US007078042B2

(12) United States Patent
Briles et al.

(10) Patent No.: US 7,078,042 B2
(45) Date of Patent: Jul. 18, 2006

(54) PNEUMOCOCCAL SURFACE PROTEIN C (PSPC), EPITOPIC REGIONS AND STRAIN SELECTION THEREOF, AND USES THEREFOR

(75) Inventors: David E. Briles, Birmingham, AL (US); Susan K. Hollingshead, Birmingham, AL (US); Alexis Brooks-Walter, Birmingham, AL (US)

(73) Assignee: UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/298,523

(22) Filed: Apr. 23, 1999

(65) Prior Publication Data

US 2003/0059438 A1 Mar. 27, 2003

Related U.S. Application Data

(63) Continuation-in-part of application No. 08/714,741, filed on Sep. 16, 1996, now Pat. No. 6,500,613, which is a continuation-in-part of application No. 08/529,055, filed on Sep. 15, 1995, now Pat. No. 6,592,876.

(60) Provisional application No. 60/082,728, filed on Apr. 23, 1998.

(51) Int. Cl.

| | |
|---|---|
| ***A61K 39/395*** | (2006.01) |
| ***A61K 39/40*** | (2006.01) |
| ***A61K 39/00*** | (2006.01) |
| ***A61K 39/38*** | (2006.01) |
| ***A61K 38/00*** | (2006.01) |
| ***C07K 14/00*** | (2006.01) |
| ***C07K 16/00*** | (2006.01) |
| ***C07K 7/00*** | (2006.01) |
| ***C07K 17/00*** | (2006.01) |
| ***C07K 5/00*** | (2006.01) |

(52) U.S. Cl. ................................ 424/244.1; 424/184.1; 424/234.1; 424/237.1; 424/139.1; 424/130.1; 424/150.1; 424/165.1; 530/300; 530/324; 530/350; 530/387.1; 514/2; 514/8

(58) Field of Classification Search ................. 530/300, 530/350, 324, 387.1; 424/184.1, 234.1, 130.1, 424/237.1, 244.1, 165.1, 150.1, 139.1; 514/2, 514/8

See application file for complete search history.

(56) References Cited

U.S. PATENT DOCUMENTS

| | | | | |
|---|---|---|---|---|
| 5,476,929 | A | * | 12/1995 | Briles et al. |
| 5,679,768 | A | * | 10/1997 | Briles et al. |
| 5,728,387 | A | | 3/1998 | Briles et al. |
| 5,753,463 | A | * | 5/1998 | Briles et al. |
| 5,804,193 | A | * | 9/1998 | Briles et al. |
| 5,856,170 | A | * | 1/1999 | Briles et al. |
| 5,871,943 | A | | 2/1999 | Briles et al. |
| 5,955,089 | A | * | 9/1999 | Briles et al. |
| 5,965,141 | A | * | 10/1999 | Briles et al. |
| 5,980,909 | A | * | 11/1999 | Briles et al. |

(Continued)

FOREIGN PATENT DOCUMENTS

| | | | | |
|---|---|---|---|---|
| CA | 2104014 | | | 8/1992 |
| CA | 2116261 | | | 10/1994 |
| CA | 2149345 | | | 11/1995 |
| CA | 2232033 | | | 3/1997 |
| CA | 2253252 | | | 11/1997 |
| EP | 0 622 081 | A1 | | 11/1994 |
| EP | 0 695 803 | | | 2/1996 |
| EP | 1 477 185 | A2 | * | 11/2004 |
| WO | WO 92/14488 | | | 9/1992 |
| WO | WO 93/24000 | | | 12/1993 |
| WO | WO 97/09994 | | | 3/1997 |
| WO | WO 98/21337 | | | 5/1998 |
| WO | WO 99/53940 | | * | 10/1999 |
| WO | WO 00/56359 | | * | 9/2000 |
| WO | WO 00/76541 | | * | 12/2000 |
| WO | WO 02/084426 | A2 | | 1/2002 |

OTHER PUBLICATIONS

Briles, "PspA's Affect on Lactoferrin Killing of Pneumococci," National Institute of Health/National Institute of Allergy and Infectious Diseases Grant No. 1 RO1 A10610 38-01, pp. 2 (2003).

Beall et al J. Clin. Microbiol, 38/10: 3663-3669, 2000.*

Talkington et al, Infection & Immunity, 59/4: 1285-1289, 1991.*

(Continued)

*Primary Examiner*—Nita Minnifield
(74) *Attorney, Agent, or Firm*—Nixon Peabody LLP

(57) ABSTRACT

Disclosed and claimed are: epitopic regions of Pneumococcal Surface Protein C or "PspC", different clades of PspC, isolated and/or purified nucleic acid molecules such as DNA encoding a fragment or portion of PspC such as an epitopic region of PspC or at least one epitope of PspC, uses for such nucleic acid molecules, e.g., to detect the presence of PspC or of *S. pneumoniae* by detecting a nucleic acid molecule therefor in a sample such as by amplification and/or a polymerase chain reaction, vectors or plasmids which contain and/or express such nucleic acid molecles, e.g., in vitro or in vivo, immunological, immunogenic or vaccine compositions including at least one PspC and/or a portion thereof (such as at least one epitopic region of at least one PspC and/or at least one polypeptide encoding at least one epitope of at least one PspC), either alone or in further combination with at least one second pneumococcal antigen, such as at least one different PspC and/or a fragment thereof and/or at least one PspA and/or at least one epitopic region of at least one PspA and/or at least one polypeptide including at least one epitope of PspA. PspC or a fragment thereof, and thus a composition including PspC or a fragment thereof, can be administered by the same routes, and in approximately the same amounts, as PspA. Thus, the invention further provides methods for administering PspC or a fragment thereof, as well as uses of PspC or a fragment thereof to formulate such compositions.

10 Claims, 50 Drawing Sheets

U.S. PATENT DOCUMENTS

| | | | | | |
|---|---|---|---|---|---|
| 6,004,802 | A | * | 12/1999 | Briles et al. | |
| 6,027,734 | A | * | 2/2000 | Briles et al. | |
| 6,042,838 | A | * | 3/2000 | Briles et al. | |
| 6,231,870 | B1 | * | 5/2001 | Briles et al. | |
| 6,232,116 | B1 | * | 5/2001 | Briles et al. | |
| 6,245,335 | B1 | * | 6/2001 | Masure et al. | 424/190.1 |
| 6,291,654 | B1 | * | 9/2001 | Hostetter et al. | 530/413 |
| 6,420,135 | B1 | * | 7/2002 | Kunsch et al. | 435/69.1 |
| 6,500,613 | B1 | * | 12/2002 | Briles et al. | 435/6 |
| 6,503,511 | B1 | * | 1/2003 | Wizemann et al. | 424/190.1 |
| 6,573,082 | B1 | * | 6/2003 | Choi et al. | 435/252.3 |
| 6,592,876 | B1 | * | 7/2003 | Briles et al. | 424/244.1 |
| 6,638,516 | B1 | | 10/2003 | Becker et al. | |
| 6,784,164 | B1 | | 8/2004 | Masure et al. | |
| 6,943,241 | B1 | * | 9/2005 | Isogai et al. | 536/23.1 |
| 2001/0016200 | A1 | | 8/2001 | Briles et al. | |
| 2002/0061545 | A1 | * | 5/2002 | Choi et al. | 435/7.34 |
| 2003/0059438 | A1 | * | 3/2003 | Briles et al. | 424/190.1 |
| 2003/0091577 | A1 | | 5/2003 | Gilbert et al. | |
| 2003/0096950 | A1 | * | 5/2003 | Tuomanen et al. | 530/350 |
| 2004/0067237 | A1 | | 4/2004 | Becker et al. | |
| 2004/0077847 | A1 | * | 4/2004 | Briles et al. | 536/23.1 |
| 2004/0081662 | A1 | * | 4/2004 | Hermand et al. | 424/190.1 |
| 2004/0241638 | A1 | * | 12/2004 | Thonnard | 435/5 |
| 2004/0241687 | A1 | * | 12/2004 | Thonnard et al. | 435/6 |
| 2005/0031646 | A1 | * | 2/2005 | Capiau et al. | 424/203.1 |
| 2005/0118659 | A1 | * | 6/2005 | Castado et al. | 435/7.32 |
| 2005/0196405 | A1 | * | 9/2005 | Briles et al. | 424/190.1 |

OTHER PUBLICATIONS

Kuroki et al, J. Biol. Chem. 263/7: 3388–3394, 1988.*

Kolberg et al FEMS Immunol & Med. Microb. 29: 289–294, 2000.*

McDaniel et al Microbial Pathogenesis 17:323–337, 1994.*

Briles et al, Vaccine 18: 1707–1711, 2000.*

Nabors et al, Vaccine 18: 1743–1754, 2000.*

Brooks–Walter et al, Infection & Immunity 67/12 :6533–6542, 1999.*

Hollingshead et al, Infection & Immunity 68/10: 5889–5900, 2000.*

HåKansson et al Infection & Immunity 69/5: 3372–3381, 2001.*

Crain et al Microbial Pathogenesis 21:265–275, 1996.*

Dave et al Infection & Immunity 69/5:3435–3437, 2001.*

Ralph et al Annals. NY. Acad. Sciences.*

Brooks–Walter ASM Annual Mtg 1997 (Abstract only) p. 35 Abstract #B–37.*

Swiatlo et al, Gene, 188: 279–284, 1997.*

Briles et al, Microbial Drug Resistance 3/4:401–408, 1997.*

Hammerschmidt et al., "SpsA, A Novel *Pneumococcal* Surface Protein With Specific Binding to Secretory Immunoglobin A and Secretory Component, Molecular Immunology", vol. 25, pp. 1113–1124, 1997.

Tomasz, A., "Choline in the Cell Wall of a Bacterium: Novel Type of Polymer–Linked Choline in *Pneumococcus*", Science, vol. 157, pp. 694–697, 1967.

Briese et al., "Interactions of the Pneumococcal Amidase with Lipoteichoic Acid and Choline", Eur. J. Biochem., vol. 146, pp. 417–427, 1985.

Sanchez–Beato et al., "Molecular Characterization of a Family of Choline–Binding Proteins of *Clostridium beijerinckii* NCIB 8052. Evolution and Gene Redundancy in Prokaryotic Cell", Gene, vol. 180, pp. 13–21, 1996.

Sanchez–Beato et al., Molecular Characterization of PcpA: A Novel Choline–Binding of *Streptococcus pneumoniae*, FEMS Microbiology Letters 164, pp. 207–214, 1997.

Banas et al., "Sequence Analysis of the Gene for the Glucan–Binding Protein of *Streptococcus mutans* Ingritt", Infection and Immunity, vol. 58, No. 3, pp. 337–673, 1990.

Briles et al., "PspA and PspC: Their Potential for Use as *Pneumococcal* Vaccines", Microbial Drug Resistance, vol. 3, No. 4, pp. 401–408, 1997.

Briles et al., "PspA, a Protection–Eliciting Pneumococcal Protein: Immunogenicity of Isolated Native PspA in Mice", Vaccine, vol. 14, No. 9, pp. 858–867, 1996.

McDaniel et al., Use of Insertional Inactivation to Facilitate Studies of Biological Properties of Pneumococcal Surface Protein A (PspA), J. Exp. Med., vol. 165, pp. 381–394, Feb. 1987.

McDaniel et al., "PspA, A Surface Protein of *Streptococcus pneumoniae*,Is Capable of Eliciting Protection Against Pneumococci of More Than One Capsular Type", Infection and Immunity, pp. 222–228, Jan. 1991.

McDaniel et al., "Molecular Localization of Variable and Conserved Regions of pspA and Identification of Additional pspA Homologous Sequences in *Streptococcus pneumoniae*", Microbial Pathogenesis, pp. 261–269, 1992.

McDaniel et al., "Localization of Protection–Eliciting Epitopes on PspA of *Streptococcus pneumoniae* Between Amino Acid Residues 192 and 260", Microbial Pathogenesis, pp. 323–327, 1994.

McDaniel et al., "Monoclonal Antibodies Against Surface Component of *Streptococcus pneumoniae*", Monoclonal Antibodies Against Antibodies, vol. III, pp. 143–164.

McDaniel et al., "Immunization with a Plasmid Expressing Pneumococcal Surface Protein A (PspA) Can Elicit Protection Against Fatal Infection with *Streptococcus pneumoniae*", Gene Therapy, vol. 4, pp. 375–377, 1997.

McDaniel et al., "Analysis of a Surface Protein of *Streptococcus pneumoniae* Recognized by Protective Monoclonal Antibodies", Microbial Pathogenesis, vol. 1, ppp. 519–531, 1986.

McDaniel et al., "Comparison of the PspA Sequence from *Streptococcus pneumoniae* EF5668 to the Previously Identified PspA Sequence from Strain Rx1 and Ability of PspA from EF5668 to Elicit Protection against *Pneumococci* of Different Capsular Types", Infection and Immunity, vol. 66, No. 10, pp. 4748–4754, Oct. 1998.

McDaniel et al. "Monoclonal Antibodies Against Protease–Sensitive *Pneumococcal* Antigens Can Protect Mice From Fatal Infection With *Streptococcus pneumoniae*", J. Exp. Med., vol. 160, pp. 386–397, Aug. 1984.

McDaniel et al. "Use of Insertional Inactivation To Facilitate Studies of Biological Properties of Pneumococcal Surface Protein A (PspA)", J. Exp. Med., vol. 165, pp. 381–394, Feb. 1987.

Devereux et al. "A Comprehensive Set of Sequence Analysis Programs for the VAX", Nucleic Acids Research, vol. 12, No. 1, pp. 387–395.

Wu et al., "Intranasal Immunization of Mice with PspA (Pneumococcal Surface Protein A) Can Prevent Intranasal Carriage, Pulmonary Infection, and Sepis with *Streptococcus pneumoniae*", The Journal of Infectious Diseases, pp. 839–846, 1997.

Yother et al., "Truncated Forms of PspA That are Secreted From *Streptococcus pneumoniae* and Their Use in Functional Studies and Cloning of the pspA Gene", Journal of Bacteriology, pp. 610–618, 1992.

Tart et al., "Truncated *Streptococcus pneumoniae* PspA Molecules Elicit Cross–Protective Immunity Against Pneumococcal Challenge in Mice", The Journal of Infectious Diseases, vol. 173, pp. 380–386, 1996.

Crain et al., "Evidence for the Simultaneous Expression of Two PspAs by a clone of capsular Serotype 6B *Strepotococcus pneumoniae*", Microbial Pathogenesis, vol. 21, pp. 265–275, 1996.

Crain et al. "Pneumococcal Surface Protein A (PspA) Is Serologically Highly Variable and Is Expressed By All Clinically Important Capsular Serotypes of *Streptococcus pneumoniae*", Infection and Immunity, vol. 58, No. 10, pp. 3293–3299, Oct. 1990.

Yamamoto et al., "Oral Immunization with PspA Elicits Protective Humoral Immunity Against *Streptococcus pneumoniae* Infection", Infection and Immunity, vol. 65, No. 2, Feb. 1997.

Yamamoto et al., "A Nontoxic Adjuvant for Mucosal Immunity to Pneumococcal Surface Protein A [1]", The Journal of Immunology, vol. 161, pp. 4115–4121, 1998.

Wortham et al., "Enhanced Protective Antibody Responses to PspA After Intranasal or Subcutaneous Injections of PspA Genetically Fused to Granulocyte–Macrophage Colony––Stimulating Factor or Interleukin–2", Infection and Immunity, vol. 66, No. 4, pp. 1513–1520, Apr, 1998.

Nayak et al., "A Live Recombinant A virulent Oral *Salmonella* Vaccine Expressing Pneumococcal Surface Protein A Induces Protective Responses Against *Streptococcus pneumoniae*", Infection and Immunity, vol. 66, No. 8, pp. 3744–3751, Aug. 1998.

Yother et al., "Structural Properties and Evolutionary Relationships of PspA, a Surface Protein of *Streptococcus pneumoniae*, as Revealed by Sequence Analysis,", Journal of Bacteriology, vol. 174, No. 2, pp. 601–609, Jan. 1992.

Ralph et al., "Cross–Reactive Protein Eliciting Epitopes of Pneumococcal Surface Protein A", Annals of New York Academy of Sciences, pp. 361–363, undated.

E. AlonsoDe Velasco et al., "*Streptococcus pneumoniae*: Virulence Factors, Pathogenesis, and Vaccines", Microbiology Reviews, vol. 59, No. 4, pp. 591–603, Dec. 1995.

Yother et al. "Pneumococcal Surface Protein A: Structural Analysis and Biological Significance", Genetics and Molecular Biology of *Streptococci, Lactococci* and *Enterococci*, American Society for Microbiology, Washington, D.C., 1991, pp. 88–91.

Talkington et al., "a 43–Kilodalton Pneumococcal Surface Protein PspA: Isolation, Protective Abilities, and Structural Analysis of the Amino–Terminal Sequence", Infection and Immunity, vol. 59, No. 4, pp. 1285–1289, Apr. 1991.

Swiatlo et al. "Oligonucleotides Identify Conserved and Variable Regions of pspA and pspA–Like Sequences of *Streptococcus pneumoniae*", Gene, vol. 188, pp. 279–284, 1997.

Barrosso et al., "Nucleotide Sequence of *Clostridium difficile* Toxin B Gene" Nucleic Acids Research, vol. 18, No. 13, p 4004.

Garcia et al., "Nucleotide Sequence and Expression of the Pneumococcal Autolysin Gene From Its Own Promoter In *Escherichia coli*", Gene, vol. 43, pp. 265–272, 1986.

Abstracts of 90th Annual Meeting of the American Society for Microbiology, p. 98, item D–106, May 1990.

Abstract of ASM Conference on *Streptococcal* Genetics, p. 77 item 2c–21, undated.

Brooks–Walter, A., et al., *The pspC gene encodes a second pneumococcal surface protein homologous to the gene encoding the protection–eliciting PspA protein of Streptococcus pneumoniae*. ASM Annual Meeting (Abstract), 1997.

Gary, B.M., *Pneumoccal infection*, in *Bacterial Infection*, P.E. Brachman, Editor. 1997, Plenum Publishing Corporation: New York.

Abstracts of 89th Annual Meeting of the American Society for Microbiology, p. 125, item D–257, May 1989.

Dove et al., "Molecular Characterization of the *Clostridium difficile* Toxin A Gene", Infection and Immunity, vol. 58, No. 2, pp. 480–488, 1990.

Yother et al., "Novel Surface Attachment of the *Streptococcus pneumoniae* Protein PspA", Journal of Bacteriology, pp. 2976–2985, May 1994.

GENBANK ACCESSION NO. AF067128 by Hostetter et al. (May 18, 1998).

Swiatlo et al., "Genetic Analysis of Pneumococcal Surface Protein A (PspA) Using Southern Blot Hybridization with Oligonucleotide Probes," *93rd ASM General Meeting,* Abstract D–70, p. 107 (1993) (abstract).

Crain et al., "Simultaneous Expression of Two Apparent PspA Molecules by Some Capsular Group 6 Isolates of *Streptococcus pneumoniae,"93rd ASM General Meeting,* Abstract D–71, p. 107 (1993) (abstract).

Brooks–Walter et al., "Restriction Fragment Length Polymorphism Analysis of the Pneuococcal Surface Protein A (PspA) of *Streptococcus pneumoniae,"*94*th ASM General Meeting,* Abstract D–61 (1994) (abstract).

Jedrzejas, "Pneumococcal Virulence Factors: Structure and Function," *Microb. Mol. Biol. Revs.* 65(2):187–207 (2001).

Donnelly et al., "Technical and Regulatory Hurdles for DNA Vaccines,"*Int. J. Parasitol.* 33:457–467 (2003).

Deonarain, "Ligand–Targeted Receptor–Mediated Vectors for Gene Delivery," *Exp. Opin. Ther. Pat.* 8(1):53–69 (1998).

Górecki, "Prospects and Problems of Gene Therapy: An Update," *Exp. Opin. Emerging Drugs* 6(2):187–198 (2001).

Verma et al., "Gene Therapy – Promises, Problems and Prospects," *Nature* 389:239–245 (1997).

Eck et al., Goodman & Gilman's The Pharmacological Basis of Therapeutics, 9*th* Ed., McGraw–Hill, New York, New York, pp. 77–101 (1996).

Balachandran et al., "Role of Pneumococcal Surface Protein C in Nasopharyngeal Carriage and Pneumonia and Its Ability to Elicit Protection Against Carriage of *Streptococcus pneumoniae," Infection and Immunity* 70(5):2526–2534 (2002).

Rosenow et al., "Contribution of Novel Choline–Binding Proteins to Adherence, Colonization and Immunogenicity of *Streptoccoccus pnuemoniae,"Molecular Biology* 25(5):819–829 (1997).

Swiatlo, E., "Studies of Surface Proteins of *Streptococcus pneumoniae,"*Database Fed Rip on Dialog, Identifying No. 116507 (1997).

Pruitt et al., "Binding of Human Complement Factor H by PspC Of *Streptococcus pneumoniae,"FAESB Journal* 16(4):A306–A307 (2002).

Hollingshead et al., "Streptococcus pneumoniae: New Tools for an Old Pathogen," *Current Opinion in Microbilogy* 4:71–77 (2001).

Briles et al., "Pneumococcal Diversity: Consinderation for New Vaccine Strategies with Emphasis on Pneumococcal Surface Protein A (PspA)," *Clinical Microbiology Reviews* 11(4):645–657 (1998).

Iannelli et al., "Allelic Variation in the Highly Polymorphic locus *pspC of Streptococcus pneumoniae,"* *Gene* 284:63–71 (2002).

Janulczyk et al., "Hic, a Novel Surface Protein of *Streptococcus pneumoniae* That Interfaces with Complement Function," *Journal of Biological Chemistry* 275(47):37257–37263 (2000).

Baltimore et al., "Pneumcoccal Infections," in *Bacterial Infection,* Chapter 28, Brachman (ed.), Plenum Publishing Corporation, New York (1997).

Jarva et al., "Complement Resistance Mechanisms of Streptococci," *Molecular Immunology* 40:95–107 (2003).

Briles et al., "Pneumococcal Proteins That May Constitute the Next Generation Vaccine for Pneumococcal Disease," *International Congress Series* 1257:27–31 (2003).

* cited by examiner

FIGURE 1: CARTOON OF THE PspC CLADES COMPARED TO A REPRESENTATIVE PspA MOLECULE. LONG ARROWS REPRESENT THE DIRECT REPEATS FOUND WITHIN α HELIX. THE HYPERVARIABLE REGION IS INDICATED BY THE ZIG-ZAG LINES THE REGION OF HOMOLOGY FOUND WITH THE ALPHA HELIX IS INDICATED BY THE HORIZONTAL LINES

| | a | b | c | d | e | f | g | |
|---|---|---|---|---|---|---|---|---|
| 1 | | | | | | | | |
| 11 | | | | | | | | Glu Gly Val Arg Ser Gly Asn Asn Leu Thr |
| 16 | | Gln | Asp | Ile | Ser | Lys | Lys | Val Thr Ser Ser Gly |
| 22 | Tyr | Ala | Asp | Glu | Val | Glu | Ser | |
| 29 | | | His | Leu | Glu | Ser | Ile | |
| 34 | Leu | Lys | Asp | Val | Lys | Lys | Asn | |
| 41 | Leu | Lys | Lys | | | | | |
| 44 | Val | Gln | His | Thr | Gln | Asn | Val | |
| 51 | | | Gly | Leu | Ile | Thr | Lys | |
| 56 | Leu | Ser | Glu | Ile | Lys | Lys | Lys | |
| 63 | | | | | | | Tyr | |
| 64 | Leu | Tyr | Asp | Leu | Lys | | | |
| 69 | Val | Asn | Val | Leu | Ser | Glu | Ala | |
| 76 | | | Glu | Leu | Thr | Ser | Lys | |
| 81 | | | | Thr | Lys | Glu | Thr | |
| 85 | Lys | Glu | Lys | Leu | Thr | Ala | Thr | |
| 92 | Phe | Glu | Gln | Phe | Lys | Lys | Asp | |
| 99 | | | | | | | | Thr Leu Pro Thr Glu Pro |
| 105 | | | | | Glu | Lys | Lys | |
| 108 | Val | Ala | Glu | Ala | Gln | Lys | Lys | |
| 115 | Val | Glu | Glu | Ala | Lys | Lys | Lys | |
| 122 | | | | Ala | Glu | Asp | Gln | |
| 126 | Lys | Glu | Lys | Asp | Arg | Arg | Asn | |
| 133 | Tyr | Pro | Thr | Ile | Thr | | | |
| 138 | Tyr | Lys | Thr | Leu | Glu | Leu | Glu | |
| 145 | Ile | Ala | Glu | Ser | Asp | Val | Glu | |
| 152 | Val | Lys | Lys | Ala | Glu | Leu | Glu | |
| 159 | Leu | Val | Lys | Val | Lys | Ala | Lys | |
| 166 | Glu | Ser | Gln | Asp | Glu | Glu | Lys | |
| 173 | Ile | Lys | Gln | Ala | Glu | Ala | Glu | |
| 180 | Val | Glu | Ser | Lys | Gln | Ala | Glu | |
| 187 | | | | Ala | Thr | Arg | | |
| 190 | Leu | Lys | Lys | Ile | Lys | Thr | Asp | |
| 197 | Arg | Glu | Glu | Ala | Lys | Arg | Lys | |
| 204 | | Ala | Asp | Ala | Lys | Leu | Lys | |
| 210 | | Glu | Ala | Val | Glu | Lys | Asn | |
| 216 | Val | Ala | Thr | Ser | Glu | Gln | Asp | |
| 223 | Lys | | | | | | | |
| 224 | | | | | | | | |
| 234 | | | | | | | | Pro Lys Arg Arg Ala Lys Arg Gly Val Ser |
| 244 | | | | | | | | Gly Glu Leu Ala Thr Pro Asp Lys Lys Glu |
| 254 | | | | | | | | Asn Asp Ala Lys Ser Ser Asp Ser Ser Val |
| 264 | | | | | | | | Gly Glu Glu Thr Leu Pro Ser Pro Ser Leu |
| 268 | | | | | Glu | Ser | Gln | Asn Met Ala Asn |
| 271 | | Thr | Glu | His | Arg | Lys | Asp | |
| 277 | Val | Asp | Glu | Tyr | | | | |
| 281 | Ile | Lys | Lys | Met | Leu | Ser | Glu | |
| 288 | Ile | Gln | Leu | Asp | Arg | Arg | Lys | |
| 295 | | | His | Thr | Gln | Asn | Val | |
| 300 | | | Asn | Leu | Asn | Ile | Lys | |
| 305 | Leu | Ser | Ala | Ile | Lys | Thr | Lys | |
| 312 | | | | Tyr | Leu | Tyr | Glu | |
| 316 | Leu | Ser | Val | Leu | Lys | Glu | Asn | |
| 323 | | | | | | Ser | Lys | |
| 325 | Lys | Glu | Glu | Leu | Thr | Ser | Lys | |
| 332 | | | | Thr | Lys | Ala | Glu | |
| 336 | Leu | Thr | Ala | Ala | Phe | Glu | Gln | |

FIG.3A

| | | | | | | | | |
|---|---|---|---|---|---|---|---|---|
| 343 | Phe | Lys | Lys | | | | | |
| 346 | | | | | | | | Asp Thr Leu Lys Pro |
| 351 | | | | | Glu | Lys | Lys | |
| 354 | Val | Ala | Glu | Ala | Glu | Lys | Lys | |
| 361 | Val | Glu | Glu | Ala | Lys | Lys | Lys | |
| 368 | | | | Ala | Lys | Asp | Gln | |
| 372 | Lys | Glu | Glu | Asp | Arg | Arg | Asn | |
| 379 | | | | Tyr | | | | |
| 380 | | | | Pro | Thr | Asn | Thr | |
| 384 | Tyr | Lys | Thr | Leu | Glu | Leu | Glu | |
| 391 | Ile | Ala | Glu | Ser | Asp | Val | Lys | |
| 398 | Val | Lys | Glu | Ala | Glu | | | |
| 403 | Leu | Glu | Leu | Val | Lys | Glu | Glu | |
| 410 | Ala | Asn | Glu | Ser | Arg | Asn | Glu | |
| 417 | | Glu | Lys | Ile | Lys | Gln | Ala | |
| 423 | Lys | Glu | Lys | Val | Glu | Ser | Lys | |
| 430 | Lys | Ala | Glu | Ala | Thr | Arg | | |
| 436 | Leu | Glu | Lys | Ile | Lys | Thr | Asp | |
| 443 | Arg | Lys | Lys | Ala | Glu | Glu | Glu | |
| 450 | | | | Ala | Lys | Arg | Lys | |
| 454 | Ala | Glu | Glu | Ser | Glu | Lys | Lys | |
| 461 | Ala | Ala | Glu | Ala | Lys | Gln | Lys | |
| 468 | Val | Asp | Ala | Glu | Glu | Tyr | Ala | |
| 475 | | | | Leu | Glu | Ala | Lys | |
| 479 | Ile | Ala | Glu | Leu | Glu | Tyr | Glu | |
| 486 | Val | Gln | Arg | Leu | Glu | Lys | Glu | |
| 493 | Leu | Lys | Glu | | | | | |
| 496 | Ile | Asp | Glu | Ser | Asp | Ser | Glu | |
| 503 | | Asp | Tyr | Leu | Lys | Glu | Gly | |
| 509 | Leu | Arg | Ala | | | | | |
| 512 | | | Pro | Leu | Gln | Ser | Lys | |
| 517 | Leu | Asp | Thr | Lys | Lys | Ala | Lys | |
| 524 | Leu | Ser | Lys | | | | | |
| 527 | Leu | Glu | Glu | Leu | Ser | Asp | Lys | |
| 534 | Ile | Asp | Glu | Leu | Asp | Ala | Glu | |
| 541 | Ile | Ala | Lys | Leu | Glu | Val | Gln | |
| 548 | Leu | Lys | Asp | Ala | Glu | Gly | Asn | |
| 555 | | | | | | Asn | Asn | |
| 557 | Val | Glu | Ala | Tyr | Phe | Lys | Glu | |
| 564 | | | Gly | Leu | Glu | Lys | Thr | |
| 569 | | | Thr | Ala | Glu | Lys | Lys | |
| 574 | | Ala | Glu | Leu | Glu | Lys | Ala | |
| 580 | Glu | Ala | Asp | Leu | Lys | Lys | Ala | |
| 587 | Val | Asp | Glu | | | | | |

The coiled-coil motif of the α-helix of PspC. Amino acids that are not in the coiled-coil motif are in the right column. This is the output from the Matcher program accessed through the Internet (http://catt.poly.edu/~jps/).

FIG. 3B

Choline-binding Domain

```
PspC consensus
               11111111112
  12345678901234567890
1 KTGWKQENGNWYFYNTDGSMA
2   TGWLQNNGSWYYLNAMGAMA
3   TGWLQNNGSWYYLNANGSMA
4   TGWLQNNGSWYYLNANGAMA
5   TGWLQYNGSWYYLNANGDMA
6   TGWLQYNGSWYYLNSNGAMA
7   TGWLQYNGSWYYLNANGDMA
8   TGWLQNNGSWYYLNANGDMA
9   TGWLQYN  SWYYLNANGDMA
10  TGWVKDGDTWYYLEASGAMKA
11  SQWFKVSDKWYYVNGSGALA
        VNTTVDGYGVNANGEWVN   18 amino acid tail PspC
                             28% identical to consensus

    TGWLQNNGSWYYLNANGAMA     PspC consensus repeat
         Y
```

For PspA/R36A alingement see Yother and Briles 1992.

```
TGWLQXNGSWYYLNANGAMA     PspA/Rx1 consensus
     Y                   95% identical to PspC consensus

VNTTVDGYKVNANGEWV_       PspA/Rx1 17 amino acid tail.
                         One AA different from PspC,
                         And one AA shorter.
```

*FIG.5A*

PspA/EF5668

```
            11111111112
   12345678901234567890
1  IGWKQENGMWYFYNTDGSM A
2  TGWLQNNGSWYYLNSNGAM A
3  TGWLQYNGSWYYLNANGAM A
4  TGWLQYNGSWYYLNANGAM A
5  TGWLQYNGSWYYLNANGDM A
6  TGWLQYNGSWYYLNANGDM A
7  TGWAKVHGSWYYLNANGSM A
8  TGWVKDGETWYYLEASGSMKA
9  NQWFQVSDKWYYVNGLGSL S
10    VNTTVDGYKVNANGEWV     17 amino acid tail EF5668 PspA

   TGWLQYNGSWYYLNANGSM A    PspA/EF5668 consensus
                            90% identical to PspC consensus
```

| | |
|---|---|
| Repeat #1 | |
| PspC consensus | KTGWKQENGNWYFYNTDGSMA |
| PspA/Rx1 | TGWKQENGMWYFYNTDGSMA |
| PspA/EF5668 | IGWKQENGMWYFYNTDGSM A |
| Repeat #N-1 | |
| PspC consensus | TGWVKDGDTWYYLEASGAMKA |
| PspA/Rx1 | TGWVKDGDTWYYLEASGAMKA |
| PspA/EF5668 | TGWVKDGETWYYLEASGSMKA |
| Repeat #N | |
| PspC consensus | SQWFKVSDKWYYVNGSGALA |
| PspA/Rx1 | SQWFKVSDKWYYVNGLGALA |
| PspA/EF5668 | NQWFQVSDKWYYVNGLGSLS |
| 17-18 AA tail | |
| PspC consensus | VNTTVDGYGVNANGEWVN |
| PspA/Rx1 | VNTTVDGYKVNANGEWV |
| PspA/EF5668 | VNTTVDGYKVNANGEWV |

FIG. 5B

Western Immunoblot of pneumococcal lyates
Panel A was developed with anti-PspC polyclonal serum and panel B was developed with anti-PspA monoclonal antibody, Xi126. The molecular weight markers are indicated. Cross-reaction of the polyclonal serum to PspC is observed with all strains tested.

Level of antibody reactive to PspC and PspA fragments present in the sera of mice immunized with PspC. Each bar represents the mean of the log reciprocal titer and upperbound of standard error of sera from five mice. The limit of detection of the log reciprocal antibody titer is 1.8.

Other Formats:
Links:

FIG. 8A

LOCUS CAA05158 539 aa BCT 14-OCT-1997
DEFINITION SpsA protein.
ACCESSION CAA05158
PID g2576331
VERSION CAA05158.1 GI:2576331
DBSOURCE embl locus SPSPSA2, accession AJ002054.1
KEYWORDS
SOURCE Streptococcus pneumoniae.
ORGANISM Streptococcus pneumoniae
Bacteria; Firmicutes; Bacillus/Clostridium group; Streptococcaceae; Streptococcus.
REFERENCE 1 (residues 1 to 539)
AUTHORS Hammerschmidt,S.
TITLE Direct Submission
JOURNAL Submitted (13-OCT-1997) Hammerschmidt S., Microbiology, Devision Microbial Pathogenesis, National Research Centre for Biotechnology, Spielmannstrasse 7, 38106 Braunschweig, GERMANY
REFERENCE 2 (residues 1 to 539)
AUTHORS Hammerschmidt,S., Talay,S.R., Brandtzaeg,P. and Chhatwal,G.S.
TITLE SpsA, a novel pneumococcal surface protein with specific binding to secretory immunoglobulin A and secretory component
JOURNAL Mol. Microbiol. 25 (6), 1113-1124 (1997)
MEDLINE 98010350
FEATURES Location/Qualifiers
source 1..539
/organism="Streptococcus pneumoniae"
/strain="type 2"
/db_xref="taxon:1313"
Protein 1..539
/function="IgA binding protein"
/product="SpsA protein"
CDS 1..539
/db_xref="SPTREMBL:O33741"
/coded_by="AJ002054.1:1..1620"
/transl_table=11
ORIGIN
1 mfaskserkv hysirkfsig vasvavaslv mgsvvhaten egstqaatss nmaktehrka
61 akqvvdeyie kmlreiqldr rkhtqnvaln iklsaiktky lrelnvleek skdelpseik
121 akldaafekf kkdtlkpgek vaeakkkvee akkkaedqke edrrnyptnt yktleleiae
181 fdvkvkeael elvkeeakef rnegtikqak ekveskkaea trleniktdr kkaeeeakrk
241 aaeedkvkek paeqpqpapa tqpekpapkp ekpaeqpkae ktddqqaeed yarrseeeyn
301 rltqqqppkt ekpaqpstpk tgwkqengmw yfyntdgsma tgwlqnngsw yylnangama
361 tgwlqnngsw yylnangsma tgwlqnngsw yylnangama tgwlqyngsw yylnsngama

Figure 8B:
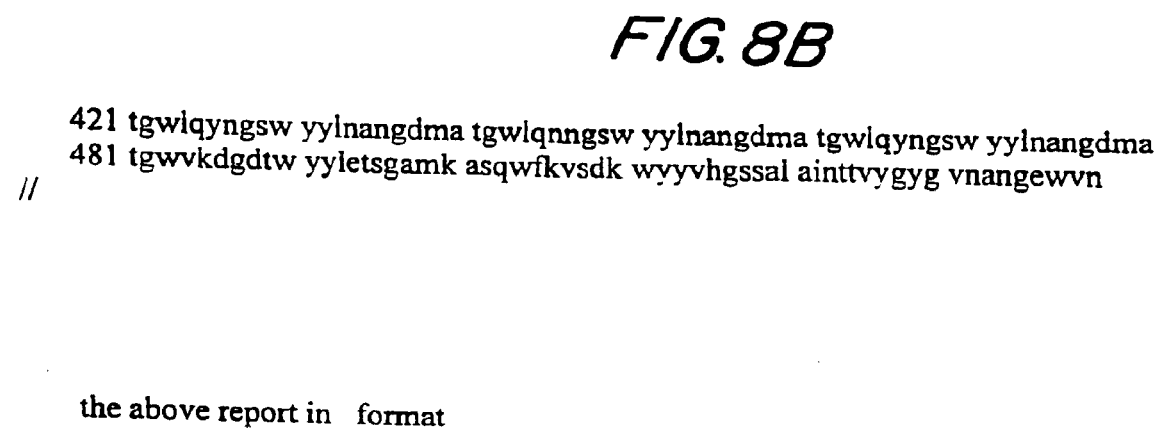

FIG. 8B 421 tgwlqyngsw yylnangdma tgwlqnngsw yylnangdma tgwlqyngsw yylnangdma
481 tgwvkdgdtw yyletsgamk asqwfkvsdk wyyvhgssal ainttvygyg vnangewvn
// the above report in format

Other Formats:
Links:

FIG. 8C

LOCUS SPSPSA2 1620 bp DNA BCT 14-OCT-1997
DEFINITION Streptococcus pneumoniae SIgA binding.
ACCESSION AJ002054
NID g2576330
VERSION AJ002054.1 GI:2576330
KEYWORDS SpsA protein.
SOURCE Streptococcus pneumoniae.
ORGANISM Streptococcus pneumoniae
Bacteria; Firmicutes; Bacillus/Clostridium group; Streptococcaceae; Streptococcus.
REFERENCE 1 (bases 1 to 1620)
AUTHORS Hammerschmidt,S.
TITLE Direct Submission
JOURNAL Submitted (13-OCT-1997) Hammerschmidt S., Microbiology, Devision Microbial Pathogenesis, National Research Centre for Biotechnology, Spielmannstrasse 7, 38106 Braunschweig, GERMANY
REFERENCE 2 (bases 1 to 1620)
AUTHORS Hammerschmidt,S., Talay,S.R., Brandtzaeg,P. and Chhatwal,G.S.
TITLE SpsA, a novel pneumococcal surface protein with specific binding to secretory immunoglobulin A and secretory component
JOURNAL Mol. Microbiol. 25 (6), 1113-1124 (1997)
MEDLINE 98010350
FEATURES Location/Qualifiers
source 1..1620
/organism="Streptococcus pneumoniae"
/strain="type 2"
/db_xref="taxon:1313"
CDS 1..1620
/function="IgA binding protein"
/codon_start=1
/transl_table=11
/product="SpsA protein"
/protein_id="CAA05158.1"
/db_xref="PID:e354783"
/db_xref="PID:g2576331"
/db_xref="GI:2576331"
/db_xref="SPTREMBL:O33741"

/translation="MFASKSERKVHYSIRKFSIGVASVAVASLVMGSVVHATENEGST

QAATSSNMAKTEHRKAAKQVVDEYIEKMLREIQLDRRKHTQNVALNIKLSAIKT
KYLR

FIG. 8D

ELNVLEEKSKDELPSEIKAKLDAAFEKFKKDTLKPGEKVAEAKKKVEEAKKKAE
DQKE

EDRRNYPTNTYKTLELEIAEFDVKVKEAELELVKEEAKEFRNEGTIKQAKEKVES
KKA

EATRLENIKTDRKKAEEEAKRKAAEEDKVKEKPAEQPQPAPATQPEKPAPKPEK
PAEQ

PKAEKTDDQQAEEDYARRSEEEYNRLTQQQPPKTEKPAQPSTPKTGWKQENGM
WYFYN

TDGSMATGWLQNNGSWYYLNANGAMATGWLQNNGSWYYLNANGSMATGW
LQNNGSWYY

LNANGAMATGWLQYNGSWYYLNSNGAMATGWLQYNGSWYYLNANGDMAT
GWLQNNGSW

YYLNANGDMATGWLQYNGSWYYLNANGDMATGWVKDGDTWYYLETSGAM
KASQWFKVS

DKWYYVHGSSALAINTTVYGYGVNANGEWVN"

repeat_region 961..1564

/rpt_type=DIRECT

BASE COUNT 625 a 294 c 370 g 331 t

ORIGIN 1 atgtttgcat caaaaagcga aagaaaagta cattattcaa ttcgtaaatt tagtattgga
61 gtagctagtg tagctgttgc cagtcttgtt atgggaagtg tggttcatgc gacagagaac
121 gagggaagta cccaagcagc cacttcttct aatatggcaa agacagaaca taggaaagct
181 gctaaacaag tcgtcgatga atatatagaa aaaatgttga gggagattca actagataga
241 agaaaacata cccaaaatgt cgccttaaac ataaagttga gcgcaattaa aacgaagtat
301 ttgcgtgaat taaatgtttt agaagagaag tcgaaagatg agttgccgtc agaaataaaa
361 gcaaagttag acgcagcttt tgagaagttt aaaaaagata cattgaaacc aggagaaaag
421 gtagcagaag ctaagaagaa ggttgaagaa gctaagaaaa aagccgagga tcaaaaagaa
481 gaagatcgtc gtaactaccc aaccaatact tacaaaacgc ttgaacttga aattgctgag
541 ttcgatgtga aagttaaaga agcggagctt gaactagtaa aagaggaagc taaagaattt
601 cgaaacgagg gcacaattaa gcaagcaaaa gagaaagttg agagtaaaaa agctgaggct
661 acaaggttag aaaacatcaa gacagatcgt aaaaaagcag aagaagaagc taaacgaaaa
721 gcagcagaag aagataaagt taaagaaaaa ccagctgaac aaccacaacc agcgccggct
781 actcaaccag aaaaaccagc tccaaaacca gagaagccag ctgaacaacc aaaagcagaa
841 aaaacagatg atcaacaagc tgaagaagac tatgctcgta gatcagaaga agaatataat
901 cgcttgactc aacagcaacc gccaaaaact gaaaaaccag cacaaccatc tactccaaaa
961 acaggctgga aacaagaaaa cggtatgtgg tacttctaca atactgatgg ttcaatggca
1021 acaggatggc tccaaaacaa cggttcatgg tactatctaa acgctaatgg tgctatggcg
1081 acaggatggc tccaaaacaa tggttcatgg tactatctaa acgctaatgg ttcaatggca
1141 acaggatggc tccaaaacaa tggttcatgg tactacctaa acgctaatgg tgctatggcg

FIG. 8E

```
1201 acaggatggc tccaatacaa tggttcatgg tactacctaa acagcaatgg cgctatggcg
1261 acaggatggc tccaatacaa tggctcatgg tactacctca acgctaatgg tgatatggcg
1321 acaggatggc tccaaaacaa cggttcatgg tactacctca acgctaatgg tgatatggcg
1381 acaggatggc tccaatacaa cggttcatgg tattacctca acgctaatgg tgatatggcg
1441 acaggttggg tgaaagatgg agatacctgg tactatcttg aaacatcagg tgctatgaaa
1501 gcaagccaat ggttcaaagt atcagataaa tggtactatg tccatggctc aagtgccctt
1561 gcaatcaaca caactgtata tggctatgga gtcaatgcca atggtgaatg ggtaaactaa
```

the above report in format

FIG. 9A

Other Formats:
Links:

LOCUS CAA05159 581 aa BCT 14-OCT-1997
DEFINITION SpsA protein.
ACCESSION CAA05159
PID g2576333
VERSION CAA05159.1 GI:2576333
DBSOURCE embl locus SPSPSA47, accession AJ002055.1
KEYWORDS
SOURCE Streptococcus pneumoniae.
 ORGANISM Streptococcus pneumoniae
 Bacteria; Firmicutes; Bacillus/Clostridium group; Streptococcaceae; Streptococcus.
REFERENCE 1 (residues 1 to 581)
 AUTHORS Hammerschmidt,S.
 TITLE Direct Submission
 JOURNAL Submitted (13-OCT-1997) Hammerschmidt S., Microbiology, Devision Microbial Pathogenesis, National Research Centre for Biotechnology, Spielmannstrasse 7, 38106 Braunschweig, GERMANY
REFERENCE 2 (residues 1 to 581)
 AUTHORS Hammerschmidt,S., Talay,S.R., Brandtzaeg,P. and Chhatwal,G.S.
 TITLE SpsA, a novel pneumococcal surface protein with specific binding to secretory immunoglobulin A and secretory component
 JOURNAL Mol. Microbiol. 25 (6), 1113-1124 (1997)
 MEDLINE 98010350
FEATURES Location/Qualifiers
 source 1..581
 /organism="Streptococcus pneumoniae"
 /strain="type 47"
 /db_xref="taxon:1313"
 Protein 1..581
 /function="IgA binding protein"
 /product="SpsA protein"
 CDS 1..581
 /db_xref="SPTREMBL:O33742"
 /coded_by="AJ002055.1:1..1746"
 /transl_table=11
ORIGIN
 1 mfaskserkv hysirkfsig vasvavaslv mgsvvhaten egstqaatss nmaktehrka
 61 akqvvdeyie kmlreiqldr rkhtqnvaln iklsaiktky lrelnvleek skdelpseik
 121 akldaafekf kkdtlkpgek vaeakkkvee akkkaedqke edrrnyptnt yktleleiae
 181 fdvkvkeael elvkeeakes rnegtikqak ekveskkaea trleniktdr kkaeeeakrk
 241 adaklkeanv atsdqgkpkg rakrgvpgel atpdkkenda kssdssvgee tlpssslksg
 301 kkvaeaekkv eeaekkakdq keedrrnypt ntyktldlei aesdvkvkea elelvkeeak
 361 eprdeekikq akakveskka eatrlenikt drkkaeeeak rkaaeedkvk ekpaeqpqpa 421 patqpekpap kpekpaeqpk aektddqqae edyarrseee ynrliqqqpp ktekpaqpft
481 pktgwkqeng mwyfyntdgs matgwlqyng swyylnangd matgwvkdgd twyyleasga
541 mkasqwfkvs dkwyyvngsg alavnttvdg ygvnangewv n
//

FIG. 9B the above report in format

FIG.9C

Other Formats:
Links:

LOCUS SPSPSA47 1746 bp DNA BCT 14-OCT-1997
DEFINITION Streptococcus pneumoniae SIgA binding.
ACCESSION AJ002055
NID g2576332
VERSION AJ002055.1 GI:2576332
KEYWORDS SpsA protein.
SOURCE Streptococcus pneumoniae.
ORGANISM Streptococcus pneumoniae
Bacteria; Firmicutes; Bacillus/Clostridium group; Streptococcaceae;
Streptococcus.
REFERENCE 1 (bases 1 to 1746)
AUTHORS Hammerschmidt,S.
TITLE Direct Submission
JOURNAL Submitted (13-OCT-1997) Hammerschmidt S., Microbiology, Devision
Microbial Pathogenesis, National Research Centre for Biotechnology,
Spielmannstrasse 7, 38106 Braunschweig, GERMANY
REFERENCE 2 (bases 1 to 1746)
AUTHORS Hammerschmidt,S., Talay,S.R., Brandtzaeg,P. and Chhatwal,G.S.
TITLE SpsA, a novel pneumococcal surface protein with specific binding to
secretory immunoglobulin A and secretory component
JOURNAL Mol. Microbiol. 25 (6), 1113-1124 (1997)
MEDLINE 98010350
FEATURES Location/Qualifiers
source 1..1746
/organism="Streptococcus pneumoniae"
/strain="type 47"
/db_xref="taxon:1313"
CDS 1..1746
/function="IgA binding protein"
/codon_start=1
/transl_table=11
/product="SpsA protein"
/protein_id="CAA05159.1"
/db_xref="PID:e354769"
/db_xref="PID:g2576333"
/db_xref="GI:2576333"
/db_xref="SPTREMBL:O33742"

/translation="MFASKSERKVHYSIRKFSIGVASVAVASLVMGSVVHATENEGST

QAATSSNMAKTEHRKAAKQVVDEYIEKMLREIQLDRRKHTQNVALNIKLSAIKT
KYLR

FIG.9D

ELNVLEEKSKDELPSEIKAKLDAAFEKFKKDTLKPGEKVAEAKKKVEEAKKKAE
DQKE

EDRRNYPTNTYKTLELEIAEFDVKVKEAELELVKEEAKESRNEGTIKQAKEKVES
KKA

EATRLENIKTDRKKAEEEAKRKADAKLKEANVATSDQGKPKGRAKRGVPGELA
TPDKK

ENDAKSSDSSVGEETLPSSSLKSGKKVAEAEKKVEEAEKKAKDQKEEDRRNYPT
NTYK

TLDLEIAESDVKVKEAELELVKEEAKEPRDEEKIKQAKAKVESKKAEATRLENIK
TDR

KKAEEEAKRKAAEEDKVKEKPAEQPQPAPATQPEKPAPKPEKPAEQPKAEKTDD
QQAE

EDYARRSEEEYNRLIQQQPPKTEKPAQPFTPKTGWKQENGMWYFYNTDGSMAT
GWLQY

NGSWYYLNANGDMATGWVKDGDTWYYLEASGAMKASQWFKVSDKWYYVN
GSGALAVNT

TVDGYGVNANGEWVN"

repeat_region 1447..1690

/rpt_type=DIRECT

BASE COUNT 722 a 290 c 408 g 326 t

ORIGIN 1 atgtttgcat caaaaagcga aagaaaagta cattattcaa ttcgtaaatt tagtattgga
61 gtagctagtg tagctgttgc cagtcttgtt atgggaagtg tggttcatgc gacagagaac
121 gagggaagta cccaagcagc cacttcttct aatatggcaa agacagaaca taggaaagct
181 gctaaacaag tcgtcgatga atatatagaa aaaatgttga gggagattca actagataga
241 agaaaacata cccaaaatgt cgccttaaac ataaagttga gcgcaattaa aacgaagtat
301 ttgcgtgaat taaatgtttt agaagagaag tcgaaagatg agttgccgtc agaaataaaa
361 gcaaagttag acgcagcttt tgagaagttt aaaaaagata cattgaaacc aggagaaaag
421 gtagcagaag ctaagaagaa ggttgaagaa gctaagaaaa aagccgagga tcaaaaagaa
481 gaagatcgtc gtaactaccc aaccaatact tacaaaacgc ttgaacttga aattgctgag
541 ttcgatgtga aagttaaaga agcggagctt gaactagtaa aagaggaagc taaagaatct
601 cgaaacgagg gcacaattaa gcaagcaaaa gagaaagttg agagtaaaaa agctgaggct
661 acaaggttag aaaacatcaa gacagatcgt aaaaaagcag aagaagaagc taaacgaaaa
721 gcagatgcta agttgaagga agctaatgta gcgacttcag atcaaggtaa accaaagggg
781 cgggcaaaac gaggagttcc tggagagcta gcaacacctg ataaaaaaga aaatgatgcg
841 aagtcttcag attctagcgt aggtgaagaa actcttccaa gctcatccct gaaatcagga
901 aaaaaggtag cagaagctga gaagaaggtt gaagaagctg agaaaaaagc caaggatcaa
961 aaagaagaag atcgccgtaa ttacccaacc aatacttaca aaacgcttga ccttgaaatt 1021 gctgagtccg atgtgaaagt taaagaagcg gagcttgaac tagtaaaaga ggaagctaag
1081 gaacctcgag acgaggaaaa aattaagcaa gcaaaagcga aagttgagag taaaaaagct
1141 gaggctacaa ggttagaaaa catcaagaca gatcgtaaaa aagcagaaga agaagctaaa
1201 cgaaaagcag cagaagaaga taaagttaaa gaaaaaccag ctgaacaacc acaaccagcg
1261 ccggctactc aaccagaaaa accagctcca aaaccagaga agccagctga acaaccaaaa
1321 gcagaaaaaa cagatgatca acaagctgaa gaagactatg ctcgtagatc agaagaagaa
1381 tataatcgct tgattcaaca gcaaccgcca aaaactgaaa aaccagcaca accatttact
1441 ccaaaaacag gctggaaaca agaaaacggt atgtggtact tctacaatac tgatggttca
1501 atggcaacag gatggctcca atacaacggt tcatggtatt acctcaacgc taatggtgat
1561 atggcgacag gttgggtgaa agatggagat acctggtact atcttgaagc atcaggtgct
1621 atgaaagcaa gccaatggtt caaagtatca gataaatggt actatgtcaa tggctcaggt
1681 gcccttgcag tcaacacaac tgtagatggc tatggagtca atgccaatgg tgaatgggta
1741 aactaa
//

FIG. 9E the above report in format ther Formats:
Links:

FIG.10A

LOCUS AAB70838 663 aa BCT 16-SEP-1997
DEFINITION choline binding protein A.
ACCESSION AAB70838
PID g2425109
VERSION AAB70838.1 GI:2425109
DBSOURCE locus AF019904 accession AF019904.1
KEYWORDS
SOURCE Streptococcus pneumoniae.
ORGANISM Streptococcus pneumoniae
Eubacteria; Firmicutes; Low G+C gram-positive bacteria;
Streptococcaceae; Streptococcus.
REFERENCE 1 (residues 1 to 663)
AUTHORS Rosenow,C., Ryan,P., Weiser,J.N., Johnson,S., Fontan,P.,
Ortqvist,A. and Masure,H.R.
TITLE Contribution of novel choline-binding proteins to adherence,
colonization and immunogenicity of Streptococcus pneumoniae
JOURNAL Mol. Microbiol. (1997) In press
REFERENCE 2 (residues 1 to 663)
AUTHORS Rosenow,C., Ryan,P., Weiser,J.N., Johnson,S., Fontan,P.,
Ortqvist,A. and Masure,H.R.
TITLE Direct Submission
JOURNAL Submitted (18-AUG-1997) Infectious Diseases, St. Jude Children's
Research Hospital, 322 North Lauderdale, Memphis, TN 38105, USA
COMMENT Method: conceptual translation supplied by author.
FEATURES Location/Qualifiers
source 1..663
/organism="Streptococcus pneumoniae"
/strain="R6x"
/db_xref="taxon:1313"
Protein <1..663
/product="choline binding protein A"
/name="CbpA"
CDS 1..663
/gene="cbpA"
/coded_by="AF019904.1:<1..1992"
/transl_table=11
ORIGIN
1 enegstqaat ssnmaktehr kaakqvvdey iekmlreiql drrkhtqnva lniklsaikt
61 kylrelnvle ekskdelpse ikakldaafe kfkkdtlkpg ekvaeakkkv eeakkkaedq
121 keedrrnypt ntyktlelei aefdvkvkea elelvkeeak esrnegtikq akekveskka
181 eatrlenikt drkkaeeeak rkadaklkea nvatsdqgkp kgrakrgvpg elatpdkken
241 dakssdssvg eetlpssslk sgkkvaeaek kveeaekkak dqkeedrrny ptntyktldl
301 eiaesdvkvk eaelelvkee akeprdeeki kqakakvesk kaeatrleni ktdrkkaeee

FIG. 10B 361 akrkaaeedk vkekpaeqpq papatqpekp apkpekpaeq pkaektddqq aeedyarrse
421 eeynrltqqq ppktekpaqp stpktgwkqe ngmwyfyntd gsmatgwlqn ngswyylnan
481 gamatgwlqn ngswyylnan gsmatgwlqn ngswyylnan gamatgwlqy ngswyylnsn
541 gamatgwlqy ngswyylnan gdmatgwlqn ngswyylnan gdmatgwlqy ngswyylnan
601 gdmatgwvkd gdtwyyleas gamkasqwfk vsdkwyyvng sgalavnttv dgygvnange
661 wvn

// the above report in format

Other Formats:
Links:

FIG. 10C

```
LOCUS       AF019904    2480 bp    DNA           BCT       22-SEP-1997
DEFINITION  Streptococcus pneumoniae choline binding protein A (cbpA) gene,
            partial cds.
ACCESSION   AF019904
NID         g2425108
VERSION     AF019904.1  GI:2425108
KEYWORDS
SOURCE      Streptococcus pneumoniae.
  ORGANISM  Streptococcus pneumoniae
            Eubacteria; Firmicutes; Low G+C gram-positive bacteria;
            Streptococcaceae; Streptococcus.
REFERENCE   1  (bases 1 to 2480)
  AUTHORS   Rosenow,C., Ryan,P., Weiser,J.N., Johnson,S., Fontan,P.,
            Ortqvist,A. and Masure,H.R.
  TITLE     Contribution of novel choline-binding proteins to adherence,
            colonization and immunogenicity of Streptococcus pneumoniae
  JOURNAL   Mol. Microbiol. (1997) In press
REFERENCE   2  (bases 1 to 2480)
  AUTHORS   Rosenow,C., Ryan,P., Weiser,J.N., Johnson,S., Fontan,P.,
            Ortqvist,A. and Masure,H.R.
  TITLE     Direct Submission
  JOURNAL   Submitted (18-AUG-1997) Infectious Diseases, St. Jude Children's
            Research Hospital, 322 North Lauderdale, Memphis, TN 38105, USA
FEATURES             Location/Qualifiers
     source          1..2480
                     /organism="Streptococcus pneumoniae"
                     /strain="R6x"
                     /db_xref="taxon:1313"
     gene            <1..1992
                     /gene="cbpA"
     CDS             <1..1992
                     /gene="cbpA"
                     /note="CbpA"
                     /codon_start=1
                     /transl_table=11
                     /product="choline binding protein A"
                     /protein_id="AAB70838.1"
                     /db_xref="PID:g2425109"
                     /db_xref="GI:2425109"

/translation="ENEGSTQAATSSNMAKTEHRKAAKQVVDEYIEKMLREIQLDRRK
```

FIG. 10D

HTQNVALNIKLSAIKTKYLRELNVLEEKSKDELPSEIKAKLDAAFEKFKKDTLKP
GEK

VAEAKKKVEEAKKKAEDQKEEDRRNYPTNTYKTLELEIAEFDVKVKEAELELV
KEEAK

ESRNEGTIKQAKEKVESKKAEATRLENIKTDRKKAEEEAKRKADAKLKEANVAT
SDQG

KPKGRAKRGVPGELATPDKKENDAKSSDSSVGEETLPSSSLKSGKKVAEAEKKV
EEAE

KKAKDQKEEDRRNYPTNTYKTLDLEIAESDVKVKEAELELVKEEAKEPRDEEKI
KQAK

AKVESKKAEATRLENIKTDRKKAEEEAKRKAAEEDKVKEKPAEQPQPAPATQPE
KPAP

KPEKPAEQPKAEKTDDQQAEEDYARRSEEEYNRLTQQQPPKTEKPAQPSTPKTG
WKQE

NGMWYFYNTDGSMATGWLQNNGSWYYLNANGAMATGWLQNNGSWYYLNA
NGSMATGWL

QNNGSWYYLNANGAMATGWLQYNGSWYYLNSNGAMATGWLQYNGSWYYL
NANGDMATG

WLQNNGSWYYLNANGDMATGWLQYNGSWYYLNANGDMATGWVKDGDTWY
YLEASGAMK

ASQWFKVSDKWYYVNGSGALAVNTTVDGYGVNANGEWVN"

BASE COUNT 933 a 452 c 575 g 520 t

ORIGIN 1 gaaaacgaag gaagtaccca agcagccact tcttctaata tggcaaagac agaacatagg
61 aaagctgcta aacaagtcgt cgatgaatat atagaaaaaa tgttgaggga gattcaacta
121 gatagaagaa aacataccca aaatgtcgcc ttaaacataa agttgagcgc aattaaaacg
181 aagtatttgc gtgaattaaa tgttttagaa gagaagtcga aagatgagtt gccgtcagaa
241 ataaaagcaa agttagacgc agcttttgag aagtttaaaa aagatacatt gaaaccagga
301 gaaaaggtag cagaagctaa gaagaaggtt gaagaagcta agaaaaaagc cgaggatcaa
361 aaagaagaag atcgtcgtaa ctacccaacc aatacttaca aaacgcttga acttgaaatt
421 gctgagttcg atgtgaaagt taaagaagcg gagcttgaac tagtaaaaga ggaagctaaa
481 gaatctcgaa acgagggcac aattaagcaa gcaaaagaga aagttgagag taaaaaagct
541 gaggctacaa ggttagaaaa catcaagaca gatcgtaaaa aagcagaaga agaagctaaa
601 cgaaaagcag atgctaagtt gaaggaagct aatgtagcga cttcagatca aggtaaacca
661 aaggggcggg caaaacgagg agttcctgga gagctagcaa cacctgataa aaaagaaaat
721 gatgcgaagt cttcagattc tagcgtaggt gaagaaactc ttccaagctc atccctgaaa

FIG. 10E 781 tcaggaaaaa aggtagcaga agctgagaag aaggttgaag aagctgagaa aaaagccaag
841 gatcaaaaag aagaagatcg ccgtaactac ccaaccaata cttacaaaac gcttgacctt
901 gaaattgctg agtccgatgt gaaagttaaa gaagcggagc ttgaactagt aaaagaggaa
961 gctaaggaac ctcgagacga ggaaaaaatt aagcaagcaa aagcgaaagt tgagagtaaa
1021 aaagctgagg ctacaaggtt agaaaacatc aagacagatc gtaaaaaagc agaagaagaa
1081 gctaaacgaa aagcagcaga agaagataaa gttaaagaaa aaccagctga acaaccacaa
1141 ccagcgccgg ctactcaacc agaaaaacca gctccaaaac cagagaagcc agctgaacaa
1201 ccaaaagcag aaaaaacaga tgatcaacaa gctgaagaag actatgctcg tagatcagaa
1261 gaagaatata atcgcttgac tcaacagcaa ccgccaaaaa ctgaaaaacc agcacaacca
1321 tctactccaa aaacaggctg gaaacaagaa aacggtatgt ggtacttcta caatactgat
1381 ggttcaatgg caacaggatg gctccaaaac aacggttcat ggtactatct aaacgctaat
1441 ggtgctatgg cgacaggatg gctccaaaac aatggttcat ggtactatct aaacgctaat
1501 ggttcaatgg caacaggatg gctccaaaac aatggttcat ggtactacct aaacgctaat
1561 ggtgctatgg cgacaggatg gctccaatac aatggttcat ggtactacct aaacagcaat
1621 ggcgctatgg cgacaggatg gctccaatac aatggctcat ggtactacct caacgctaat
1681 ggtgatatgg cgacaggatg gctccaaaac aacggttcat ggtactacct caacgctaat
1741 ggtgatatgg cgacaggatg gctccaatac aacggttcat ggtattacct caacgctaat
1801 ggtgatatgg cgacaggttg ggtgaaagat ggagatacct ggtactatct tgaagcatca
1861 ggtgctatga aagcaagcca atggttcaaa gtatcagata aatggtacta tgtcaatggc
1921 tcaggtgccc ttgcagtcaa cacaactgta gatggctatg gagtcaatgc caatggtgaa
1981 tgggtaaact aaacctaata taactagtta atactgactt cctgtaagaa ctttttaaag
2041 tattccctac aaataccata tcctttcagt agataatata cccttgtagg aagtttagat
2101 taaaaaataa ctctgtaatc tctagccgga tttatagcgc tagagactac ggagtttttt
2161 tgatgaggaa agaatggcgg cattcaagag actctttaag agagttacgg gttttaaact
2221 attaagcctt ctccaattgc aagaggcttc aatctctgct agggtgctag cttgcgaaat
2281 ggctccacgg agtttggcag cgccagatgt tccacggaga tagtgaggag cgaggccgcg
2341 gaattcacga actgcgacgt ttctcctttt gaggttaatc aatcgtttca agtgttcgta
2401 ggcgatcttc atcttgtctt caaaggtcaa atcaggtagg atttctcctg tttcaaagtt
2461 tatggtggcc ctggttgaag
// the above report in format

FIG. 11A

Other Formats:
Links:

LOCUS AAD00184 929 aa BCT 07-OCT-1996
DEFINITION surface protein C.
ACCESSION AAD00184
PID g4097980
VERSION AAD00184.1 GI:4097980
DBSOURCE locus SPU72655 accession U72655.1
KEYWORDS
SOURCE Streptococcus pneumoniae.
 ORGANISM Streptococcus pneumoniae
 Eubacteria; Firmicutes; Low G+C gram-positive bacteria;
 Streptococcaceae; Streptococcus.
REFERENCE 1 (residues 1 to 929)
 AUTHORS Brooks-Walter,A., Tart,R.C., Briles,D.E. and Hollingshead,S.K.
 TITLE The pspC gene encodes a second pneumococcal surface protein
 homologous to the protection-eliciting PspA protein of
 Streptococcus pneumoniae
 JOURNAL Unpublished
REFERENCE 2 (residues 1 to 929)
 AUTHORS Brooks-Walter,A., Tart,R.C., Briles,D.E. and Hollingshead,S.K.
 TITLE Direct Submission
 JOURNAL Submitted (26-SEP-1996) Microbiology, University of Alabama at
 Birmingham, 19th Street South, Box 10, Birmingham, AL 35294-2170,
 USA
FEATURES Location/Qualifiers
 source 1..929
 /organism="Streptococcus pneumoniae"
 /strain="EF6796"
 /db_xref="taxon:1313"
 Protein 1..929
 /product="surface protein C"
 CDS 1..929
 /gene="pspC"
 /coded_by="U72655.1:319..3108"
 /transl_table=11
ORIGIN 1 mfaskserkv hysirkfsig vasvavaslf lggvvhaegv rsgnnltvts sgqdiskkya
61 deveshlesi lkdvkknlkk vqhtqnvgli tklseikkky lydlkvnvls eaeltsktke
121 tkekltatfe qfkkdtlpte pekkvaeaqk kveeakkkae dqkekdrrny ptitykktlel
181 eiaesdvevk kaelelvkvk akesqdeeki kqaeaevesk qaeatrlkki ktdreeakrk
241 adaklkeave knvatseqdk pkrrakrgvs gelatpdkke ndakssdssv geetlpspsl
301 nmanesqteh rkdvdeyikk mlseiqldrr khtqnvnlni klsaiktkyl yelsvlkens
361 kkeeltsktk aeltaafeqf kkdtlkpekk vaeaekkvee akkkakdqke edrrnyptnt
421 yktleleiae sdvkvkeael elvkeeanes rneekikqak ekveskkaea trlekiktdr 481 kkaeeeakrk aeesekkaae akqkvdaeey aleakiaele yevqrlekel keidesdsed
541 ylkeglrapl qskldtkkak lskleelsdk ideldaeiak levqlkdaeg nnnveayfke
601 glekttaekk aelekaeadl kkavdepetp apapqpapap ekpaekpapa pekpapapek
661 papapekpap apekpapape kpaptpetpk tgwkqengmw yfyntdgsma tgwlqnngsw
721 yylnsngama tgwlqnngsw yylnsngama tgwlqyngsw yylnangdma tgwlqyngsw
781 yylnangdma tgwfqyngsw yylnangdma tgwfqyngsw yylnangdma tgwlqyngsw
841 yylnsngamv tgwlqnngsw yylnangsma tdwvkdgdtw yyleasgamk asqwfkvsdk
901 wyyvngsgal avnttvdsyr vnangewvn
// the above report in format

*FIG. 11B*

Other Formats:
Links:

FIG. 11C

```
LOCUS       SPU72655    3463 bp    DNA          BCT       02-JAN-1999
DEFINITION  Streptococcus pneumoniae surface protein C (pspC) gene, complete
            cds.
ACCESSION   U72655
NID         g4097979
VERSION     U72655.1  GI:4097979
KEYWORDS
SOURCE      Streptococcus pneumoniae.
  ORGANISM  Streptococcus pneumoniae
            Eubacteria; Firmicutes; Low G+C gram-positive bacteria;
            Streptococcaceae; Streptococcus.
REFERENCE   1  (bases 1 to 3463)
  AUTHORS   Brooks-Walter,A., Tart,R.C., Briles,D.E. and Hollingshead,S.K.
  TITLE     The pspC gene encodes a second pneumococcal surface protein
            homologous to the protection-eliciting PspA protein of
            Streptococcus pneumoniae
  JOURNAL   Unpublished
REFERENCE   2  (bases 1 to 3463)
  AUTHORS   Brooks-Walter,A., Tart,R.C., Briles,D.E. and Hollingshead,S.K.
  TITLE     Direct Submission
  JOURNAL   Submitted (26-SEP-1996) Microbiology, University of Alabama at
            Birmingham, 19th Street South, Box 10, Birmingham, AL 35294-2170,
            USA
FEATURES             Location/Qualifiers
     source          1..3463
                     /organism="Streptococcus pneumoniae"
                     /strain="EF6796"
                     /db_xref="taxon:1313"
     gene            319..3108
                     /gene="pspC"
     CDS             319..3108
                     /gene="pspC"
                     /codon_start=1
                     /transl_table=11
                     /product="surface protein C"
                     /protein_id="AAD00184.1"
                     /db_xref="PID:g4097980"
                     /db_xref="GI:4097980"

/translation="MFASKSERKVHYSIRKFSIGVASVAVASLFLGGVVHAEGVRSGN

NLTVTSSGQDISKKYADEVESHLESILKDVKKNLKKVQHTQNVGLITKLSEIKKK
YLY
```

FIG. 11D

DLKVNVLSEAELTSKTKETKEKLTATFEQFKKDTLPTEPEKKVAEAQKKVEEAK
KKAE

DQKEKDRRNYPTITYKTLELEIAESDVEVKKAELELVKVKAKESQDEEKIKQAEA
EVE

SKQAEATRLKKIKTDREEAKRKADAKLKEAVEKNVATSEQDKPKRRAKRGVSG
ELATP

DKKENDAKSSDSSVGEETLPSPSLNMANESQTEHRKDVDEYIKKMLSEIQLDRR
KHTQ

NVNLNIKLSAIKTKYLYELSVLKENSKKEELTSKTKAELTAAFEQFKKDTLKPEK
KVA

EAEKKVEEAKKKAKDQKEEDRRNYPTNTYKTLELEIAESDVKVKEAELELVKEE
ANES

RNEEKIKQAKEKVESKKAEATRLEKIKTDRKKAEEEAKRKAEESEKKAAEAKQK
VDAE

EYALEAKIAELEYEVQRLEKELKEIDESDSEDYLKEGLRAPLQSKLDTKKAKLSK
LEE

LSDKIDELDAEIAKLEVQLKDAEGNNNVEAYFKEGLEKTTAEKKAELEKAEADL
KKAV

DEPETPAPAPQPAPAPEKPAEKPAPAPEKPAPAPEKPAPAPEKPAPAPEKPAPAPE
KP

APTPETPKTGWKQENGMWYFYNTDGSMATGWLQNNGSWYYLNSNGAMATG
WLQNNGSW

YYLNSNGAMATGWLQYNGSWYYLNANGDMATGWLQYNGSWYYLNANGDM
ATGWFQYNG

SWYYLNANGDMATGWFQYNGSWYYLNANGDMATGWLQYNGSWYYLNSNG
AMVTGWLQN

NGSWYYLNANGSMATDWVKDGDTWYYLEASGAMKASQWFKVSDKWYYVNG
SGALAVNT
TVDSYRVNANGEWVN"

BASE COUNT 1326 a 591 c 755 g 790 t 1 others
ORIGIN
1 aagcttatgc ttgtcaataa tcacaaatat gtagatcata tcttgtttag gacagtaaaa

FIG. 11E 61 catcctaatt actttttaaa tattttacct gagttgattg gcttgacctt gttgagtcat
121 gcctatatga cttttgtttt agtttttcca gtttatgcag ttattttgta tcgacgaata
181 gctgaagagg aaaagttatt acatgaagtt ataatcccaa atggaagcat aaagagataa
241 atacaaaatt cgatttatat acagttcata ttgaagtgat atagtaaggt taaagaaaaa
301 atatagaagg aaataaacat gtttgcatca aaaagcgaaa gaaaagtaca ttattcaatt
361 cgtaaattta gtattggagt agctagtgta gctgttgcca gcttgttctt aggaggagta
421 gtccatgcag aaggggttag aagtgggaat aacctcacgg ttacatctag tgggcaagat
481 atatcgaaga agtatgctga tgaagtcgag tcgcatctag aaagtatatt gaaggatgtc
541 aaaaaaaatt tgaaaaaagt tcaacatacc caaaatgtcg gcttaattac aaagttgagc
601 gaaattaaaa agaagtattt gtatgactta aaagttaatg ttttatcgga agctgagttg
661 acgtcaaaaa caaaagaaac aaaagaaaag ttaaccgcaa cttttgagca gtttaaaaaa
721 gatacattac caacagaacc agaaaaaaag gtagcagaag ctcagaagaa ggttgaagaa
781 gctaagaaaa aagccgagga tcaaaaagaa aaagatcgcc gtaactaccc aaccattact
841 tacaaaacgc ttgaacttga aattgctgag tccgatgtgg aagttaaaaa agcggagctt
901 gaactagtaa aagtgaaagc taaggaatct caagacgagg aaaaaattaa gcaagcagaa
961 gcggaagttg agagtaaaca agctgaggct acaaggttaa aaaaaatcaa gacagatcgt
1021 gaagaagcta aacgaaaagc agatgctaag ttgaaggaag ctgttgaaaa gaatgtagcg
1081 acttcagagc aagataaacc aaagaggcgg gcaaaacgag gagtttctgg agagctagca
1141 acacctgata aaaaagaaaa tgatgcgaag tcttcagatt ctagcgtagg tgaagaaact
1201 cttccaagcc catcccttaa tatggcaaat gaaagtcaga cagaacatag gaaagatgtc
1261 gatgaatata taaaaaaaat gttgagtgag atccaattag atagaagaaa acatacccaa
1321 aatgtcaact taaacataaa gttgagcgca attaaaacga agtatttgta tgaattaagt
1381 gttttaaaag agaactcgaa aaaagaagag ttgacgtcaa aaaccaaagc agagttaacc
1441 gcagcttttg agcagtttaa aaaagataca ttgaaaccag aaaaaaaggt agcagaagct
1501 gagaagaagg ttgaagaagc taagaaaaaa gccaaggatc aaaaagaaga agatcgccgt
1561 aactacccaa ccaatactta caaaacgctt gaacttgaaa ttgctgagtc cgatgtgaaa
1621 gttaaagaag cggagcttga actagtaaaa gaggaagcta acgaatctcg aaacgaggaa
1681 aaaattaagc aagcaaaaga gaaagttgag agtaaaaaag ctgaggctac aaggttagaa
1741 aaaatcaaga cagatcgtaa aaaagcagaa gaagaagcta aacgaaaagc agaagaatct
1801 gagaaaaaag ctgctgaagc caaacaaaaa gtggatgctg aagaatatgc tcttgaagct
1861 aaaatcgctg agttggaata tgaagttcag agactagaaa aagagctcaa agagattgat
1921 gagtctgact cagaagatta tcttaaagaa ggcctccgtg ctcctcttca atctaaattg
1981 gataccaaaa aagctaaact atcaaaactt gaagagttga gtgataagat tgatgagtta
2041 gacgctgaaa ttgcaaaact tgaagttcaa cttaaagatg ctgaaggaaa caataatgta
2101 gaagcctact ttaaagaagg tttagagaaa actactgctg agaaaaaagc tgaattagaa
2161 aaagctgaag ctgaccttaa gaaagcagtt gatgagccag aaactccagc tccggctcct
2221 caaccagctc cagctccaga aaaaccagct gaaaaaccag ctccagctcc agaaaaacca
2281 gctccagctc cagaaaaacc agctccagct ccagaaaaac cagctccagc tccagaaaaa
2341 ccagctccag ctccagaaaa accagctcca actccagaaa ctccaaaaac aggctggaaa
2401 caagaaaacg gtatgtggta cttctacaat actgatggtt caatggcaac aggctggctc
2461 caaaacaatg gctcatggta ctacctcaac agcaatggcg ctatggcgac aggatggctc
2521 caaaacaatg gctcatggta ctacctcaac agcaatggcg ctatggcgac aggatggctc
2581 caatacaatg gttcatggta ctacctcaac gctaatggtg atatggcgac aggatggctc
2641 caatacaatg gttcatggta ctacctcaac gctaatggtg atatggcgac aggatggttc
2701 caatacaatg gttcatggta ctacctcaac gctaatggtg atatggcgac aggatggttc
2761 caatacaatg gttcatggta ctacctcaac gctaatggtg atatggcgac aggatggctc

FIG. 11F 2821 caatacaatg gttcatggta ctacctaaac agcaatggtg ctatggtaac aggatggctc
2881 caaaacaatg gctcatggta ctacctaaac gctaacggtt caatggcaac agattgggtg
2941 aaagatggag atacctggta ctatcttgaa gcatcaggtg ctatgaaagc aagccaatgg
3001 ttcaaagtat cagataaatg gtactatgtc aatggctcag gtgcccttgc agtcaacaca
3061 actgtagata gctatagagt caatgccaat ggtgaatggg taaactaaac ttaatataac
3121 tagttaatac tgacttcctg taagaactct ttaaagtatt ccctacaaat accatatcct
3181 ttcagtagat aatataccct tgtaggaagt ttagattaaa aaataactct gtaatctcta
3241 gccggattta tagcgctaga gactacggag ttttttgat gaggaaagaa tggcggcatt
3301 caagagactc tttaagagag ttacgggttt taaactatta agctttctcc aattgcaaga
3361 gggcttcaat ctctgctagg tgctagcttg cgaaatggct cccacggagt ttggcrgcgc
3421 cagatgttcc acggaggtag tgaggagcga ggccgcggaa ttc
// the above report in format

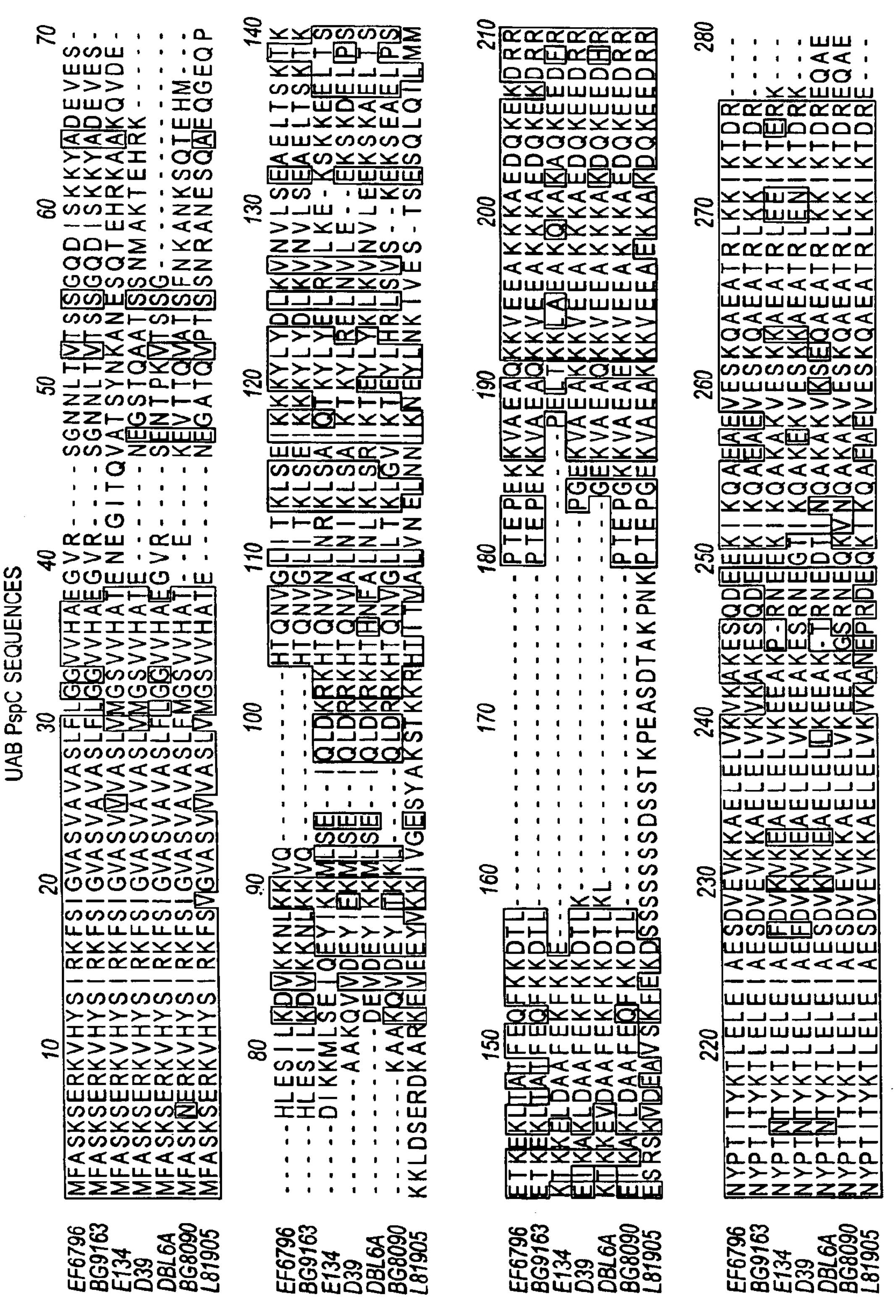

FIG. 13A

UAB PspC SEQUENCES

```
            10         20         30         40         50         60         70
EF6796  MFASKSERKVHYSIRKFSIGVASVAVASLFLGGVVHAEGVR----SGNNLTVTSSGGQDISKKYADEVES-
BG9163  MFASKSERKVHYSIRKFSIGVASVAVASLFLGGVVHAEGVR----SGNNLTVTSSGGQDISKKYADEVES-
E134    MFASKSERKVHYSIRKFSIGVASVAVASLVMGSVVHATENEGITQVATSYNKANESQTEHRKAAKQVDE-
D39     MFASKSERKVHYSIRKFSIGVASVAVASLVMGSVVHATE------NEGSTQAATSSNMAKTEHRK-----
DBL6A   MFASKSERKVHYSIRKFSIGVASVAVASLFMGSVVHATE--E---SENTPKVTSSG-------------
BG8090  MFASKNERKVHYSIRKFSIGVASVAVASLFMGSVVHATE------KEVTTQAVTQVPTISNRANESQAEQGEQP
L81905  MFASKSERKVHYSIRKFSVGVASSVAVSLFMGSVVHATE------NEGATQVPTISNRANESQAEQGEQP

            80         90        100        110        120        130        140
EF6796  ----HLESILKDVKKNLKKIVQ--------------HTQNVGLITKLSEIKKKYLYDLKVNVLSEAELTSKTK
BG9163  ----HLESILKDVKKNLKKIVQ--------------HTQNVGLITKLSEIKKKYLYDLKVNVLSEAELTSKTK
E134    --DIKKMLSELQEYIEKMLSE---IQLDKRKKHTQNVLLNRKLSAIQTKYLYELRVLKE-KSKKEELTS
D39     ----AAKQVIDEYIEKMLSE---IQLDKRKHTQNVALNLNIKLSRIKTEYLKLKVNVLE--EKSKDELPIS
DBL6A   ---DEVDEYIEKMLSE------IQLDKRRKHTQNVNFEALNLNVGLLTKLGVIKTEYLHRLSVIS--EEKSKEALPIS
BG8090  ---KAAKQVDEYIEKMLKL---IQLDKRRKHTQNVDTLLLKLNEIISTKKRHITTWALLVNELNNIKNEYLNKIVES-TSESQLQTLMM
L81905  KKLDSERDKARKEVEEYKKI IVGESYAKSTKKRHI TVGESYAKSTKKRHIT

           150        160        170        180        190        200        210
EF6796  ETKEKLTATFEQFKKDTL-----------------PTEPEKKVAEAQKKVEEAKKKKAEDQKEKDRR
BG9163  ETKEKLTATFEQFKKDTL-----------------PTEPEKKVAEAQKKVEEAKKKKAEDQKEKDRR
E134    KIKKELDAAFEKFKKDTLK----------------PIELTKKLAEAKKKKVAEAKQKAEKDQKEEDER
D39     EIKAKLDAAFEKFKKDTLK----------------PGEKVAEAKKKVAEAQKKVAEAKKKKAEDQKEEDRR
DBL6A   KIKKEVDAAFEQFKKDTL-----------------PGEKVAEAKKKVAEAQKKVAEAKDKAEDQKEEDHR
BG8090  ETKAKLDAAFEQFKKDTL-----------------PTEPGEKPTEPGEKVAEAKKKKVAEAKKKKAEKKAEKKAEDRR
L81905  ESRSKVDEAVSKEEIKDSSSSSSSDSSTKPEASDTAKPNKPTEPGEKVAEAKKKKVEEAKKKKAEDQKEEDRR

           220        230        240        250        260        270        280
EF6796  NYPTITYKTLELEIAESDVEVKKAELELVKIVKAKESQDEEEKIKQAEAEVESKQAEATRLKKIKTDR---
BG9163  NYPTITYKTLELEIAESDVEVKKAELELVKVKAKESQDEEEKIKQAEAEVESKQAEATRLKKIKTDR---
E134    NYPTNTYKTLELEIAEFDVKVKEAELELVKEESKNRNE---RNEEKIKQAAKEVESKKIAEATRLEEIKTERK---
D39     NYPTNTYKTLELEIAESDVKVKEAKGSRNE-AKP-RNEEKKQAAKEVESKKSEQAEATRLKKIKTDRK---
DBL6A   NYPTNTYKTLELEIAESDVKVKEAK-TRNEDTLNQAKAKVKSEQAEATRLKKIKTDREQAE-
BG8090  NYPTNTYKTLELEIAESDVEVKKAELELVKEELKVKEENEGTILNQAKAKVKSEQAEATRLKKIKTDREQAE-
L81905  NYPTITYKTLELEIAESDVEVKKANEPRDEQKTKQAEAEVESKQAEATRLKKIKTDRE-----
```

FIG. 15A

```
LOCUS      PSPC.V26      730 AA   PROT          SYN
DEFINITION Streptococcus pneumoniae PspC protein from strain V26
ACCESSION  -
KEYWORDS   -
SOURCE     -
FEATURES            Location/Qualifiers
    PROPEP          <1..731
                    /note="3 to 2349 of V26.pspC (translated)"
ORIGIN     -
      1 MFASKSERKV HYSIRKFSIG VASVVVASLF LGGVVHAEEV RRGNNLTVTS SGDEVESHYQ
     61 SILEKVRKSL EKDRHTQNVD LIKKLQDIKR TYLYNLKEKP EAELTSKTNK ELDAAFEKFK
    121 KEPELTKKLA EAEKKAKDQK EEDHRNYPTN TYKTIELEIA EAEVGVAKAE LELAQAQVQI
    181 PQDTEKINAA KAKVEAAKSN VKKLEKIKSD IEKTYLYKLD NSTKETPKSR VRRNSPQVGD
    241 SRELKETIDK AKETLSTYMV TRLTKLDPSV FWFADLLMDA KKVVEEYKTK LEDASDKKSV
    301 EDLRKEAEGK IESLIVTHQN REKENQPAPQ PGGQAGGSMV VPPVTQTPPS TSQSPGQKAT
    361 EAEKKKLQDL IRQFQEALNK LDDETKTVPD GAKLTGEAGK AYNETRTYAK EVVDKSKKLL
    421 SQTAVTMDEL AMQLTKLNDA MSKLKEAKAK LVPEVKPQPE NPEPKPQPEG EKPSVPDINQ
    481 EKEKAKLAIA TYMSKILDDI KKHHLKKEKH HQIVALIKDL DKLRKQALSE IDNVNTKVEI
    541 ENTVHKVFAD MDTVVTKFQK GLIQNTPQVP EAQRAQRYQR FQIHQKAPDT PQVPEAPKSP
    601 EVPKVPEAPK APDTPQVPEA PKSPEVPKVS DTPKAPDTPQ VPEAPKSPEV PKVPEAPKAP
    661 DTPQVPEAPK SPEVPKVPDT PKAPDTPQVP EAPKAPDTPQ IPEAPAPETP APAPEAPKTG
    721 WKQENGMWKG
//
```

FIG. 15B

```
LOCUS      V26DNA.PSP  2349 BP SS-DNA        SYN
DEFINITION Streptococcus pneumoniae PspC gene from strain V26
ACCESSION  -
KEYWORDS   -
SOURCE     -
BASE COUNT    937 A   457 C   505 G   450 T    0 OTHER
ORIGIN     -
      1 AATTCGCCCT TCGACGAATA GCTGAAGAGG AAAAGCTATT ACATGAAGTT ATAATCCCAA
     61 ATGGAAGCAT AAAGAGATAA ATACAAAATT CGATTTATAT ACAGTTCATA TTGAAGTGAT
    121 ATAGTAAGGC TAAAGAAAAA ATATAGAAGG AAATAAACAT GTTTGCATCA AAAAGCGAAA
    181 GAAAAGTACA TTATTCAATT CGTAAATTTA GTATTGGAGT AGCTAGTGTA GTAGTTGCTA
    241 GTTTGTTCTT AGGAGGAGTA GTTCACGCAG AAGAGGTTAG AAGAGGGAAT AACCTCACGG
    301 TTACATCTAG TGGGGATGAA GTCGAGTCGC ATTATCAAAG TATATTGGAG AAGGTCAGAA
    361 AAAGTTTGGA AAAAGATCGA CATACCCAAA ATGTCGACTT AATCAAAAAG TTGCAAGACA
    421 TTAAGAGAAC GTATTTGTAT AATTTAAAAG AGAAGCCGGA AGCTGAGTTG ACGTCAAAAA
    481 CAAATAAAGA GTTAGACGCA GCTTTTGAGA AGTTTAAAAA AGAACCAGAA CTTACTAAAA
    541 AATTAGCAGA AGCTGAGAAA AAAGCCAAGG ATCAAAAAGA AGAAGATCAC CGTAACTACC
    601 CAACCAATAC TTACAAAACA ATCGAACTGG AAATTGCGGA AGCAGAAGTA GGGGTCGCCA
    661 AGGCAGAGCT TGAGCTTGCA CAAGCTCAAG TCCAAATACC TCAAGATACT GAGAAAATTA
    721 ATGCTGCTAA AGCTAAAGTA GAAGCTGCTA AAAGTAATGT TAAAAAACTA GAAAAAATTA
    781 AATCAGATAT TGAAAAAACG TATTTGTATA AATTAGATAA CTCAACCAAA GAAACGCCAA
    841 AATCTAGAGT GCGAAGAAAT TCTCCGCAAG TAGGCGATTC GAGAGAACTT AAGGAAACGA
    901 TAGACAAAGC GAAAGAAACT CTGTCTACCT ATATGGTAAC TCGTTTAACG AAGCTGGATC
    961 CATCTGTTTT TTGGTTTGCA GATCTTCTTA TGGATGCTAA GAAAGTTGTG GAAGAATACA
   1021 AGACAAAATT AGAGGATGCT TCAGATAAAA AATCGGTAGA AGACTTGCGA AAGGAAGCAG
   1081 AAGGAAAAAT AGAGTCTCTT ATCGTGACTC ACCAAAATAG AGAAAAAGAA AACCAACCAG
   1141 CACCCCAACC AGGAGGACAA GCAGGTGGTT CAATGGTTGT ACCACCGGTG ACGCAAACAC
   1201 CTCCATCAAC TTCCCAAAGT CCAGGACAAA AGGCGACCGA AGCTGAAAAG AAAAAGTTAC
   1261 AAGACTTGAT TCGTCAATTC CAAGAAGCCT TGAACAAACT AGACGATGAA ACAAAGACTG
   1321 TTCCAGATGG GGCTAAACTC ACAGGAGAAG CTGGAAAAGC CTATAATGAG ACTAGAACTT
   1381 ATGCGAAAGA AGTTGTTGAC AAGAGCAAGA AGCTTCTATC ACAGACAGCA GTGACAATGG
   1441 ATGAATTGGC AATGCAATTA ACCAAATTGA ACGATGCCAT GTCTAAATTG AAAGAAGCTA
   1501 AAGCGAAATT GGTACCAGAG GTTAAACCAC AGCCGGAAAA CCCAGAGCCA AAACCACAAC
   1561 CAGAGGGTGA GAAACCAAGC GTACCAGATA TTAATCAGGA GAAAGAAAAA GCTAAACTTG
   1621 CTATAGCAAC ATACATGAGC AAGATTTTAG ATGATATAAA GAAACATCAT CTGAAGAAAG
   1681 AAAAACATCA TCAGATTGTT GCTCTTATTA AGGACCTTGA TAAACTTAGA AAGCAAGCAC
   1741 TTTCTGAAAT TGATAATGTA AATACCAAAG TAGAAATTGA GAATACAGTC CACAAGGTAT
   1801 TTGCAGACAT GGATACGGTT GTTACTAAAT TCCAAAAAGG CTTAATTCAG AACACACCGC
   1861 AGGTTCCAGA AGCCCAAAGA GCCCAGAGGT ACCAAAGGTT TCAGATACAC CAAAAGGCTC
```

1921 CGGACACACC GCAGGTTCCA GAAGCACCAA AGAGCCCAGA GGTACCAAAG GTTCCAGAAG
1981 CACCAAAGGC TCCGGACACA CCGCAAGTTC CGGAAGCACC AAAGAGCCCA GAGGTACCAA
2041 AGGTTTCAGA TACACCAAAG GCTCCGGACA CACCGCAGGT TCCAGAAGCA CCAAAGAGCC
2101 CAGAGGTACC AAAGGTTCCA GAAGCACCAA AGGCTCCGGA CACACCGCAA GTTCCGGAAG
2161 CACCAAAGAG CCCAGAGGTA CCAAAGGTTC CAGATACACC AAAGGCTCCG GACACACCGC
2221 AGGTTCCAGA AGCACCAAAG GCTCCAGACA CACCGCAAAT TCCGGAAGCA CCAGCTCCAG
2281 AAACTCCGGC TCCAGCTCCA GAAGCTCCAA AAACAGGCTG GAAACAAGAA AACGGTATGT
2341 GGAAGGGCG
//

LOCUS E134.DNA 2405 BP SS-DNA SYN
DEFINITION -
ACCESSION -
KEYWORDS -
SOURCE -
FEATURES Location/Qualifiers
CDS 187..2405
BASE COUNT 1046 A 386 C 505 G 468 T 0 OTHER
ORIGIN -

1 CGGCCGCCAG TGTGATGGAT ATCTGCAGAA TTCGCCCTTC GACGAATAGC TGAAGAGGAA
61 AAGCTATTAC ATGAAGTTAT AATCCCAAAT GGAAGCATAA AGAGATAAAT ACAAAATTCG
121 ATTTATATAC AGTTCATATT GAAGTGATAT AGTAAGGTTA AAGAAAAAAT ATAGAAGGAA
181 ATAAACATGT TTGCATCAAA AAGCGAAAGA AAAGTACATT ATTCAATTCG TAAATTTAGT
241 ATTGGAGTAG CTAGTGTAGT AGTTGCTAGT CTTGTTATGG GAAGTGTGGT TCATGCGACG
301 GAGAATGAGG GAATTACCCA AGTAGCCACT TCTTATAATA AGGCAAATGA AAGTCAGACA
361 GAACATAGGA AAGCTGCTAA ACAAGTCGAT GAAGATATAA AAAAAATGTT GAGTGAGATC
421 CAAGAATATA TAAAAAAAAT GTTGAGTGAG ATCCAATTAG ATAAAAGAAA ACATACCCAA
481 AATGTCAACT TAAACAGAAA GTTGAGCGCA ATTCAAACGA AGTATTTGTA TGAATTAAGA
541 GTTTTAAAAG AGAAGTCGAA AAAAGAAGAG TTGACGTCAA AAACAAAAAA AGAGTTAGAC
601 GCAGCTTTTG AGAAGTTTAA AAAAGAACCA GAACTTACTA AAAAATTAGC AGAAGCTAAA
661 CAAAAAGCCA AGGCTCAAAA AGAAGAAGAT TTCCGTAACT ACCCAACCAA TACTTACAAA
721 ACGCTTGAAC TTGAAATTGC TGAGTTCGAT GTGAAAGTTA AAGAAGCGGA GCTTGAACTA
781 GTAAAAGAGG AAGCTAAACC CCGAAACGAG GAAAAAATTA AGCAAGCAAA AGCGAAAGTT
841 GAGAGTAAAA AAGCTGAGGC TACAAGGTTA GAAGAAATCA AGACAGAACG TAAAAAAGCA
901 GAAGAAGAAG CTAAACGAAA AGCAGAAGAA TCTGAGAAAA AAGCTGCTGA AGCCAAACAA
961 AAAGTGGATA CTAAAGAGCA AGGTAAACCA AAGAGGCGGG CAAAACGAGG
AGTTTCTGGA

1021 GAGCTAGCAA CACCTGATAA AAAAGAAAAT GATGCGAAGT CTTCAGATTC TAGCGTAGGT
1081 GAAGAAACTC TTCCAAGCCC ATCCCTTAAT ATGGCAAATG AAAGTCAGAC AGAACATAGG
1141 AAAGATGTCG ATGAATATAT AAAAAAAATG TTGAGTGAGA TCCAATTAGA TAGAAGAAAA
1201 CATACCCAAA ATGTCAACTT AAACATAAAG TTGAGCGCAA TTAAAACGAA GTATTTGTAT
1261 GAATTAAGTG TTTTAAAAGA GAACTCGAAA AAAGAAGAGT TGACGTCAAA AACCAAAGCA
1321 GAGTTAACCG CAGCTTTTGA GCAGTTTAAA AAAGATACAT TGAAACCAGA AAAAAAGGTA
1381 GCAGAAGCTG AGAAGAAGGT TGAAGAAGCT AAGAAAAAAG CCAAGGATCA
AAAAGAAGAA

1441 GATCGCCGTA ACTACCCAAC CAATACTTAC AAAACGCTTG AACTTGAAAT TGCTGAGTCC
1501 GATGTGAAAG TTAAAAAAGC GGAGCTTGAA CTAGTAAAAG AGGAAGCTAA CGAATCTCGA
1561 AACGAGGAAA AAATTAAGCA AGCAAAAGAG AAAGTTGAGA GTAAAAAAGC TGAGGCTACA
1621 AGGTTAGAAA AAATCAAGAC AGATCGTAAA AAAGCAGAAG AAGAAGCTAA ACGAAAAGCA
1681 GAAGAATCTG AGAAAAAAGC TGCTGAAGCC AAACAAAAAG TGGATGCTGA AGAATATGCT
1741 CTTGAAGCTA AAATCGCTGA GTTGGAATAT GAAGTTCAGA GACTAGAAAA AGAGCTCAAA
1801 GAGATTGATG AGTCTGACTC AGAAGATTAT CTTAAAGAAG GCCTCCGTGC TCCTCTTCAA
1861 TCTAAATTGG ATACCAAAAA AGCTAAACTA TCAAAACTTG AAGAGTTGAG TGATAAGATT
1921 GATGAGTTAG ACGCTGAAAT TGCAAAACTT GAAGTTCAAC TTAAAGATGC TGAAGGAAAC
1981 AATAATGTAG AAGCCTACTT TAAAGAAGGT TTAGAGAAAA CTACTGCTGA GAAAAAAGCT
2041 GAATTAGAAA AAGCTGAAGC TGACCTTAAG AAAGCAGTTG ATGAGCCAGA AACTCCAGCT
2101 CCGGCTCCTC AACCAGCTCC AGCTCCAGAA AAACCAGCTG AAAAACCAGC
TCCAGCTCCA

2161 GCTCCAGAAA AACCAGCTCC AGCTCCAGAA AAACCAGCTG AAAAACCAGC
TGAAAAACCA

2221 GCTGAAGAAC CAGCTGAAAA ACCAGCTCCA GCTCCAGAAA AACCAGCTCC
AACTCCAGAA

2281 AAACCAGCTC CAACTCCAGA AACTCCAAAA ACAGGCTGGA AACAAGAAAA
CGGTATGTGG

2341 TACTTCTACA ATACTGATGG TTCAATGGCA ACAGGCTGGC TCCAAAACAA TGGTTCATGG
2401 TACTA
//

FIG. 16B

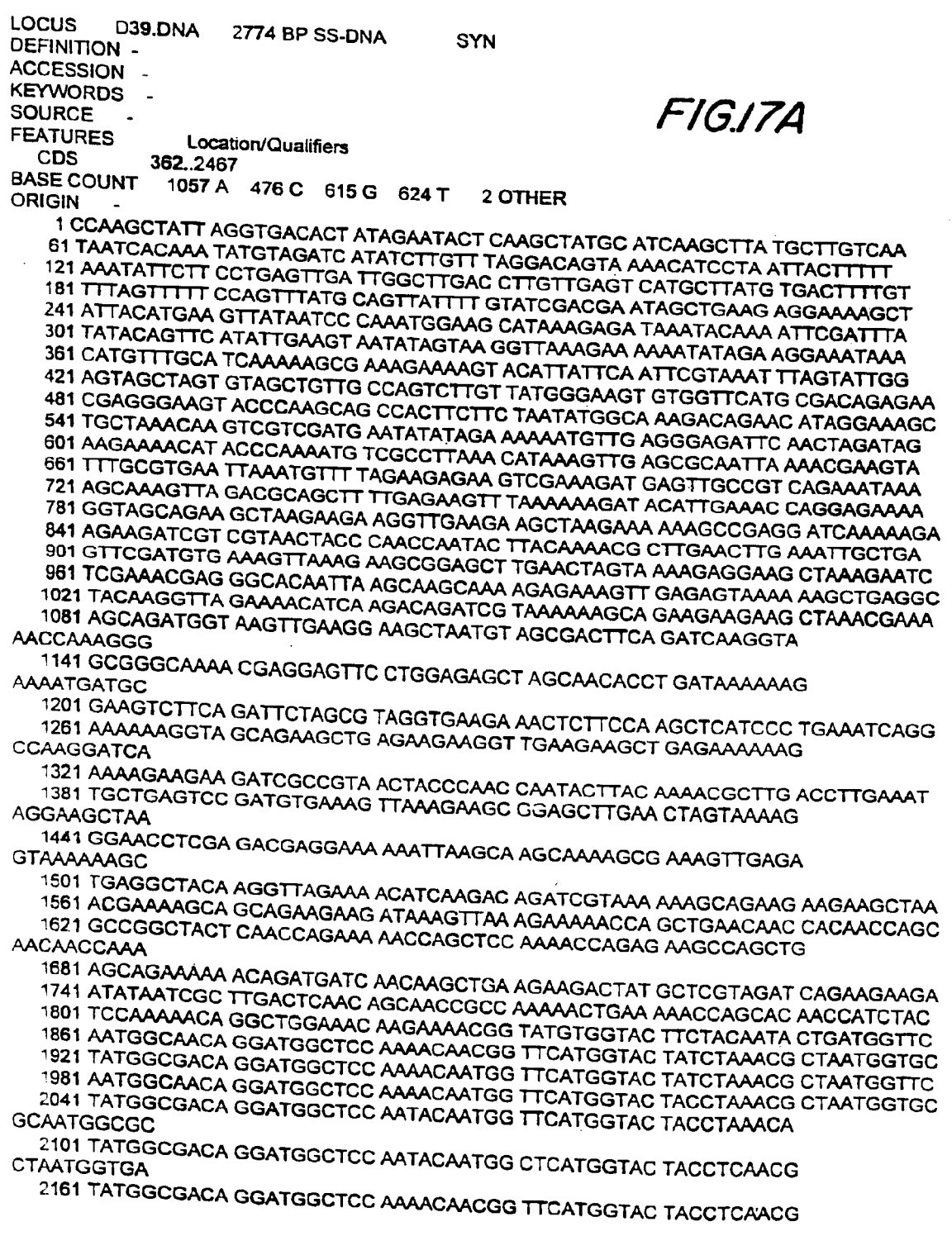

LOCUS D39.DNA 2774 BP SS-DNA SYN
DEFINITION -
ACCESSION -
KEYWORDS -
SOURCE -
FEATURES Location/Qualifiers
CDS 362..2467
BASE COUNT 1057 A 476 C 615 G 624 T 2 OTHER
ORIGIN -

FIG.17A

1 CCAAGCTATT AGGTGACACT ATAGAATACT CAAGCTATGC ATCAAGCTTA TGCTTGTCAA
61 TAATCACAAA TATGTAGATC ATATCTTGTT TAGGACAGTA AAACATCCTA ATTACTTTTT
121 AAATATTCTT CCTGAGTTGA TTGGCTTGAC CTTGTTGAGT CATGCTTATG TGACTTTTGT
181 TTTAGTTTTT CCAGTTTATG CAGTTATTTT GTATCGACGA ATAGCTGAAG AGGAAAAGCT
241 ATTACATGAA GTTATAATCC CAAATGGAAG CATAAAGAGA TAAATACAAA ATTCGATTTA
301 TATACAGTTC ATATTGAAGT AATATAGTAA GGTTAAAGAA AAAATATAGA AGGAAATAAA
361 CATGTTTGCA TCAAAAAGCG AAAGAAAAGT ACATTATTCA ATTCGTAAAT TTAGTATTGG
421 AGTAGCTAGT GTAGCTGTTG CCAGTCTTGT TATGGGAAGT GTGGTTCATG CGACAGAGAA
481 CGAGGGAAGT ACCCAAGCAG CCACTTCTTC TAATATGGCA AAGACAGAAC ATAGGAAAGC
541 TGCTAAACAA GTCGTCGATG AATATATAGA AAAAATGTTG AGGGAGATTC AACTAGATAG
601 AAGAAAACAT ACCCAAAATG TCGCCTTAAA CATAAAGTTG AGCGCAATTA AAACGAAGTA
661 TTTGCGTGAA TTAAATGTTT TAGAAGAGAA GTCGAAAGAT GAGTTGCCGT CAGAAATAAA
721 AGCAAAGTTA GACGCAGCTT TTGAGAAGTT TAAAAAAGAT ACATTGAAAC CAGGAGAAAA
781 GGTAGCAGAA GCTAAGAAGA AGGTTGAAGA AGCTAAGAAA AAAGCCGAGG ATCAAAAAGA
841 AGAAGATCGT CGTAACTACC CAACCAATAC TTACAAAACG CTTGAACTTG AAATTGCTGA
901 GTTCGATGTG AAAGTTAAAG AAGCGGAGCT TGAACTAGTA AAAGAGGAAG CTAAAGAATC
961 TCGAAACGAG GGCACAATTA AGCAAGCAAA AGAGAAAGTT GAGAGTAAAA AAGCTGAGGC
1021 TACAAGGTTA GAAAACATCA AGACAGATCG TAAAAAAGCA GAAGAAGAAG CTAAACGAAA
1081 AGCAGATGGT AAGTTGAAGG AAGCTAATGT AGCGACTTCA GATCAAGGTA AACCAAAGGG
1141 GCGGGCAAAA CGAGGAGTTC CTGGAGAGCT AGCAACACCT GATAAAAAAG AAAATGATGC
1201 GAAGTCTTCA GATTCTAGCG TAGGTGAAGA AACTCTTCCA AGCTCATCCC TGAAATCAGG
1261 AAAAAAGGTA GCAGAAGCTG AGAAGAAGGT TGAAGAAGCT GAGAAAAAAG CCAAGGATCA
1321 AAAAGAAGAA GATCGCCGTA ACTACCCAAC CAATACTTAC AAAACGCTTG ACCTTGAAAT
1381 TGCTGAGTCC GATGTGAAAG TTAAAGAAGC GGAGCTTGAA CTAGTAAAAG AGGAAGCTAA
1441 GGAACCTCGA GACGAGGAAA AAATTAAGCA AGCAAAAGCG AAAGTTGAGA GTAAAAAAGC
1501 TGAGGCTACA AGGTTAGAAA ACATCAAGAC AGATCGTAAA AAAGCAGAAG AAGAAGCTAA
1561 ACGAAAAGCA GCAGAAGAAG ATAAAGTTAA AGAAAAACCA GCTGAACAAC CACAACCAGC
1621 GCCGGCTACT CAACCAGAAA AACCAGCTCC AAAACCAGAG AAGCCAGCTG AACAACCAAA
1681 AGCAGAAAAA ACAGATGATC AACAAGCTGA AGAAGACTAT GCTCGTAGAT CAGAAGAAGA
1741 ATATAATCGC TTGACTCAAC AGCAACCGCC AAAAACTGAA AAACCAGCAC AACCATCTAC
1801 TCCAAAAACA GGCTGGAAAC AAGAAAACGG TATGTGGTAC TTCTACAATA CTGATGGTTC
1861 AATGGCAACA GGATGGCTCC AAAACAACGG TTCATGGTAC TATCTAAACG CTAATGGTGC
1921 TATGGCGACA GGATGGCTCC AAAACAATGG TTCATGGTAC TATCTAAACG CTAATGGTTC
1981 AATGGCAACA GGATGGCTCC AAAACAATGG TTCATGGTAC TACCTAAACG CTAATGGTGC
2041 TATGGCGACA GGATGGCTCC AATACAATGG TTCATGGTAC TACCTAAACA GCAATGGCGC
2101 TATGGCGACA GGATGGCTCC AATACAATGG CTCATGGTAC TACCTCAACG CTAATGGTGA
2161 TATGGCGACA GGATGGCTCC AAAACAACGG TTCATGGTAC TACCTCAACG

*FIG.17B*

CTAATGGTGA
2221 TATGGCGACA GGATGGCTCC AATACAACGG TTCATGGTAT TACCTCAACG CTAATGGTGA
2281 TATGGCGACA GGTTGGGTGA AAGATGGANA TACCTGGTAC TATCTTAAAG
CATCAGGTGC
2341 TATGAAAGCA AGCCAATGGT TCAAAGTATC AGATAAATGG TACTATGTCA ATGGCTCAGG
2401 TGCCCTTGCA GTCAACACAA CTGTAGATGG CTATGGAGTC AATGCCAATG
GTGAATGGGT
2461 AAACTAAACC TAATATAACT AGTTAATACT GACTTCCTGT AAGAACTTTT TAAAGTATTC
2521 CCTACAAATA CCATATCCTT TCAGTAGATA ATATACCCTT GTAGGAAGTT TAGATTAAAA
2581 AATAACTCTG TAATCTCTAG CCGGATTTAT AGCGCTAGAG ACTACGGAGT TTTTTTGATG
2641 AGGAAAGAAT GGCGGCATTC AAGAGACTCT TTAAGAGAGT TACGGGTTTT AAACTATTAA
2701 GCCTTCTCCA ATTGCAAGAG GGCTTCAATC TCTGCTAGGG TGCTAGCTTG
CGAAATGGCT
2761 CCACGGAGTT TNGC
//

LOCUS BG9163.DNA 2489 BP SS-DNA SYN
DEFINITION -
ACCESSION -
KEYWORDS -
SOURCE -

FIG. 18A

FEATURES Location/Qualifiers
CDS 221..2489
BASE COUNT 1026 A 429 C 541 G 493 T 0 OTHER
ORIGIN -

1 GATTGTATAC GACCACTATA GGGCGAATTG GGCCCGACGT CGCATGCTCC CGGCCGCCAT
61 GGCCGCGGGT ATTCGACGAA TAGCTGAAGA GGAAAAGCTA TTACATGAAG TTATAATCCC
121 AAATGGAAGC ATAAAGAGAT AAATACAACA TTCGATTTAT ATACAGTTCC TATTGAAGTG
181 ATATAATAAG GTTAAAGAAA AAATATAGAA GGAAATAAAC ATGTTTGCAT CAAAAAGCGA
241 AAGAAAAGTA CATTATTCAA TTCGTAAATT TAGTATTGGA GTAGCTAGTG TAGCTGTTGC
301 CAGCTTGTTC TTAGGAGGAG TAGTCCATGC AGAAGGGGTT AGAAGTGGGA ATAACCTCAC
361 GGTTACATCT AGTGGGCAAG ATATATCGAA GAAGTATGCT GATGAAGTCG AGTCGCATCT
421 AGAAAGTATA TTGAAGGATG TCAAAAAAAA TTTGAAAAAA GTTCAACATA CCCAAAATGT
481 CGGCTTAATT ACAAAGTTGA GCGAAATTAA AAAGAAGTAT TTGTATGACT TAAAAGTTAA
541 TGTTTTATCG GAAGCTGAGT TGACGTCAAA AACAAAAGAA ACAAAAGAAA AGTTAACCGC
601 AACTTTTGAG CAGTTTAAAA AAGATACATT ACCAACAGAA CCAGAAAAAA AGGTAGCAGA
661 AGCTCAGAAG AAGGTTGAAG AAGCTAAGAA AAAAGCCGAG GATCAAAAAG AAAAAGATCG
721 CCGTAACTAC CCAACCATTA CTTACAAAAC GCTTGAACTT GAAATTGCTG AGTCCGATGT
781 GGAAGTTAAA AAAGCGGAGC TTGAACTAGT AAAAGTGAAA GCTAAGGAAT CTCAAGACGA
841 GGAAAAAATT AAGCAAGCAG AAGCGGAAGT TGAGAGTAAA CAAGCTGAGG CTACAAGGTT
901 AAAAAAAATC AAGACAGATC GTGAAGAAGC TAAACGAAAA GCAGATGCTA AGTTGAAGGA
961 AGCTGTTGAA AAGAATGTAG CGACTTCAGA GCAAGATAAA CCAAAGAGGC
GGGCAAAACG
1021 AGGAGTTTCT GGAGAGCTAG CAACACCTGA TAAAAAAGAA AATGATGCGA AGTCTTCAGA
1081 TTCTAGCGTA GGTGAAGAAA CTCTTCCAAG CCCATCCCTT AATATGGCAA ATGAAAGTCA
1141 GACAGAACAT AGGAAAGATG TCGATGAATA TATAAAAAAA ATGTTGAGTG AGATCCAATT
1201 AGATGGAAGA AAACATACCC CAAATGTCAA CTTAAACATA AAGTTGAGCG CAATTAAAAC
1261 GAAGTATTTG TATGAATTAA GTGTTTTAAA AGAGAACTCG AAAAAAGAAG AGTTGACGTC
1321 AAAAACCAAA GCAGAGTTAA CCGCAGCTTT TGAGCAGTTT AAAAAAGATA CATTGAAACC
1381 AGAAAAAAAA GTAGCAGAAG CTGAGAAGAA GGTTGAAGAA GCTAAGAAAA
AAGCCAAGGA
1441 TCAAAAAGAA GAAGATCGCC GTAACTACCC AACCAATACT TACAAAACGC TTGAACTTGA
1501 AATTGCTGAG TCCGATGTGA AAGTTAAAGA AGCGGAGCTT GAACTAGTAA
AAGAGGAAGC
1561 TAACGAATCT CGAAACGAGG AAAAAATTAA GCAAGCAAAA GAGAAAGTTG AGAGTAAAAA
1621 AGCTGAGGCT ACAAGGTTAG AAAAAATCAA GACAGATCGT AAAAAAGCAG AAGAAGAAGC
1681 TAAACGAAAA GCAGAAGAAT CTGAGAAAAA AGCTGCTGAA GCCAAACAAA AAGTGGATGC
1741 TGAAGAATAT GCTCTTGAAG CTAAAATCGC TGAGTTGGAA TATGAAGTTC AGAGACTAGA
1801 AAAAGAGCTC AAAGAGATTG ATGAGTCTGA CTCAGAAGAT TATCTTAAAG AAGGCCTCCG
1861 TGCTCCTCTT CAATCTAAAT TGGATACCAA AAAAGCTAAA CTATCAAAAC TTGAAGAGTT
1921 GAGTGATAAG ATTGATGAGT TAGACGCTGA AATTGCAAAA CTTGAAGTTC AACTTAAAGA
1981 TGCTGAAGGA AACAATAATG TAGAAGCCTA CTTTAAAGAA GGTTTAGAGA AAACTACTGC
2041 TGAGAAAAAA GCTGAATTAG AAAAAGCTGA AGCTGACCTT AAGAAAGCAG TTGATGAGCC
2101 AGAAACTCCA GCTCCGGCTC CTCAACCAGC TCCGGCTCCA GAAAAACCAG
CTGAAAAACC
2161 AGCTCCAGCT CCAGCTCCAG AAAAACCAGC TCCAGCTCCA GAAAAACCAG
CTCCAGCTCC
2221 AGAAAAACCA GCTCCAGCTC CAGAAAAACC AGCTCCAGCT CCAGAAAAAC
CAGCTCCAGC
2281 TCCAGAAAAA CCAGCTCCAG CTCCAGAAAA ACCAGCTCCA GCTCCTAAAC CAGAAACTCC

FIG. 18B

2341 AGAAACAGGC TGGAAACAAG AAAACGGTAT GTGGTACTTC TACAATACTG ATGGTTCAAT
2401 GGCAACAGGC TGGCTCCAAA ACAATGGCTC ATGGTACTAC CTCAACAGCA
ATGGCGTTAT
2461 GGCGACAGGA TGGTTCCCAA ACAATGGTC
//

FIG. 19

```
LOCUS       BG8090.DNA  1680 BP SS-DNA          SYN
DEFINITION  -
ACCESSION   -
KEYWORDS    -
SOURCE      -
FEATURES          Location/Qualifiers
   CDS          220..1680
BASE COUNT    714 A   287 C   375 G   304 T    0 OTHER
ORIGIN      -
      1 ATTGTATACG ACTCACTATA GGGCGAATTG GGCCCGACGT CGCATGCTCC CGGCCGCCAT
     61 GGCCGCGGGA TTCGACGAAT AGCTGAAGAG GAAAAGCTAT TACATGAAGT TATAATCCCA
    121 AATGGAAGCA TAAAGAGATA AATACAAAAT TCGATTTATA TACAGTTCAT ATTGAAGTGA
    181 TATAGTAAGG TTAAAGAAAA AATATAGAAG GAAATAAACA TGTTTGCATC AAAAAACGAA
    241 AGAAAAGTAC ATTATTCAAT TCGTAAATTT AGTATTGGAG TAGCTAGTGT AGCTGTTGCC
    301 AGTCTTTTTA TGGGAAGTGT GGTTCATGCG ACAGAGAAGG AGGTAACTAC CCAAGTAGCC
    361 ACTTCTTTTA ATAAGGCAAA TAAAAGTCAG ACAGAACATA TGAAAGCTGC TAAACAAGTC
    421 GATGAATATA TAACAAAAAA GCTCCAATTA GATAGAAGAA AACATACCCA AAATGTCGGC
    481 TTACTCACAA AGTTGGGCGT AATTAAAACG GAGTATTTGC ATAGATTAAG TGTTTCAAAA
    541 GAGAAGTCGG AAGCTGAGTT GCCGTCAGAA ATAAAAGCAA AGTTAGACGC AGCTTTTGAG
    601 CAGTTTAAAA AAGATACATT ACCAACAGAA CCAGGAAAAA AGGTAGCAGA AGCTGAGAAG
    661 AAGGTTGAAG AAGCTAAGAA AAAAGCCGAG GATCAAAAAG AAGAAGATCG TCGTAACTAC
    721 CCAACCATTA CTTACAAAAC GCTTGAACTT GAAATTGCTG AGTCCGATGT GGAAGTTAAA
    781 AAAGCGGAGC TTGAACTAGT AAAAGAGGAA GCTAAGGGAT CTCGAAACGA GCAAAAAGTT
    841 AACCAAGCAA AAGCGAAAGT TGAGAGTAAA CAAGCTGAGG CTACAAGGTT AAAAAAAATC
    901 AAGACAGATC GTGAACAAGC TGAGACTACA AGGTTAGAAA ACATCAAGAC AGATCGTGAA
    961 AAAGCAGAAG AAGCTAAACG AAAAGCAGAT GCTAAAGAGC AAGATGAATC
AAAGAGGCGG
   1021 GTAAAAGGAG GAGTTCCGGG AGAGCAAGCA ACACTTGATA AAAAAGAAAA
TGATGCGAAG
   1081 TCTTCAGATT CTAGCGTAGG TGAAGAAACT CTTCCAAGCC CATCCCTGAA ATCAGGAAAA
   1141 AAGGTAGCAG AAGCTGAGAA GAAGGTTGCA GAAGCTGAGA AAAAAGCCAA
GGATCAAAAA
   1201 GAAGAAGATC GCCGTAACTA CCCAACCAAT ACTTACAAAA CGCTTGAACT TGAAATTGCT
   1261 GAGTCCGATG TGAAAGTTAA AGAAGCGGAG CTTGAACTAG TAAAAGAGGA
AGCTAAGGAA
   1321 TCTCGAAACG AGGAAAAAGT TAAGCAAGCA AAAGCGGAAG TTGAGAGTAA
AAAAGCTGAG
   1381 GCTACAAGGT TAGAAAAAAT CAAGACAGAT CGTAAAAAAG CAGAAGAAGC TAAACGAAAA
   1441 GCAGCAGAAG AAGATAAAGT TAAAGAAAAA CCAGCTGAAC AACCACAACC
AGCGCCGGCT
   1501 CCTCAACCAG AAAAACCAGC TCCAGCTCCA AAACCAGAGA ATCCAGCTGA ACAACCAAAA
   1561 GCAGAAAAAC CAGCTGATCA ACAAGCTGAA GAAGACTATG CTCGTAGATC AGAAGAAGAA
   1621 TATAATCGCT TGACTCAACA GCAACCGCCA AAAACTGAAA AACCAGCACA ACCATCTACT
//
```

FIG. 20

```
LOCUS       L81905.DNA   1766 BP SS-DNA        SYN
DEFINITION  -
ACCESSION   -
KEYWORDS    -
SOURCE      -
FEATURES             Location/Qualifiers
   CDS           217..1766
BASE COUNT    741 A   313 C   402 G   309 T    1 OTHER
ORIGIN      -
      1 GTATACGACT CACTATAGGG CGAATTGGGC CCGACGTCGC ATGCTCCCGG
CCGCCATGGC
     61 CGCGGGATTC GACGAATAGC TGAAGAGGAA AAGCTATTAC ATGAAGTTAT AATCCCAAAT
    121 GGAAGCATAA AGAGATAAAT ACAAAATTCG ATTTATATAC AGTTCATATT GAAGTGATAT
    181 AGTAAGGTTA AAGAAAAAAT ATAGAAGGAA ATAAACATGT TTGCATCAAA AAGCGAAAGA
    241 AAAGTACATT ATTCAATTCG TAAATTTAGT GTTGGAGTAG CTAGTGTAGT TGTTGCCAGT
    301 CTTGTTATGG GAAGTGTGGT TCATGCGACA GAGAACGAGG GAGCTACCCA
AGTACCCACT
    361 TCTTCTAATA GGGCAAATGA AAGTCAGGCA GAACAAGGAG AACAACCTAA AAAACTCGAT
    421 TCAGAACGAG ATAAGGCAAG GAAAGAGGTC GAGGAATATG TAAAAAAAAT AGTGGGTGAG
    481 AGCTATGCAA AATCAACTAA AAAGCGACAT ACAATTACTG TAGCTCTAGT TAACGAGTTG
    541 AACAACATTA AGAACGAGTA TTTGAATAAA ATAGTTGAAT CAACCTCAGA AAGCCAACTA
    601 CAGATACTGA TGATGGAGAG TCGATCAAAA GTAGATGAAG CTGTGTCTAA GTTTGAAAAG
    661 GACTCATCTT CTTCGTCAAG TTCAGACTCT TCCACTAAAC CGGAAGCTTC AGATACAGCG
    721 AAGCCAAACA AGCCGACAGA ACCAGGAGAA AAGGTAGCAG AAGCTAAGAA
GAAGGTTGAA
    781 GAAGCTGAGA AAAAAGCCAA GGATCAAAAA GAAGAAGATC GTCGTAACTA CCCAACCATT
    841 ACTTACAAAA CGCTTGAACT TGAAATTGCT GAGTCCGATG TGGAAGTTAA AAAAGCGGAG
    901 CTTGAACTAG TAAAAGTGAA AGCTAACGAA CCTCGAGACG AGCAAAAAAT TAAGCAAGCA
    961 GAAGCGGAAG TTGAGAGTAA ACAAGCTGAG GCTACAAGGT TAAAAAAAAT CAAGACAGAT
   1021 CGTGAAGAAG CAGAAGAAGA AGCTAAACGA AGAGCAGATG CTAAAGAGCA
AGGTAAACCA
   1081 AAGGGGCGGG CAAAACGAGG AGTTCCTGGA GAGCTAGCAA CACCTGATAA
AAAAGAAAAT
   1141 GATGCGAAGT CTTCAGATTC TAGCGTAGGT GAAGAAACTC TTCCAAGCCC ATCCCTGAAA
   1201 CCAGAAAAAA AGGTAGCAGA AGCTGAGAAG AAGGTTGAAG AAGCTAAGAA
AAAAGCCGAG
   1261 GATCAAAAAG AAGAAGATCG CCGTAACTAC CCAACCAATA CTTACAAAAC GCTTGAACTT
   1321 GAAATTGCTG AGTCCGATGT GGAAGTTAAA AAAGCGGAGC TTGAACTAGT AAAAGAGGAA
   1381 GCTAAGGAAC CTCGAAACGA GGAAAAAGTT AAGCAAGCAA AAGCGGAAGT
TGAGAGTAAA
   1441 AAAGCTGAGG CTACTAGGTT AGAAAAAATC AAGACAGATC GTAAAAAAGC AGAAGAAGAA
   1501 GCTAAACGAA AAGCAGCAGA AGAAGATAAA GTTAAAGAAA AACCAGCTGA ACAACCACAA
   1561 CCAGCGCCGG CTCCAAAAGC AGAAAAACCA GCTCCAGCTC CAAAACCAGA
GAATCCAGCT
   1621 GAACAACCAA AAGCAGAAAA ACCAGCTGAT CAACAAGCTG AAGAAGAGTA TGCTCGTAGA
   1681 TCAGAAGAAG AATATAATCG CTTGACTCTA CAGCAACCGC CAAAAACTGA AAAACCAGCA
   1741 CAACCATCTA CTCCAAAAAC AAANAC
//
```

FIG. 21

```
LOCUS       DBL6A.DNA    1590 BP SS-DNA          SYN
DEFINITION  -
ACCESSION   -
KEYWORDS    -
SOURCE      -
FEATURES          Location/Qualifiers
   CDS          127:.1590
BASE COUNT     701 A   261 C   339 G   288 T    1 OTHER
ORIGIN      -
       1 AAACTATTAC ATGAAGTTAT AATCCCAAAT GGAAGCATAA AGAGATAAAT ACAAAATTCG
      61 ATTTATATAC AGTTCATATT GAAGTGATAT AGTAAGGTTA AAGAAAAAAT ATAGAAGGAA
     121 ATAATTATGT TTGCATCYAA AAGCGAAAGA AAAGTACATT ATTCAATTCG TAAATTTAGT
     181 ATTGGAGTAG CTAGTGTAGC TGTTGCTAGC TTGTTCTTAG GAGGAGTAGT CCATGCAGAA
     241 GGGGTTAGAA GTGAGAATAC CCCCAAGGTT ACATCTAGTG GGGATGAAGT CGATGAATAT
     301 ATAAAAAAAA TGTTGAGTGA GATCCAATTA GATAAAAGAA AACATACCCA CAATTTCGCC
     361 TTAAACCTAA AGTTGAGCAG AATTAAAACG GAGTATTTGT ATAAATTAAA AGTTAATGTT
     421 TTAGAAGAAA AGTCAAAAGC TGAGTTGACG TCAAAAACAA AAAAAGAGGT AGACGCAGCT
     481 TTTGAGAAGT TTAAAAAAGA TACATTGAAA CTAGGAGAAA AGGTAGCAGA AGCTCAGAAG
     541 AAGGTTGAAG AAGCTAAGAA AAAAGCCAAG GATCAAAAAG AAGAAGATCA CCGTAACTAC
     601 CCAACCAATA CTTACAAAAC GCTTGAACTT GAAATTGCTG AGTCCGATGT GAAAGTTAAA
     661 GAAGCGGAGC TTGAACTATT GAAAGAGGAA GCTAAAACTC GAAACGAGGA CACAATTAAC
     721 CAAGCAAAAG CGAAAGTTAA GAGTGAACAA GCTGAGGCTA CAAGGTTAAA AAAAATCAAG
     781 ACAGATCGTG AACAAGCTGA GGCTACAAGG TTAGAAAACA TCAAGACAGA TCGTGAAAAA
     841 GCAGAAGAAG CTAAACGAAA AGCAGAAGCA GAAGAAGTTA AAGATAAACT AAAGAGGCGG
     901 ACAAAACGAG CAGTTCCTGG AGAGCCAGCA ACACCTGATA AAAAAGAAAA TGATGCGAAG
     961 TCTTCAGATT CTAGCGTAGG TGAAGAAACT CTTCCAAGCC CATCCCTGAA ATCAGGAAAA
    1021 AAGGTAGCAG AAGCTCAGAA GAAGGTAGCA GAAGCTGAGA AAAAAGCCAA
GGATCAAAAA
    1081 GAAGAAGATC GCCGTAACTA CCCAACCAAT ACTTACAAAA CGCTTGACCT TGAAATTGCT
    1141 GAGTCCGATG TGAAAGTTAA AGAAGCGGAG CTTGAACTAG TAAAAGAGGA
AGCTAAGGAA
    1201 TCTCGAAACG AGGAAAAAGT TAAGCAAGCA AAAGCGAAAG TTGAGAGTAA AAAAGCTGAG
    1261 GCTACAAGGT TAGAAAAAAT CAAGACAGAT CGTAAAAAAG CAGAAGAAGC TAAACGAAGA
    1321 GCAGCAGAAG AAGATAAAGT TAAAGAAAAA CCAGCTGAAC AACCACAACC
AGCGCCGGCT
    1381 CCTCAACCAG AAAAACCAAC TGAAGAGCCT GAGAATCCAG CTCCAGCTCC
AAAACCTGAG
    1441 AATCCAGCTG AACAACCAAA AGCAGAAAAA CCAGCTGATC AACAAGCTGA AGAAGACTAT
    1501 GCTCGTAGAT CAGAAGAAGA ATATAATCGC TTGACTCAAC AGCAACCGCC AAAAACTGAA
    1561 AAACCAGCAC AACCATCTAC TCCAAAAACA
//
```

PNEUMOCOCCAL SURFACE PROTEIN C (PSPC), EPITOPIC REGIONS AND STRAIN SELECTION THEREOF, AND USES THEREFOR

RELATED APPLICATIONS/PATENTS

This application is a continuation-in-part ("CIP") of U.S. application Ser. No. 08/714,741, filed Sep. 16, 1996, now U. S. Pat. No. 6,500,613, which is a CIP of U.S. application Ser. No. 08/529,055, filed Sep. 15, 1995, now U.S. Pat. No. 6,592,876. This application is also based upon and claims priority from U.S. Provisional application Ser. No. 60/082, 728, filed Apr. 23, 1998.

STATEMENT OF GOVERNMENT SUPPORT

This work was supported in part by National Institute of Health Grants A121548 and HL58418.

Reference also is made to: Briles et al., "Strain Selection of Pneumnococcal Surface Proteins," U.S. application Ser. No. 08/710,749, filed Sep. 20, 1996, now U.S. Pat. No. 5,955,089; PCT applications PCT/US96/14819, filed Sep. 16, 1996 and WO 97/09994, published Mar. 20, 1997; Briles et al. "Oral Administration . . . ," U.S. application Ser. No. 08/482,981, filed Jun. 7, 1995, now U.S. Pat. No. 6,232,116, U.S. application Ser. No. 08/458,399, filed Jun. 2, 1995, now U.S. Pat. No. 6,231,870 and U.S. application Ser. No. 08/657,751, filed May 30, 1996, now U.S. Pat. No. 6,004, 802; "Mucosal Administration . . . ," Briles et al., U.S. application Ser. No. 08/446,201, filed May 19, 1995, now U.S. Pat. No. 6,042,832 (filed as a CIP of U.S. Ser No. 08/246,636, filed May 20,1994, now U.S. Pat. No. 5,965, 141) and Briles et al., U.S. application Ser. No. 08/312,949, filed Sep. 30, 1994, now U.S. Pat. No. 6,027,734; Briles et al., "Epitopic Regions of Pneunococcal Surface Protein A," U.S. application Ser. No. 08/319,795, filed May 20, 1994 now U.S. Pat. No. 5,980,909; Briles et al., "Structural Gene of Pneumococcal Protein", U.S. application Ser. No. 08/467, 852, filed June 6, 1995, now U.S. Pat. No. 5,856,170 (filed as a cont. of U.S. application Ser. No. 08/247,491, filed May 23, 1994, now U.S. Pat. No. 5,965,400), U.S. application Ser. No. 08/072,070, filed Jun. 3, 1993, now U.S. Pat. No. 5,476,929, U.S. application Ser. No. 08/469,434, filed Jun. 6, 1995, now U.S. Pat. No. 5,753,463 and U.S. application Ser. No. 08/214,164, filed Mar. 14,1994, now U.S. Pat. No. 5,728,387; Briles et al., "Truncated PspA . . . ," U.S. application Ser. No. 08/214,222, filed Mar. 17, 1994, now U.S. Pat. No. 5,804,193 and Briles et al., U.S. application Ser. No. 08/468,985, now U.S. Pat. No. 5,997,882; Briles et al., "Immunoassay Comprising a Truncated Pneumococcal Surface Protein A (PspA)," U.S. application Ser. No. 08/468, 718, filed Jun. 6, 1995, now U.S. Pat. No. 5,871,943; U.S. application Ser. No. 08/226,844, filed May 29, 1992; U.S. applications Ser. Nos. 08/093,907, filed Jul. 5, 1994 and 07/889,918, filed Jul. 5, 1994, both abandoned; PCT/US93/ 05191; and Briles et al., WO 92/1448.

Each of these applications and patents, as well as each document or reference cited in each of these applications and patents (including during the prosecution of each issued patent) and PCT and foreign applications or patents corresponding to and/or claiming priority from any of the foregoing applications and patents, is hereby expressly incorporated herein by reference. Documents or references are also cited in the following text, either in a Reference List before the claims, or in the text itself; and, each of these documents or references ("herein-cited documents or references"), as well as each document or reference cited in each of the herein-cited documents or references, is hereby expressly incorporated herein by reference.

FIELD OF THE INVENTION

The present invention relates to epitopic regions of Pneumococcal Surface Protein C or "PspC", different clades of PspC, isolated and/or purified nucleic acid molecules, such as DNA encoding a fragment or portion of PspC such as an epitopic region of PspC or at least one epitope of PspC, uses for such nucleic acid molecules, e.g., to detect the presence of PspC or of *Streptococcus pneumoniae* by detecting a nucleic acid molecule therefor in a sample such as by amplification and/or a polymerase chain reaction, vectors or plasmids which contain and/or express such nucleic acid molecules, e.g, in vitro or in vivo, immunological, immunogenic or vaccine compositions comprising at least one PspC and/or a portion thereof (such as at least one epitopic region of at least one PspC and/or at least one polypeptide encoding at least one epitope of at least one PspC), either alone or in further combination with at least one second pneumococcal antigen, such as at least one different PspC and/or a fragment thereof and/or at least one PspA and/or at least one epitopic region of at least one PspA and/or at least polypeptide comprising at least one epitope of PspA.

PspC or a fragment thereof, and thus a composition comprising PspC or a fragment thereof, can be administered by the same routes, and in approximately the same amounts, as PspA. Thus, the invention further provides methods for administering PspC or a fragment thereof, as well as uses of PspC or a fragment thereof to formulate such compositions.

Other aspects of the invention are described in or are obvious from (and within the ambit of the invention) the following disclosure.

BACKGROUND OF THE INVENTION

*S. pneumoniae* is an important cause of otitis media, meningitis, bacteremia and pneumonia, and a leading cause of fatal infections in the elderly and persons with underlying medical conditions, such as pulmonary disease, liver disease, alcoholism, sickle cell anemia, cerebrospinal fluid leaks, acquired immune deficiency syndrome (AIDS), and in patients undergoing immunosuppressive therapy. It is also a leading cause of morbidity in young children. Pneumococcal infections cause approximately 40,000 deaths in the U.S. yearly. The most severe pneumococcal infections involve invasive meningitis and bacteremia infections, of which there are 3,000 and 50,000 cases annually, respectively.

Despite the use of antibiotics and vaccines, the prevalence of pneumococcal infections has declined little over the last twenty-five years; the case-fatality rate for bacteremia is reported to be 15–20% in the general population, 30–40% in the elderly, and 36% in inner-city African Americans. Less severe forms of pneumococcal disease are pneumonia, of which there are 500,000 cases annually in the U.S., and otitis media in children, of which there are an estimated 7,000,000 cases annually in the U.S. caused by pneumococcus. Strains of drug-resistant *S. pneumoniae* are becoming ever more common in the U.S. and worldwide. In some areas, as many as 30% of pneumococcal isolates are resistant to penicillin. The increase in antimicrobial resistant pneumococcus further emphasizes the need for preventing pneumococcal infections.

Pneumococcus asymptomatically colonizes the upper respiratory tract of normal individuals; disease often results from the spread of organisms from the nasopharynx to other tissues during opportunistic events. The incidence of carriage in humans varies with age and circumstances. Carrier rates in children are typically higher than those of adults. Studies have demonstrated that 38 to 60% of preschool children, 29 to 35% of grammar school children and 9 to 25% of junior high school children are carriers of pneumococcus. Among adults, the rate of carriage drops to 6% for those without children at home, and to 18 to 29% for those with children at home. It is not surprising that the higher rate of carriage in children than in adults parallels the incidence of pneumococcal disease in these populations.

An attractive goal for streptococcal vaccination is to reduce carriage in the vaccinated populations and subsequently reduce the incidence of pneumococcal disease. There is speculation that a reduction in pneumococcal carriage rates by vaccination could reduce the incidence of the disease in non-vaccinated individuals as well as in vaccinated individuals. This "herd immunity" induced by vaccination against upper respiratory bacterial pathogens has been observed using the *Haemophilus influenzae* type b conjugate vaccines (Takala, A. K., et al., J. Infect. Dis. 1991; 164: 982–986; Takala, A. K., et al., Pediatr. Infect. Dis. J., 1993; 12: 593–599; Ward, J., et al., Vaccines, S. A. Plotkin and E. A. Mortimer, eds., 1994, pp. 337–386; Murphy, T. V., et al., J. Pediatr., 1993; 122; 517–523; and Mohle-Boetani, J. C., et al., Pediatr. Infect. Dis. J., 1993; 12: 589–593).

It is generally accepted that immunity to *S. pneumoniae* can be mediated by specific antibodies against the polysaccharide capsule of the pneumococcus. However, neonates and young children fail to make an adequate immune response against most capsular polysaccharide antigens and can have repeated infections involving the same capsular serotype. One approach to immunizing infants against a number of encapsulated bacteria is to conjugate the capsular polysaccharide antigens to protein to make them immunogenic. This approach has been successful, for example, with *H. influenzae b* (see U.S. Pat. No. 4,496,538 to Gordon and U.S. Pat. No. 4,673,574 to Anderson).

However, there are over ninety known capsular serotypes of *S. pneumoniae*, of which twenty-three account for about 95% of the disease. For a pneumococcal polysaccharide-protein conjugate to be successful, the capsular types responsible for most pneumococcal infections would have to be made adequately immunogenic. This approach may be difficult, because the twenty-three polysaccharides included in the presently-available vaccine are not all adequately immunogenic, even in adults.

Protection mediated by anti-capsular polysaccharide antibody responses are restricted to the polysaccharide type. Different polysaccharide types differentially facilitate virulence in humans and other species. Pneumococcal vaccines have been developed by combining 23 different capsular polysaccharides that are the prevalent types of human pneumococcal disease. These 23 polysaccharide types have been used in a licensed pneumococcal vaccine since 1983 (D. S. Fedson and D. M. Musher, Vaccines, S. A. Plotkin and J. E. A. Montimer, eds., 1994, pp. 517–564). The licensed 23-valent polysaccharide vaccine has a reported efficacy of approximately 60% in preventing bacteremia caused pneumococci in healthy adults.

However, the efficacy of the vaccine has been controversial, and at times, the justification for the recommended use of the vaccine questioned. It has been speculated that the efficacy of this vaccine is negatively affected by having to combine 23 different antigens. Having a large number of antigens combined in a single formulation may negatively affect the antibody responses to individual types within this mixture because of antigenic competition. The efficacy is also affected by the fact that the 23 serotypes encompass all serological types associated with human infections and carriage.

An alternative approach to protecting against pneumococcal infection, especially for protecting children, and also the elderly, would be to identify protein antigens that could elicit protective immune responses. Such proteins may serve as a vaccine by themselves, may be used in conjunction with successful polysaccharide-protein conjugates, or as carriers for polysaccharides.

Pneumococcal Surface Protein A or PspA has been identified as an antigen; and, its DNA and amino acid sequences have been investigated. PspA is useful in eliciting protective immune responses. PspA or fragments thereof can be used in immunological, immunogenic or vaccine compositions; and, such compositions can contain different types of PspAs or fragments from different types of PspAs. Further, such compositions can be administered by injection, or mucosally or orally, or by means of a vector expressing the PspA or fragment thereof.

Studies on PspA led to the discovery of a PspA-like protein and a pspA-like gene, now termed PspC and pspC. Indeed, early patent literature termed PspC as "PspA-like".

It is believed that heretofore that epitopic regions of PspC have not been disclosed or suggested. It is likewise believed that heretofore different clades of PspC have not been taught or suggested. Further, it is believed that heretofore DNA encoding epitopic regions of PspC have not been disclosed or suggested. Further still, it is believed that heretofore immunological, immunogenic or vaccine compositions comprising at least one PspC and/or portions thereof (such as at least one epitopic region of at least one PspC and/or at least one polypeptide encoding at least one epitope of at least one PspC), either alone or in further combination with at least one second pneumococcal antigen, such as at least one different PspC and/or a fragment thereof and/or at least one PspA and/or at least one epitopic region of at least one PspA and/or at least one polypeptide comprising at least one epitope of PspA, have not been taught or suggested.

Alternative vaccination strategies are desirable as such provide alternative immunological, immunogenic or vaccine compositions, as well as alternative routes to administration or alternative routes to responses. It would be advantageous to provide an immunological composition or vaccination regimen which elicits protection against various diversified pneumococcal strains, without having to combine a large number of possibly competitive antigens within the same formulation. And, it is advantageous to provide additional antigens and epitopes for use in immunological, immunogenic and/or vaccine compositions, e.g., to provide alternative compositions containing or comprising such antigens or epitopes either alone or in combination with different antigens.

Furthermore it is advantageous to provide a better understanding of the pathogenic mechanisms of pneumococci, as this can lead to the development of improved vaccines, diagnoses and treatments.

OBJECTS AND SUMMARY OF THE INVENTION

An object of the invention can include providing one or more of: epitopic regions of PspC, different clades of PspC, isolated and/or purified nucleic acid molecules such as DNA encoding a fragment or portion of PspC such as an epitopic region of PspC or at least one epitope of PspC, uses for such nucleic acid molecules, vectors or plasmids which contain and/or express such nucleic acid molecules, e.g., in vitro or in vivo, immunological, immunogenic or vaccine compositions comprising such a vector or plasmid and/or at least one PspC and/or a portion thereof (such as at least one epitopic region of at least one PspC and/or at least one polypeptide encoding at least one epitope of at least one PspC), either alone or in further combination with at least one second pneumococcal antigen, such as at least one different PspC and/or a fragment thereof and/or at least one PspA and/or at least one epitopic region of at least one PspA and/or at least one polypeptide comprising at least one epitope of PspA and/or at least one vector or plasmid expressing said second pneumococcal antigen (which vector or plasmid could be the same as the aforementioned vector or plasmid comprising a nucleic acid molecule encoding PspC or a portion or fragment thereof); and, methods for administering PspC or a fragment thereof, as well as uses of PspC or a fragment thereof to formulate such compositions, inter alia.

Accordingly, the invention can provide one or more of: epitopic regions of PspC, different clades of PspC, isolated and/or purified nucleic acid molecules such as DNA encoding a fragment or portion of PspC such as an epitopic region of PspC or at least one epitope of PspC, uses for such nucleic acid molecules, vectors or plasmids which contain and/or express such nucleic acid molecules, e.g., in vitro or in vivo, immunological, immunogenic or vaccine compositions comprising such a vector or plasmid and/or at least one PspC and/or a portion thereof (such as at least one epitopic region of at least one PspC and/or at least one polypeptide encoding at least one epitope of at least one PspC), either alone or in further combination with at least one second pneumococcal antigen, such as at least one different PspC and/or a fragment thereof and/or at least one PspA and/or at least one epitopic region of at least one PspA and/or at least one polypeptide comprising at least one epitope of PspA and/or at least one vector or plasmid expressing said second pneumococcal antigen (which vector or plasmid could be the same as the aforementioned vector or plasmid comprising a nucleic acid molecule encoding PspC or a portion or fragment thereof); and, methods for administering PspC or a fragment thereof, as well as uses of PspC or a fragment thereof to formulate such compositions, inter alia.

PspC or a fragment thereof, and thus a composition comprising PspC or a fragment thereof, can be administered by the same routes, and in approximately the same amounts, as PspA. Thus, the invention further provides methods for administering PspC or a fragment thereof, as well as uses of PspC or a fragment thereof to formulate such compositions.

Still further, the invention provides PspC epitopic regions, e.g., the alpha helical region, or the proline region or the combination of the alpha helical and proline regions, or the entire PspC molecule, or aa 1–590 of PspC clade A, or amino acid(s) ("aa") 1–204 or aa 46–204 or aa 1–295 or aa 46–295 or aa 1–454 or aa 46–454 or aa 295–454 or aa 1–590 or aa 46–590 or aa 204–590 or aa 295–590 or aa 454–590 or aa 46–652 or aa 204–652 or aa 295–652 or aa 454–652 or aa 590–652 or aa 1–892 or aa 46–892 or aa 204–892 or aa 295–892 or aa 454–892 or 590–892 of PspC clade A. A prototypic clade A PspC is PspC.EF6796. In other clade A PspCs, the epitopic regions may have slightly different amino acid numbers. Thus, the invention comprehends regions of other lade A PspCs which are substantially homologous, or significantly homologous, or highly homologous, or very highly homologous, or identical, or highly conserved, with respect to the foregoing particularly recited epitopic regions. Also, where possible, these regions can extend in either the N-terminal or COOH-terminal direction; e.g., by about another 1–25 or 1–50 amino acids in either or both directions. The invention further provides a polypeptide comprising at least one epitopic region or at least one epitope in any one of these various regions.

Similarly, the invention provides clade B epitopic regions, e.g., the alpha helical region, the proline region, the combination of the alpha helical and proline regions, and the entire molecule, as well as by aa such as aa 1–664, or aa 1–375, or aa 14–45 or aa 1–101, or aa 1–193, or aa 1–262, or aa 1–355, or aa 101–193, or aa 101–262, or aa 101–355, or aa 101–375, or aa 101–455 or aa 193–262, or aa 193–355, or aa 193–375, or aa 193–445 or aa 262–355, or aa 262–375, or aa 262–445 or aa 355–375, or aa 355–445 or aa 3754–445 or aa 101–664, or aa 193–664, or aa 262–664, or aa 355–664 or aa 375–664 or aa 1-end of proline subregion A, or aa 1-beginning of proline subregion B, or aa 101-end of proline subregion A, or aa 101-beginning of proline subregion B, or aa 193-end of proline subregion A, or aa 193-beginning of proline subregion B, or aa 262-end of proline subregion A, or aa 262-beginning of proline subregion B, or aa 355-end of proline subregion A, or aa 355-beginning of proline subregion B, or aa 375-end of proline subregion A, or proline subregion A, or aa 375-beginning of proline subregion B, or proline subregion B, or beginning of proline subregion B-aa 664. A prototypic clade B PspC is PspC.D39. In other clade B PspCs, the epitopic regions may have slightly different amino acid numbers. Thus, the invention comprehends regions of other clade B PspCs which are substantially homologous, or significantly homologous, or highly homologous, or very highly homologous, or identical, or highly conserved, with respect to the foregoing particularly recited epitopic regions. Also, where possible, these regions can extend in either the N-terminal or COOH-terminal direction; e.g., by about another 1–25 or 1–50 amino acids in either or both directions. For instance, interesting epitopic regions include: aa 263–482, 14–45 and 255–445. And, the invention further provides a polypeptide comprising at least one epitopic region or at least one epitope in any one of these regions.

A polypeptide comprising at least one epitope of PspC or PspA can be shorter than natural or full length PspC or PspA, e.g., a truncated PspC or PspA, such as comprising up to about 90% of natural or full length PspC or PspA.

The invention further provides an isolated nucleic acid molecule, e.g., DNA comprising a sequence encoding any one of these epitopic regions or a polypeptide comprising at least one of these epitopic regions, or an epitope of PspC; such a nucleic acid molecule is advantageously at least about 12 nucleotides in length, for instance, at least about 15, about 18, about 21, about 24 or about 27 nucleotides in length, such as at least about 30, about 33, about 36, about 39 or about 42 nucleotides in length, for example, a nucleic acid molecule of at least about 12 nucleotides in length such as about 12 to about 30, about 12 to about 50 or about 12 to about 60, or about 12 to about 75 or about 12 to about 100 or more nucleotides in length. A nucleic acid molecule comprising a sequence encoding at least one epitope of PspC or PspA can be shorter than natural or full length pspC or pspA, e.g., a truncated pspC or pspA, such as comprising up to about 90% of natural or full length pspC or pspA or encoding up to about 90% of natural or full length PspA or PspC.

Moreover, in this disclosure, Applicants demonstrate cross-reactivity between PspC and PspA, as well as regions of PspC and PspA and/or of pspC and pspA which are highly conserved, substantially homologous, highly homologous, and identical. This information allows the skilled artisan to identify nucleic acid molecules which can hybridize, e.g., specifically ("specific hybridization"), to pspC or pspA or both pspC and pspA, e.g, under stringent conditions. The term "specific hybridization" will be understood to mean that the nucleic acid probes of the invention are capable of stable, double-stranded hybridization to bacterially-derived DNA or RNA under conditions of high stringency, as the term "high stringency" would be understood by those with skill in the art (see, for example, Sambrook et al., 1989, Molecular Cloning: A Laboratory Manual, Cold Spring Harbor Laboratory Press, Cold Spring Harbor, N.Y. and Hames and Higgins, eds., 1985, Nucleic Acid Hybridization, IRL Press, Oxford, U.K.). Hybridization will be understood to be accomplished using well-established techniques, including but not limited to Southern blot hybridization, Northern blot hybridization, in situ hybridization and, most preferably, Southern hybridization to PCR-amplified DNA fragments. In a preferred alternative, the nucleic acid hybridization probe of the invention may be obtained by use of the polymerase chain reaction (PCR) procedure, using appropriate pairs of PCR oligonucleotide primers as provided herein or from the teachings herein. See U.S. Pat. Nos. 4,683,195 to Mullis et al. and 4,683,202 to Mullis. A probe or primer can be any stretch of at least 8, preferably at least 10, more preferably at least 12, 13, 14, or 15, such as at least 20, e.g., at least 23 or 25, for instance at least 27 or 30 nucleotides in pspC which are unique to pspC, e.g., not also in pspA (when amplification of just pspC is desired) or unique to both pspC and pspA or in both pspC and pspA (when amplification of both is acceptable or desired) or which are in pspC and are least conserved among the pspC/pspA genes. As to PCR or hybridization primers or probes and optimal lengths therefor, reference is also made to Kajimura et al., GATA 7(4):71–79 (1990). The invention will thus be understood to provide oligonucleotides, such as, pairs of oligonucleotides, for use as primers for the in vitro amplification of bacterial DNA samples and fragments thereof, or for use in expressing a portion of bacterial DNA, either in vitro or in vivo. The oligonucleotides preferably specifically hybridize to sequences flanking a nucleic acid to be amplified, wherein the oligonucleotides hybridize to different and opposite strands of the double-stranded DNA target. The oligonucleotides of the invention are preferably derived from the nucleic acid molecules and teachings herein. As used in the practice of this invention, the term "derived from" is intended to encompass the development of such oligonucleotides from the nucleic acid molecules and teachings disclosed herein, from which a multiplicity of alternative and variant oligonucleotides can be prepared.

And, the invention further comprehends vectors or plasmids containing and/or expressing such a nucleic acid molecule, as well as uses of such nucleic acid molecules, e.g., for expression of PspC or an epitopic region thereof or at least an epitope thereof or a polypeptide comprising at least one epitope thereof either in vitro or in vivo, or for amplifying or detecting PspC or *S. pneumoniae* in a sample, for instance by a PCR.

With respect to the herein mentioned nucleic acid molecules and polypeptides, e.g., the aforementioned nucleic acid molecules and polypeptides, the invention further comprehends isolated and/or purified nucleic acid molecules and isolated and/or purified polypeptides having at least about 70%, preferably at least about 75% or about 77% identity or homology ("substantially homologous or identical"), advantageously at least about 80% or about 83%, such as at least about 85% or about 87% homology or identity ("significantly homologous or identical"), for instance at least about 90% or about 93% identity or homology ("highly homologous or identical"), more advantageously at least about 95%, e.g., at least about 97%, about 98%, about 99% or even about 100% identity or homology ("very highly homologous or identical" to "identical"; or from about 84–100% identity considered "highly conserved"). The invention also comprehends that these nucleic acid molecules and polypeptides can be used in the same fashion as the herein or aforementioned nucleic acid molecules and polypeptides.

Nucleotide sequence homology can be determined using the "Align" program of Myers and Miller, ("Optimal Alignments in Linear Space", CABIOS, 4, 11–17, 1988, incorporated herein by reference) and available at NCBI. Alternatively or additionally, the terms "homology" or "identity", for instance, with respect to a nucleotide or amino acid sequence, can indicate a quantitative measure of homology between two sequences. The percent sequence homology can be calculated as $(N_{ref-Ndif})$* $100/N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence similarity of 75% with the sequence AATCAATC ($N_{ref}$=8; $N_{dif}$=2).

Alternatively or additionally, "homology" or "identity" with respect to sequences can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur and Lipman, 1983 PNAS USA 80:726, incorporated herein by reference), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity or homology with DNA sequences, thymidine (T) in the DNA sequence is considered equal to uracil (U) in the RNA sequence.

RNA sequences within the scope of the invention can be derived from DNA sequences, by thymidine (T) in the DNA sequence being considered equal to uracil (U) in RNA sequences.

Additionally or alternatively, amino acid sequence similarity or identity or homology can be determined using the BlastP program (Altschul et al., Nucl. Acids Res. 25: 3389–3402, incorporated herein by reference) and available at NCBI. The following references (each incorporated herein by reference) provide algorithms for comparing the relative identity or homology of amino acid residues of two proteins, and additionally or alternatively with respect to the foregoing, the teachings in these references can be used for determining percent homology or identity: Needleman S B and Wunsch C D, "A general method applicable to the search for similarities in the amino acid sequences of two proteins," J. Mol. Biol. 48:444–453 (1970); Smith TF and Waterman MS, "Comparison of Bio-sequences," Advances in Applied Mathematics 2:482–489 (1981); Smith T F, Waterman M S and Sadler J R, "Statistical characterization of nucleic acid sequence functional domains," Nucl. Acids Res., 11:2205–2220 (1983); Feng D F and Dolittle R F, J. Molec. Evol., 25:351–360 (1987); Higgins D G and Sharp P M, CABIOS, 5, 151–153 (1989); Thompson J D, Higgins D G and Gibson T J, Nucl. Acids Res., 22:4673–480 (1994);

and, Devereux J, Haeberlie P and Smithies 0, Nucl. Acids Res., 12:387–395 (1984).

A polypeptide comprising at least a fragment or epitope of PspC, e.g., an epitopic region of PspC or PspC, can be a fusion protein; for instance, fused to a protein which enhances immnunogenicity, such as a Cholera Toxin, e.g., Cholera Toxin B (CTB).

Similarly, a polypeptide comprising at least a fragment or epitope of PspC, e.g., an epitopic region of PspC or PspC, can be administered with an adjuvant or a vehicle which enhances immunogenicity, such as CTB.

Thus, the invention provides an immunological, immunogenic or vaccine composition comprising at least one PspC and/or a portion thereof (such as at least one epitopic region of at least one PspC and/or at least one polypeptide encoding at least one epitope of at least one PspC), either alone or in further combination with at least one second pneumococcal antigen, such as at least one different PspC and/or a fragment thereof and/or at least one PspA and/or at least one epitopic region of at least one PspA and/or at least one polypeptide comprising at least one epitope of PspA. The epitopic region of PspA can be as in applications cited under "Related Applications", supra, e.g., aa 1 to 115, 1 to 314, 1 to 260, 192 to 260, 192 to 588, 192 to 299, 1–301, 1–314 or 1–370 of PspA. From the teachings herein and in the applications cited under "Related Applications", the skilled artisan can select an epitope of interest, e.g, of PspC and/or PspA.

This invention also provides strain selection of PspCs from strains for vaccine compositions, based upon sequence homology and cross-reactivity, akin to that which Applicants have done with PspA. PspC strains can be classified according to sequence homology in the alpha helical and/or proline rich regions, and assigned to a clade, and subsequently, each clade is assigned to a family. Applicants have thus determined that so far there is at least one PspC family with at least two major clades.

Inventive compositions, such as immunogenic, immunological or vaccine compositions, can comprise at least one PspC (or immunogenic fragment thereof or polypeptide comprising at least one PspC epitope or epitopic region or at least one vector or plasmid expressing such PspC or fragment thereof, or at least one PspC epitope or epitopic region), preferably at least two (2), for instance up to ten (10), from strains from each clade (and/or family), alone, or in further combination with at least one PspA (or immunogenic fragment thereof or polypeptide comprising at least one PspA or at least one epitope or epitopic region of PspA or at least one vector or plasmid expressing such PspA or fragment thereof, or at least one PspA epitope or epitopic region, which vector or plasmid can be the same as the aforementioned vector or plasmid) or preferably at least two (2), for instance up to ten (10), from strains from each PspA clade (and/or family), for a broadly efficacious pneumococcal vaccine with a limited number of strains.

Immunogenic, immunological or vaccine compositions of the invention can be administered in the same ways as PspA immunogenic, immunological or vaccine compositions, e.g., by injection, mucosally, orally, nasally, and the like, and/or by way of in vivo expression thereof by a plasmid or vector, as well as in same or similar regimens (e.g., such as by prime boost) (see applications cited under Related Applications, as well as documents cited herein). (Thus, there can be PspA, an epitopic region of PspA, a polypeptide comprising an epitope within an epitopic region of PspA, an immunogenic, immunological or vaccine composition comprising at least one PspA and/or at least one fragment or portion thereof, e.g., an epitopic region thereof or a polypeptide comprising at least one epitope from PspA and/or a vector or plasmid expressing a nucleic acid molecule encoding PspA or a fragment or portion thereof, administration of PspA or such a polypeptide or such a composition by injection, mucosally, nasally, orally, and the like and/or as part of a prime-boost regimen with another antigen which can also be PspA.) The amount of PspC in such compositions can be analogous to the amount of PspA in PspA immunogenic, immunological or vaccine compositions (see applications cited under Related Applications). (Accordingly, there can be PspC, an epitopic region of PspC, a polypeptide comprising an epitope within an epitopic region of PspC, an immunogenic, immunological or vaccine composition comprising at least one PspC and/or at least one fragment or portion thereof, e.g., an epitopic region thereof or a polypeptide comprising at least one epitope from PspC and/or a vector or plasmid expressing a nucleic acid molecule encoding PspC or a fragment or portion thereof, administration of PspC or such a polypeptide or such a composition by injection, mucosally, nasally, orally, and the like and/or as part of a prime-boost regimen with another antigen which can also be PspC.)

Such compositions are useful in eliciting an immune response in an animal or a host, such as a protective immune response; or, for generating antibodies, which can be subsequently used in kits, tests or assays for detecting the presence of PspC and/or PspA and PspC and/or *S. pneumoniae.*

These and other embodiments are disclosed or are obvious from and encompassed by, the following Detailed Description.

BRIEF DESCRIPTION OF FIGURES

The following Detailed Description, given by way of example, and not intended to limit the invention to specific embodiments described, may be understood in conjunction with the accompanying Figures, incorporated herein by reference, in which:

FIGS. 3A to 3B show the coiled-coil motif of the alpha-helix of PspC (amino acids that are not in the coiled-coil motif are in the right column; this is the output from the Matcher program) (SEQ ID NO: 14);

FIGS. 5A to 5B show PspC and PspA consensus of the choline binding region (SEQ ID NOs: 15–52);

FIGS. 8A to 8E show amino acid and DNA sequences for SpsA and spsA from Genbank (SEQ ID NOs: 53 and 54) (accession CAA05158; AJ002054.1; AJ002054; Hammerschmidt et al. 1997);

FIGS. 9A to 9E show an additional amino acid and DNA sequences for SpsA and spsA from Genbank (SEQ ID NOs: 55 and 56) (accession CAA05159; AJ002055; AJ002055.1; Hammerschmidt et al. 1997);

FIGS. 10A to 10E show amino acid and DNA sequences for CbpA and cbpA from Genbank (SEQ ID NOS: 57 and 58)(accession AAB70838; AF019904; AF019904.1; Rosenow et al. 1997);

FIGS. 11A to 11F show amino acid and DNA sequences for PspC and pspC from Genbank (SEQ ID NOs: 59 and 60)(from EF6796; accession AAD00184; U72655.1; U72655; Brooks-Walter et al.);

FIGS. 13A to 13C show the alignment of PspCs (SEQ ID NOs: 61–67) from this disclosure from the University of Alabama, analogous to the alignment shown in FIG. 2;

FIGS. 15A to 15C show the amino acid and DNA sequences (SEQ ID NOs: 68 to 69) of the divergent PspC (PspC from *S. pneumoniae* strain V26);

FIGS. 16A to 16B show the sequence of PspC from strain E134 (SEQ ID NO: 70).

FIGS. 17A to 17B show the DNA sequence of PspC from strain D39 (SEQ ID NO: 71).

FIGS. 18A to 18B show the DNA sequence of PspC from strain BG9163 (SEQ ID NO: 72).

FIG. 19 shows the DNA sequence of PspC from strain BG8090 (SEQ ID NO: 73).

FIG. 20 shows the DNA sequence of PspC from strain L81905 (SEQ ID NO: 74).

FIG. 21 shows the DNA sequence of PspC from strain DBL6a (SEQ ID NO: 75).

DETAILED DESCRIPTION

Figure 1:
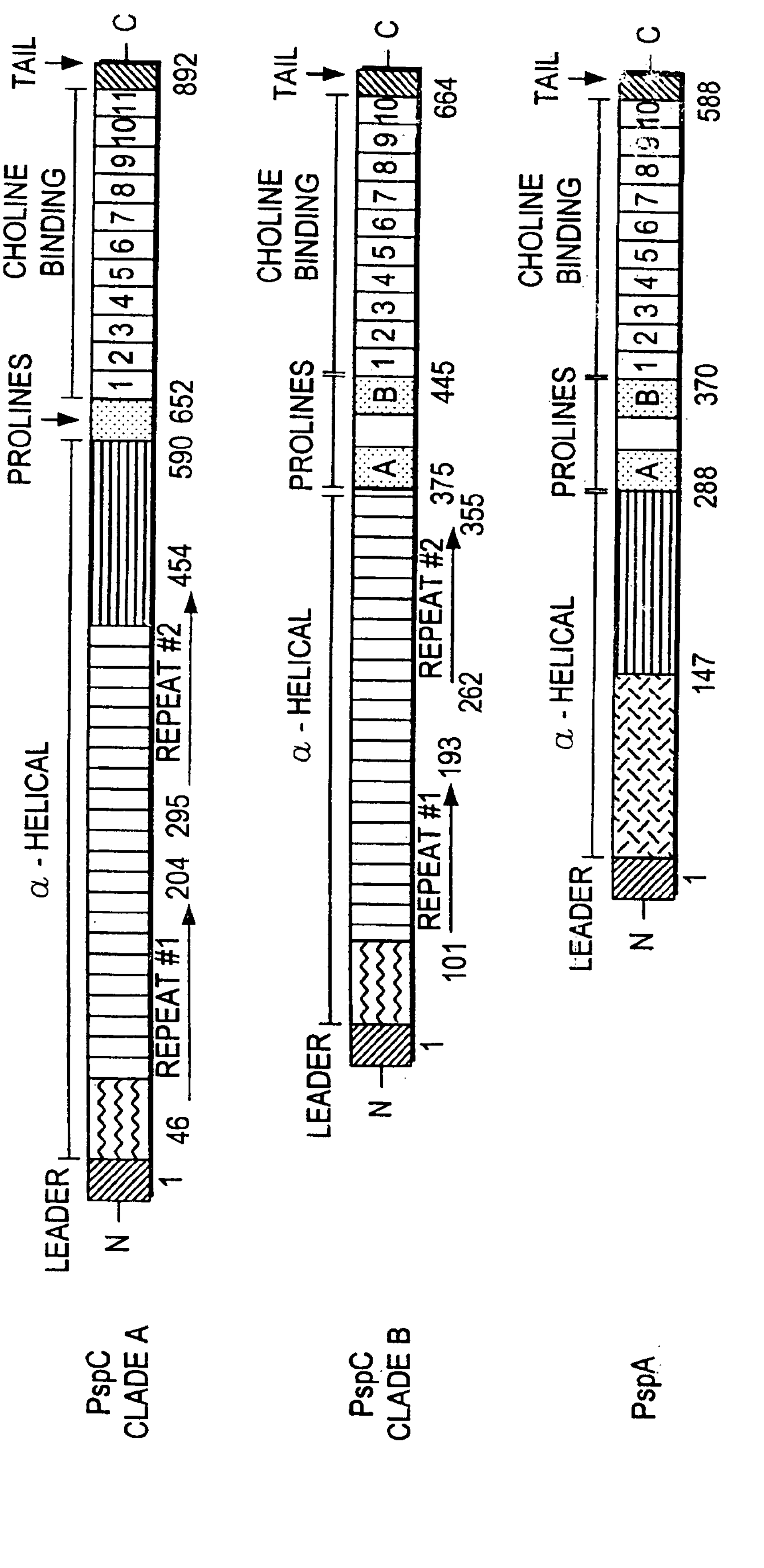
FIG. 1 shows a schematic representation of the PspC clade A and clade B and PspA polypeptides in comparison with each other (long arrows represent direct repeats found within the alpha helix; the hypervariable region is indicated by zig-zag lines; and the region of homology of pspC with pspA found within the alpha helix is indicated by horizontal lines)
Figure 2A:
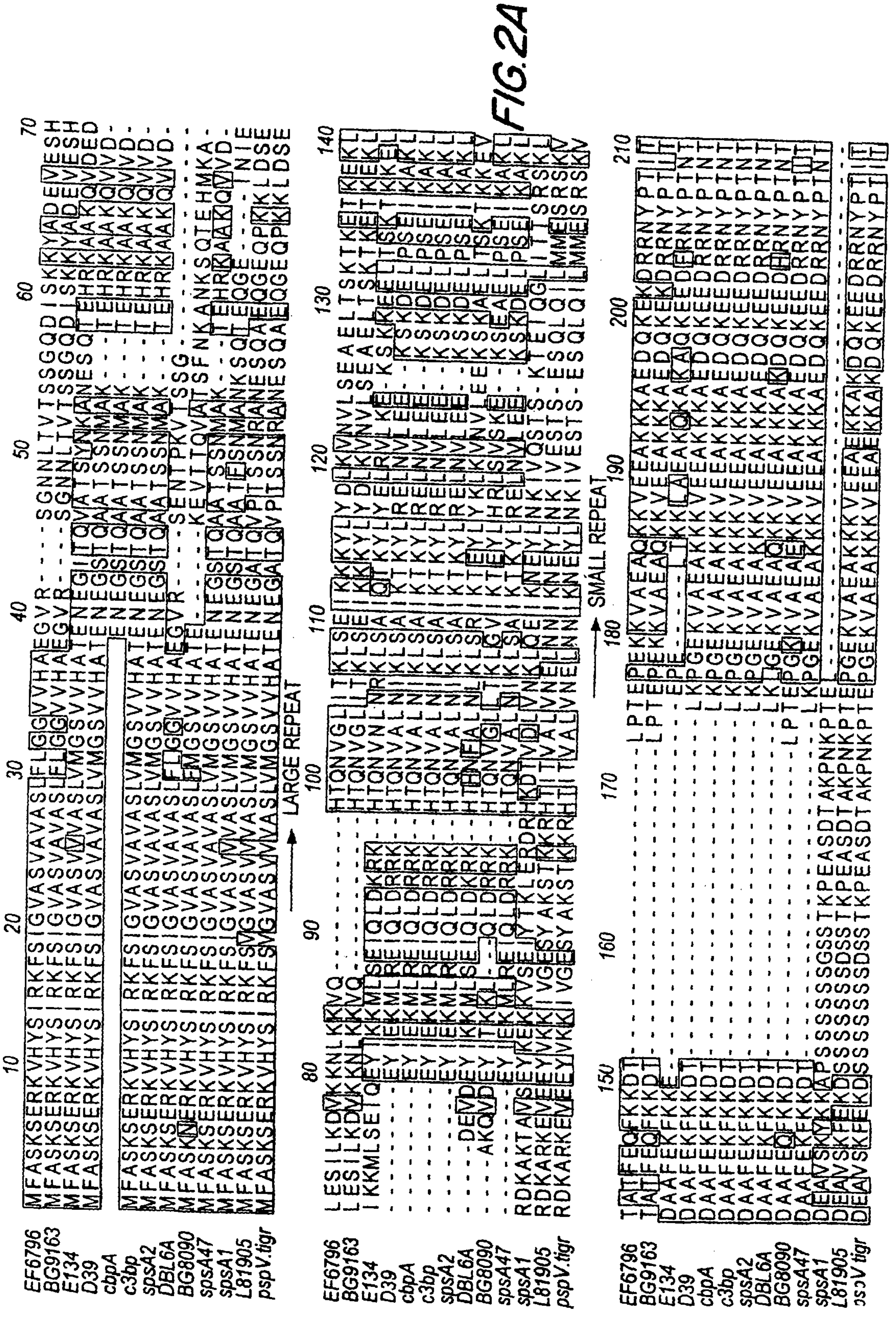
FIGS. 2A to 2D show the alignment of PspCs (SEQ ID NOs: 1 to 13) (the amino acid sequences which include the o helical region and the proline-rich region of PspC were aligned using MacVector 6.0; the direct repeats within the α helix, the non-coiled-coil block, and the proline-rich region are indicated with arrows; conserved regions are shaded, and gaps are shown with a dash (-); taxons are named for the strain from which the gene was cloned with the exception of Genbank entrees: SpsA1 (Y10818) from strain ATCC33400 (serotype 1), SpsA2 (AJ002054) from strain ATCC1 1733 (serotype 2), SpsA47 (AJ002055) from strain NCTC10319 (serotype 47), CbpA (AF019904) from strain LM91 (serotype 2), C3bp (AF067128), and tigr from a serotype 4 clinical isolate; the capsular serotypes of the other strains are as follows: EF6796 (6A), BG8090 (19), L81905 (4), DBL6A (6A), BG9163 (6B), D39 (2) and E134 (23))
Figure 2B:
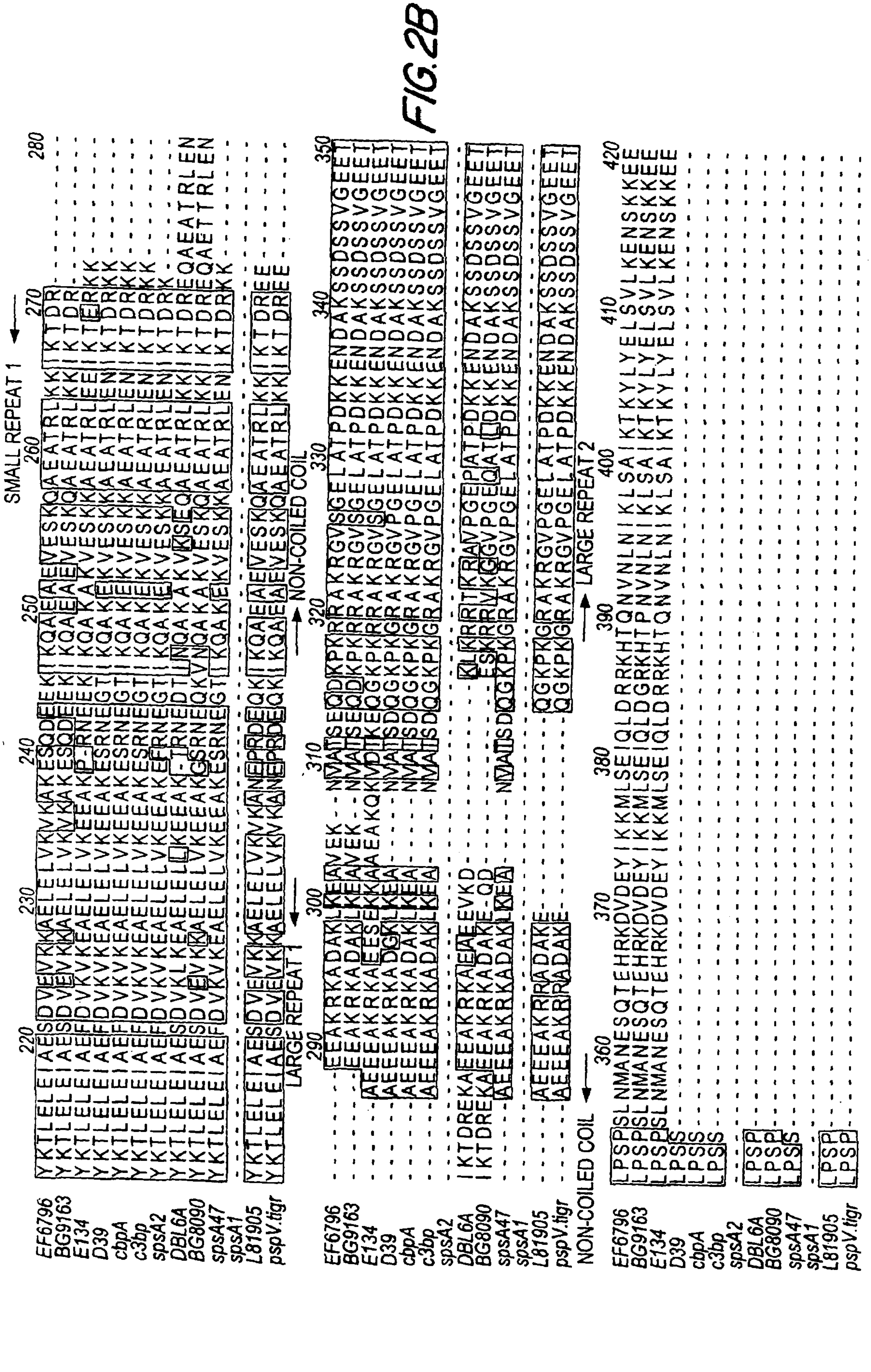
Figure 2C:
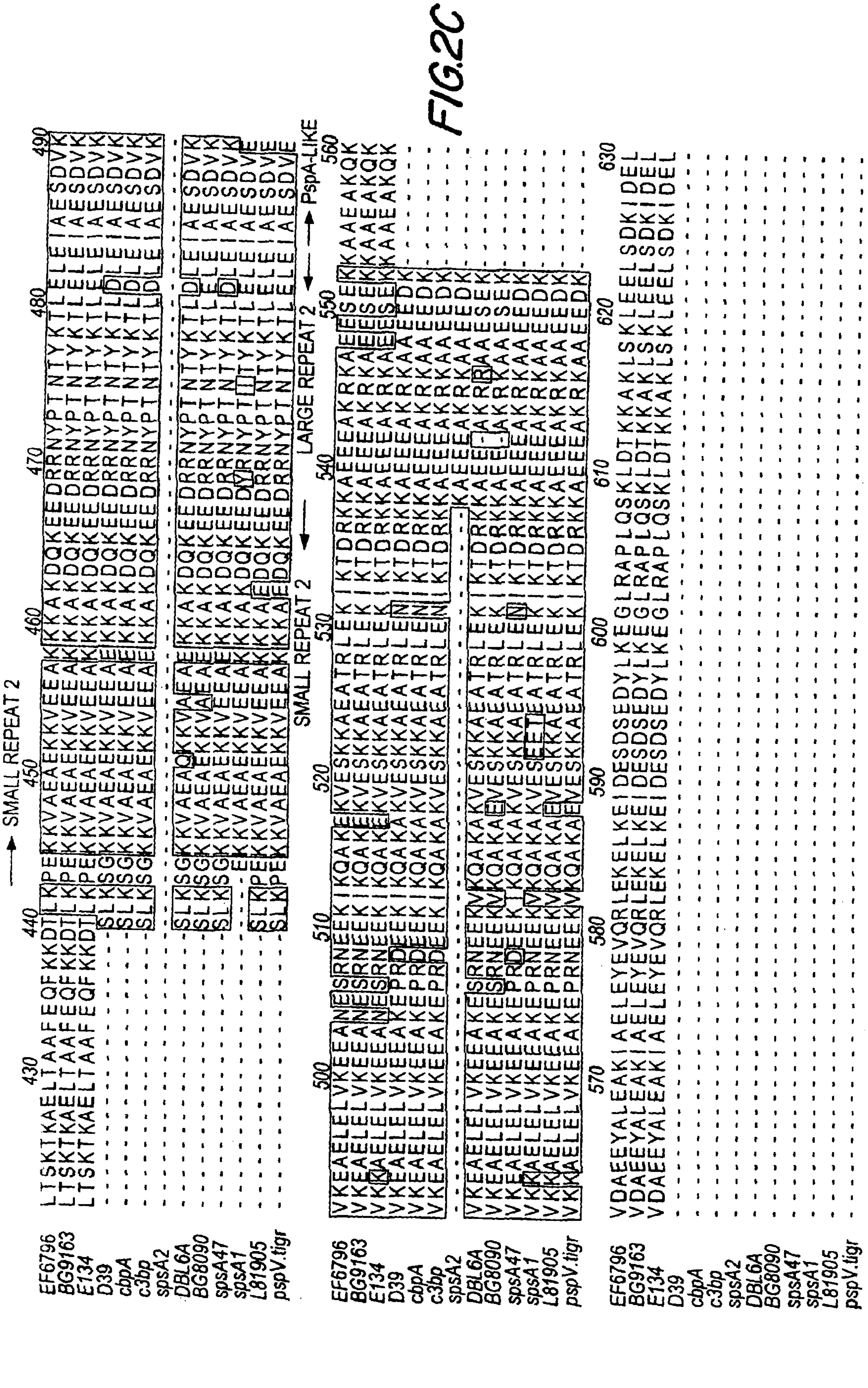
Figure 2D:
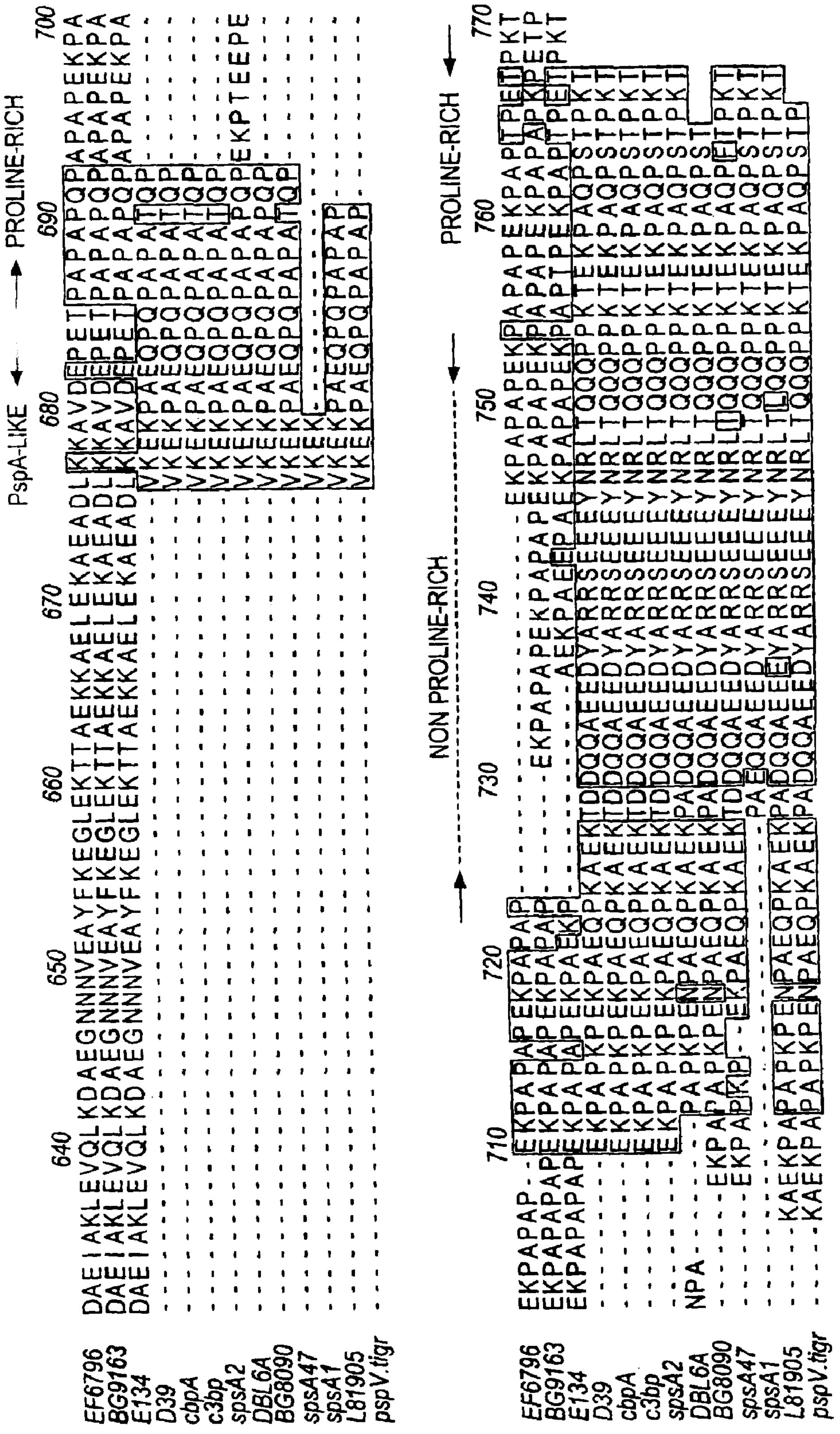

PspC (see FIGS. 1, 2, 3, 4, 5, 11, 12, 13, 14, 15) is one of three designations for a pneumococcal surface protein which is PspA-like, and whose gene is present in approximately 75% of all *S. pneumoniae*. Applicants have cloned and sequenced the pspC gene and have expressed the PspC protein (See, e.g., FIGS. 1, 2, 4, 5, 11, 12, 13, and patent applications cited under the heading Related Applications, supra, as well as to articles or literature cited herein; see also FIGS. 14, 15). Under the designation SpsA (see FIGS. 8, 9), PspC has been shown to bind secretory IgA (Hammerschmidt et al. 1997). Under the designation CbpA (see FIG. 10), PspC has been shown to interact with human epithelial and endothelial cells (Rosenow et al. 1997).

The pspC gene is paralogous to the pspA gene in *S. pneumoniae* and was thus called pspC (Brooks-Walter et al. 1997; see also applications cited in Related Applications, supra).

The present invention provides epitopic regions of PspC, different clades of PspC, DNA encoding epitopic regions of PspC, vectors which express such epitopic regions, immunological, immunogenic or vaccine compositions comprising at least one PspC and/or a portion thereof (such as at least one epitopic region of at least one PspC and/or at least one polypeptide encoding at least one epitope of at least one PspC), either alone or in further combination with at least one second pneumococcal antigen, such as at least one different PspC and/or a fragment thereof and/or at least one PspA and/or at least one epitopic region of at least one PspA and/or at least one polypeptide comprising at least one epitope of PspA.

PspC or a fragment thereof, and thus a composition comprising PspC or a fragment thereof, can be administered by the same routes, and in approximately the same amounts, as PspA. Thus, the invention further provides methods for administering PspC or a fragment thereof or a polypeptide comprising at least one epitope of PspC, as well as uses of PspC or a fragment thereof to formulate such compositions.

Furthermore, in this disclosure, pspC genes from seven different clinical *S. pneumoniae* strains were cloned and sequenced. Examination of the sequences of twelve alleles reveals that this gene exists in diverse forms among Pneumococci and has a mosaic structure in which sequence modules encoding protein domains have contributed to the pattern of variation during gene evolution.

Two major clades exist: clade A alleles are larger and contain an extra module that is shared by many pspA genes; clade B alleles are smaller and lack this pspA-like domain. All genes in both lade A and clade B maintain a proline-rich domain and a choline-binding repeat domain that are indistinguishable from similar domains in the pspA gene at the nucleotide and protein level.

Thus, this invention also relates to strain selection of PspCs from strains for vaccine compositions, based upon sequence homology and cross-reactivity, akin to that which Applicants have done with PspA. PspC strains can be classified according to sequence homology in the alpha helical and/or proline rich regions, and assigned to a clade, and subsequently, each clade is assigned to a family. Applicants have thus determined that so far there is one PspC family with at least two major clades.

Figure 14:
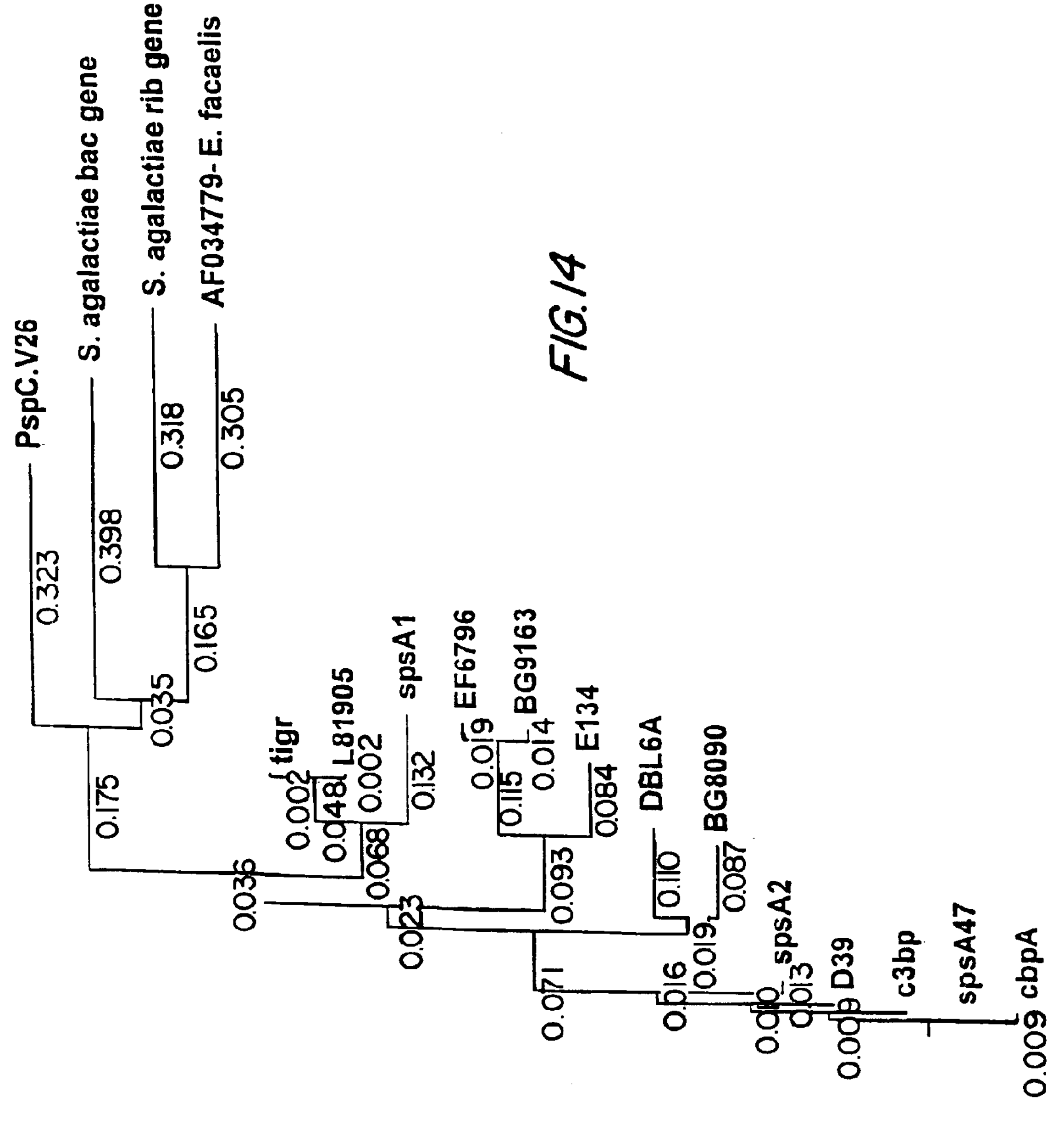
FIG. 14 shows a dendrogram showing the distance of a divergent PspC (from other PspCs), indicating that it likely belongs to a second family (Dendrogram of the PspC/SpsA/Cbpa from Genbank and nearest relative genes from other species; PspC proteins were truncated after the proline-rich region—see FIG. 1—before being aligned using the ClustalW algorithm and the Blosum3O amino acid scoring matrix in MacVector; the dendrogram is the guide tree used in alignment by MacVector; small numbers on the tree indicate distances along the branch lengths as calculated during the ClustalW alignment; sequences of two proteins from *Streptococcus agalactiae* bac and rib, and one from *Enterococcus facaelis* are included for comparison; the PspC.V26 is a highly divergent PspC protein from *S. pneumoniae* strain V26)

There is, however, a single PspC (PspC.V26, from *S. pneumoniae* strain V26, a capsular-type 14 *S. pneumoniae* strain) that appears to be a member of a second family because it seems only distantly related to members of the first major PspC family. FIG. 14 provides a dendrogram showing the distance of this divergent PspC from the other PspCs. FIG. 15 provides the amino acid and DNA sequences of the divergent PspC.

Inventive compositions, such as immunogenic, immunological or vaccine compositions, can comprise at least one PspC (or immunogenic fragment thereof or polypeptide comprising at least one PspC epitope or epitopic region or at least one vector or plasmid expressing such PspC or fragment thereof, or at least one PspC epitope or epitopic region), preferably at least two (2), for instance up to ten ( 10), from strains from each clade, alone, or in further combination with at least one PspA (or immunogenic fragment thereof or polypeptide comprising at least one PspA or at least one epitope or epitopic region of PspA or at least one vector or plasmid expressing such PspA or fragment thereof, or at least one PspA epitope or epitopic region, which vector or plasmid can be the same as the aforementioned vector or plasmid) or preferably at least two (2), for instance up to ten (10), from strains from each PspA lade, for a broadly efficacious pneumococcal vaccine with a limited number of strains.

Accordingly, in an aspect, the invention provides an immunogenic, immunological or vaccine composition containing an epitope of interest from at least one PspC and/or PspA, and a pharmaceutically acceptable carrier or diluent. An immunological composition elicits an immunological response—local or systemic. The response can, but need not be, protective. An immunogenic composition likewise elicits a local or systemic immunological response which can, but need not be, protective. A vaccine composition elicits a local or systemic protective response. Accordingly, the terms “immunological composition” and “immunogenic composition” include a “vaccine composition” (as the two former terms can be protective compositions).

The invention therefore also provides a method of inducing an immunological response in a host mammal comprising administering to the host an immunogenic, immunological or vaccine composition. From the disclosure herein and the documents cited herein, including the applications cited under “Related Applications”, the skilled artisan can obtain an epitope of interest of PspC and/or PspA, without undue experimentation.

Further, the invention demonstrates that more than one serologically complementary PspC molecule can be in an antigenic, immunological or vaccine composition, so as to elicit better response, e.g., protection, for instance, against a variety of strains of Pneumococci; and, the invention provides a system of selecting PspCs for a multivalent composition which includes cross-protection evaluation so as to provide a maximally efficacious composition.

The determination of the amount of antigen, e.g., PspC or truncated portion thereof or a polypeptide comprising an epitope or epitopic region of PspC, and optional adjuvant in the inventive compositions and the preparation of those compositions can be in accordance with standard techniques well known to those skilled in the pharmaceutical or veterinary arts.

In particular, the amount of antigen and adjuvant in the inventive compositions and the dosages administered are determined by techniques well known to those skilled in the medical or veterinary arts taking into consideration such factors as the particular antigen, the adjuvant (if present), the age, sex, weight, species and condition of the particular patient, and the route of administration.

For instance, dosages of particular PspC antigens for suitable hosts in which an immunological response is desired, can be readily ascertained by those skilled in the art from this disclosure, as is the amount of any adjuvant typically administered therewith. Thus, the skilled artisan can readily determine the amount of antigen and optional adjuvant in compositions to be administered in methods of the invention. Typically, an adjuvant is commonly used as 0.001 to 50 wt % solution in phosphate buffered saline, and the antigen is present on the order of micrograms to milligrams, such as about 0.0001 to about 5 wt %, preferably about 0.0001 to about 1 wt %, most preferably about 0.0001 to about 0.05 wt % (see, e.g., Examples below or in applications cited herein). Typically, however, the antigen is present in an amount on the order of micrograms to milligrams, or, about 0.001 to about 20 wt %, preferably about 0.01 to about 10 wt %, and most preferably about 0.05 to about 5 wt %.

Of course, for any composition to be administered to an animal or human, including the components thereof, and for any particular method of administration, it is preferred to determine therefor: toxicity, such as by determining the lethal dose (LD) and $LD_{50}$ in a suitable animal model, e.g., rodent such as mouse; and, the dosage of the composition(s), concentration of components therein and timing of administering the composition(s), which elicit a suitable immunological response, such as by titrations of sera and analysis thereof for antibodies or antigens, e.g., by ELISA and/or RFFIT analysis. Such determinations do not require undue experimentation from the knowledge of the skilled artisan, this disclosure and the documents cited herein. And, the time for sequential administrations can be ascertained without undue experimentation.

Examples of compositions of the invention include liquid preparations for orifice, e.g., oral, nasal, anal, vaginal, peroral, intragastric, mucosal (e.g., perlingual, alveolar, gingival, olfactory or respiratory mucosa) etc., administration, such as suspensions, syrups or elixirs; and, preparations for parenteral, subcutaneous, intradermal, intramuscular or intravenous administration (e.g., injectable administration), such as sterile suspensions or emulsions. Such compositions may be in admixture with a suitable carrier, diluent, or excipient, such as sterile water, physiological saline, glucose or the like. The compositions can also be lyophilized. The compositions can contain auxiliary substances, such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Compositions of the invention, are conveniently provided as liquid preparations, e.g., isotonic aqueous solutions, suspensions, emulsions or viscous compositions which may be buffered to a selected pH. If digestive tract absorption is preferred, compositions of the invention can be in the "solid" form of pills, tablets, capsules, caplets and the like, including "solid" preparations that are time-released or that have a liquid filling, e.g., gelatin covered liquid, whereby the gelatin is dissolved in the stomach for delivery to the gut. If nasal or respiratory (mucosal) administration is desired, compositions may be in a form and dispensed by a squeeze spray dispenser, pump dispenser or aerosol dispenser. Aerosols are usually under pressure by means of a hydrocarbon. Pump dispensers can preferably dispense a metered dose or, a dose having a particular particle size.

Compositions of the invention can contain pharmaceutically acceptable flavors and/or colors for rendering them more appealing, especially if they are administered orally. The viscous compositions may be in the form of gels, lotions, ointments, creams and the like and will typically contain a sufficient amount of a thickening agent so that the viscosity is from about 2500 to 6500 cps, although more viscous compositions, even up to 10,000 cps, may be employed. Viscous compositions have a viscosity preferably of 2500 to 5000 cps, since above that range they become more difficult to administer. However, above that range, the compositions can approach solid or gelatin forms which are then easily administered as a swallowed pill for oral ingestion.

Liquid preparations are normally easier to prepare than gels, other viscous compositions, and solid compositions. Additionally, liquid compositions are somewhat more convenient to administer, especially by injection or orally, to animals, children, particularly small children, and others who may have difficulty swallowing a pill, tablet, capsule or the like, or in multi-dose situations. Viscous compositions, on the other hand, can be formulated within the appropriate viscosity range to provide longer contact periods with mucosa, such as the lining of the stomach or nasal mucosa Obviously, the choice of suitable carriers and other additives will depend on the exact route of administration and the nature of the particular dosage form, e.g., liquid dosage form (e.g., whether the composition is to be formulated into a solution, a suspension, gel or another liquid form), or solid dosage form (e.g., whether the composition is to be formulated into a pill, tablet, capsule, caplet, time release form or liquid-filled form).

Solutions, suspensions and gels, normally contain a major amount of water (preferably purified water) in addition to the antigen, lipoprotein and optional adjuvant. Minor amounts of other ingredients, such as pH adjusters (e.g., a base such as NaOH), emulsifiers or dispersing agents, buffering agents, preservatives, wetting agents, jelling agents (e.g., methylcellulose), colors and/or flavors may also be present. The compositions can be isotonic, i.e., it can have the same osmotic pressure as blood and lacrimal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions may be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount that will achieve the selected viscosity. Viscous compositions are normally prepared from solutions by the addition of such thickening agents.

A pharmaceutically acceptable preservative can be employed to increase the shelf-life of the compositions. Benzyl alcohol may be suitable, although a variety of preservatives, including, for example, parabens, thimerosal, chlorobutanol, or benzalkonium chloride, may also be employed. A suitable concentration of the preservative will be from 0.02% to 2% based on the total weight although there may be appreciable variation depending upon the agent selected.

Those skilled in the art will recognize that the components of the compositions must be selected to be chemically inert with respect to the PspC antigen and optional adjuvant. This will present no problem to those skilled in chemical and pharmaceutical principles, or problems can be readily avoided by reference to standard texts or by simple experiments (not involving undue experimentation), from this disclosure and the documents cited herein.

The immunologically effective compositions of this invention are prepared by mixing the ingredients following generally accepted procedures. For example the selected components may be simply mixed in a blender, or other standard device to produce a concentrated mixture which may then be adjusted to the final concentration and viscosity by the addition of water or thickening agent and possibly a buffer to control pH or an additional solute to control tonicity. Generally the pH may be from about 3 to 7.5. Compositions can be administered in dosages and by techniques well known to those skilled in the medical and veterinary arts taking into consideration such factors as the age, sex, weight, and condition of the particular patient or animal, and the composition form used for administration (e.g., solid vs. liquid). Dosages for humans or other mammals can be determined without undue experimentation by the skilled artisan, from this disclosure, the documents cited herein, and the Examples below (e.g., from the Examples involving mice and from the applications cited herein, e.g., under "Related Applications", especially since PspC can be administered in a manner and dose analogous to PspA).

Suitable regimes for initial administration and booster doses or for sequential administrations also are variable, may include an initial administration followed by subsequent administrations; but nonetheless, may be ascertained by the skilled artisan, from this disclosure, the documents cited herein, including applications cited herein, and the Examples below. The compositions can be administered alone, or can be co-administered or sequentially administered with other compositions of the invention or with other prophylactic or therapeutic compositions. Given that PspC is PspA-like, the skilled artisan can readily adjust concentrations of PspA in compositions comprising PspA or a portion thereof to take into account the presence of PspC or a portion thereof in accordance with the herein teachings of compositions comprising at least one PspC or portion thereof and optionally at least one PspA or a portion thereof.

The PspC antigen (PspC or a portion thereof), as well as a PspA antigen (PspA or a portion thereof) can be expressed recombinantly, e.g., in *E. coli* or in another vector or plasmid for either in vivo expression or in vitro expression. The methods for making and/or administering a vector or recombinant or plasmid for expression of PspC or a portion thereof either in vivo or in vitro can be any desired method, e.g., a method which is by or analogous to the methods disclosed in: U.S. Pat. Nos. 4,603,112; 4,769,330; 5,174,993; 5,505,941; 5,338,683; 5,494,807; 4,722,848; WO 94/16716; WO 96/39491; Paoletti, Proc. Natl. Acad. Sci., USA 93:11349–11353, 1996: Moss, Proc. Natl. Acad. Sci., USA 93:11341–11348, 1996: Smith et al., U.S. Pat. No. 4,745,051 (recombinant baculovirus); Richardson, C. D. (Editor), Methods in Molecular Biology 39, "Baculovirus Expression Protocols" (1995 Humana Press Inc.); Smith et al., Molecular and Cellular Biology, 1983, Vol.3, No. 12, p. 2156–2165; Pennock et al., Molecular and Cellular Biology 1984, Vol. 4, No.3, p. 399–406; EPA 0 370 573; U.S. application Ser. No. 920,197, filed Oct. 16, 1986; EP Patent publication No. 265785; U.S. Pat. No. 4,769,331 (recombinant herpesvirus); Roizman, Proc. Natl. Acad. Sci. USA 93:11307–11312, 1996; Andreansky et al., Proc. Natl. Acad. Sci. USA 93:11313–11318, 1996; Robertson et al., Proc. Natl. Acad. Sci. USA 93:11334–11340, 1996; Frolov et al., Proc. Natl. Acad. Sci. USA 93:11371–11377, 1996; Kitson et al., J. Virol. 65, 3068–3075, 1991; U.S. Pat. Nos. 5,591,439 and 5,552,143 (recombinant adenovirus); Grunhaus et al., 1992, Seminars in Virology (Vol.3) p. 237–52, 1993; Ballay et al. EMBO Journal, vol. 4, p. 3861–65; Graham, Tibtech 8, 85–87, 1990; Prevec et al., J. Gen. Virol. 70, 429–434; PCT WO91/11525, Felgner et al. (1994), J. Biol. Chem. 269, 2550–2561; Science, 259:1745–49, 1993; McClements et al., Proc. Natl. Acad. Sci. USA 93:1141–411420, 1996; and U.S. Pat. Nos. 5,591,639; 5,589,466; and 5,580,859 relating to DNA expression vectors, inter alia. See also WO 98/33510; Ju et al., Diabetologia, 41:736–739, 1998 (lentiviral expression system); Sanford et al., U.S. Pat. No. 4,945,050 (method for transporting substances into living cells and tissues and apparatus therefor); Fischbach et al. (Intracel), WO 90/01543 (method for the genetic expression of heterologous proteins by cells transfected); Robinson et al., [s]Seminars in IMMUNOLOGY, vol. 9, pp. 271–283 (1997) (DNA vaccines); Szoka et al., U.S. Pat. No. 4,394,448 (method of inserting DNA into living cells); and McCormick et al., U.S. Pat. No. 5,677,178 (use of cytopathic viruses for therapy and prophylaxis of neoplasia).

The expression product generated by vectors or recombinants in this invention optionally can also be isolated and/or purified from infected or transfected cells; for instance, to prepare compositions for administration to patients. However, in certain instances, it may be advantageous to not isolate and/or purify an expression product from a cell; for instance, when the cell or portions thereof enhance the effect of the polypeptide.

An inventive vector or recombinant expressing PspC or a portion thereof and/or PspA or a portion thereof can be administered in any suitable amount to achieve expression at a suitable dosage level, e.g., a dosage level analogous to the aforementioned dosage levels (wherein the antigen or epitope of interest is directly present). The inventive vector or recombinant can be administered to a patient or infected or transfected into cells in an amount of about at least $10^3$ pfu; more preferably about $10^4$ pfu to about $10^{10}$ pfu, e.g., about $10^5$ pfu to about $10^9$ pfu, for instance about $10^6$ pfu to about $10^8$ pfu. In plasmid compositions, the dosage should be a sufficient amount of plasmid to elicit a response analogous to compositions wherein PspC or a portion thereof and/or PspA or a portion thereof are directly present; or to have expression analogous to dosages in such compositions; or to have expression analogous to expression obtained in vivo by recombinant compositions. For instance, suitable quantities of plasmid DNA in plasmid compositions can be 1 μg to 100 mg, preferably 0.1 to 10 mg, e.g., 500 micrograms, but lower levels such as 0.1 to 2 mg or preferably 1–10 μg may be employed. Documents cited herein regarding DNA plasmid vectors may be consulted for the skilled artisan to ascertain other suitable dosages for DNA plasmid vector compositions of the invention, without undue experimentation.

Returning to our discussion of the examples and results presented herein, a rabbit polyclonal serum to PspC was made by immunization with a recombinant truncated clade B allele. The serum reacted with both PspC and PspA from fifteen (15) pneumococcal isolates indicating that PspC and PspA share extensive cross-reactive epitopes. The cross-reactive antibodies appeared to cause cross-protection in a mouse model system. Mice immunized with recombinant clade B PspC were protected against challenge with a strain that expressed PspA but not PspC. In this experiment, the PspA-PspC cross-reactive antibodies were directed to the proline-rich domain present in both molecules.

More in particular, *S. pneumonae* possess a family of proteins that bind phosphocholine (Brooks-Walter et al. 1997; Garcia et al. 1986; McDaniel et al. 1992) present in the teichoic acid and the lipoteichoic acid of the cell membrane and the cell wall (Tomasz 1967). The choline-binding proteins of *Pneumococci* and other Gram-positive organisms all contain structurally similar choline-binding domains, which are composed of multiple tandem amino acid repeats (Breise et al. 1985). Autolysin, PspA (pneumococcal surface protein A), and PcpA (pneumococcal choline-binding protein A) of *S. pneumoniae*, toxins A and B of *Clostridium difficile*, glucosyltransferases from *Streptococcus downei* and *Streptococcus mutans*, CspA of *Clostridium acetobiltylicum*, and PspA of *Clostridium perfringens* all contain similar regions (Sanchez-Beato et al. 1995; Banas et al. 1990; Barroso et al. 1990; Dove et al. 1990; Garcia et al. 1986; Sanchez-Beato et al. 1998).

In PspA from *S. pneumoniae*, these choline-binding repeats are responsible for the attachment of PspA to the surface of the pneumococcus (Yother et al. 1994). PspA molecules interfere with complement activation (Briles et al. 1997), slow clearance of Pneumococci from the blood of infected mice (McDaniel et al. 1987), and elicit protection against pneumococcal sepsis and nasal carriage (McDaniel et al. 1991; Wu et al. 1997). A single non-pspA locus has been identified which has greater similarity to the choline-binding and proline rich regions of pspA than any of the other choline-binding genes (McDaniel et al. 1992). Applicants have designated the molecule PspC because of its strong molecular and serologic similarities to PspA (Brooks-Walter et al. 1997; see also applications cited under Related Applications, supra, note that in those applications initially PspC was called “PspA-like”, and pspC was considered pspA-like).

Figure 9B:
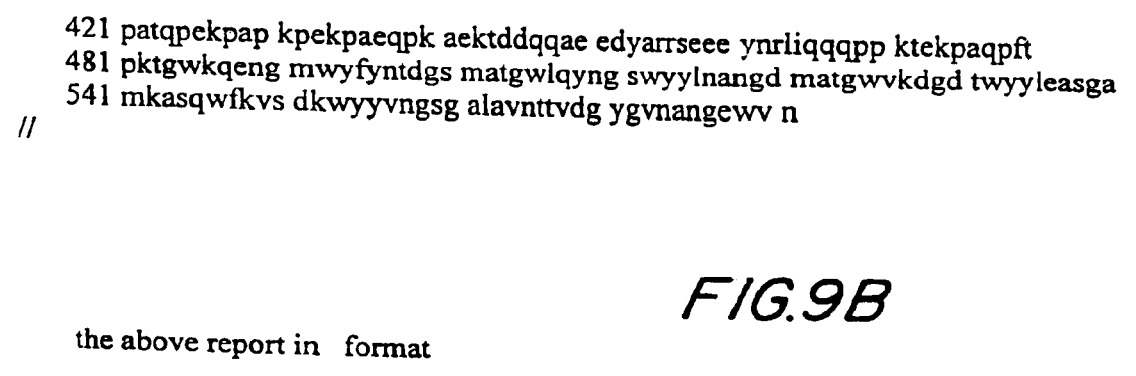

Other PspA-like proteins and pspA-like loci, which could be the same as PspC and pspC, have also been characterized and sequenced (SpsA, which reportedly binds secretory IgA, Hammerschmidt et al. 1997; choline-binding protein (for binding a moiety on eukaryotic surfaces), CbpA, Rosenow et. al. 1997; see, e.g., FIGS. 8, 9, 10). Immunization with a crude extract of pooled non-PspA choline-binding proteins containing CbpA elicited protection to a lethal challenge of Pneumococci introduced intraperitoneally into mice (Rosenow et al. 1997).

In the present studies, Applicants have demonstrated that immunization with purified PspC is able to elicit protection against sepsis, and this protection is apparently mediated by antibodies cross-reactive with PspA. Applicants have also examined the genetic diversity present within this genetic locus, herein called pspC, by the examination of 12 sequenced alleles. These include the previously sequenced alleles of cbpA and spsA, an allele from the genomic sequencing project, and seven newly sequenced pspC genes presented here for the first time.

The sequences of cbpA and spsA both included sequences of D39 or its derivatives. Rosenow et al. sequenced cbpA from LM91 a pspA-mutant of D39 (Rosenow et al. 1997); and Hammerschmidt et al. sequenced spsA from an encapsulated derivative of R36A (ATCC11733) (Hammerschmidt et al. 1997; see also FIGS. 8, 9, 10). From a comparison of these two sequences, it was apparent that spsA sequence contained a 480 bp deletion within the gene. Because of this discrepancy, Applicants also reported a sequence of pspC from a cloned HindIII-EcoRI chromosomal fragment of D39 that was determined prior to the cbpA and spsA sequence (Brooks-Walter et al. 1997; see also applications cited under Related Applications, supra). This sequence matched exactly that of cbpA. Other sequences that were used for sequence alignment comparisons included two spsA sequences from capsular serotype 1 and 47 strains (Hammerschmidt et al. 1997), and the pspC/cbpA/spsA sequence from the capsular serotype 4 strain sequenced in the TIGR genome project.

The invention shall be further described by way of the following Examples and Results, provided for illustration and not to be considered a limitation of the invention.

EXAMPLES AND RESULTS

Materials and Methods

Bacterial Strains, Plasmids, and Recombinant DNA Techniques

Chromosomal DNA from *S. pneumoniae* EF6796, a serotype 6A clinical isolate (Salser et al. 1993), and D39, a serotype 2 isolate, was isolated using a cesium chloride gradient procedure. The HindIII-EcoRI fragment of EF6796 and D39 was cloned in a modified pZero vector (Invitrogen, San Diego, Calif.) in which the Zeocin-resistance cassette was replaced by a kanamycin cassette, kindly provided by Randall Harris. Recombinant plasmids were electroporated into *E. coli* TOP10F' cells [F'{lac$^q$Tet$^R$} mcrA_(mrr-hsdRMS-mcrBC) f80lacZ_M15_acX74 deoR recAl araD139_(ara-leu)7697 galU galk rpsL end A1 nupG] (Invitrogen). DNA was purified from agarose using Gene Clean (Bio101, Inc., Vista, Calif.).

Chromosomal DNA used for PCR was isolated using a chloroform-isoamyl alcohol procedure. Oligonucleotide primers, ABW13 (5' CGACGAATAGCTGAAGAGG 3') (SEQ ID NO: 76) and SKH2 (5'CATACCGTTTTCTTGTTTCCAGCC 3') (SEQ ID NO: 77), were used to amplify the DNA encoding the alpha-helical region and the proline-rich region of pspC in 100 additional *S. pneumoniae strains*. These primers correspond to nucleotides 215–235 and nucleotides 1810–1834, respectively, of the pspC/EF6796 gene. PCR products from L81905 (serotype 4), BG9163 (serotype 6B), DBL6A (serotype 6A), BG8090 (serotype 19) and E134 (serotype 23) were cloned into pGem (Promega) or Topo TA vector (Invitrogen) which utilize the A overhangs generated by Taq polymerase.

Sequencing and DNA Analysis

Sequencing of pspC was completed using automated DNA sequencing (ABI 377, Applied Biosystems, Inc., Foster City, Calif.). Sequence analyses were performed using the University of Wisconsin Genetics Computer Group (GCG) programs (Devereux et al. 1984), MacVector 6.5 (Oxford Molecular), Sequencer 3.0 (GeneCodes, Inc.), and DNA Strider programs (Salser et al. 1993). Sequence similarities of pspC were determined using the NCBI BLAST. Coil structure predicted by the pspC sequence was analyzed using Matcher (Fischetti et al. 1993). The accession number by Genbank/EMBL for the nucleotide sequences of PspC are as follows: EF6796-U72655, DBL6A-AF068645, D39-AF068646, E134 -AF068647, BG8090-AF068648, L81905-AF068649, BG9163-AF068650, DBL6A-AF068645, D39-AF068646, E134-AF068647, BG8090-AF068648, L81905-AF068649, and BG9163-AF068650; and each of these sequences and GenBank results from the accession numbers are hereby expressly incorporated herein by reference (See also FIGS. 11 and 15–21). Preliminary sequence data was obtained from The Institute for Genomic Research website.

Deposit

*E. coli* containing a cloned PspC gene from Streptococcus pneumoniae strain EF6796 was deposited on Jul. 24, 2001 with the American Type Culture Collection (ATCC), University Boulevard, Manassas, Va. 20110–2209, USA, under accession number ATCC No. PTA-3526.

Example/Result 1

Figure 13B:
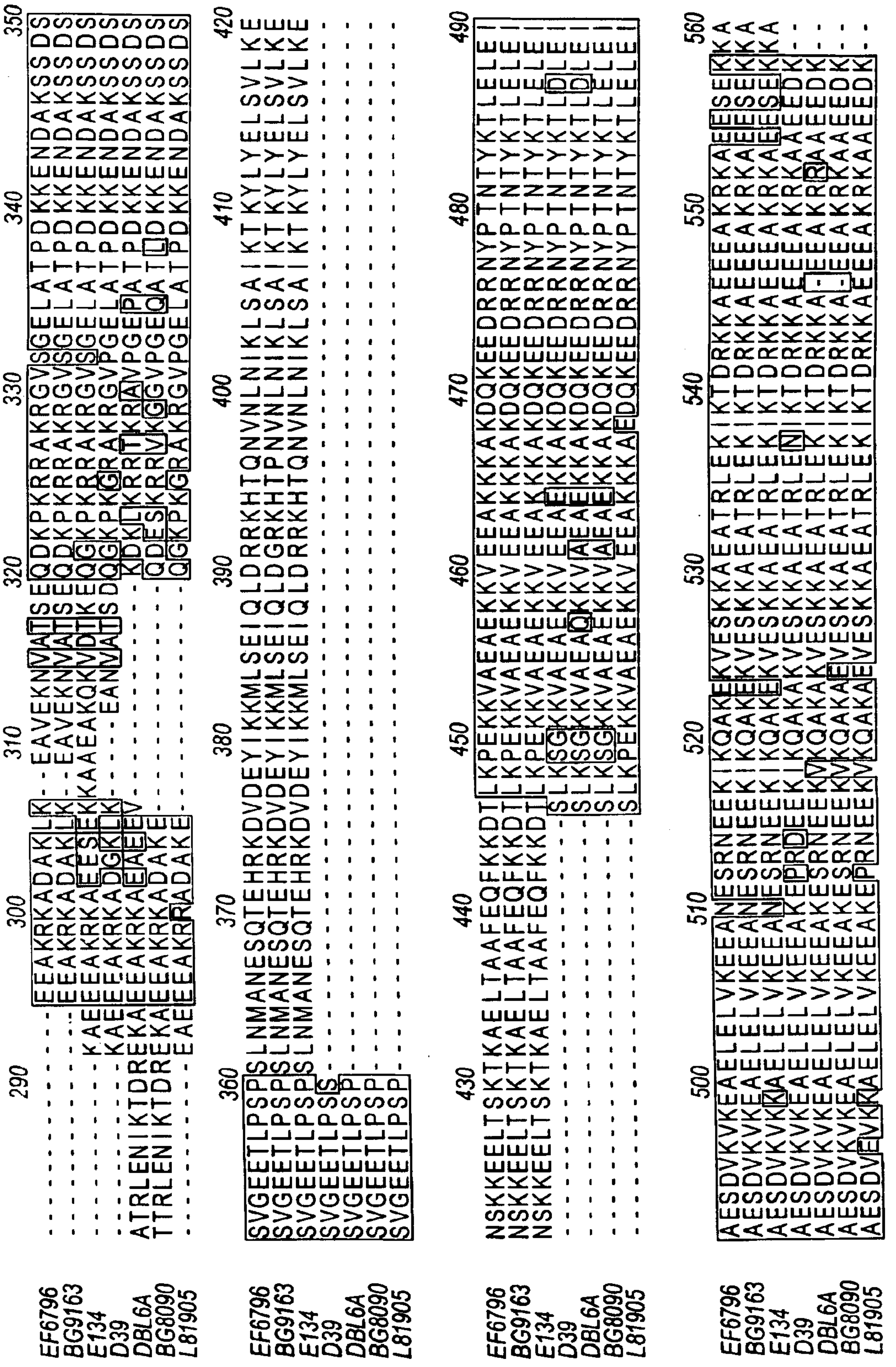
Figure 13C:
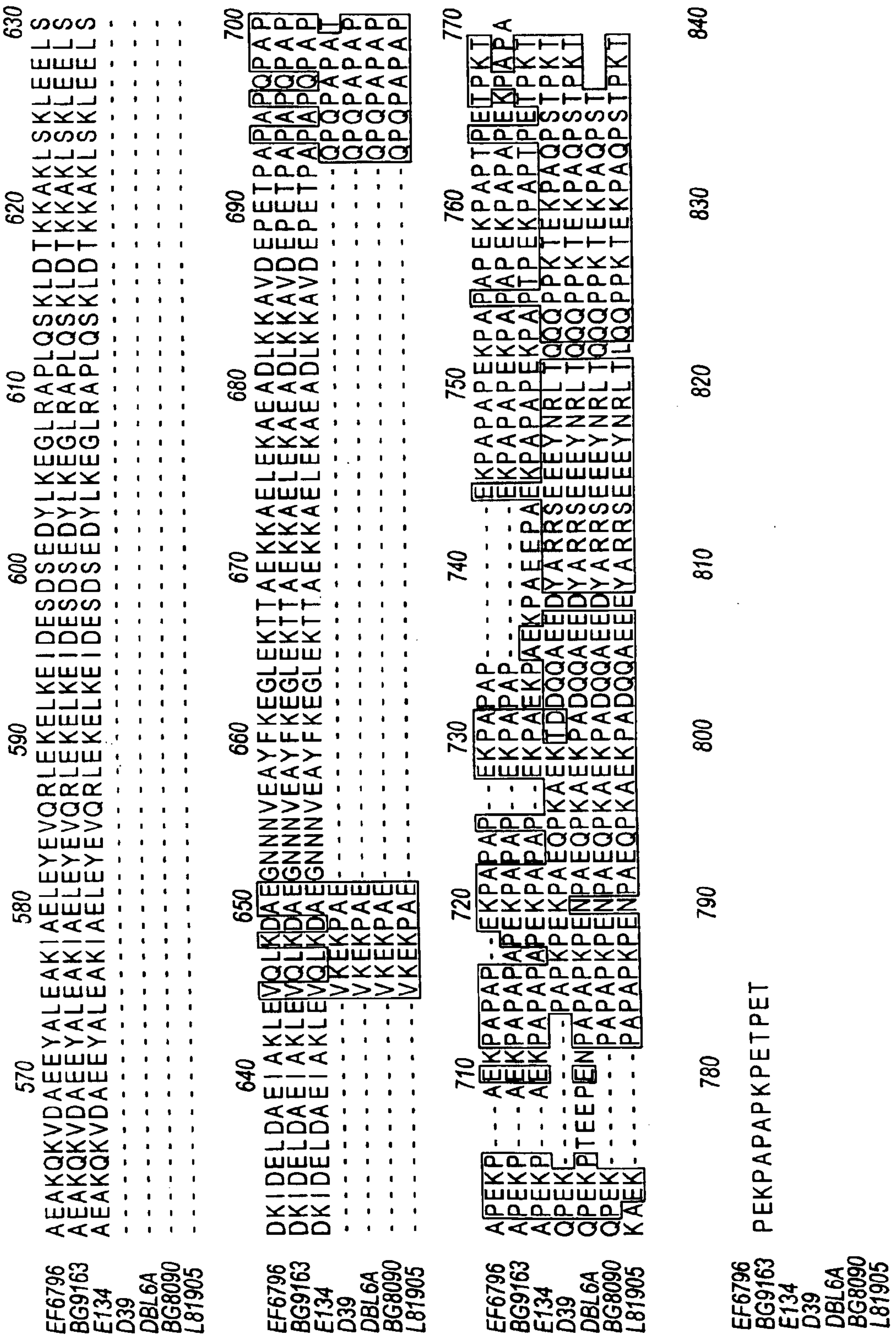

Sequence Analysis of pspC Gene-aspects Relating to Domain Structure and Function:

The protein sequences of pspC, spsA, and cbpA were aligned using MacVector 6.5 (FIGS. 1, 2, and 13). The predicted amino acid sequences encode proteins ranging in size from 59 to 105 kDa protein. The signal sequences of 37 amino acids are highly conserved (84–100% Identity). The major part of each protein is composed of a large alpha-helical domain (FIGS. 1, 2, and 13). The N-terminal 100 to 150 amino acids of this alpha-helical domain are hypervariable in both size and sequence and are unique for each strain sequence of unrelated parentage (FIG. 2, D39, SpsA2, CbpA, and Cb3P are all from a related lineage; see also FIG. 13). In the hypervariable regions of capsular serotype 1 and 4 strains, there is a unique 23 amino acid serine-rich sequence (amino acid positions 112 to 135).

Downstream of the hypervariable region and central to the alpha-helical domain is the first of two direct repeats. The amino acid repeats (FIGS. 2, 13) vary in size in individual PspCs from 101 to 205 amino acids and are approximately 79–89% identical at the amino acid level. Smaller-sized amino acid repeats in some strains differ from the larger repeats of other strains only by lack of sequence at the $NH_2$-terminal end, which accounts for their smaller size. The first repeat in each strain is more like the corresponding first repeat of other strains than it is like the second repeat of the same strain. This pattern suggests that duplication forming this repeat happened in an ancestral gene, prior to the diversification of pspC into the numerous divergent alleles seen today. These repeats are highly charged with approximately 45% of their sequence being either lysine or glutamic acid residues. These alpha-helical repeats were present in all alleles that were examined except for the spsA//serotype I and spsA//serotype 2 (Hammerschmidt et al. 1997) (FIGS. 2, 13).

Between the amino acid repeats of the alpha-helical domain is a highly conserved 40 amino acid sequence break in the coiled-coil motif which was identified using the Matcher program (Fischetti et al. 1993) (FIGS. 2, 13 and 3). Matcher examines the characteristic seven residue periodicity of coiled-coil proteins arising largely from the predominance of hydrophobic residues in the first and fourth positions (a and d) and non-hydrophobic residues in the remaining positions (Fischetti et al. 1993). The coiled-coil region of the alpha-helix of PspC/EF6796 has three breaks in the heptad repeat motif (FIG. 3). These interruptions of the heptad motif in the 7-residue periodicity were respectively 6, 44 and 5 amino acids in length. Similar breaks at corresponding sequence positions were found in all PspC alleles.

Figure 4:
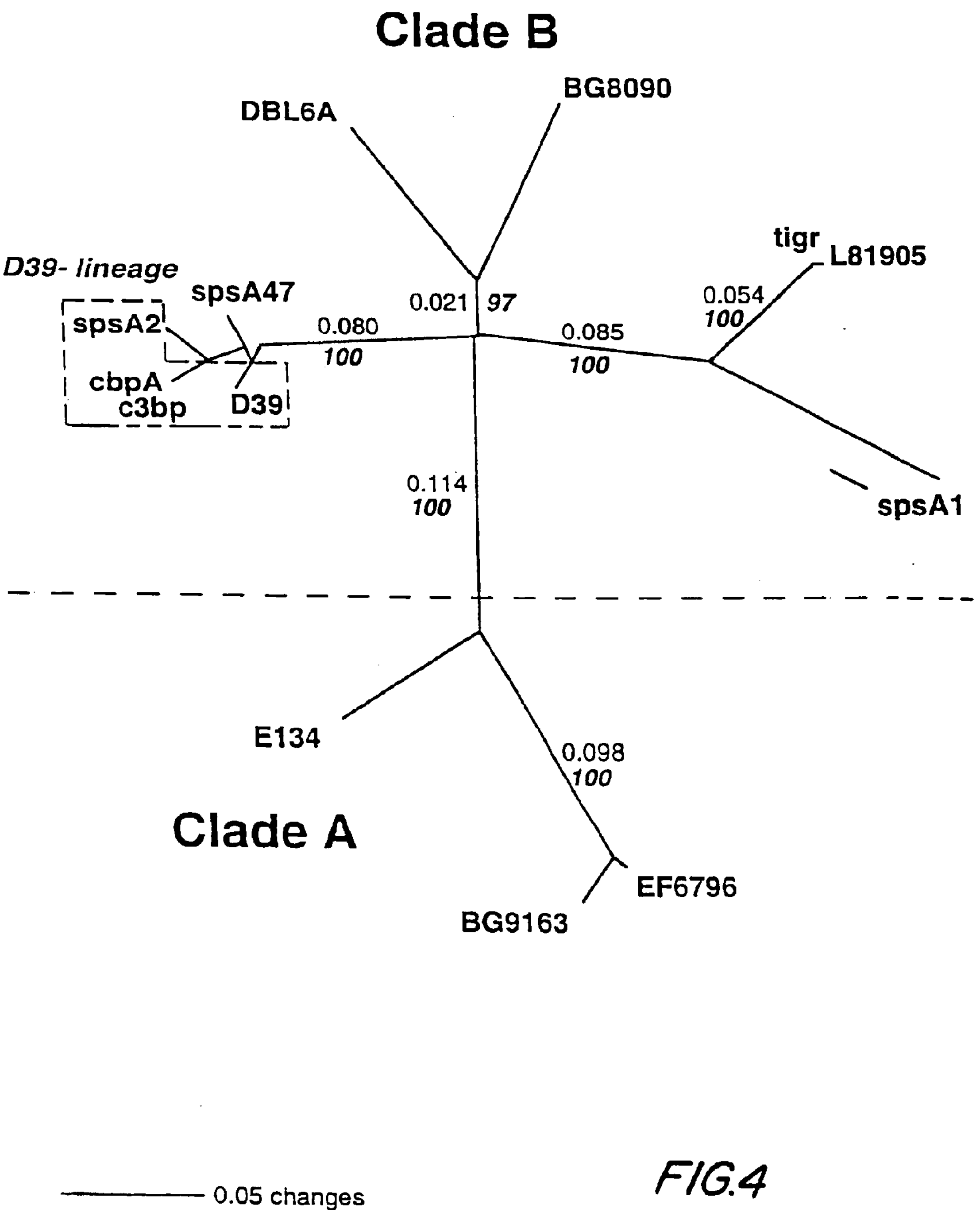
FIG. 4 shows a tree of the PspC proteins from this disclosure and related proteins SpsA and CbpA from Genbank (PspC proteins were truncated after the proline-rich region (FIG. 1) before being aligned using the ClustalW algorithm and the Blosum30 amino acid scoring matrix in MacVector; the tree is an unrooted phylogram generated by the neighbor-joining method using mean character distances in the program PAUP4.0b (Swofford); non-italic numbers on the tree indicate distances along the branch lengths as calculated by PAUP; italic bolded numbers indicate the percentage of time each branch was joined together under bootstrap analysis (1000 replicates performed); Clade A and Clade B are each monophyletic groups separated by greater than 0.1 distance which clustered together 100% of the time; Clade A PspC proteins share a 120 amino acid domain with many PspA proteins (FIG. 2); Clade B proteins lack the 120 AA domain, but all PspC/SpsA/CbpA proteins share the proline-rich domain with PspA proteins; the boxed D39-lineage indicates different sequences for this locus originating from strains that are laboratory descendents of the strain D39; the taxons used were the same as those described for FIG. 2)
Figure 12:
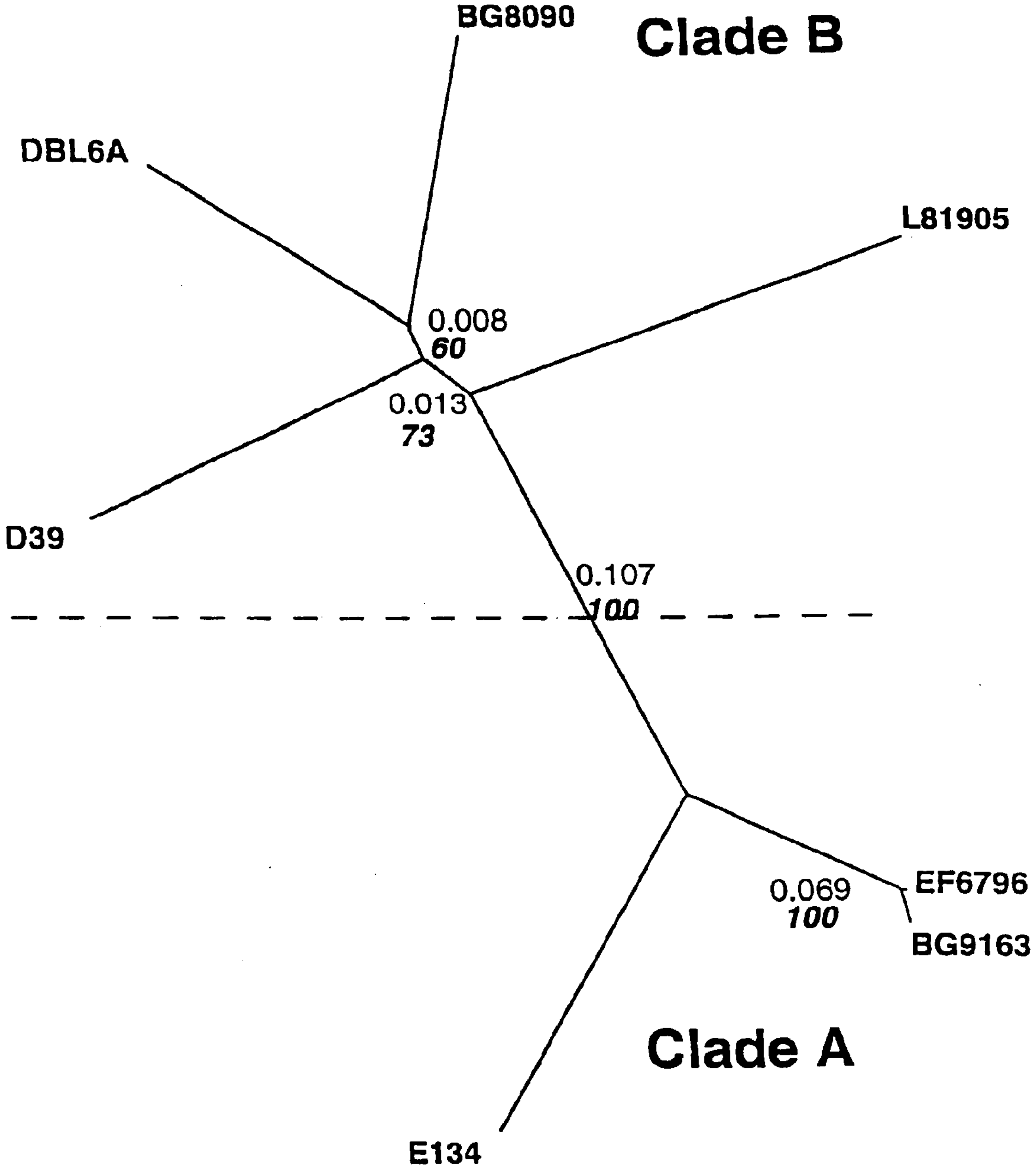
FIG. 12 shows a tree of PspC proteins from this disclosure from the University of Alabama, analogous to the tree shown in FIG. 4 (PspC proteins sequenced at the University of Alabama; PspC proteins were truncated after the proline-rich region—see FIG. 1—before aligned using the ClustalW algorithm and the Blosum30 amino acid scoring matrix in MacVector; the tree is an unrooted phylogram generated by the neighbor-joining method using mean character distances in the program PAUP4.0b (Swofford); non-italic numbers on the tree indicate distances along the branch lengths as calculated by PAUP; italic bolded numbers indicate the percentage of time each branch was joined together under bootstrap analysis (1000 replicates performed); Clade A and Clade B are monophyletic groups separated by greater than 0.1 distance which clustered together 100% of the time; Clade A PspC proteins share a 120 amino acid domain with many PspA protein—see FIG. 2; taxons are named for the strain from which the gene was cloned, with the capsular serotypes as follows—EF6796 (6A), BG8090 (19), L81905 (4), DBL6A (6a), BG9163 (6B), D39 (2) and E134 (23))

In some molecules of PspC, the proline-rich region followed the second amino acid repeat (FIGS. 1, 2, and 13). However, in the three larger PspC molecules, a region very similar to a corresponding region of the pspA genetic locus is present. Based on whether this pspA-like region was present or absent and on a distance-based cluster analysis, PspC molecules were classified into two clades (FIGS. 4, 12). Clade A molecules contained the pspA-like element and were larger in size. PspC clade B molecules were smaller and lacked this pspA-like region. This pspA-like region (alpha-helical-2) was present in PspC/BG9163, EF6796 and BG7322 (FIGS. 1, 2, and 13 and Table 1) as well as in many pspA genes.

Although there is some variation within the proline-rich region of the sequenced PspCs (FIGS. 1, 2, 13), the region is not distinguishable from the proline-rich region of PspA molecules. Within PspA molecules, two types of proline-rich regions have been identified. One type, which corresponds to about 60% of PspAs, contains a central region of 27 non-proline amino acids, which is highly conserved. The other type of proline-rich region in PspA lacks this conserved non-proline region. In the case of PspC, clade A strains lacked the 27 amino acid non-proline-rich block, whereas the four clade B PspC molecules had this conserved block. When present, the sequence of the 27 amino acid non-proline-rich region is highly conserved between PspC and PspA molecules. No correlation was observed between the expression of this conserved region within PspA and PspC molecules produced by the same strain. The proline-region of SpsA/serotype 1 was different from that of all other PspC molecules. This proline-rich region of this SpsA molecule has a truncated proline-rich region, which contains the 27 amino acid non-proline break but lacks the $NH_2$ end of the proline-rich region.

The choline-binding repeat domains of PspC, CbpA and SpsA proteins each contain between 4 and 11 repeats of about 20 amino acids (FIG. 5). The repeats found in the center of the choline-binding domain were closest to the consensus sequence, while repeats on the NH2-terminal and COOH-terminal ends of the block were more distant from the consensus sequence. The arrangement of repeats over the entire choline-binding region in PspC was examined relative to the arrangement of similar repeats in the choline-binding region of five PspC and three PspA genes for which the entire choline-binding domain was sequenced. The following findings all suggested a very close relationship between PspA and PspC in the choline-binding region of the molecule: 1) the $NH_2$-terminal divergent repeat is identical between the paralogous proteins (PspA and PspC); 2) similarly, the COOH-terminal divergent repeats are very similar between PspC and PspA (see repeats 10 and 11 of PspC consensus and repeats 9 and 10 of PspA consensus—FIG. 5), yet these repeats are highly diverged from the rest of the repeat block; 3) the conserved central repeats of the choline-binding domain in each case have a single amino acid at position 6 which is frequently asparagine in PspC, but usually tyrosine in PspA proteins (other than position 6, the consensus repeat for both genes is identical); 4) divergence of individual amino acids within the 20 amino acid repeat from the repeat consensus sequence was identical between PspA and PspC (position number 4, 6, 9, 12, 13, 15, 16, and 18); and 5). The repeat blocks are followed by a 17 amino acid partially hydrophobic "tail" that is nearly identical for PspC or PspA except for an additional asparagine present at the end of the PspC proteins that is missing from PspA proteins. Overall, the choline-binding domains of PspA and PspC are so similar that it would not be possible to determine with certainty whether any particular choline-binding domain from these two proteins belongs to PspA or PspC without knowledge of its flanking DNA.

Example/Result 2

Phylogenetic Analysis

The pspA and pspC genes are paralogs of each other because they are both present in the genome of most pneumococci, and because they share high identity in the sequence encoding their COOH-terminal halves (Table 1). An alignment of the 12 PspC/CbpA/SpsA sequences was constructed using the Clustal W algorithm (FIGS. 2, 13). An unrooted phylogram was produced with PAUP 4.0B with the neighbor-joining method from the mean amino acid distances as calculated over this alignment (FIGS. 4, 12). The figure as shown incorporates both distance measurements along the branch lengths and bootstrap analysis of 1000 repetitions. Branch length between molecules is proportional to the similarity of the sequences. The tree represents the evolutionary hypothesis that PspC molecules arose in two main clusters representing clades A and B. One clade, A, consisted of the larger PspC molecules, and contained strong identity in alpha-helical region-2 with some pspA alleles. The second clade, B, did not contain this region of identity with pspA alpha-helical region pspAs.

Example/Result 3

Analysis of pspC Using PCR

PCR was used to amplify pspC from different strains of *S. pneumoniae* to permit studies of the variability of PspC. Two oligonucleotides which recognized the common sequence regions of pspC, but which did not amplify the pspA genes, were designed in an effort to permit specific amplification of pspC alleles from all pneumococcal strains. Oligonucleotide ABW13 is specific to DNA upstream of the promoter sequence of the pspC gene locus. Oligonucleotide SKH2 is specific to the DNA encoding the C-terminal end of the proline-rich region of both the pspA and pspC gene loci. These oligonucleotides were used to amplify fragments of pspC from 100 *S. pneumoniae* strains. Seventy-eight of the 100 strains produced PCR-generated fragments, which varied from 1.5 kb to 2.2 kb in size. The remaining 22 strains failed to produce a PCR product. Based on the strains of known sequence it was observed that the size of the amplified products correlated with whether they were clade A or clade B. Because of the absence of this pspA-conserved region, the clade B pspC sequences were smaller than the clade A pspC. The amplified product using oligonucleotide ABW13 and SKH2 of clade A molecules was 2.0 kb or greater. The amplified fragment of clade B molecules was approximately 1.6 kb. Approximately 4% of the 75 strains from which a pspC gene was amplified were found to be clade A by this criterion and 96% were clade B.

Example/Result 4

Cloning and Expression of a Recombinant Truncated PspC Molecules

Oligonucleotides were used to amplify a 1.2 kb fragment of L81905, which encodes amino acids 263–482 of the alpha-helix and proline-rich region of PspC. The amplified PCR fragment was cloned into pQE40 (Qiagen, Chatsworth, Calif.) which allows expression of a fusion product with a polyhistidine tag at the amino-terminal end, followed by dihydrofolate reductase (DHFR), and then by the fragment of PspC/L81905 (263–482). Expression of the fusion protein in *E. coli* strain BL21 (DE3) was induced during growth at room temperature by the addition of 1 mM isopropyl-b-d-thiogalactopyranoside (IPTG). The overexpressed fusion protein was purified by affinity chromatography under non-denaturing conditions over a nickel resin according to the manufacturer's protocols. Purified fusion protein was then analyzed by SDS-PAGE and quantitated using a BioRad Protein Assay (Hercules, Calif.). Two fragments of PspC/D39 (AA 1–445 and AA 255–445), and three fragments of PspA/Rx1 (AA 1–301, AA 1–314 and AA 1–370) were expressed as fusion proteins with 6X His tag in the pET20b expression system (Novagen, Madison, Wis.). In this case, the overexpressed fusion proteins contain a PelB leader peptide, followed by the PspC or PspA fragments and the His tag at the carboxy-terminus. Expression was induced for pET20b-based constructs with 0.4mM IPTG in the expression strain BL21(DE3), and purified according the manufacturer's protocol.

Example/Result 5

Production of a Polyclonal Antiserum, SDS-PAGE, and Immunoblots

The truncated product (AA 263 to 482) of PspC/L81905 was purified by metal affinity chromatography and used to immunize a rabbit. Approximately 4 μg of purified PspC from L81905 was injected two times subcutaneously into a rabbit twice on consecutive weeks and blood was collected 10 days after the last injection. The primary immunization was with Freund's complete adjuvant and the booster immunization was given in saline. Polyclonal rabbit antiserum was diluted 1:50 and used to analyze pneumococcal lysates on a 7.5% SDS-PAGE gel (BioRad, Hercules, CA). Pneumococcal lysates and immunoblots were performed as described by Yother et al. 1994.

Example/Result 6

Figures 6A, 6B:
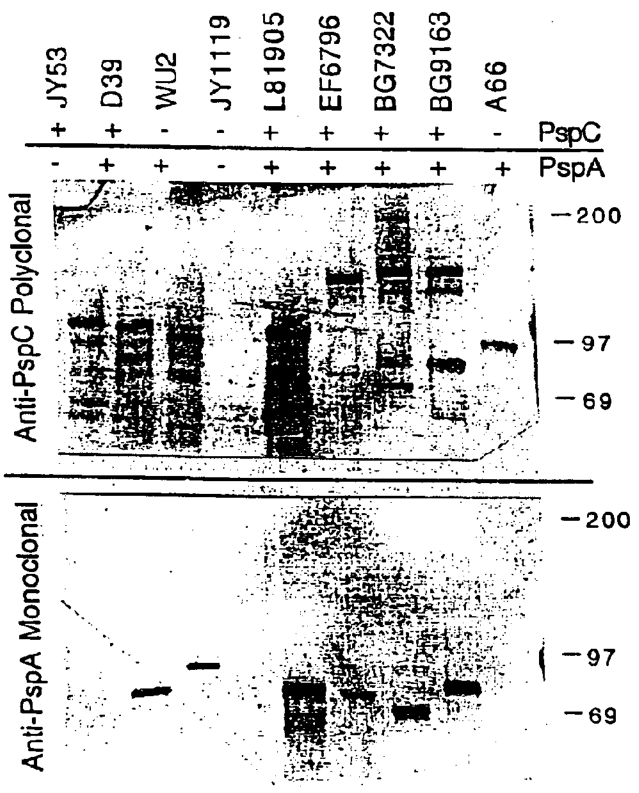
FIGS. 6A and 6B show the reactivity of PspC antiserum with selected pneumococcal lysates run in a Western immunoblot.

Cross-reactivity of Antisera Made to PspC/L81905 with pspA and other PspC Molecules:

A truncated product (AA 263482) of the PspC/L81905 clade B pspC protein was expressed in *E. coli* using the Qiagen Expression system. It should be noted that PspC/L81905 is clade B and lacks the pspA-like region in its alpha-helix. The truncated (AA 263–482) clade B PspC protein was purified by metal affinity chromatography and used to immunize a rabbit to generate a polyclonal antiserum to PspC. Pneumococcal lysates were separated on SDS-polyacrylamide gels and blotted to nitrocellulose. The blots were developed either with xi126, a monoclonal antibody to PspA, or with the anti-PspC rabbit polyclonal antiserum. The reactivity of the PspC antiserum with selected pneumococcal lysates run in a Western immunoblot is shown in FIG. 6.

The reactivity pattern of the antiserum to PspC was deciphered in part using lysates from *S. pneumoniae* strains JY1119 and JY53. These strains are derivatives of the pneumococcal strains WU2 and D39, respectively, in which the pspA genes have been insertionally inactivated (Yother et al 1992). From the Western blot, it is apparent that the polyclonal serum reacts with a 90 kDa band in JY53 even though the pspA gene has been inactivated in this strain. This band is assumed to represent PspC. Both JY1119 and its parent, WU2, lack the pspC gene altogether (McDaniel et al. 1992). An 85 kDa molecule from WU2 reacts with the anti-PspC antiserum and with the anti-PspA MAb. This band is not present in JY1119, which contains an insertionally inactivated PspA.

The rabbit antiserum was reactive with proteins in the lysates from all pneumococcal strains tested. The relative molecular weights of the proteins detected also made it apparent that the antiserum was reacting with both PspA and PspC molecules. To distinguish cross-reactivity with the PspA molecule from direct reactivity with the PspC molecule in untested strain lysates a second identical Western blot was developed with a monoclonal antibody specific to PspA molecules (FIG. 6, part B). PspC bands could be identified through the comparison of banding patterns in parts A and B of FIG. 6. The bands reactive with the anti-PspC rabbit antiserum but not with the anti-PspA MAb were identified as PspC. Bands stained by the rabbit antiserum that co-migrate with those also stained by the MAb were PspA molecules that cross-reacted with the antiserum to PspC. Besides failing to react with the MAb, it was also noted that PspC bands were of higher molecular weight than the PspA bands. By these criteria the anti-PspC serum cross-reacted with PspA in all strains tested except A66. For A66, a single band was detected. Further testing determined this band to be PspA-derived, rather than PspC-derived. In this case, A66 lacked a pspC gene and the PspA of A66 was not reactive with the MAb used, Xi126, even though anti-PspA immune sera does detect PspA in this strain. From the above patterns of reactivity, it was concluded that the PspC polyclonal antiserum is cross-reacting specifically with the PspA molecule.

Example/Result 7

Immunization and Challenge Studies

CBA/N mice were immunized with purified recombinant PspC proteins originating from strain L81905 (AA 263–482), the full alpha-helical region of PspC in strain D39

(AA 1–445), or a truncated portion of the PspC protein in strain D39 (AA 255–445). Each mouse received only one of the above recombinant proteins and groups of 5–6 mice were immunized in each experiment. The mice were immunized subcutaneously with approximately 1 μg of purified protein emulsified in 0.2 ml of complete Freund's adjuvant. Three weeks later they were boosted with 1 μg of purified protein in saline. Three weeks after the boost, the mice were challenged with approximately 700 colony-forming units (CFU) of pneumococcal strain WU2. Control mice were immunized with buffer and complete Freund's adjuvant without PspC.

Analysis of Immune Sera: Mice were bled retroorbitally 24 hours before challenge. The blood was collected into 0.5 ml 1% BSA/phosphate buffered saline. Samples were centrifuged for 1 min (2000 rpm) and the supernatant was collected and stored at −20° C. until used in direct ELISAs (enzyme-linked immunosorbent assays). Microtiter 96 well plates (Nunc, Weisbaden, Germany) were coated overnight at 4° C. with 0.5 μg of expressed protein which included PspC (AA 1–445) and PspA (UAB55-AA 1–301, UAB15-AA 1–314 and UAB103-AA 1–370). Plates were blocked with 1% bovine serum albumin/phosphate buffered saline (PBS) followed by incubation with immune sera for 3 hours at 37° C. Plates were washed with PBS/DAKO with 0.15% Tween and incubated with goat anti-mouse immunoglobulin biotin-conjugated antiserum and streptavidin alkaline phosphatase (Southern Biotechnology Assoc., Birmingham Ala.). They were developed with p-nitrophenyl phosphate (Sigma, St. Louis, Mo.). The log reciprocal titer giving 33% maximum binding to the mouse immune sera was determined to evaluate the reactivity.

Ability of PspC to elicit protective immunity in mice: Mice were immunized with one of three purified fragments of clade B PspC: L81905 (AA 263–482), D39 (AA 1–445) and D39 (AA 255–445). None of these immunogens contained the pspA-like alpha-helical region 2 noted earlier, but all of the immunogens contained the proline-rich region. Mice immunized with PspC and control mice then immunized with adjuvant only were challenged with WU2 or BG7322. WU2 is a capsular serotype 3 strain that produces no detectable PspC and does not contain the structural gene for pspC (FIG. 6). BG7322 is a capsular serotype 6B strain and contains a clade A PspC molecule. Significant protection against death was seen with both challenge strains in mice immunized with the three different PspC clade B molecules (Table 2). Protective immunity in mice challenged with WU2 must derive from the ability of the PspC immunogen to elicit immunity (presumably mediated by antibodies) in the mice that cross-reacts with the PspA molecule present on surface of strain WU2 because this strain lacks PspC. The ability of PspC to elicit immunity that is directed against PspA was expected from the data herein since PspC had been shown to elicit antibodies cross-reactive with PspA (FIG. 6). Protection of the mice challenged with BG7322 was statistically significant even though only 62% of the mice were protected as opposed to 96% when challenged with WU2.

Example/Result 8

Antibody Elicited to Recombinant PspC

Figure 7:
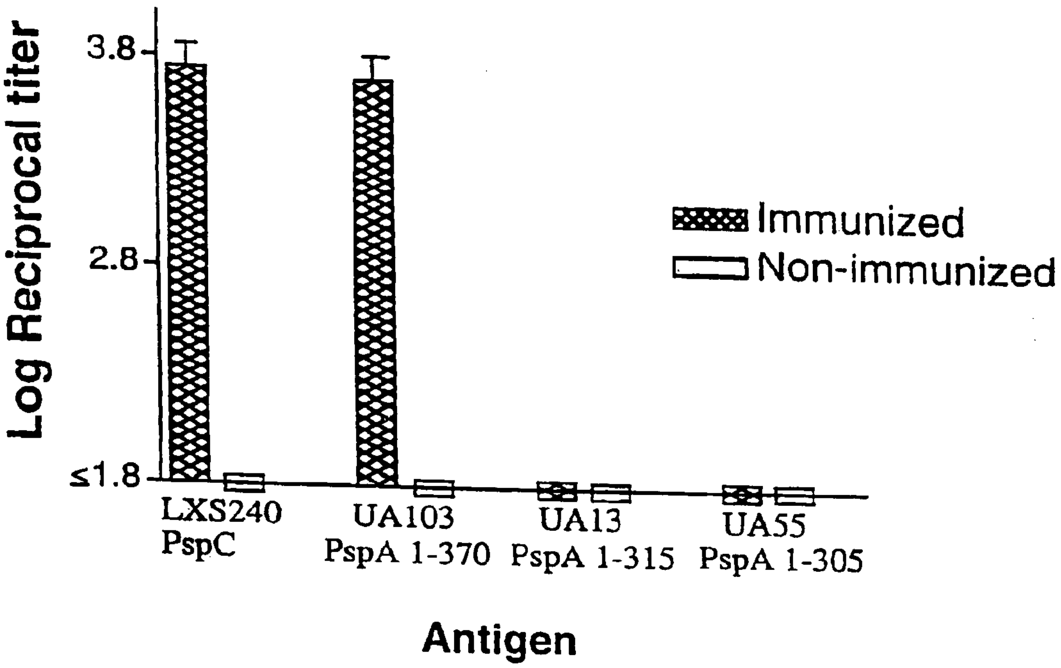
FIG. 7 shows the level of antibody reactivity to PspC and PspA fragments present in the sera of mice immunized with PspC (each bar represents the mean of the log reciprocal titer and upperbound of the standard error of sera from five mice; the limit of detection of the log reciprocal antibody titer is 1.8)

For this study sera was used from mice immunized with LXS240, which encoded amino acids 255–445 of clade B PspC/D39. This sequence contains the entire proline-rich region of PspC/D39. Direct binding ELISAs were conducted to localize the epitope yielding the cross-reactivity with PspA. Microtiter 96 well plates were coated with fragments of PspC/D39 and PspA/Rx1. Each of the cloned PspA/Rx1 molecules used in these assays expressed the PspA alpha-helical region and differed only in the number of the amino acids it contained in the proline-rich region. UAB55 contained 15 amino acids in the proline-rich region, UAB 15 contained 26 amino acids in the proline-rich region, and UAB103 contained the entire proline-rich region. The results from the ELISA are depicted in FIG. 7. Mouse antisera only reacted with the PspA/Rx1 molecules containing the entire proline-rich region. The antisera did not react with the PspA molecules UAB55 and UAB 15 that contained truncated proline regions. These results strongly suggest that the antibodies elicited by PspC that cross-protect against PspA are probably directed at the proline-rich regions of these molecules. Accordingly, the invention comprehends a method for eliciting anti-PspA antibodies comprising administering PspC or an epitopic region thereof or a polypeptide comprising an epitope of PspC.

Example/Result 9

Modular Evolution and Chimeric Structure of pspC

PspC is a chimeric protein which has acquired domains from both interspecies and intraspecies genetic exchanges. The protein contains a signal sequence that has 75% nucleotide identity to the bac gene from group B streptococci (accession numbers X59771 and X58470) (Hammerschmidt et al. 1997). The bac gene encodes the b antigen of Group B streptococci, a cell surface receptor that binds the constant region of human IgA. This similar sequence in the signal peptide region suggests that potential interspecies genetic exchange between group B streptococci and *S. pneumoniae* may have formed a chimeric locus including the bac regulatory region and a partial pspA or a pspA-like locus to create an ancestral gene for pspC. The origin of the central region specific to the current pspC genes is unknown. The direct amino acid repeats of the alpha-helix suggest that this region of PspC has evolved by a domain duplication event. This internal duplication of a portion of the alpha-helix led to gene elongation. The region of the alpha-helix is presumably the functional region of the molecule and reportedly binds SIGA (Hammerschmidt et al. 1997). Further intraspecies variation events are hinted at in the finding that 4% of PspC proteins are of clade A. This clade appears to have derived from a recombination event with PspA (or visa versa) providing further evidence of chimeric structure of PspC and possibly PspA molecules.

Several functions have been attributed to the PspC molecule. In addition to binding secretory IgA and a moiety on the surface of epithelial cells, Hoistetter et al. have reported that PspC binds the complement component C3 (Hostetter et al. 1997). Recent studies have shown that PspA inhibits complement activation by inhibiting the formation of the C3 convertase. With the similar structural domains of PspA and PspC, it is conceivable that the virulence properties of the two proteins may complement each other in the host. WU2 is a strain of *S. pneumoniae* that does not contain a structural gene for PspC. When mutants of PspA are produced in WU2 that lacks PspC there is a 10,000-fold decrease in virulence (Briles et al. 1997). When PspA is mutated in D39, a strain that contains both PspA and PspC, there is only a 10-fold decrease in virulence (Briles et al. 1997). From the data herein, PspA and PspC may complement each other in their abilities to block the clearance of pneumococci by interfering with the complement pathway (see also the preliminary data of Hostetter et al. 1997 and the data of Briles et al. 1997).

Rosenow et al. demonstrated that CbpA is expressed more strongly by pneumococci in the nasopharynx than by pneumococci in the blood (Rosenow et al. 1997). Thus, it is feasible that the two molecules may serve the same general function, possibly in different host tissues and in different stages of infection. Furthermore, either molecule may be more critical to virulence in the absence of the other. This hypothesis is further strengthened by data from ongoing studies that show that mutants lacking in both PspC and PspA are significantly decreased in virulence.

In PspC immunization studies, Applicants challenged mice with a strain expressing both PspC and PspA and a strain expressing PspA but not PspC. By including strains lacking the pspC gene Applicants could determine if protection elicited by PspC required the expression of PspC or might act, at least in part, through cross-reactions with PspA. For the study presented, mice were immunized with clade B PspC. This molecule lacks the PspA-PspC homology region near the C-terminal end of the alpha-helical region of PspC. Thus, this immunogen was expected to be one that would give less cross-reaction with PspA than would a clade A PspC. Even so, immunization with PspC/D39 resulted in protection when mice were challenged either with strain BG7322, which expresses both PspA and PspC, or with strain WU2, which expresses PspA but lacks PspC.

The protection-eliciting PspC immunogen contained the entire proline-rich region. The alpha-helical regions of PspA/WU2 and PspC/D39 have essentially no homology. However, the proline-rich region of PspC is repetitive and homologous with PspA. It was possible that antibody to this region was responsible for the cross-protection we observed. This hypothesis was supported by the observation that antibody elicited to PspC reacted with PspA fragments that contained the proline-rich region but not with those that lacked the proline-rich region in direct ELISAs. Antibodies elicited by PspC also cross-reacted with PspA on Western blots. The likelihood that the protective cross-reaction of PspC immune sera is mediated through PspA was further strengthened by the sequence data released by TIGR. Extensive searches of the largely completed genome failed to find other pneumococcal gene sequences with as high a similarity with the PspC sequence domains as the proline-rich region of PspA.

Electron microscopy surface labeling studies and epitope mapping studies have localized PspA on the surface of pneumococci with the largely exposed alpha-helical region (Gray, *Pneumococcal infection*, in Bacterial Infection, P. E. Brachman, Ed. 1997, Plenum Pub. Corp. NY; McDaniel et al. 1994; McDaniel et al., *Monoclonal antibodies against surface components of Streptococcus pneumoniae*, in Monoclonal antibodies against bacteria, A. J. L. Macario and E. C. de Macario, Eds. 1986, Academic Press, Inc. Orlando). Studies by Yother and White have shown that PspA is attached by the C-terminal end to lipoteichoic acids (Yother et al. 1994). No information has been available, however, about whether or not the proline-rich domain is surface exposed. Results from these experiments indicating that antibodies to the proline-rich domain are protective suggest that this domain of PspA is probably accessible on the surface of the pneumococci. This study also provides the first published evidence that antibodies reactive with the proline-rich region of PspA can be protective against pneumococcal infection.

PspA, PspC/CbpA/SpsA, LytA and PcpA are proteins of *S. pneumoniae* that contain choline-binding domains. The choline-binding domains of PspC/CbpA/SpsA contain between 4 and 11 repeats of about 20 amino acids. The consensus sequences of these repeats are from 90 to 95% identical. The middle region of the choline-binding domain of PspA and PspC is conserved. The first and last two repeats of PspA and PspC differ substantially (by 40 to 65%) from the consensus sequence. Even so, PspA and PspC sequences in these areas generally have the same deviations from the consensus sequence and in most cases are within 95% identical. The choline-binding domains of LytA and PcpA are quite different from that of PspA or PspC (42–62% identity) (Garcia et al. 1986; Sanchez-Beato et al. 1998). Whereas PspA and PspC have most likely evolved by gene duplication, PcpA has probably arisen from horizontal gene transfer. The choline-binding regions of these proteins all support a modular form of evolution of this group of proteins.

This disclosure provides a comprehensive study of the sequence of pspC and shows that PspCs can be divided into two clades based on the sequences in their alpha-helical and proline-rich domains. The disclosure also demonstrates that immunity to the proline-rich domain of PspC can be protective through its recognition of the proline-rich domain of the PspA molecule. The fact that the N-terminal alpha-helical domain of PspC is different from the alpha-helical domain of PspA suggests that PspC and PspA may serve somewhat distinct roles in virulence. However, the fact that the two molecules have a very similar domain structure and have similarity in much of their sequences raises the possibility that these two molecules may have similar functions. Although there are sequences of a few pspC alleles, this is the first report that the PspC family contains two clades and that the PspC molecules contain homology to PspA within the cross-protective region of the alpha-helix. The identification of two clades of PspC is pertinent to PspC-containing vaccine, immunological or immunogenic compositions, as well as to methods for identifying PspA, pspA, PspC, pspC, and/or *S. pneumoniae*. Moreover, the observation that antibodies to the proline-rich regions of PspA and PspC can be cross-protective facilitates the design of more efficacious vaccines, as well as of alternate vaccines, immunogenic or immunological compositions, e.g., by providing epitopic regions of PspC, epitopes of PspC and nucleic acid molecules encoding the same, and methods for identifying PspA, pspA, PspC, pspC, and/or *S. pneumoniae*.

TABLE 1

Conservation of PspC domains shown as percent amino acid identities.

| PspC Domain | PspC vs. PspC Orthologous | Clade A PspC vs. PspA Paralogous | Clade B PspC vs. PspA Paralogous | PspA vs. PspA Orthologous |
|---|---|---|---|---|
| Upstream through signal Peptide | >97% | no alignment possible | no alignment possible | >95% |
| Whole gene | 67.6–99% | 14–29% | 14–21% | 22–79% |
| Alpha-helical 1 | 66.9–99.6% | 11.8–22.0% | 14.8–23.1% | not present |
| Alpha-helical 2 | 100% | 13.1–88.7% | not present | 14–99% |

TABLE 1-continued

Conservation of PspC domains shown as percent amino acid identities.

| PspC Domain | PspC vs. PspC Orthologous | Clade A PspC vs. PspA Paralogous | Clade B PspC vs. PspA Paralogous | PspA vs. PspA Orthologous |
|---|---|---|---|---|
| Proline-rich* | High** | high | high | high |
| Choline-binding | 87% | 77% | 79.1–99% | 77–98% |
| 17 AA tail | 100% | 88.9% | 88.9–94.4% | 98–100% |
| 3' downstream | 99% | no alignment possible | no alignment possible | N.D. |

Percentages calculated using a distance matrix from PAUP 3.0.
*All PspA and PspC molecules have a repetitive segment of protein in this region with the motif PEPK or PAPAP. Clade B PspC molecules have a conserved non-repetitive break in the proline-rich region. Distance ranges are uninformative because it is not possible to align these sequences in a meaningful way.

TABLE 2

Cross-Protection of CBA/N Mice immunized with Recombinant PspC

| Immunogen | | Challenge | | Non- | |
|---|---|---|---|---|---|
| PspC fragment | Capsular Serotype of PspC donor | Strain and Capsular Serotype | Immunized[2] # of mice alive/dead[3] | immunized[2] # of mice alive/dead[3] | P value[1] |
| L81905 (AA 263–248) | 4 | WU2 (3) | 13/0 | 1/12 | <.0001 |
| D39 (AA 1–445) | 2 | WU2 (3) | 5/0 | 0/5 | .008 |
| D39 (AA 255–445) | 2 | WU2 (3) | 4/1 | 0/5 | .048 |
| D39 (AA 255–445) | 2 | BG7322 (6B) | 13/8 | 1/19 | .0002 |

[1]The statistical difference between immunized and non-immunized was calculated using the Fisher exact test.
[2]Mice were either immunized with PspC with complete Freund's adjuvant or with adjuvant and buffer but no antigen.
[3]Mice were challenged 21 days post immunization with 700 CFU of WU2 or 2000 CFU of BG7322 injected i.v. in 0.2 Ringer's injection solution.

Having thus described in detail preferred embodiments of the present invention, it is to be understood that the invention defined by the appended claims is not to be limited to particular details set forth in the above description as many apparent variations thereof are possible without departing from the spirit or scope of the present invention.

References

1. S. Hammerschmidt et al., *SpsA, a Novel Pneumococcal Surface Protein with Specific Binding to Secretory Immunoglobulin A and Secretory Component*. Mol. Microbiol., 1997, 25, 1113–1124.

2. C. Rosenow et al., *Contribution of Novel Choline-Binding Proteins to Adherance, Colonization and Immunogenicity of Streptococcus Pneumoniae*. Mol. Microbiol., 1997, 25, 819–829.

3. A. Brooks-Walter et al., *The pspC Gene Encodes a Second Pneumococcal Surface Protein Homologous to the Gene Encoding the Protection-Eliciting PspA Protein of Streptococcus Pneumoniae*. ASM Annual Meeting (Abstract), 1997.

4. A. Tomasz, *Choline in the Cell Wall of a Bacterium: Novel Type of Polymer-Linked Choline in Pneumococcus*. Science, 1967, 57, 694–697.

5. T. Breise and R. Hackenbeck, *Interactions of Pneumococcal Amidase with Lipoteichoic Acid and Choline*. Eur. J. Biochem., 1985, 146, 417–427.

6. A. Sanchez-Beato and J. Garcia, *Molecular Characterization of a Family of Choline-Binding Proteins of Costridium Acetobutylicum NCIB*8052 *Accession Number Z*50008, 1995.

7. J. A. Banas, R. R. B. Russell, and J. J. Ferretti, *Sequence Analysis of the Gene for the Glucan-Binding Protein of Streptococcus Mutans Ingbritt,* 1990.

8. L. A. Barroso et al., *Nucleotide Sequence of Clostridium Difficile Toxin B Gene*. Nuc. Acids Res., 1990, 18, 4004.

9. C. H. Dove et al., *Molecular Characterization of the Clostridium Difficile Toxin A Gene*. Infect. Immun., 1990, 58, 480–488.

10. P. Garcia et al., *Nucleotide Sequence and Expression of the Pneumococcal Autolysin Gene from its Own Promoter in Escherichia Coli.* Gene, 1986, 43, 265–272.

11. A. R. Sanchez-Beato, R. Lopez, and J. L. Garcia, *Molecular Characterization of PcpA: a Novel Choline-Binding Protein of Streptococcus Pneumoniae*. FEMS Microbiol. Lett., 1998, 164(1), 207–214.

12. J. Yother and J. M. White, *Novel Surface Attachment Mechanism for the Streptococcus Pneumoniae Protein PspA*. J. Bact., 1994, 176, 2976–2985.

13. D. E. Briles et al., *PspA and PspC: Their Potential for Use as Pneumococcal Vaccines*. Microb. Drug Resist., 1997, 3, 401–408.

14. L. S. McDaniel et al., *Use of insertional Inactivation to Facilitate Studies of Biological Properties of Pneumococcal Surface Protein A* (*PspA*). J. Exp. Med., 1987, 165, 381–394.

15. L. S. McDaniel et al., *PspA, a Surface Protein of Streptococcus Pneumoniae, is Capable of Eliciting Protection Against Pneumococci of More Than One Capsular Type*. Infect. Immun., 1991, 59, 222–228.

16. H. Y. Wu et al., *Intranasal Immunization of Mice with PspA (Pneumococcal Surface Protein A) Can Prevent Intranasal Carriage and Infection with Streptococcus Pneumoniae*. J. Infect. Dis., 1997, 175, 893–846.

17. L. S. McDaniel et al., *Molecular Localization of Variable and Conserved Regions of pspA, and Identification of Additional pspA Homologous Sequences in Streptococcus Pneumoniae*. Microb. Pathog., 1992, 13, 261–269.

18. V. A. Fischetti et al., *Identifying Periodic Occurrences of a Template with Applications to Protein Structure*. Inform. Proc. Letters, 1993, 11–18.

19. J. Yother, G. L. Handsome, and D. E. Briles, *Truncated Forms of PspA That Are Secreted from Streptococcus Pneumoniae and Their Use in Functional Studies and Cloning of the pspA Gene*. J. Bact., 1992, 174, 610–618.

20. M. K. Hostetter, Q. Cheng, and D. A. Finkel, C3-*Binding Protein (pbcA) in Streptococcus Pneumoniae: Accession Number AF*067128. ASM Meeting Miami Beach, Fla. 1997.

21. B. M. Gray, *Pneumococcal Infection*, in *Bacterial Infection*, P. E. Brachman, Editor, 1997, Plenum Publishing Corporation: New York.

22. L. S. McDaniel et al., *Localization of Protection-Eliciting Epitopes on PspA of Streptococcus Pneumoniae Between Amino Acid Residues* 192 *and* 260. Microb. Pathog., 1994, 17, 323–337.

23. L. S. McDaniel, and D. E. Briles, *Monoclonal Antibodies Against Surface Components of Streptococcus Pneumoniae,* in *Monoclonal Antibodies Against Bacteria* A. J. L. Macario and E. C. de Macario, Editors, Academic Press, Inc.: Orlando, 1986, 143.

24. J. Devereux, P. Haeberli, and O. Smithies, A *Comprehensive Set of Sequence Analysis Programs for the VAX*. Nuc. Acids Res., 1984, 12, 387–395.

25. W. Salser et al., *DNA Sequence Assembly and Editing Products Which Permits Direct Visualization of Raw Data Traces from Automated (Fluorescent) Sequencing Data*. J. NIH Res., 1993, (5), 81–82.

26. R. C. Tart, L. S. McDaniel, B. A. Ralph, D. E. Briles. *Truncated Streptococcus Pneumoniae PspA Molecules Elicit Cross-Protective Immunity Against Pneumococcal Challenge in Mice*. J. Infect. Dis., 1996, 173, 380–4393.

27. D. E. Briles, J. D. King, M. A. Gray, L. S. McDaniel, E. Swiatlo, K. A. Benton. *Pspa, a Protection-Eliciting Pneumococcal Protein: Immunogenicity of Isolated Native Pspa in Mice*. Vaccine, 1996, 14, 858–67.

28. M. J. Crain, J. S. Scott, D. A. Robinson, T. J. Coffey, A. Brooks-Walter, L. S. McDaniel, D. E. Briles. *Evidence for the Simultaneous Expression of Two PspAs by a Clone of Capsular Serotype 6B Streptococcus Pneumoniae*. Microbiol. Patho., 1996, 21, 265–275.

29. M. Yamamoto, L. S. McDaniel, K. Kawabata, D. E. Briles, R. J. Jackson, J. R. McGhee, H. Kiyono. *Oral Immunization with PspA Elicits Protective Humoral Immunity Against Streptococcus Pneumoniae Infection*. Infect. Immun., 1997, 56, 640–644.

30. H. Y. Wu, M. Nahm, Y. Guo, M. W. Russell, and D. E. Briles *Intranasal Immunization of Mice with PspA (Pneumococcal Surface Protein A) Can Prevent Carriage, and Infection with Streptococcus Pneumoniae*. J. Infect. Dis. In Press, 1997.

31. E. Swiatlo, A. Brooks-Walter, D. E. Briles, L. S. McDaniel. *Oligonucleotides Identify Conserved and Variable Regions of pspA and pspA-Like Sequences of Streptoccus Pneumoniae*. Gene, 1997, 188(2), 279–284.

32. L. S. McDaniel, F. Loechel, C. Benedict, T. Greenway, D. E. Briles, R. M. Conry, D. T. Curiel. *Immunization with a Plasmid Expressing Pneumococcal Surface Protein A (PspA) Can Elicit Protection Against Fatal Infection with Streptococcus Pneumoniae*. Gene Therapy, 1997, 4(4), 375–377.

33. C. Wortham, L. Grinberg, D. C. Kaslow, D. E. Briles, L. S. McDaniel, A. Lees, M. Flora, C. M. Snapper, J. J. Mond. *Enhanced Protective Antibody Responses to PspA After Intranasal or Subcutaneous Injection of PspA Genetically Fused to Granulocyte-Macrophage Colony-Stimulating Factor or Interlukin*-2. Infect. Immun., 1998, 66, 1513–1520.

34. A. R. Nayak, S. A. Tinge, R. C. Tart, L. S. McDaniel, D. E. Briles, R. Curtiss III. *A Live Recombinant Avirulent Oral Salmonella Vaccine Expressing Pneumococcal Surface Protein a (PspA) Induced Protective Responses Against Streptococcus Pneumoniae*. Infect. Immun., 1998, 66, 3744–3751.

35. L. S. McDaniel, D. O. McDaniel, S. K. Hollingshead, D. E. Briles. *Comparison of the PspA Sequence from Streptococcus Pneumoniae EF*5668 *to the Previously Identified PspA Sequence from Strain RxI and the Ability of Pspa from EF*5668 to *Elicit Protection Against Pneumococci of Different Capsular Types. Infect. Immun.,* 1998, 66, 4748–4754.

36. M. Yamamoto, D. E. Briles, S. Yamamoto, M. Ohmura, H. Kiyono, J. R. McGhee. *A Non-Toxic Adjuvant of Mucosal Immunity to Pneumococcal Surface Protein A*. J. Immunol., 1998,161,4115–4121.

37. Abstracts of 89th Annual Meeting of the American Society for Microbiology, p. 125, item D-257, May 1989.

38. Abstracts of 90th Annual Meeting of the American Society for Microbiology, p. 98, item D-106, May 1990.

39. Abstracts of 3rd International ASM Conference on Streptococcal Genetics, p. 11, item 12, June 1990.

40. Talkington et al, Infect. Immun., 1991, 59, 1285–1289.

41. Yother et al., J. Bacteriol., 1992, 174, 601–609.

42. McDaniel et al., J. Exp. Med., 1984, 160, 386–397.

43. McDaniel et al., Microbial Pathogenesis, 1986,1, 519–531.

44. McDaniel et al., Exp. Med., 1987, 165, 381–394.

45. Crain et al, Infect. Immun., 1990, 56, 3293–3299.

46. B. A. Ralph et al., Ann. N. Y. Acad. Sci., 1994, 730,361–363.

47. E. Alonson DeVelasco et al., Microbiological Rev., 1995, 59, 591–603.

What is claimed is:

1. An isolated or purified polypeptide comprising PspC, wherein the polypeptide has the amino acid sequence of SEQ ID NO: 13.

2. An immunogenic, immunological, or vaccine composition comprising the polypeptide of claim 1.

3. A method for eliciting an immunological response in a subject against *Streptococcus pneumoniae* comprising administering to the subject the polypeptide of claim 1.

4. The method of claim 3, wherein said method is preformed by administering an injection or by oral, nasal, or mucosal administration.

5. A method for eliciting an anti-PspA antibody in a subject comprising administering to the subject the polypeptide of claim 1.

6. The method of claim 5, wherein said method is preformed by administering an injection or by oral, nasal, or mucosal administration.

7. A method for eliciting an immunological response in a subject against *Streptococcus pneumoniae* comprising administering to the subject the composition of claim 2.

8. The method of claim 7, wherein said method is preformed by administering an injection or by oral, nasal, or mucosal administration.

9. A method for eliciting an anti-PspA antibody in a subject comprising administering to the subject the composition of claim 2.

10. The method of claim 9, wherein said method is preformed by administering an injection or by oral, nasal, or mucosal administration.

* * * * *

SEQUENCE LISTING

<160> NUMBER OF SEQ ID NOS: 77

<210> SEQ ID NO 1
<211> LENGTH: 691
<212> TYPE: PRT
<213> ORGANISM: Streptococcus pneumoniae

<400> SEQUENCE: 1

```
Met Phe Ala Ser Lys Ser Glu Arg Lys Val His Tyr Ser Ile Arg Lys
  1               5                  10                  15

Phe Ser Ile Gly Val Ala Ser Val Ala Val Ala Ser Leu Phe Leu Gly
             20                  25                  30

Gly Val Val His Ala Glu Gly Val Arg Ser Gly Asn Asn Leu Thr Val
         35                  40                  45

Thr Ser Ser Gly Gln Asp Ile Ser Lys Lys Tyr Ala Asp Glu Val Glu
     50                  55                  60

Ser His Leu Glu Ser Ile Leu Lys Asp Val Lys Lys Asn Leu Lys Lys
 65                  70                  75                  80

Val Gln His Thr Gln Asn Val Gly Leu Ile Thr Lys Leu Ser Glu Ile
                 85                  90                  95

Lys Lys Lys Tyr Leu Tyr Asp Leu Lys Val Asn Val Leu Ser Glu Ala
            100                 105                 110

Glu Leu Thr Ser Lys Thr Lys Glu Thr Lys Glu Lys Leu Thr Ala Thr
        115                 120                 125

Phe Glu Gln Phe Lys Lys Asp Thr Leu Pro Thr Glu Pro Glu Lys Lys
    130                 135                 140

Val Ala Glu Ala Gln Lys Lys Val Glu Glu Ala Lys Lys Lys Ala Glu
145                 150                 155                 160

Asp Gln Lys Glu Lys Asp Arg Arg Asn Tyr Pro Thr Ile Thr Tyr Lys
                165                 170                 175

Thr Leu Glu Leu Glu Ile Ala Glu Ser Asp Val Glu Val Lys Lys Ala
            180                 185                 190

Glu Leu Glu Leu Val Lys Val Lys Ala Lys Glu Ser Gln Asp Glu Glu
        195                 200                 205

Lys Ile Lys Gln Ala Glu Ala Glu Val Glu Ser Lys Gln Ala Glu Ala
    210                 215                 220

Thr Arg Leu Lys Lys Ile Lys Thr Asp Arg Glu Glu Ala Lys Arg Lys
225                 230                 235                 240

Ala Asp Ala Lys Leu Lys Glu Ala Val Glu Lys Asn Val Ala Thr Ser
                245                 250                 255

Glu Gln Asp Lys Pro Lys Arg Arg Ala Lys Arg Gly Val Ser Gly Glu
            260                 265                 270

Leu Ala Thr Pro Asp Lys Lys Glu Asn Asp Ala Lys Ser Ser Asp Ser
        275                 280                 285

Ser Val Gly Glu Glu Thr Leu Pro Ser Pro Ser Leu Asn Met Ala Asn
    290                 295                 300

Glu Ser Gln Thr Glu His Arg Lys Asp Val Asp Glu Tyr Ile Lys Lys
305                 310                 315                 320

Met Leu Ser Glu Ile Gln Leu Asp Arg Arg Lys His Thr Gln Asn Val
                325                 330                 335

Asn Leu Asn Ile Lys Leu Ser Ala Ile Lys Thr Lys Tyr Leu Tyr Glu
            340                 345                 350

Leu Ser Val Leu Lys Glu Asn Ser Lys Lys Glu Glu Leu Thr Ser Lys
```

-continued

```
        355                 360                 365

Thr Lys Ala Glu Leu Thr Ala Ala Phe Glu Gln Phe Lys Lys Asp Thr
    370                 375                 380

Leu Lys Pro Glu Lys Lys Val Ala Glu Ala Glu Lys Lys Val Glu Glu
385                 390                 395                 400

Ala Lys Lys Lys Ala Lys Asp Gln Lys Glu Glu Asp Arg Arg Asn Tyr
                405                 410                 415

Pro Thr Asn Thr Tyr Lys Thr Leu Glu Leu Glu Ile Ala Glu Ser Asp
            420                 425                 430

Val Lys Val Lys Glu Ala Glu Leu Glu Leu Val Lys Glu Glu Ala Asn
        435                 440                 445

Glu Ser Arg Asn Glu Glu Lys Ile Lys Gln Ala Lys Glu Lys Val Glu
    450                 455                 460

Ser Lys Lys Ala Glu Ala Thr Arg Leu Glu Lys Ile Lys Thr Asp Arg
465                 470                 475                 480

Lys Lys Ala Glu Glu Glu Ala Lys Arg Lys Ala Glu Glu Ser Glu Lys
                485                 490                 495

Lys Ala Ala Glu Ala Lys Gln Lys Val Asp Ala Glu Glu Tyr Ala Leu
            500                 505                 510

Glu Ala Lys Ile Ala Glu Leu Glu Tyr Glu Val Gln Arg Leu Glu Lys
        515                 520                 525

Glu Leu Lys Glu Ile Asp Glu Ser Asp Ser Glu Asp Tyr Leu Lys Glu
    530                 535                 540

Gly Leu Arg Ala Pro Leu Gln Ser Lys Leu Asp Thr Lys Lys Ala Lys
545                 550                 555                 560

Leu Ser Lys Leu Glu Glu Leu Ser Asp Lys Ile Asp Glu Leu Asp Ala
                565                 570                 575

Glu Ile Ala Lys Leu Glu Val Gln Leu Lys Asp Ala Glu Gly Asn Asn
            580                 585                 590

Asn Val Glu Ala Tyr Phe Lys Glu Gly Leu Glu Lys Thr Thr Ala Glu
        595                 600                 605

Lys Lys Ala Glu Leu Glu Lys Ala Glu Ala Asp Leu Lys Lys Ala Val
    610                 615                 620

Asp Glu Pro Glu Thr Pro Ala Pro Ala Pro Gln Pro Ala Pro Ala Pro
625                 630                 635                 640

Glu Lys Pro Ala Glu Lys Pro Ala Pro Ala Pro Glu Lys Pro Ala Pro
                645                 650                 655

Ala Pro Glu Lys Pro Ala Pro Ala Pro Glu Lys Pro Ala Pro Ala Pro
            660                 665                 670

Glu Lys Pro Ala Pro Ala Pro Glu Lys Pro Ala Pro Thr Pro Glu Thr
        675                 680                 685

Pro Lys Thr
    690


<210> SEQ ID NO 2
<211> LENGTH: 707
<212> TYPE: PRT
<213> ORGANISM: Streptococcus pneumoniae

<400> SEQUENCE: 2

Met Phe Ala Ser Lys Ser Glu Arg Lys Val His Tyr Ser Ile Arg Lys
  1               5                  10                  15

Phe Ser Ile Gly Val Ala Ser Val Ala Val Ala Ser Leu Phe Leu Gly
             20                  25                  30
```

-continued

```
Gly Val Val His Ala Glu Gly Val Arg Ser Gly Asn Asn Leu Thr Val
         35                  40                  45

Thr Ser Ser Gly Gln Asp Ile Ser Lys Lys Tyr Ala Asp Glu Val Glu
     50                  55                  60

Ser His Leu Glu Ser Ile Leu Lys Asp Val Lys Lys Asn Leu Lys Lys
 65                  70                  75                  80

Val Gln His Thr Gln Asn Val Gly Leu Ile Thr Lys Leu Ser Glu Ile
                 85                  90                  95

Lys Lys Lys Tyr Leu Tyr Asp Leu Lys Val Asn Val Leu Ser Glu Ala
            100                 105                 110

Glu Leu Thr Ser Lys Thr Lys Glu Thr Lys Glu Lys Leu Thr Ala Thr
        115                 120                 125

Phe Glu Gln Phe Lys Lys Asp Thr Leu Pro Thr Glu Pro Glu Lys Lys
    130                 135                 140

Val Ala Glu Ala Gln Lys Lys Val Glu Glu Ala Lys Lys Lys Ala Glu
145                 150                 155                 160

Asp Gln Lys Glu Lys Asp Arg Arg Asn Tyr Pro Thr Ile Thr Tyr Lys
                165                 170                 175

Thr Leu Glu Leu Glu Ile Ala Glu Ser Asp Val Glu Val Lys Lys Ala
            180                 185                 190

Glu Leu Glu Leu Val Lys Val Lys Ala Lys Glu Ser Gln Asp Glu Glu
        195                 200                 205

Lys Ile Lys Gln Ala Glu Ala Glu Val Glu Ser Lys Gln Ala Glu Ala
    210                 215                 220

Thr Arg Leu Lys Lys Ile Lys Thr Asp Arg Glu Glu Ala Lys Arg Lys
225                 230                 235                 240

Ala Asp Ala Lys Leu Lys Glu Ala Val Glu Lys Asn Val Ala Thr Ser
                245                 250                 255

Glu Gln Asp Lys Pro Lys Arg Arg Ala Lys Arg Gly Val Ser Gly Glu
            260                 265                 270

Leu Ala Thr Pro Asp Lys Lys Glu Asn Asp Ala Lys Ser Ser Asp Ser
        275                 280                 285

Ser Val Gly Glu Glu Thr Leu Pro Ser Pro Ser Leu Asn Met Ala Asn
    290                 295                 300

Glu Ser Gln Thr Glu His Arg Lys Asp Val Asp Glu Tyr Ile Lys Lys
305                 310                 315                 320

Met Leu Ser Glu Ile Gln Leu Asp Gly Arg Lys His Thr Pro Asn Val
                325                 330                 335

Asn Leu Asn Ile Lys Leu Ser Ala Ile Lys Thr Lys Tyr Leu Tyr Glu
            340                 345                 350

Leu Ser Val Leu Lys Glu Asn Ser Lys Lys Glu Glu Leu Thr Ser Lys
        355                 360                 365

Thr Lys Ala Glu Leu Thr Ala Ala Phe Glu Gln Phe Lys Lys Asp Thr
    370                 375                 380

Leu Lys Pro Glu Lys Lys Val Ala Glu Ala Glu Lys Lys Val Glu Glu
385                 390                 395                 400

Ala Lys Lys Lys Ala Lys Asp Gln Lys Glu Glu Asp Arg Arg Asn Tyr
                405                 410                 415

Pro Thr Asn Thr Tyr Lys Thr Leu Glu Leu Glu Ile Ala Glu Ser Asp
            420                 425                 430

Val Lys Val Lys Glu Ala Glu Leu Glu Leu Val Lys Glu Glu Ala Asn
        435                 440                 445

Glu Ser Arg Asn Glu Glu Lys Ile Lys Gln Ala Lys Glu Lys Val Glu
```

-continued

```
    450                 455                 460

Ser Lys Lys Ala Glu Ala Thr Arg Leu Glu Lys Ile Lys Thr Asp Arg
465                 470                 475                 480

Lys Lys Ala Glu Glu Glu Ala Lys Arg Lys Ala Glu Glu Ser Glu Lys
                485                 490                 495

Lys Ala Ala Glu Ala Lys Gln Lys Val Asp Ala Glu Glu Tyr Ala Leu
            500                 505                 510

Glu Ala Lys Ile Ala Glu Leu Glu Tyr Glu Val Gln Arg Leu Glu Lys
        515                 520                 525

Glu Leu Lys Glu Ile Asp Glu Ser Asp Ser Glu Asp Tyr Leu Lys Glu
    530                 535                 540

Gly Leu Arg Ala Pro Leu Gln Ser Lys Leu Asp Thr Lys Lys Ala Lys
545                 550                 555                 560

Leu Ser Lys Leu Glu Glu Leu Ser Asp Lys Ile Asp Glu Leu Asp Ala
                565                 570                 575

Glu Ile Ala Lys Leu Glu Val Gln Leu Lys Asp Ala Glu Gly Asn Asn
            580                 585                 590

Asn Val Glu Ala Tyr Phe Lys Glu Gly Leu Glu Lys Thr Thr Ala Glu
        595                 600                 605

Lys Lys Ala Glu Leu Glu Lys Ala Glu Ala Asp Leu Lys Lys Ala Val
    610                 615                 620

Asp Glu Pro Glu Thr Pro Ala Pro Ala Pro Gln Pro Ala Pro Ala Pro
625                 630                 635                 640

Glu Lys Pro Ala Glu Lys Pro Ala Pro Ala Pro Ala Pro Glu Lys Pro
                645                 650                 655

Ala Pro Ala Pro Glu Lys Pro Ala Pro Ala Pro Glu Lys Pro Ala Pro
            660                 665                 670

Ala Pro Glu Lys Pro Ala Pro Ala Pro Glu Lys Pro Ala Pro Ala Pro
        675                 680                 685

Glu Lys Pro Ala Pro Ala Pro Glu Lys Pro Ala Pro Ala Thr Pro Lys
    690                 695                 700

Pro Glu Thr
705


<210> SEQ ID NO 3
<211> LENGTH: 711
<212> TYPE: PRT
<213> ORGANISM: Streptococcus pneumoniae

<400> SEQUENCE: 3

Met Phe Ala Ser Lys Ser Glu Arg Lys Val His Tyr Ser Ile Arg Lys
  1               5                  10                  15

Phe Ser Ile Gly Val Ala Ser Val Val Val Ala Ser Leu Val Met Gly
             20                  25                  30

Ser Val Val His Ala Thr Glu Asn Glu Gly Ile Thr Gln Val Ala Thr
         35                  40                  45

Ser Tyr Asn Lys Ala Asn Glu Ser Gln Thr Glu His Arg Lys Ala Ala
     50                  55                  60

Lys Gln Val Asp Glu Asp Ile Lys Lys Met Leu Ser Glu Ile Gln Glu
 65                  70                  75                  80

Tyr Ile Lys Lys Met Leu Ser Glu Ile Gln Leu Asp Lys Arg Lys His
                 85                  90                  95

Thr Gln Asn Val Asn Leu Asn Arg Lys Leu Ser Ala Ile Gln Thr Lys
            100                 105                 110
```

-continued

```
Tyr Leu Tyr Glu Leu Arg Val Leu Lys Glu Lys Ser Lys Lys Glu Glu
        115                 120                 125

Leu Thr Ser Lys Thr Lys Lys Glu Leu Asp Ala Ala Phe Glu Lys Phe
    130                 135                 140

Lys Lys Glu Glu Pro Glu Leu Thr Lys Lys Leu Ala Glu Ala Lys Gln
145                 150                 155                 160

Lys Ala Lys Ala Gln Lys Glu Glu Asp Phe Arg Asn Tyr Pro Thr Asn
                165                 170                 175

Thr Tyr Lys Thr Leu Glu Leu Glu Ile Ala Glu Phe Asp Val Lys Val
            180                 185                 190

Lys Glu Ala Glu Leu Glu Leu Val Lys Glu Glu Ala Lys Pro Arg Asn
        195                 200                 205

Glu Glu Lys Ile Lys Gln Ala Lys Ala Lys Val Glu Ser Lys Lys Ala
    210                 215                 220

Glu Ala Thr Arg Leu Glu Glu Ile Lys Thr Glu Arg Lys Lys Ala Glu
225                 230                 235                 240

Glu Glu Ala Lys Arg Lys Ala Glu Glu Ser Glu Lys Lys Ala Ala Glu
                245                 250                 255

Ala Lys Gln Lys Val Asp Thr Lys Glu Gln Gly Lys Pro Lys Arg Arg
            260                 265                 270

Ala Lys Arg Gly Val Ser Gly Glu Leu Ala Thr Pro Asp Lys Lys Glu
        275                 280                 285

Asn Asp Ala Lys Ser Ser Asp Ser Ser Val Gly Glu Glu Thr Leu Pro
    290                 295                 300

Ser Pro Ser Leu Asn Ala Met Ala Asn Glu Ser Gln Thr Glu His Arg
305                 310                 315                 320

Lys Asp Val Asp Glu Tyr Ile Lys Lys Met Leu Ser Glu Ile Gln Leu
                325                 330                 335

Asp Arg Arg Lys His Thr Gln Asn Val Asn Leu Asn Ile Lys Leu Ser
            340                 345                 350

Ala Ile Lys Thr Lys Tyr Leu Tyr Glu Leu Ser Val Leu Lys Glu Asn
        355                 360                 365

Ser Lys Lys Glu Glu Leu Thr Ser Lys Thr Lys Ala Glu Leu Thr Ala
    370                 375                 380

Ala Phe Glu Gln Phe Lys Lys Asp Thr Leu Lys Pro Glu Lys Lys Val
385                 390                 395                 400

Ala Glu Ala Glu Lys Lys Val Glu Glu Ala Lys Lys Lys Ala Lys Asp
                405                 410                 415

Gln Lys Glu Glu Asp Arg Arg Asn Tyr Pro Thr Asn Thr Tyr Lys Thr
            420                 425                 430

Leu Glu Leu Glu Ile Ala Glu Ser Asp Val Lys Val Lys Lys Ala Glu
        435                 440                 445

Leu Glu Leu Val Lys Glu Glu Ala Asn Glu Ser Arg Asn Glu Glu Lys
    450                 455                 460

Ile Lys Gln Ala Lys Glu Lys Val Glu Ser Lys Lys Ala Glu Ala Thr
465                 470                 475                 480

Arg Leu Glu Lys Ile Lys Thr Asp Arg Lys Lys Ala Glu Glu Glu Ala
                485                 490                 495

Lys Arg Lys Ala Glu Glu Ser Glu Lys Lys Ala Ala Glu Ala Lys Gln
            500                 505                 510

Lys Val Asp Ala Glu Glu Tyr Ala Leu Glu Ala Lys Ile Ala Glu Leu
        515                 520                 525

Glu Tyr Glu Val Gln Arg Leu Glu Lys Glu Leu Lys Glu Ile Asp Glu
```

-continued

```
    530                 535                 540

Ser Asp Ser Glu Asp Tyr Leu Lys Glu Gly Leu Arg Ala Pro Leu Gln
545                 550                 555                 560

Ser Lys Leu Asp Thr Lys Lys Ala Lys Leu Ser Lys Leu Glu Glu Leu
                565                 570                 575

Ser Asp Lys Ile Asp Glu Leu Asp Ala Glu Ile Ala Lys Leu Glu Val
            580                 585                 590

Gln Leu Lys Asp Ala Glu Gly Asn Asn Asn Val Glu Ala Tyr Phe Lys
        595                 600                 605

Glu Gly Leu Glu Lys Thr Thr Ala Glu Lys Lys Ala Glu Leu Glu Lys
    610                 615                 620

Ala Glu Ala Asp Leu Lys Lys Ala Val Asp Glu Pro Glu Thr Pro Ala
625                 630                 635                 640

Pro Ala Pro Gln Pro Ala Pro Ala Pro Glu Lys Pro Ala Glu Lys Pro
                645                 650                 655

Ala Pro Ala Pro Ala Pro Glu Lys Pro Ala Pro Ala Pro Glu Lys Pro
            660                 665                 670

Ala Glu Lys Pro Ala Glu Lys Pro Ala Glu Glu Pro Ala Glu Lys Pro
        675                 680                 685

Ala Pro Ala Pro Glu Lys Pro Ala Pro Thr Pro Glu Lys Pro Ala Pro
    690                 695                 700

Thr Pro Glu Thr Pro Lys Thr
705                 710


<210> SEQ ID NO 4
<211> LENGTH: 496
<212> TYPE: PRT
<213> ORGANISM: Streptococcus pneumoniae

<400> SEQUENCE: 4

Met Phe Ala Ser Lys Ser Glu Arg Lys Val His Tyr Ser Ile Arg Lys
  1               5                  10                  15

Phe Ser Ile Gly Val Ala Ser Val Ala Val Ala Ser Leu Val Met Ser
            20                  25                  30

Val Val His Ala Thr Glu Asn Glu Gly Ser Thr Gln Ala Ala Thr Ser
        35                  40                  45

Ser Asn Met Ala Lys Thr Glu His Arg Lys Ala Ala Lys Gln Val Val
     50                  55                  60

Asp Ile Lys Lys Met Leu Ser Glu Ile Gln Glu Tyr Ile Lys Lys Met
 65                  70                  75                  80

Leu Ser Glu Ile Gln Leu Asp Lys Arg Lys His Thr Gln Asn Val Asn
                 85                  90                  95

Leu Asn Arg Lys Leu Ser Ala Ile Gln Thr Lys Tyr Leu Tyr Glu Leu
            100                 105                 110

Arg Val Leu Lys Glu Lys Ser Lys Lys Glu Glu Leu Thr Ser Lys Thr
        115                 120                 125

Lys Lys Glu Leu Asp Ala Ala Phe Glu Lys Phe Lys Lys Asp Thr Leu
    130                 135                 140

Lys Pro Gly Glu Lys Val Ala Glu Ala Lys Lys Lys Val Glu Glu Ala
145                 150                 155                 160

Lys Lys Lys Ala Glu Asp Gln Lys Glu Glu Asp Arg Arg Asn Tyr Pro
                165                 170                 175

Thr Asn Thr Tyr Lys Thr Leu Glu Leu Glu Ile Ala Glu Phe Asp Val
            180                 185                 190
```

-continued

```
Lys Val Lys Glu Ala Glu Leu Glu Leu Val Lys Glu Glu Ala Lys Glu
        195                 200                 205

Ser Arg Asn Glu Gly Thr Ile Lys Gln Ala Lys Glu Lys Val Glu Ser
    210                 215                 220

Lys Lys Ala Glu Ala Thr Arg Leu Glu Asn Ile Lys Thr Asp Arg Lys
225                 230                 235                 240

Lys Ala Glu Glu Glu Ala Lys Arg Lys Ala Glu Glu Ser Glu Lys Lys
                245                 250                 255

Ala Ala Glu Ala Lys Gln Lys Val Asp Thr Lys Glu Gln Gly Lys Pro
            260                 265                 270

Lys Arg Arg Ala Lys Arg Gly Val Ser Gly Glu Leu Ala Thr Pro Asp
        275                 280                 285

Lys Lys Glu Asn Asp Ala Lys Ser Ser Asp Ser Ser Val Gly Glu Glu
    290                 295                 300

Thr Leu Pro Ser Ser Ser Leu Lys Ser Gly Lys Lys Val Ala Glu Ala
305                 310                 315                 320

Glu Lys Lys Val Glu Glu Ala Glu Lys Lys Ala Lys Asp Gln Lys Glu
                325                 330                 335

Glu Asp Arg Arg Asn Tyr Pro Thr Asn Thr Tyr Lys Thr Leu Asp Leu
            340                 345                 350

Glu Ile Ala Glu Ser Asp Val Lys Val Lys Glu Ala Glu Leu Glu Leu
        355                 360                 365

Val Lys Glu Glu Ala Lys Glu Pro Arg Asp Glu Glu Lys Ile Lys Gln
    370                 375                 380

Ala Lys Ala Lys Val Glu Ser Lys Lys Ala Glu Ala Thr Arg Leu Glu
385                 390                 395                 400

Asn Ile Lys Thr Asp Arg Lys Lys Ala Glu Glu Glu Ala Lys Arg Lys
                405                 410                 415

Ala Ala Glu Glu Asp Lys Val Lys Glu Lys Pro Ala Glu Gln Pro Gln
            420                 425                 430

Pro Ala Pro Ala Thr Gln Pro Glu Lys Pro Ala Pro Lys Pro Glu Lys
        435                 440                 445

Pro Ala Glu Gln Pro Lys Ala Glu Lys Thr Asp Asp Gln Gln Ala Glu
    450                 455                 460

Glu Asp Tyr Ala Arg Arg Ser Glu Glu Tyr Asn Arg Leu Thr Gln Gln
465                 470                 475                 480

Gln Pro Pro Lys Thr Glu Lys Pro Ala Gln Pro Ser Thr Pro Lys Thr
                485                 490                 495
```

<210> SEQ ID NO 5
<211> LENGTH: 444
<212> TYPE: PRT
<213> ORGANISM: Streptococcus pneumoniae

<400> SEQUENCE: 5

```
Glu Asn Glu Gly Ser Thr Gln Ala Ala Thr Ser Ser Asn Met Ala Lys
  1               5                  10                  15

Thr Glu His Arg Lys Ala Ala Lys Gln Val Val Asp Glu Tyr Ile Glu
            20                  25                  30

Lys Met Leu Glu Arg Ile Gln Leu Asp Arg Arg Lys His Thr Gln Asn
        35                  40                  45

Val Ala Leu Asn Ile Lys Leu Ser Ala Ile Lys Thr Lys Tyr Leu Arg
    50                  55                  60

Glu Leu Asn Val Leu Glu Glu Lys Ser Lys Asp Glu Leu Pro Ser Glu
65                  70                  75                  80
```

-continued

```
Ile Lys Ala Lys Leu Asp Ala Ala Phe Glu Lys Phe Lys Lys Asp Thr
                85                  90                  95

Leu Lys Pro Gly Glu Lys Val Ala Glu Ala Lys Lys Val Glu Glu Ala
            100                 105                 110

Lys Lys Lys Ala Glu Asp Gln Lys Glu Glu Asp Arg Arg Asn Tyr Pro
        115                 120                 125

Thr Asn Thr Tyr Lys Thr Glu Leu Glu Ile Ala Glu Phe Asp Val Lys
    130                 135                 140

Val Lys Glu Ala Glu Leu Glu Leu Val Lys Glu Glu Ala Lys Glu Ser
145                 150                 155                 160

Arg Asn Glu Gly Thr Ile Lys Gln Ala Lys Glu Lys Val Glu Ser Lys
                165                 170                 175

Lys Ala Glu Ala Thr Arg Leu Glu Asn Ile Lys Thr Asp Arg Lys Lys
            180                 185                 190

Ala Glu Glu Glu Ala Lys Arg Lys Ala Asp Ala Lys Leu Lys Glu Ala
        195                 200                 205

Asn Val Ala Thr Ser Asp Gln Gly Lys Pro Lys Gly Arg Ala Lys Arg
    210                 215                 220

Gly Val Pro Gly Glu Leu Ala Thr Pro Asp Lys Lys Glu Asn Asp Ala
225                 230                 235                 240

Lys Ser Ser Asp Ser Ser Val Gly Glu Glu Thr Leu Pro Ser Ser Ser
                245                 250                 255

Leu Lys Leu Ser Gly Lys Lys Val Ala Glu Ala Glu Lys Lys Val Glu
            260                 265                 270

Glu Ala Glu Lys Lys Ala Lys Asp Gln Lys Glu Glu Asp Arg Arg Asn
        275                 280                 285

Tyr Pro Thr Asn Thr Tyr Lys Thr Leu Asp Leu Glu Ile Ala Glu Ser
    290                 295                 300

Asp Val Lys Val Lys Glu Ala Glu Leu Glu Leu Val Lys Glu Glu Ala
305                 310                 315                 320

Lys Glu Pro Arg Asp Glu Glu Lys Ile Lys Gln Ala Lys Ala Lys Val
                325                 330                 335

Glu Ser Lys Lys Ala Glu Ala Thr Arg Leu Glu Asn Ile Lys Thr Asp
            340                 345                 350

Arg Lys Lys Ala Glu Glu Glu Ala Lys Arg Lys Ala Ala Glu Glu Asp
        355                 360                 365

Lys Val Lys Glu Lys Pro Ala Glu Gln Pro Gln Pro Ala Pro Ala Thr
    370                 375                 380

Gln Pro Glu Lys Pro Ala Pro Lys Pro Glu Lys Pro Ala Glu Gln Pro
385                 390                 395                 400

Lys Ala Glu Lys Thr Asp Asp Gln Gln Ala Glu Glu Asp Tyr Ala Arg
                405                 410                 415

Arg Ser Glu Glu Glu Tyr Asn Arg Leu Thr Gln Gln Gln Pro Pro Lys
            420                 425                 430

Thr Glu Lys Pro Ala Gln Pro Ser Thr Pro Lys Thr
        435                 440
```

<210> SEQ ID NO 6
<211> LENGTH: 481
<212> TYPE: PRT
<213> ORGANISM: Streptococcus pneumoniae

<400> SEQUENCE: 6

```
Met Phe Ala Ser Lys Ser Glu Arg Lys Val His Tyr Ser Ile Arg Lys
```

-continued

```
 1               5                  10                  15

Phe Ser Ile Gly Val Ala Ser Val Ala Val Ala Ser Leu Val Met Gly
            20                  25                  30

Ser Val Val His Ala Thr Glu Asn Glu Gly Ser Thr Gln Ala Ala Thr
        35                  40                  45

Ser Ser Asn Met Ala Lys Thr Glu His Arg Lys Ala Ala Lys Gln Val
    50                  55                  60

Val Asp Glu Tyr Ile Glu Lys Met Leu Arg Glu Ile Gln Leu Asp Arg
65                  70                  75                  80

Arg Lys His Thr Gln Asn Val Ala Leu Asn Ile Lys Leu Ser Ala Ile
                85                  90                  95

Lys Thr Lys Tyr Leu Arg Glu Leu Asn Val Leu Glu Glu Lys Ser Lys
            100                 105                 110

Asp Glu Leu Pro Ser Glu Ile Lys Ala Lys Leu Asp Ala Ala Phe Glu
        115                 120                 125

Lys Phe Lys Lys Asp Thr Leu Lys Pro Gly Glu Lys Val Ala Glu Ala
    130                 135                 140

Lys Lys Lys Val Glu Glu Ala Lys Lys Lys Ala Glu Asp Gln Lys Glu
145                 150                 155                 160

Glu Asp Arg Arg Asn Tyr Pro Thr Asn Thr Tyr Lys Thr Leu Glu Leu
                165                 170                 175

Glu Ile Ala Glu Phe Asp Val Lys Val Lys Glu Ala Glu Leu Glu Leu
            180                 185                 190

Val Lys Glu Glu Ala Lys Glu Ser Arg Asn Glu Gly Thr Ile Lys Gln
        195                 200                 205

Ala Lys Glu Lys Val Glu Ser Lys Lys Ala Glu Ala Thr Arg Leu Glu
    210                 215                 220

Asn Ile Lys Thr Asp Arg Lys Lys Ala Glu Glu Glu Ala Lys Arg Lys
225                 230                 235                 240

Ala Asp Ala Lys Leu Lys Glu Ala Asn Val Ala Thr Ser Asp Gln Gly
                245                 250                 255

Lys Pro Lys Gly Arg Ala Lys Arg Gly Val Pro Gly Glu Leu Ala Thr
            260                 265                 270

Pro Asp Lys Lys Glu Asn Asp Ala Lys Ser Ser Asp Ser Ser Val Gly
        275                 280                 285

Glu Glu Thr Leu Pro Ser Ser Ser Leu Lys Ser Gly Lys Lys Val Glu
    290                 295                 300

Ala Glu Lys Lys Val Glu Glu Ala Glu Lys Lys Ala Lys Asp Gln Lys
305                 310                 315                 320

Glu Glu Asp Arg Arg Asn Tyr Pro Thr Asn Thr Tyr Lys Thr Leu Asp
                325                 330                 335

Leu Glu Ile Ala Glu Ser Asp Val Lys Val Lys Glu Ala Glu Leu Glu
            340                 345                 350

Leu Val Lys Glu Glu Ala Lys Glu Pro Arg Asp Glu Glu Lys Ile Lys
        355                 360                 365

Gln Ala Lys Ala Lys Val Glu Ser Lys Lys Ala Glu Ala Thr Arg Leu
    370                 375                 380

Glu Asn Ile Lys Thr Asp Arg Lys Lys Ala Glu Glu Glu Ala Lys Arg
385                 390                 395                 400

Lys Ala Ala Glu Glu Asp Lys Val Lys Glu Lys Pro Ala Glu Gln Pro
                405                 410                 415

Gln Pro Ala Pro Ala Thr Gln Pro Glu Lys Pro Ala Pro Lys Pro Glu
            420                 425                 430
```

-continued

```
Lys Pro Ala Glu Gln Pro Lys Ala Glu Lys Thr Asp Asp Gln Gln Ala
        435                 440                 445

Glu Glu Asp Tyr Ala Arg Ser Glu Glu Glu Tyr Asn Arg Leu Thr Gln
    450                 455                 460

Gln Gln Pro Pro Lys Thr Glu Lys Pro Ala Gln Pro Ser Thr Pro Lys
465                 470                 475                 480

Thr


<210> SEQ ID NO 7
<211> LENGTH: 307
<212> TYPE: PRT
<213> ORGANISM: Streptococcus pneumoniae

<400> SEQUENCE: 7

Met Phe Ala Ser Lys Ser Glu Arg Lys Val His Tyr Ser Ile Arg Lys
  1               5                  10                  15

Phe Ser Ile Gly Val Ala Ser Val Ala Val Ala Ser Leu Phe Leu Gly
             20                  25                  30

Gly Val Val His Ala Glu Gly Val Arg Ser Glu Asn Thr Pro Lys Val
         35                  40                  45

Thr Ser Ser Gly Glu Tyr Ile Glu Lys Met Leu Arg Glu Ile Gln Leu
     50                  55                  60

Asp Arg Arg Lys His Thr Gln Asn Val Ala Leu Asn Ile Lys Ile Ser
 65                  70                  75                  80

Ala Ile Lys Thr Lys Tyr Leu Arg Glu Leu Asn Val Leu Glu Glu Lys
                 85                  90                  95

Ser Lys Asp Glu Leu Pro Ser Glu Ile Lys Ala Lys Leu Asp Ala Ala
            100                 105                 110

Phe Glu Lys Phe Lys Lys Asp Thr Leu Lys Pro Gly Glu Lys Val Ala
        115                 120                 125

Glu Ala Lys Lys Lys Val Glu Glu Ala Lys Lys Lys Ala Glu Asp Gln
    130                 135                 140

Lys Glu Glu Asp Arg Arg Asn Tyr Pro Thr Asn Thr Tyr Lys Thr Leu
145                 150                 155                 160

Glu Leu Glu Ile Ala Glu Phe Asp Val Lys Val Lys Glu Ala Glu Leu
                165                 170                 175

Glu Leu Val Lys Glu Glu Ala Lys Glu Phe Arg Asn Glu Gly Thr Ile
            180                 185                 190

Lys Gln Ala Lys Glu Lys Val Glu Ser Lys Lys Ala Glu Ala Thr Arg
        195                 200                 205

Leu Glu Asn Ile Lys Thr Asp Arg Lys Lys Ala Glu Glu Glu Ala Lys
    210                 215                 220

Arg Lys Ala Ala Glu Glu Asp Lys Val Lys Glu Lys Pro Ala Glu Gln
225                 230                 235                 240

Pro Gln Pro Ala Pro Ala Thr Gln Pro Glu Lys Pro Ala Pro Lys Pro
                245                 250                 255

Glu Lys Pro Ala Glu Gln Pro Lys Ala Glu Lys Thr Asp Asp Gln Gln
            260                 265                 270

Ala Glu Glu Asp Tyr Ala Arg Arg Ser Glu Glu Glu Tyr Asn Arg Leu
        275                 280                 285

Thr Gln Gln Gln Pro Pro Lys Thr Glu Lys Pro Ala Gln Pro Ser Thr
    290                 295                 300

Pro Lys Thr
305
```

-continued

<210> SEQ ID NO 8
<211> LENGTH: 434
<212> TYPE: PRT
<213> ORGANISM: Streptococcus pneumoniae

<400> SEQUENCE: 8

```
Met Phe Ala Ser Lys Ser Glu Arg Lys Val His Tyr Ser Ile Arg Lys
  1               5                  10                  15

Phe Ser Ile Gly Val Ala Ser Val Ala Val Ala Ser Leu Phe Leu Gly
             20                  25                  30

Gly Val Val His Ala Glu Gly Val Arg Ser Glu Asn Thr Pro Lys Val
         35                  40                  45

Thr Ser Ser Gly Asp Glu Val Asp Glu Tyr Ile Lys Lys Met Leu Ser
     50                  55                  60

Glu Ile Gln Leu Asp Lys Arg Lys His Thr His Asn Phe Ala Leu Asn
 65                  70                  75                  80

Leu Lys Leu Ser Arg Ile Lys Thr Glu Tyr Leu Tyr Lys Leu Lys Val
                 85                  90                  95

Asn Val Leu Glu Glu Lys Ser Lys Ala Glu Leu Thr Ser Lys Thr Lys
            100                 105                 110

Lys Glu Val Asp Ala Ala Phe Glu Lys Phe Lys Lys Asp Thr Leu Lys
        115                 120                 125

Leu Gly Glu Lys Val Ala Glu Ala Gln Lys Lys Val Glu Glu Ala Lys
    130                 135                 140

Lys Lys Ala Lys Asp Gln Lys Glu Glu Asp His Arg Asn Tyr Pro Thr
145                 150                 155                 160

Asn Thr Tyr Lys Thr Leu Glu Leu Glu Ile Ala Glu Ser Asp Val Lys
                165                 170                 175

Leu Lys Glu Ala Glu Leu Glu Leu Leu Lys Glu Glu Ala Lys Thr Arg
            180                 185                 190

Asn Glu Asp Thr Ile Asn Gln Ala Lys Ala Lys Val Lys Ser Glu Gln
        195                 200                 205

Ala Glu Ala Thr Arg Leu Lys Lys Ile Lys Thr Asp Arg Glu Gln Ala
    210                 215                 220

Glu Ala Thr Arg Leu Glu Asn Ile Lys Thr Asp Arg Glu Lys Ala Glu
225                 230                 235                 240

Glu Ala Lys Arg Lys Ala Glu Ala Glu Glu Val Lys Asp Lys Leu Lys
                245                 250                 255

Arg Arg Thr Lys Arg Ala Val Pro Gly Glu Pro Ala Thr Pro Asp Lys
            260                 265                 270

Lys Glu Asn Asp Ala Lys Ser Ser Asp Ser Ser Val Gly Glu Glu Thr
        275                 280                 285

Leu Pro Ser Pro Ser Leu Lys Ser Gly Lys Lys Val Ala Glu Ala Gln
    290                 295                 300

Lys Lys Val Ala Glu Ala Glu Lys Lys Ala Lys Asp Gln Lys Glu Glu
305                 310                 315                 320

Asp Arg Arg Asn Tyr Pro Thr Asn Thr Tyr Lys Thr Leu Asp Leu Glu
                325                 330                 335

Ile Ala Glu Ser Asp Val Lys Val Lys Glu Lys Pro Ala Glu Gln Pro
            340                 345                 350

Gln Pro Ala Pro Ala Pro Gln Pro Glu Lys Pro Thr Glu Glu Pro Glu
        355                 360                 365

Asn Pro Ala Pro Ala Pro Lys Pro Glu Asn Pro Ala Pro Lys Pro Glu
```

-continued

```
    370                 375                 380

Asn Pro Ala Glu Gln Pro Lys Ala Glu Lys Pro Ala Asp Gln Gln Ala
385                 390                 395                 400

Glu Glu Asp Tyr Ala Arg Arg Ser Glu Glu Glu Tyr Asn Arg Leu Thr
                405                 410                 415

Gln Gln Gln Pro Pro Lys Thr Glu Lys Pro Ala Gln Pro Ser Thr Pro
            420                 425                 430

Lys Thr


<210> SEQ ID NO 9
<211> LENGTH: 487
<212> TYPE: PRT
<213> ORGANISM: Streptococcus pneumoniae

<400> SEQUENCE: 9

Met Phe Ala Ser Lys Asn Glu Arg Lys Val His Tyr Ser Ile Arg Lys
  1               5                  10                  15

Phe Ser Ile Gly Val Ala Ser Val Ala Val Ala Ser Leu Phe Met Gly
             20                  25                  30

Ser Val Val His Ala Thr Glu Lys Glu Val Thr Thr Gln Val Ala Thr
         35                  40                  45

Ser Phe Asn Lys Ala Asn Lys Ser Gln Thr Glu His Met Lys Ala Ala
     50                  55                  60

Lys Gln Val Asp Glu Tyr Ile Thr Lys Lys Leu Gln Leu Asp Arg Arg
 65                  70                  75                  80

Lys His Thr Gln Asn Val Gly Leu Leu Thr Lys Leu Gly Val Ile Lys
                 85                  90                  95

Thr Glu Tyr Leu His Arg Leu Ser Val Ser Lys Glu Lys Ser Glu Ala
            100                 105                 110

Glu Leu Pro Ser Glu Ile Lys Ala Lys Leu Asp Ala Ala Phe Glu Gln
        115                 120                 125

Phe Lys Lys Asp Thr Leu Pro Thr Glu Pro Gly Lys Lys Val Ala Glu
    130                 135                 140

Ala Glu Lys Lys Val Glu Glu Ala Lys Lys Lys Ala Glu Asp Gln Lys
145                 150                 155                 160

Glu Glu Asp Arg Arg Asn Tyr Pro Thr Ile Thr Tyr Lys Thr Leu Glu
                165                 170                 175

Leu Glu Ile Ala Glu Ser Asp Val Glu Val Lys Lys Ala Glu Leu Glu
            180                 185                 190

Leu Val Lys Glu Glu Ala Lys Gly Ser Arg Asn Glu Gln Lys Val Asn
        195                 200                 205

Gln Ala Lys Ala Lys Val Glu Ser Lys Gln Ala Glu Ala Thr Arg Leu
    210                 215                 220

Lys Lys Ile Lys Thr Asp Arg Glu Gln Ala Glu Thr Thr Arg Leu Glu
225                 230                 235                 240

Asn Ile Lys Thr Asp Arg Glu Lys Ala Glu Glu Ala Lys Arg Lys Ala
                245                 250                 255

Asp Ala Lys Glu Gln Asp Glu Ser Lys Arg Arg Val Lys Gly Gly Val
            260                 265                 270

Pro Gly Glu Gln Ala Thr Leu Asp Lys Lys Glu Asn Asp Ala Lys Ser
        275                 280                 285

Ser Asp Ser Ser Val Gly Glu Glu Thr Leu Pro Ser Pro Ser Leu Lys
    290                 295                 300

Ser Gly Lys Lys Val Ala Glu Ala Glu Lys Lys Val Ala Glu Ala Glu
```

-continued

```
305                 310                 315                 320

Lys Lys Ala Lys Asp Gln Lys Glu Glu Asp Arg Arg Asn Tyr Pro Thr
                325                 330                 335

Asn Thr Tyr Lys Thr Leu Glu Leu Glu Ile Ala Glu Ser Asp Val Lys
            340                 345                 350

Val Lys Glu Ala Glu Leu Glu Leu Val Lys Glu Glu Ala Lys Glu Ser
        355                 360                 365

Arg Asn Glu Glu Lys Val Lys Gln Ala Lys Ala Glu Val Glu Ser Lys
    370                 375                 380

Lys Ala Glu Ala Thr Arg Leu Glu Lys Ile Lys Thr Asp Arg Lys Lys
385                 390                 395                 400

Ala Glu Glu Ala Lys Arg Lys Ala Ala Glu Ser Glu Lys Val Lys Glu
                405                 410                 415

Lys Pro Ala Glu Gln Pro Gln Pro Ala Pro Ala Pro Gln Pro Glu Lys
            420                 425                 430

Pro Ala Pro Ala Pro Lys Pro Glu Asn Pro Ala Glu Gln Pro Lys Ala
        435                 440                 445

Glu Lys Pro Ala Asp Gln Gln Ala Glu Glu Asp Tyr Ala Arg Arg Ser
    450                 455                 460

Glu Glu Glu Tyr Asn Arg Leu Thr Gln Gln Gln Pro Pro Lys Thr Glu
465                 470                 475                 480

Lys Pro Ala Gln Pro Ser Thr
                485


<210> SEQ ID NO 10
<211> LENGTH: 483
<212> TYPE: PRT
<213> ORGANISM: Streptococcus pneumoniae

<400> SEQUENCE: 10

Met Phe Ala Ser Lys Ser Glu Arg Lys Val His Tyr Ser Ile Arg Lys
  1               5                  10                  15

Phe Ser Ile Gly Val Ala Ser Val Ala Val Ala Ser Leu Val Met Gly
            20                  25                  30

Ser Val Val His Ala Thr Glu Asn Glu Gly Ser Thr Gln Ala Ala Thr
        35                  40                  45

Ser Ser Asn Met Ala Lys Thr Glu His Arg Lys Ala Ala Lys Gln Val
     50                  55                  60

Val Asp Glu Tyr Ile Glu Lys Met Leu Arg Glu Ile Gln Leu Asp Arg
 65                  70                  75                  80

Arg Lys His Thr Gln Asn Val Ala Leu Asn Ile Lys Leu Ser Ala Ile
                 85                  90                  95

Lys Thr Lys Tyr Leu Arg Glu Leu Asn Val Leu Glu Glu Lys Ser Lys
            100                 105                 110

Asp Glu Leu Pro Ser Glu Ile Lys Ala Lys Leu Asp Ala Ala Phe Glu
        115                 120                 125

Lys Phe Lys Lys Asp Thr Leu Lys Pro Gly Glu Lys Val Ala Glu Ala
    130                 135                 140

Lys Lys Lys Val Glu Glu Ala Lys Lys Lys Ala Glu Asp Gln Lys Glu
145                 150                 155                 160

Glu Asp Arg Arg Asn Tyr Pro Thr Asn Thr Tyr Lys Thr Leu Glu Leu
                165                 170                 175

Glu Ile Ala Glu Phe Asp Val Lys Val Lys Glu Ala Glu Leu Glu Leu
            180                 185                 190
```

-continued

```
Val Lys Glu Glu Ala Lys Glu Ser Arg Asn Glu Gly Thr Ile Lys Gln
        195                 200                 205

Ala Lys Glu Lys Val Glu Ser Lys Lys Ala Glu Ala Thr Arg Leu Glu
    210                 215                 220

Asn Ile Lys Thr Asp Arg Lys Lys Ala Glu Glu Glu Ala Lys Arg Lys
225                 230                 235                 240

Ala Asp Ala Lys Leu Lys Glu Ala Asn Val Ala Thr Ser Asp Gln Gly
                245                 250                 255

Lys Pro Lys Gly Arg Ala Lys Arg Gly Val Pro Gly Glu Leu Ala Thr
            260                 265                 270

Pro Asp Lys Lys Glu Asn Asp Ala Lys Ser Ser Asp Ser Ser Val Gly
        275                 280                 285

Glu Glu Thr Leu Pro Ser Ser Ser Leu Lys Ser Gly Lys Lys Val Ala
    290                 295                 300

Glu Ala Glu Lys Lys Val Glu Glu Ala Glu Lys Lys Ala Lys Asp Gln
305                 310                 315                 320

Lys Glu Glu Asp Arg Arg Asn Tyr Pro Thr Asn Thr Tyr Lys Thr Leu
                325                 330                 335

Asp Leu Glu Ile Ala Glu Ser Asp Val Lys Val Lys Glu Ala Glu Leu
            340                 345                 350

Glu Leu Val Lys Glu Glu Ala Lys Glu Pro Arg Asp Glu Glu Lys Thr
        355                 360                 365

Lys Gln Ala Lys Ala Lys Val Glu Ser Lys Lys Ala Glu Ala Thr Arg
    370                 375                 380

Leu Glu Asn Ile Lys Thr Asp Arg Lys Lys Ala Glu Glu Glu Ala Lys
385                 390                 395                 400

Arg Lys Ala Ala Glu Glu Asp Lys Val Lys Glu Lys Pro Ala Glu Gln
                405                 410                 415

Pro Gln Pro Ala Pro Ala Thr Gln Pro Glu Lys Pro Ala Pro Lys Pro
            420                 425                 430

Glu Lys Pro Ala Glu Gln Pro Lys Ala Glu Lys Thr Asp Asp Gln Gln
        435                 440                 445

Ala Glu Glu Asp Tyr Ala Arg Arg Ser Glu Glu Glu Tyr Asn Arg Leu
    450                 455                 460

Ile Gln Gln Gln Pro Pro Lys Thr Glu Lys Pro Ala Gln Pro Phe Thr
465                 470                 475                 480

Pro Lys Thr


<210> SEQ ID NO 11
<211> LENGTH: 329
<212> TYPE: PRT
<213> ORGANISM: Streptococcus pneumoniae

<400> SEQUENCE: 11

Met Phe Ala Ser Lys Ser Glu Arg Lys Val His Tyr Ser Ile Arg Lys
  1               5                  10                  15

Phe Ser Val Gly Val Ala Ser Val Val Val Ala Ser Leu Val Met Gly
             20                  25                  30

Ser Val Val His Ala Thr Glu Asn Glu Gly Ala Thr Gln Val Pro Thr
         35                  40                  45

Ser Ser Asn Arg Ala Asn Glu Ser Gln Ala Glu Gln Gly Glu Gln Pro
     50                  55                  60

Lys Lys Leu Asp Ser Glu Arg Asp Lys Ala Lys Thr Ala Val Ser Glu
 65                  70                  75                  80
```

-continued

Tyr Lys Glu Lys Lys Val Ser Glu Ile Tyr Thr Lys Leu Glu Arg Asp
85 90 95

Arg His Lys Asp Thr Val Asp Leu Val Asn Lys Leu Gln Glu Ile Lys
100 105 110

Asn Glu Tyr Leu Asn Lys Ile Val Gln Ser Thr Ser Lys Thr Glu Ile
115 120 125

Gln Gly Leu Ile Thr Thr Ser Arg Ser Lys Leu Asp Glu Ala Val Ser
130 135 140

Lys Tyr Lys Lys Ala Pro Ser Ser Ser Ser Ser Ser Gly Ser Ser Thr
145 150 155 160

Lys Pro Glu Ala Ser Asp Thr Ala Lys Pro Asn Lys Pro Thr Glu Leu
165 170 175

Glu Lys Lys Val Ala Glu Ala Glu Lys Lys Val Glu Glu Ala Lys Lys
180 185 190

Lys Ala Lys Asp Gln Lys Glu Glu Asp Tyr Arg Asn Tyr Pro Thr Ile
195 200 205

Thr Tyr Lys Thr Leu Glu Leu Glu Ile Ala Glu Ser Asp Val Glu Val
210 215 220

Lys Lys Ala Glu Leu Glu Leu Val Lys Glu Glu Ala Lys Glu Pro Arg
225 230 235 240

Asn Glu Glu Lys Val Lys Gln Ala Lys Ala Lys Val Glu Ser Glu Glu
245 250 255

Thr Glu Ala Thr Arg Leu Glu Lys Ile Lys Thr Asp Arg Lys Lys Ala
260 265 270

Glu Glu Glu Ala Lys Arg Lys Ala Ala Glu Glu Asp Lys Val Lys Glu
275 280 285

Lys Pro Ala Glu Gln Gln Ala Glu Glu Asp Tyr Ala Arg Arg Ser Glu
290 295 300

Glu Glu Tyr Asn Arg Leu Thr Gln Gln Gln Pro Pro Lys Thr Glu Lys
305 310 315 320

Pro Ala Gln Pro Ser Thr Pro Lys Thr
325

<210> SEQ ID NO 12
<211> LENGTH: 515
<212> TYPE: PRT
<213> ORGANISM: Streptococcus pneumoniae

<400> SEQUENCE: 12

Met Phe Ala Ser Lys Ser Glu Arg Lys Val His Tyr Ser Ile Arg Lys
1 5 10 15

Phe Ser Val Gly Val Ala Ser Val Val Val Ala Ser Leu Val Met Gly
20 25 30

Ser Val Val His Ala Thr Glu Asn Glu Gly Ala Thr Gln Val Pro Thr
35 40 45

Ser Ser Asn Arg Ala Asn Glu Ser Gln Ala Glu Gln Gly Glu Gln Pro
50 55 60

Lys Lys Leu Asp Ser Glu Arg Asp Lys Ala Arg Lys Glu Val Glu Glu
65 70 75 80

Tyr Val Lys Lys Ile Val Gly Glu Ser Tyr Ala Lys Ser Thr Lys Lys
85 90 95

Arg His Thr Ile Thr Val Ala Leu Val Asn Glu Leu Asn Asn Ile Lys
100 105 110

Asn Glu Tyr Leu Asn Lys Ile Val Glu Ser Thr Ser Glu Ser Gln Leu
115 120 125

-continued

```
Gln Ile Leu Met Met Glu Ser Arg Ser Lys Val Asp Glu Ala Val Ser
    130                 135                 140

Lys Phe Glu Lys Asp Ser Ser Ser Ser Ser Ser Ser Asp Ser Ser Thr
145                 150                 155                 160

Lys Pro Glu Ala Ser Asp Thr Ala Lys Pro Asn Lys Pro Thr Glu Pro
                165                 170                 175

Gly Glu Lys Val Ala Glu Ala Lys Lys Lys Val Glu Glu Ala Glu Lys
            180                 185                 190

Lys Ala Lys Asp Gln Lys Glu Glu Asp Arg Arg Asn Tyr Pro Thr Ile
        195                 200                 205

Thr Tyr Lys Thr Leu Glu Leu Glu Ile Ala Glu Ser Asp Val Glu Val
    210                 215                 220

Lys Lys Ala Glu Leu Glu Leu Val Lys Val Lys Ala Asn Glu Pro Arg
225                 230                 235                 240

Asp Glu Gln Lys Ile Lys Gln Ala Glu Ala Glu Val Glu Ser Lys Gln
                245                 250                 255

Ala Glu Ala Thr Arg Leu Lys Lys Ile Lys Thr Asp Arg Glu Glu Ala
            260                 265                 270

Glu Glu Glu Ala Lys Arg Arg Ala Asp Ala Lys Glu Gln Gly Lys Pro
        275                 280                 285

Lys Gly Arg Ala Lys Arg Gly Val Pro Gly Glu Leu Ala Thr Pro Asp
    290                 295                 300

Lys Lys Glu Asn Asp Ala Lys Ser Ser Asp Ser Ser Val Gly Glu Glu
305                 310                 315                 320

Thr Leu Pro Ser Pro Ser Leu Lys Pro Glu Lys Lys Val Ala Glu Ala
                325                 330                 335

Glu Lys Lys Val Glu Glu Ala Lys Lys Lys Ala Glu Asp Gln Lys Glu
            340                 345                 350

Glu Asp Arg Arg Asn Tyr Pro Thr Asn Thr Tyr Lys Thr Leu Glu Leu
        355                 360                 365

Glu Ile Ala Glu Ser Asp Val Glu Val Lys Lys Ala Glu Leu Glu Leu
    370                 375                 380

Val Lys Glu Glu Ala Lys Glu Pro Arg Asn Glu Glu Lys Val Lys Gln
385                 390                 395                 400

Ala Lys Ala Glu Val Glu Ser Lys Lys Ala Glu Ala Thr Arg Leu Glu
                405                 410                 415

Lys Ile Lys Thr Asp Arg Lys Lys Ala Glu Glu Glu Ala Lys Arg Lys
            420                 425                 430

Ala Ala Glu Glu Asp Lys Val Lys Glu Lys Pro Ala Glu Gln Pro Gln
        435                 440                 445

Pro Ala Pro Ala Pro Lys Ala Glu Lys Pro Ala Pro Ala Pro Lys Pro
    450                 455                 460

Glu Asn Pro Ala Glu Gln Pro Lys Ala Glu Lys Pro Ala Asp Gln Gln
465                 470                 475                 480

Ala Glu Glu Glu Tyr Ala Arg Arg Ser Glu Glu Glu Tyr Asn Arg Leu
                485                 490                 495

Thr Leu Gln Gln Pro Pro Lys Thr Glu Lys Pro Ala Gln Pro Ser Thr
            500                 505                 510

Pro Lys Thr
        515
```

<210> SEQ ID NO 13
<211> LENGTH: 513

-continued

```
<212> TYPE: PRT
<213> ORGANISM: Streptococcus pneumoniae

<400> SEQUENCE: 13

Met Phe Ala Ser Lys Ser Glu Arg Lys Val His Tyr Ser Ile Arg Lys
  1               5                  10                  15

Phe Ser Val Gly Val Ala Ser Val Val Val Ala Ser Leu Val Met Gly
             20                  25                  30

Ser Val Val His Ala Thr Glu Asn Glu Gly Ala Thr Gln Val Pro Thr
         35                  40                  45

Ser Ser Asn Arg Ala Asn Glu Ser Gln Ala Glu Gln Gly Glu Gln Pro
     50                  55                  60

Lys Lys Leu Asp Ser Glu Arg Asp Lys Ala Arg Lys Glu Val Glu Glu
 65                  70                  75                  80

Tyr Val Lys Lys Ile Val Gly Glu Ser Tyr Ala Lys Ser Thr Lys Lys
                 85                  90                  95

Arg His Thr Ile Thr Val Ala Leu Val Asn Glu Leu Asn Asn Ile Lys
            100                 105                 110

Asn Glu Tyr Leu Asn Lys Ile Val Glu Ser Thr Ser Glu Ser Gln Leu
        115                 120                 125

Gln Ile Leu Met Met Glu Ser Arg Ser Lys Val Asp Glu Ala Val Ser
    130                 135                 140

Lys Phe Glu Lys Asp Ser Ser Ser Ser Ser Ser Ser Asp Ser Ser Thr
145                 150                 155                 160

Lys Pro Glu Ala Ser Asp Thr Ala Lys Pro Asn Lys Pro Thr Glu Pro
                165                 170                 175

Gly Glu Lys Val Ala Glu Ala Lys Lys Lys Val Glu Glu Ala Glu Lys
            180                 185                 190

Lys Ala Lys Asp Gln Lys Glu Glu Asp Arg Arg Asn Tyr Pro Thr Ile
        195                 200                 205

Thr Tyr Lys Thr Leu Glu Leu Glu Ile Ala Glu Ser Asp Val Glu Val
    210                 215                 220

Lys Lys Ala Glu Leu Glu Leu Val Lys Val Lys Ala Asn Glu Pro Arg
225                 230                 235                 240

Asp Glu Gln Lys Ile Lys Gln Ala Glu Ala Glu Val Glu Ser Lys Gln
                245                 250                 255

Ala Glu Ala Thr Arg Leu Lys Lys Ile Lys Thr Asp Arg Glu Glu Ala
            260                 265                 270

Glu Glu Glu Ala Lys Arg Arg Ala Asp Ala Lys Glu Gln Gly Lys Pro
        275                 280                 285

Lys Gly Arg Ala Lys Arg Gly Val Pro Gly Glu Leu Ala Thr Pro Asp
    290                 295                 300

Lys Lys Glu Asn Asp Ala Lys Ser Ser Asp Ser Ser Val Gly Glu Glu
305                 310                 315                 320

Thr Leu Pro Ser Pro Ser Leu Lys Pro Glu Lys Lys Val Ala Glu Ala
                325                 330                 335

Glu Lys Lys Val Glu Glu Ala Lys Lys Lys Ala Glu Asp Gln Lys Glu
            340                 345                 350

Glu Asp Arg Arg Asn Tyr Pro Thr Asn Thr Tyr Lys Thr Leu Glu Leu
        355                 360                 365

Glu Ile Ala Glu Ser Asp Val Glu Val Lys Lys Ala Glu Leu Glu Leu
    370                 375                 380

Val Lys Glu Glu Ala Lys Glu Pro Arg Asn Glu Glu Lys Val Lys Gln
385                 390                 395                 400
```

-continued

```
Ala Lys Ala Glu Val Glu Ser Lys Lys Ala Glu Ala Thr Arg Leu Glu
                405                 410                 415

Lys Ile Lys Thr Asp Arg Lys Lys Ala Glu Glu Glu Ala Lys Arg Lys
            420                 425                 430

Ala Ala Glu Glu Asp Lys Val Lys Glu Lys Pro Ala Glu Gln Pro Gln
        435                 440                 445

Pro Ala Pro Ala Pro Lys Ala Glu Lys Pro Ala Pro Ala Pro Lys Pro
    450                 455                 460

Glu Asn Pro Ala Glu Gln Pro Lys Ala Glu Lys Pro Ala Asp Gln Gln
465                 470                 475                 480

Ala Glu Glu Asp Tyr Ala Arg Arg Ser Glu Glu Glu Tyr Asn Arg Leu
                485                 490                 495

Thr Gln Gln Gln Pro Pro Lys Thr Glu Lys Pro Ala Gln Pro Ser Thr
            500                 505                 510

Pro


<210> SEQ ID NO 14
<211> LENGTH: 589
<212> TYPE: PRT
<213> ORGANISM: Streptococcus pneumoniae

<400> SEQUENCE: 14

Glu Gly Val Arg Ser Gly Asn Asn Leu Thr Val Thr Ser Ser Gly Gln
  1               5                  10                  15

Asp Ile Ser Lys Lys Tyr Ala Asp Glu Val Glu Ser His Leu Glu Ser
            20                  25                  30

Ile Leu Lys Asp Val Lys Lys Asn Leu Lys Lys Val Gln His Thr Gln
        35                  40                  45

Asn Val Gly Leu Ile Thr Lys Leu Ser Glu Ile Lys Lys Lys Tyr Leu
    50                  55                  60

Tyr Asp Leu Lys Val Asn Val Leu Ser Glu Ala Glu Leu Thr Ser Lys
 65                  70                  75                  80

Thr Lys Glu Thr Lys Glu Lys Leu Thr Ala Thr Phe Glu Gln Phe Lys
                85                  90                  95

Lys Asp Thr Leu Pro Thr Glu Pro Glu Lys Lys Val Ala Glu Ala Gln
            100                 105                 110

Lys Lys Val Glu Glu Ala Lys Lys Lys Ala Glu Asp Gln Lys Glu Lys
        115                 120                 125

Asp Arg Arg Asn Tyr Pro Thr Ile Thr Tyr Lys Thr Leu Glu Leu Glu
    130                 135                 140

Ile Ala Glu Ser Asp Val Glu Val Lys Lys Ala Glu Leu Glu Leu Val
145                 150                 155                 160

Lys Val Lys Ala Lys Glu Ser Gln Asp Glu Glu Lys Ile Lys Gln Ala
                165                 170                 175

Glu Ala Glu Val Glu Ser Lys Gln Ala Glu Ala Thr Arg Leu Lys Lys
            180                 185                 190

Ile Lys Thr Asp Arg Glu Glu Ala Lys Arg Lys Ala Asp Ala Lys Leu
        195                 200                 205

Lys Glu Ala Val Glu Lys Asn Val Ala Thr Ser Glu Gln Asp Lys Pro
    210                 215                 220

Lys Arg Arg Ala Lys Arg Gly Val Ser Gly Glu Leu Ala Thr Pro Asp
225                 230                 235                 240

Lys Lys Glu Asn Asp Ala Lys Ser Ser Asp Ser Ser Val Gly Glu Glu
                245                 250                 255
```

-continued

```
Thr Leu Pro Ser Pro Ser Leu Asn Met Ala Asn Glu Ser Gln Thr Glu
            260                 265                 270

His Arg Lys Asp Val Asp Glu Tyr Ile Lys Lys Met Leu Ser Glu Ile
        275                 280                 285

Gln Leu Asp Arg Arg Lys His Thr Gln Asn Val Asn Leu Asn Ile Lys
    290                 295                 300

Leu Ser Ala Ile Lys Thr Lys Tyr Leu Tyr Glu Leu Ser Val Leu Lys
305                 310                 315                 320

Glu Asn Ser Lys Lys Glu Glu Leu Thr Ser Lys Thr Lys Ala Glu Leu
                325                 330                 335

Thr Ala Ala Phe Glu Gln Phe Lys Lys Asp Thr Leu Lys Pro Glu Lys
            340                 345                 350

Lys Val Ala Glu Ala Glu Lys Lys Val Glu Glu Ala Lys Lys Lys Ala
        355                 360                 365

Lys Asp Gln Lys Glu Glu Asp Arg Arg Asn Tyr Pro Thr Asn Thr Tyr
    370                 375                 380

Lys Thr Leu Glu Leu Glu Ile Ala Glu Ser Asp Val Lys Val Lys Glu
385                 390                 395                 400

Ala Glu Leu Glu Leu Val Lys Glu Glu Ala Asn Glu Ser Arg Asn Glu
                405                 410                 415

Glu Lys Ile Lys Gln Ala Lys Glu Lys Val Glu Ser Lys Lys Ala Glu
            420                 425                 430

Ala Thr Arg Leu Glu Lys Ile Lys Thr Asp Arg Lys Lys Ala Glu Glu
        435                 440                 445

Glu Ala Lys Arg Lys Ala Glu Glu Ser Glu Lys Lys Ala Ala Glu Ala
    450                 455                 460

Lys Gln Lys Val Asp Ala Glu Glu Tyr Ala Leu Glu Ala Lys Ile Ala
465                 470                 475                 480

Glu Leu Glu Tyr Glu Val Gln Arg Leu Glu Lys Glu Leu Lys Glu Ile
                485                 490                 495

Asp Glu Ser Asp Ser Glu Asp Tyr Leu Lys Glu Gly Leu Arg Ala Pro
            500                 505                 510

Leu Gln Ser Lys Leu Asp Thr Lys Lys Ala Lys Leu Ser Lys Leu Glu
        515                 520                 525

Glu Leu Ser Asp Lys Ile Asp Glu Leu Asp Ala Glu Ile Ala Lys Leu
    530                 535                 540

Glu Val Gln Leu Lys Asp Ala Glu Gly Asn Asn Asn Val Glu Ala Tyr
545                 550                 555                 560

Phe Lys Glu Gly Leu Glu Lys Thr Thr Ala Glu Lys Lys Ala Glu Leu
                565                 570                 575

Glu Lys Ala Glu Ala Asp Leu Lys Lys Ala Val Asp Glu
            580                 585
```

```
<210> SEQ ID NO 15
<211> LENGTH: 21
<212> TYPE: PRT
<213> ORGANISM: Streptococcus pneumoniae

<400> SEQUENCE: 15

Lys Thr Gly Trp Lys Gln Glu Asn Gly Asn Trp Tyr Phe Tyr Asn Thr
  1               5                  10                  15

Asp Gly Ser Met Ala
             20
```

-continued

<210> SEQ ID NO 16
<211> LENGTH: 20
<212> TYPE: PRT
<213> ORGANISM: Streptococcus pneumoniae

<400> SEQUENCE: 16

Thr Gly Trp Leu Gln Asn Asn Gly Ser Trp Tyr Tyr Leu Asn Ala Met
1 5 10 15

Gly Ala Met Ala
20

<210> SEQ ID NO 17
<211> LENGTH: 20
<212> TYPE: PRT
<213> ORGANISM: Streptococcus pneumoniae

<400> SEQUENCE: 17

Thr Gly Trp Leu Gln Asn Asn Gly Ser Trp Tyr Tyr Leu Asn Ala Asn
1 5 10 15

Gly Ser Met Ala
20

<210> SEQ ID NO 18
<211> LENGTH: 20
<212> TYPE: PRT
<213> ORGANISM: Streptococcus pneumoniae

<400> SEQUENCE: 18

Thr Gly Trp Leu Gln Asn Asn Gly Ser Trp Tyr Tyr Leu Asn Ala Asn
1 5 10 15

Gly Ala Met Ala
20

<210> SEQ ID NO 19
<211> LENGTH: 20
<212> TYPE: PRT
<213> ORGANISM: Streptococcus pneumoniae

<400> SEQUENCE: 19

Thr Gly Trp Leu Gln Tyr Asn Gly Ser Trp Tyr Tyr Leu Asn Ala Asn
1 5 10 15

Gly Asp Met Ala
20

<210> SEQ ID NO 20
<211> LENGTH: 20
<212> TYPE: PRT
<213> ORGANISM: Streptococcus pneumoniae

<400> SEQUENCE: 20

Thr Gly Trp Leu Gln Tyr Asn Gly Ser Trp Tyr Tyr Leu Asn Ser Asn
1 5 10 15

Gly Ala Met Ala
20

<210> SEQ ID NO 21
<211> LENGTH: 20
<212> TYPE: PRT
<213> ORGANISM: Streptococcus pneumoniae

<400> SEQUENCE: 21

Thr Gly Trp Leu Gln Tyr Asn Gly Ser Trp Tyr Tyr Leu Asn Ala Asn
1 5 10 15

-continued

```
Gly Asp Met Ala
            20


<210> SEQ ID NO 22
<211> LENGTH: 20
<212> TYPE: PRT
<213> ORGANISM: Streptococcus pneumoniae

<400> SEQUENCE: 22

Thr Gly Trp Leu Gln Asn Asn Gly Ser Trp Tyr Tyr Leu Asn Ala Asn
  1               5                  10                  15

Gly Asp Met Ala
            20


<210> SEQ ID NO 23
<211> LENGTH: 19
<212> TYPE: PRT
<213> ORGANISM: Streptococcus pneumoniae

<400> SEQUENCE: 23

Thr Gly Trp Leu Gln Tyr Asn Ser Trp Tyr Tyr Leu Asn Ala Asn Gly
  1               5                  10                  15

Asp Met Ala


<210> SEQ ID NO 24
<211> LENGTH: 21
<212> TYPE: PRT
<213> ORGANISM: Streptococcus pneumoniae

<400> SEQUENCE: 24

Thr Gly Trp Val Lys Asp Gly Asp Thr Trp Tyr Tyr Leu Glu Ala Ser
  1               5                  10                  15

Gly Ala Met Lys Ala
            20


<210> SEQ ID NO 25
<211> LENGTH: 20
<212> TYPE: PRT
<213> ORGANISM: Streptococcus pneumoniae

<400> SEQUENCE: 25

Ser Gln Trp Phe Lys Val Ser Asp Lys Trp Tyr Tyr Val Asn Gly Ser
  1               5                  10                  15

Gly Ala Leu Ala
            20


<210> SEQ ID NO 26
<211> LENGTH: 18
<212> TYPE: PRT
<213> ORGANISM: Streptococcus pneumoniae

<400> SEQUENCE: 26

Val Asn Thr Thr Val Asp Gly Tyr Gly Val Asn Ala Asn Gly Glu Trp
  1               5                  10                  15

Val Asn


<210> SEQ ID NO 27
<211> LENGTH: 20
<212> TYPE: PRT
<213> ORGANISM: Streptococcus pneumoniae

<400> SEQUENCE: 27
```

-continued

Thr Gly Trp Leu Gln Asn Asn Gly Ser Trp Tyr Tyr Leu Asn Ala Asn
1 5 10 15

Gly Ala Met Ala
20

<210> SEQ ID NO 28
<211> LENGTH: 20
<212> TYPE: PRT
<213> ORGANISM: Streptococcus pneumoniae
<220> FEATURE:
<221> NAME/KEY: UNSURE
<222> LOCATION: (1)..(20)
<223> OTHER INFORMATION: amino acid "X" can be any amino acid

<400> SEQUENCE: 28

Thr Gly Trp Leu Gln Xaa Asn Gly Ser Trp Tyr Tyr Leu Asn Ala Asn
1 5 10 15

Gly Ala Met Ala
20

<210> SEQ ID NO 29
<211> LENGTH: 17
<212> TYPE: PRT
<213> ORGANISM: Streptococcus pneumoniae

<400> SEQUENCE: 29

Val Asn Thr Thr Val Asp Gly Tyr Lys Val Asn Ala Asn Gly Glu Trp
1 5 10 15

Val

<210> SEQ ID NO 30
<211> LENGTH: 20
<212> TYPE: PRT
<213> ORGANISM: Streptococcus pneumoniae

<400> SEQUENCE: 30

Ile Gly Trp Lys Gln Glu Asn Gly Met Trp Tyr Phe Tyr Asn Thr Asp
1 5 10 15

Gly Ser Met Ala
20

<210> SEQ ID NO 31
<211> LENGTH: 20
<212> TYPE: PRT
<213> ORGANISM: Streptococcus pneumoniae

<400> SEQUENCE: 31

Thr Gly Trp Leu Gln Asn Asn Gly Ser Trp Tyr Tyr Leu Asn Ser Asn
1 5 10 15

Gly Ala Met Ala
20

<210> SEQ ID NO 32
<211> LENGTH: 20
<212> TYPE: PRT
<213> ORGANISM: Streptococcus pneumoniae

<400> SEQUENCE: 32

Thr Gly Trp Leu Gln Tyr Asn Gly Ser Trp Tyr Tyr Leu Asn Ala Asn
1 5 10 15

Gly Ala Met Ala
20

-continued

<210> SEQ ID NO 33
<211> LENGTH: 20
<212> TYPE: PRT
<213> ORGANISM: Streptococcus pneumoniae

<400> SEQUENCE: 33

Thr Gly Trp Leu Gln Tyr Asn Gly Ser Trp Tyr Tyr Leu Asn Ala Asn
1 5 10 15

Gly Ala Met Ala
20

<210> SEQ ID NO 34
<211> LENGTH: 20
<212> TYPE: PRT
<213> ORGANISM: Streptococcus pneumoniae

<400> SEQUENCE: 34

Thr Gly Trp Leu Gln Tyr Asn Gly Ser Trp Tyr Tyr Leu Asn Ala Asn
1 5 10 15

Gly Asp Met Ala
20

<210> SEQ ID NO 35
<211> LENGTH: 20
<212> TYPE: PRT
<213> ORGANISM: Streptococcus pneumoniae

<400> SEQUENCE: 35

Thr Gly Trp Leu Gln Tyr Asn Gly Ser Trp Tyr Tyr Leu Asn Ala Asn
1 5 10 15

Gly Asp Met Ala
20

<210> SEQ ID NO 36
<211> LENGTH: 20
<212> TYPE: PRT
<213> ORGANISM: Streptococcus pneumoniae

<400> SEQUENCE: 36

Thr Gly Trp Ala Lys Val His Gly Ser Trp Tyr Tyr Leu Asn Ala Asn
1 5 10 15

Gly Ser Met Ala
20

<210> SEQ ID NO 37
<211> LENGTH: 21
<212> TYPE: PRT
<213> ORGANISM: Streptococcus pneumoniae

<400> SEQUENCE: 37

Thr Gly Trp Val Lys Asp Gly Glu Thr Trp Tyr Tyr Leu Glu Ala Ser
1 5 10 15

Gly Ser Met Lys Ala
20

<210> SEQ ID NO 38
<211> LENGTH: 20
<212> TYPE: PRT
<213> ORGANISM: Streptococcus pneumoniae

<400> SEQUENCE: 38

-continued

```
Asn Gln Trp Phe Gln Val Ser Asp Lys Trp Tyr Tyr Val Asn Gly Leu
  1               5                  10                  15

Gly Ser Leu Ser
             20


<210> SEQ ID NO 39
<211> LENGTH: 17
<212> TYPE: PRT
<213> ORGANISM: Streptococcus pneumoniae

<400> SEQUENCE: 39

Val Asn Thr Thr Val Asp Gly Tyr Lys Val Asn Ala Asn Gly Glu Trp
  1               5                  10                  15

Val


<210> SEQ ID NO 40
<211> LENGTH: 20
<212> TYPE: PRT
<213> ORGANISM: Streptococcus pneumoniae

<400> SEQUENCE: 40

Thr Gly Trp Leu Gln Tyr Asn Gly Ser Trp Tyr Tyr Leu Asn Ala Asn
  1               5                  10                  15

Gly Ser Met Ala
             20


<210> SEQ ID NO 41
<211> LENGTH: 21
<212> TYPE: PRT
<213> ORGANISM: Streptococcus pneumoniae

<400> SEQUENCE: 41

Lys Thr Gly Trp Lys Gln Glu Asn Gly Asn Trp Tyr Phe Tyr Asn Thr
  1               5                  10                  15

Asp Gly Ser Met Ala
             20


<210> SEQ ID NO 42
<211> LENGTH: 20
<212> TYPE: PRT
<213> ORGANISM: Streptococcus pneumoniae

<400> SEQUENCE: 42

Thr Gly Trp Lys Gln Glu Asn Gly Met Trp Tyr Phe Tyr Asn Thr Asp
  1               5                  10                  15

Gly Ser Met Ala
             20


<210> SEQ ID NO 43
<211> LENGTH: 20
<212> TYPE: PRT
<213> ORGANISM: Streptococcus pneumoniae

<400> SEQUENCE: 43

Ile Gly Trp Lys Gln Glu Asn Gly Met Trp Tyr Phe Tyr Asn Thr Asp
  1               5                  10                  15

Gly Ser Met Ala
             20


<210> SEQ ID NO 44
<211> LENGTH: 21
<212> TYPE: PRT
```

-continued

<213> ORGANISM: Streptococcus pneumoniae

<400> SEQUENCE: 44

Thr Gly Trp Val Lys Asp Gly Asp Thr Trp Tyr Tyr Leu Glu Ala Ser
1 5 10 15

Gly Ala Met Lys Ala
20

<210> SEQ ID NO 45
<211> LENGTH: 21
<212> TYPE: PRT
<213> ORGANISM: Streptococcus pneumoniae

<400> SEQUENCE: 45

Thr Gly Trp Val Lys Asp Gly Asp Thr Trp Tyr Tyr Leu Glu Ala Ser
1 5 10 15

Gly Ala Met Lys Ala
20

<210> SEQ ID NO 46
<211> LENGTH: 21
<212> TYPE: PRT
<213> ORGANISM: Streptococcus pneumoniae

<400> SEQUENCE: 46

Thr Gly Trp Val Lys Asp Gly Glu Thr Trp Tyr Tyr Leu Glu Ala Ser
1 5 10 15

Gly Ser Met Lys Ala
20

<210> SEQ ID NO 47
<211> LENGTH: 20
<212> TYPE: PRT
<213> ORGANISM: Streptococcus pneumoniae

<400> SEQUENCE: 47

Ser Gln Trp Phe Lys Val Ser Asp Lys Trp Tyr Tyr Val Asn Gly Ser
1 5 10 15

Gly Ala Leu Ala
20

<210> SEQ ID NO 48
<211> LENGTH: 20
<212> TYPE: PRT
<213> ORGANISM: Streptococcus pneumoniae

<400> SEQUENCE: 48

Ser Gln Trp Phe Lys Val Ser Asp Lys Trp Tyr Tyr Val Asn Gly Leu
1 5 10 15

Gly Ala Leu Ala
20

<210> SEQ ID NO 49
<211> LENGTH: 20
<212> TYPE: PRT
<213> ORGANISM: Streptococcus pneumoniae

<400> SEQUENCE: 49

Asn Gln Trp Phe Gln Val Ser Asp Lys Trp Tyr Tyr Val Asn Gly Leu
1 5 10 15

Gly Ser Leu Ser
20

-continued

```
<210> SEQ ID NO 50
<211> LENGTH: 18
<212> TYPE: PRT
<213> ORGANISM: Streptococcus pneumoniae

<400> SEQUENCE: 50

Val Asn Thr Thr Val Asp Gly Tyr Gly Val Asn Ala Asn Gly Glu Trp
  1               5                  10                  15

Val Asn


<210> SEQ ID NO 51
<211> LENGTH: 17
<212> TYPE: PRT
<213> ORGANISM: Streptococcus pneumoniae

<400> SEQUENCE: 51

Val Asn Thr Thr Val Asp Gly Tyr Lys Val Asn Ala Asn Gly Glu Trp
  1               5                  10                  15

Val


<210> SEQ ID NO 52
<211> LENGTH: 17
<212> TYPE: PRT
<213> ORGANISM: Streptococcus pneumoniae

<400> SEQUENCE: 52

Val Asn Thr Thr Val Asp Gly Tyr Lys Val Asn Ala Asn Gly Glu Trp
  1               5                  10                  15

Val


<210> SEQ ID NO 53
<211> LENGTH: 1620
<212> TYPE: DNA
<213> ORGANISM: Streptococcus pneumoniae
<220> FEATURE:
<221> NAME/KEY: CDS
<222> LOCATION: (1)..(1617)
<223> OTHER INFORMATION: coding sequence for SpsA

<400> SEQUENCE: 53

atg ttt gca tca aaa agc gaa aga aaa gta cat tat tca att cgt aaa       48
Met Phe Ala Ser Lys Ser Glu Arg Lys Val His Tyr Ser Ile Arg Lys
  1               5                  10                  15

ttt agt att gga gta gct agt gta gct gtt gcc agt ctt gtt atg gga       96
Phe Ser Ile Gly Val Ala Ser Val Ala Val Ala Ser Leu Val Met Gly
             20                  25                  30

agt gtg gtt cat gcg aca gag aac gag gga agt acc caa gca gcc act      144
Ser Val Val His Ala Thr Glu Asn Glu Gly Ser Thr Gln Ala Ala Thr
         35                  40                  45

tct tct aat atg gca aag aca gaa cat agg aaa gct gct aaa caa gtc      192
Ser Ser Asn Met Ala Lys Thr Glu His Arg Lys Ala Ala Lys Gln Val
     50                  55                  60

gtc gat gaa tat ata gaa aaa atg ttg agg gag att caa cta gat aga      240
Val Asp Glu Tyr Ile Glu Lys Met Leu Arg Glu Ile Gln Leu Asp Arg
 65                  70                  75                  80

aga aaa cat acc caa aat gtc gcc tta aac ata aag ttg agc gca att      288
Arg Lys His Thr Gln Asn Val Ala Leu Asn Ile Lys Leu Ser Ala Ile
                 85                  90                  95

aaa acg aag tat ttg cgt gaa tta aat gtt tta gaa gag aag tcg aaa      336
Lys Thr Lys Tyr Leu Arg Glu Leu Asn Val Leu Glu Glu Lys Ser Lys
            100                 105                 110
```

-continued

```
gat gag ttg ccg tca gaa ata aaa gca aag tta gac gca gct ttt gag      384
Asp Glu Leu Pro Ser Glu Ile Lys Ala Lys Leu Asp Ala Ala Phe Glu
        115                 120                 125

aag ttt aaa aaa gat aca ttg aaa cca gga gaa aag gta gca gaa gct      432
Lys Phe Lys Lys Asp Thr Leu Lys Pro Gly Glu Lys Val Ala Glu Ala
    130                 135                 140

aag aag aag gtt gaa gaa gct aag aaa aaa gcc gag gat caa aaa gaa      480
Lys Lys Lys Val Glu Glu Ala Lys Lys Lys Ala Glu Asp Gln Lys Glu
145                 150                 155                 160

gaa gat cgt cgt aac tac cca acc aat act tac aaa acg ctt gaa ctt      528
Glu Asp Arg Arg Asn Tyr Pro Thr Asn Thr Tyr Lys Thr Leu Glu Leu
                165                 170                 175

gaa att gct gag ttc gat gtg aaa gtt aaa gaa gcg gag ctt gaa cta      576
Glu Ile Ala Glu Phe Asp Val Lys Val Lys Glu Ala Glu Leu Glu Leu
            180                 185                 190

gta aaa gag gaa gct aaa gaa ttt cga aac gag ggc aca att aag caa      624
Val Lys Glu Glu Ala Lys Glu Phe Arg Asn Glu Gly Thr Ile Lys Gln
        195                 200                 205

gca aaa gag aaa gtt gag agt aaa aaa gct gag gct aca agg tta gaa      672
Ala Lys Glu Lys Val Glu Ser Lys Lys Ala Glu Ala Thr Arg Leu Glu
    210                 215                 220

aac atc aag aca gat cgt aaa aaa gca gaa gaa gaa gct aaa cga aaa      720
Asn Ile Lys Thr Asp Arg Lys Lys Ala Glu Glu Glu Ala Lys Arg Lys
225                 230                 235                 240

gca gca gaa gaa gat aaa gtt aaa gaa aaa cca gct gaa caa cca caa      768
Ala Ala Glu Glu Asp Lys Val Lys Glu Lys Pro Ala Glu Gln Pro Gln
                245                 250                 255

cca gcg ccg gct act caa cca gaa aaa cca gct cca aaa cca gag aag      816
Pro Ala Pro Ala Thr Gln Pro Glu Lys Pro Ala Pro Lys Pro Glu Lys
            260                 265                 270

cca gct gaa caa cca aaa gca gaa aaa aca gat gat caa caa gct gaa      864
Pro Ala Glu Gln Pro Lys Ala Glu Lys Thr Asp Asp Gln Gln Ala Glu
        275                 280                 285

gaa gac tat gct cgt aga tca gaa gaa gaa tat aat cgc ttg act caa      912
Glu Asp Tyr Ala Arg Arg Ser Glu Glu Glu Tyr Asn Arg Leu Thr Gln
    290                 295                 300

cag caa ccg cca aaa act gaa aaa cca gca caa cca tct act cca aaa      960
Gln Gln Pro Pro Lys Thr Glu Lys Pro Ala Gln Pro Ser Thr Pro Lys
305                 310                 315                 320

aca ggc tgg aaa caa gaa aac ggt atg tgg tac ttc tac aat act gat     1008
Thr Gly Trp Lys Gln Glu Asn Gly Met Trp Tyr Phe Tyr Asn Thr Asp
                325                 330                 335

ggt tca atg gca aca gga tgg ctc caa aac aac ggt tca tgg tac tat     1056
Gly Ser Met Ala Thr Gly Trp Leu Gln Asn Asn Gly Ser Trp Tyr Tyr
            340                 345                 350

cta aac gct aat ggt gct atg gcg aca gga tgg ctc caa aac aat ggt     1104
Leu Asn Ala Asn Gly Ala Met Ala Thr Gly Trp Leu Gln Asn Asn Gly
        355                 360                 365

tca tgg tac tat cta aac gct aat ggt tca atg gca aca gga tgg ctc     1152
Ser Trp Tyr Tyr Leu Asn Ala Asn Gly Ser Met Ala Thr Gly Trp Leu
    370                 375                 380

caa aac aat ggt tca tgg tac tac cta aac gct aat ggt gct atg gcg     1200
Gln Asn Asn Gly Ser Trp Tyr Tyr Leu Asn Ala Asn Gly Ala Met Ala
385                 390                 395                 400

aca gga tgg ctc caa tac aat ggt tca tgg tac tac cta aac agc aat     1248
Thr Gly Trp Leu Gln Tyr Asn Gly Ser Trp Tyr Tyr Leu Asn Ser Asn
                405                 410                 415

ggc gct atg gcg aca gga tgg ctc caa tac aat ggc tca tgg tac tac     1296
Gly Ala Met Ala Thr Gly Trp Leu Gln Tyr Asn Gly Ser Trp Tyr Tyr
```

-continued

```
          420                 425                 430

ctc aac gct aat ggt gat atg gcg aca gga tgg ctc caa aac aac ggt      1344
Leu Asn Ala Asn Gly Asp Met Ala Thr Gly Trp Leu Gln Asn Asn Gly
        435                 440                 445

tca tgg tac tac ctc aac gct aat ggt gat atg gcg aca gga tgg ctc      1392
Ser Trp Tyr Tyr Leu Asn Ala Asn Gly Asp Met Ala Thr Gly Trp Leu
    450                 455                 460

caa tac aac ggt tca tgg tat tac ctc aac gct aat ggt gat atg gcg      1440
Gln Tyr Asn Gly Ser Trp Tyr Tyr Leu Asn Ala Asn Gly Asp Met Ala
465                 470                 475                 480

aca ggt tgg gtg aaa gat gga gat acc tgg tac tat ctt gaa aca tca      1488
Thr Gly Trp Val Lys Asp Gly Asp Thr Trp Tyr Tyr Leu Glu Thr Ser
                485                 490                 495

ggt gct atg aaa gca agc caa tgg ttc aaa gta tca gat aaa tgg tac      1536
Gly Ala Met Lys Ala Ser Gln Trp Phe Lys Val Ser Asp Lys Trp Tyr
            500                 505                 510

tat gtc cat ggc tca agt gcc ctt gca atc aac aca act gta tat ggc      1584
Tyr Val His Gly Ser Ser Ala Leu Ala Ile Asn Thr Thr Val Tyr Gly
        515                 520                 525

tat gga gtc aat gcc aat ggt gaa tgg gta aac taa                      1620
Tyr Gly Val Asn Ala Asn Gly Glu Trp Val Asn
    530                 535


<210> SEQ ID NO 54
<211> LENGTH: 539
<212> TYPE: PRT
<213> ORGANISM: Streptococcus pneumoniae

<400> SEQUENCE: 54

Met Phe Ala Ser Lys Ser Glu Arg Lys Val His Tyr Ser Ile Arg Lys
  1               5                  10                  15

Phe Ser Ile Gly Val Ala Ser Val Ala Val Ala Ser Leu Val Met Gly
             20                  25                  30

Ser Val Val His Ala Thr Glu Asn Glu Gly Ser Thr Gln Ala Ala Thr
         35                  40                  45

Ser Ser Asn Met Ala Lys Thr Glu His Arg Lys Ala Ala Lys Gln Val
     50                  55                  60

Val Asp Glu Tyr Ile Glu Lys Met Leu Arg Glu Ile Gln Leu Asp Arg
 65                  70                  75                  80

Arg Lys His Thr Gln Asn Val Ala Leu Asn Ile Lys Leu Ser Ala Ile
                 85                  90                  95

Lys Thr Lys Tyr Leu Arg Glu Leu Asn Val Leu Glu Glu Lys Ser Lys
            100                 105                 110

Asp Glu Leu Pro Ser Glu Ile Lys Ala Lys Leu Asp Ala Ala Phe Glu
        115                 120                 125

Lys Phe Lys Lys Asp Thr Leu Lys Pro Gly Glu Lys Val Ala Glu Ala
    130                 135                 140

Lys Lys Lys Val Glu Glu Ala Lys Lys Lys Ala Glu Asp Gln Lys Glu
145                 150                 155                 160

Glu Asp Arg Arg Asn Tyr Pro Thr Asn Thr Tyr Lys Thr Leu Glu Leu
                165                 170                 175

Glu Ile Ala Glu Phe Asp Val Lys Val Lys Glu Ala Glu Leu Glu Leu
            180                 185                 190

Val Lys Glu Glu Ala Lys Glu Phe Arg Asn Glu Gly Thr Ile Lys Gln
        195                 200                 205

Ala Lys Glu Lys Val Glu Ser Lys Lys Ala Glu Ala Thr Arg Leu Glu
    210                 215                 220
```

-continued

```
Asn Ile Lys Thr Asp Arg Lys Lys Ala Glu Glu Glu Ala Lys Arg Lys
225                 230                 235                 240

Ala Ala Glu Glu Asp Lys Val Lys Glu Lys Pro Ala Glu Gln Pro Gln
                245                 250                 255

Pro Ala Pro Ala Thr Gln Pro Glu Lys Pro Ala Pro Lys Pro Glu Lys
            260                 265                 270

Pro Ala Glu Gln Pro Lys Ala Glu Lys Thr Asp Asp Gln Gln Ala Glu
        275                 280                 285

Glu Asp Tyr Ala Arg Arg Ser Glu Glu Glu Tyr Asn Arg Leu Thr Gln
    290                 295                 300

Gln Gln Pro Pro Lys Thr Glu Lys Pro Ala Gln Pro Ser Thr Pro Lys
305                 310                 315                 320

Thr Gly Trp Lys Gln Glu Asn Gly Met Trp Tyr Phe Tyr Asn Thr Asp
                325                 330                 335

Gly Ser Met Ala Thr Gly Trp Leu Gln Asn Asn Gly Ser Trp Tyr Tyr
            340                 345                 350

Leu Asn Ala Asn Gly Ala Met Ala Thr Gly Trp Leu Gln Asn Asn Gly
        355                 360                 365

Ser Trp Tyr Tyr Leu Asn Ala Asn Gly Ser Met Ala Thr Gly Trp Leu
    370                 375                 380

Gln Asn Asn Gly Ser Trp Tyr Tyr Leu Asn Ala Asn Gly Ala Met Ala
385                 390                 395                 400

Thr Gly Trp Leu Gln Tyr Asn Gly Ser Trp Tyr Tyr Leu Asn Ser Asn
                405                 410                 415

Gly Ala Met Ala Thr Gly Trp Leu Gln Tyr Asn Gly Ser Trp Tyr Tyr
            420                 425                 430

Leu Asn Ala Asn Gly Asp Met Ala Thr Gly Trp Leu Gln Asn Asn Gly
        435                 440                 445

Ser Trp Tyr Tyr Leu Asn Ala Asn Gly Asp Met Ala Thr Gly Trp Leu
    450                 455                 460

Gln Tyr Asn Gly Ser Trp Tyr Tyr Leu Asn Ala Asn Gly Asp Met Ala
465                 470                 475                 480

Thr Gly Trp Val Lys Asp Gly Asp Thr Trp Tyr Tyr Leu Glu Thr Ser
                485                 490                 495

Gly Ala Met Lys Ala Ser Gln Trp Phe Lys Val Ser Asp Lys Trp Tyr
            500                 505                 510

Tyr Val His Gly Ser Ser Ala Leu Ala Ile Asn Thr Thr Val Tyr Gly
        515                 520                 525

Tyr Gly Val Asn Ala Asn Gly Glu Trp Val Asn
    530                 535


<210> SEQ ID NO 55
<211> LENGTH: 1746
<212> TYPE: DNA
<213> ORGANISM: Streptococcus pneumoniae
<220> FEATURE:
<221> NAME/KEY: CDS
<222> LOCATION: (1)..(1743)
<223> OTHER INFORMATION: additional coding sequence for SpsA

<400> SEQUENCE: 55

atg ttt gca tca aaa agc gaa aga aaa gta cat tat tca att cgt aaa       48
Met Phe Ala Ser Lys Ser Glu Arg Lys Val His Tyr Ser Ile Arg Lys
  1               5                  10                  15

ttt agt att gga gta gct agt gta gct gtt gcc agt ctt gtt atg gga       96
Phe Ser Ile Gly Val Ala Ser Val Ala Val Ala Ser Leu Val Met Gly
```

-continued

```
             20                  25                  30

agt gtg gtt cat gcg aca gag aac gag gga agt acc caa gca gcc act      144
Ser Val Val His Ala Thr Glu Asn Glu Gly Ser Thr Gln Ala Ala Thr
         35                  40                  45

tct tct aat atg gca aag aca gaa cat agg aaa gct gct aaa caa gtc      192
Ser Ser Asn Met Ala Lys Thr Glu His Arg Lys Ala Ala Lys Gln Val
     50                  55                  60

gtc gat gaa tat ata gaa aaa atg ttg agg gag att caa cta gat aga      240
Val Asp Glu Tyr Ile Glu Lys Met Leu Arg Glu Ile Gln Leu Asp Arg
 65                  70                  75                  80

aga aaa cat acc caa aat gtc gcc tta aac ata aag ttg agc gca att      288
Arg Lys His Thr Gln Asn Val Ala Leu Asn Ile Lys Leu Ser Ala Ile
                 85                  90                  95

aaa acg aag tat ttg cgt gaa tta aat gtt tta gaa gag aag tcg aaa      336
Lys Thr Lys Tyr Leu Arg Glu Leu Asn Val Leu Glu Glu Lys Ser Lys
            100                 105                 110

gat gag ttg ccg tca gaa ata aaa gca aag tta gac gca gct ttt gag      384
Asp Glu Leu Pro Ser Glu Ile Lys Ala Lys Leu Asp Ala Ala Phe Glu
        115                 120                 125

aag ttt aaa aaa gat aca ttg aaa cca gga gaa aag gta gca gaa gct      432
Lys Phe Lys Lys Asp Thr Leu Lys Pro Gly Glu Lys Val Ala Glu Ala
    130                 135                 140

aag aag aag gtt gaa gaa gct aag aaa aaa gcc gag gat caa aaa gaa      480
Lys Lys Lys Val Glu Glu Ala Lys Lys Lys Ala Glu Asp Gln Lys Glu
145                 150                 155                 160

gaa gat cgt cgt aac tac cca acc aat act tac aaa acg ctt gaa ctt      528
Glu Asp Arg Arg Asn Tyr Pro Thr Asn Thr Tyr Lys Thr Leu Glu Leu
                165                 170                 175

gaa att gct gag ttc gat gtg aaa gtt aaa gaa gcg gag ctt gaa cta      576
Glu Ile Ala Glu Phe Asp Val Lys Val Lys Glu Ala Glu Leu Glu Leu
            180                 185                 190

gta aaa gag gaa gct aaa gaa tct cga aac gag ggc aca att aag caa      624
Val Lys Glu Glu Ala Lys Glu Ser Arg Asn Glu Gly Thr Ile Lys Gln
        195                 200                 205

gca aaa gag aaa gtt gag agt aaa aaa gct gag gct aca agg tta gaa      672
Ala Lys Glu Lys Val Glu Ser Lys Lys Ala Glu Ala Thr Arg Leu Glu
    210                 215                 220

aac atc aag aca gat cgt aaa aaa gca gaa gaa gaa gct aaa cga aaa      720
Asn Ile Lys Thr Asp Arg Lys Lys Ala Glu Glu Glu Ala Lys Arg Lys
225                 230                 235                 240

gca gat gct aag ttg aag gaa gct aat gta gcg act tca gat caa ggt      768
Ala Asp Ala Lys Leu Lys Glu Ala Asn Val Ala Thr Ser Asp Gln Gly
                245                 250                 255

aaa cca aag ggg cgg gca aaa cga gga gtt cct gga gag cta gca aca      816
Lys Pro Lys Gly Arg Ala Lys Arg Gly Val Pro Gly Glu Leu Ala Thr
            260                 265                 270

cct gat aaa aaa gaa aat gat gcg aag tct tca gat tct agc gta ggt      864
Pro Asp Lys Lys Glu Asn Asp Ala Lys Ser Ser Asp Ser Ser Val Gly
        275                 280                 285

gaa gaa act ctt cca agc tca tcc ctg aaa tca gga aaa aag gta gca      912
Glu Glu Thr Leu Pro Ser Ser Ser Leu Lys Ser Gly Lys Lys Val Ala
    290                 295                 300

gaa gct gag aag aag gtt gaa gaa gct gag aaa aaa gcc aag gat caa      960
Glu Ala Glu Lys Lys Val Glu Glu Ala Glu Lys Lys Ala Lys Asp Gln
305                 310                 315                 320

aaa gaa gaa gat cgc cgt aat tac cca acc aat act tac aaa acg ctt     1008
Lys Glu Glu Asp Arg Arg Asn Tyr Pro Thr Asn Thr Tyr Lys Thr Leu
                325                 330                 335

gac ctt gaa att gct gag tcc gat gtg aaa gtt aaa gaa gcg gag ctt     1056
```

-continued

Asp Leu Glu Ile Ala Glu Ser Asp Val Lys Val Lys Glu Ala Glu Leu
            340                 345                 350 gaa cta gta aaa gag gaa gct aag gaa cct cga gac gag gaa aaa att      1104
Glu Leu Val Lys Glu Glu Ala Lys Glu Pro Arg Asp Glu Glu Lys Ile
        355                 360                 365 aag caa gca aaa gcg aaa gtt gag agt aaa aaa gct gag gct aca agg      1152
Lys Gln Ala Lys Ala Lys Val Glu Ser Lys Lys Ala Glu Ala Thr Arg
    370                 375                 380 tta gaa aac atc aag aca gat cgt aaa aaa gca gaa gaa gaa gct aaa      1200
Leu Glu Asn Ile Lys Thr Asp Arg Lys Lys Ala Glu Glu Glu Ala Lys
385                 390                 395                 400 cga aaa gca gca gaa gaa gat aaa gtt aaa gaa aaa cca gct gaa caa      1248
Arg Lys Ala Ala Glu Glu Asp Lys Val Lys Glu Lys Pro Ala Glu Gln
                405                 410                 415 cca caa cca gcg ccg gct act caa cca gaa aaa cca gct cca aaa cca      1296
Pro Gln Pro Ala Pro Ala Thr Gln Pro Glu Lys Pro Ala Pro Lys Pro
            420                 425                 430 gag aag cca gct gaa caa cca aaa gca gaa aaa aca gat gat caa caa      1344
Glu Lys Pro Ala Glu Gln Pro Lys Ala Glu Lys Thr Asp Asp Gln Gln
        435                 440                 445 gct gaa gaa gac tat gct cgt aga tca gaa gaa gaa tat aat cgc ttg      1392
Ala Glu Glu Asp Tyr Ala Arg Arg Ser Glu Glu Glu Tyr Asn Arg Leu
    450                 455                 460 att caa cag caa ccg cca aaa act gaa aaa cca gca caa cca ttt act      1440
Ile Gln Gln Gln Pro Pro Lys Thr Glu Lys Pro Ala Gln Pro Phe Thr
465                 470                 475                 480 cca aaa aca ggc tgg aaa caa gaa aac ggt atg tgg tac ttc tac aat      1488
Pro Lys Thr Gly Trp Lys Gln Glu Asn Gly Met Trp Tyr Phe Tyr Asn
                485                 490                 495 act gat ggt tca atg gca aca gga tgg ctc caa tac aac ggt tca tgg      1536
Thr Asp Gly Ser Met Ala Thr Gly Trp Leu Gln Tyr Asn Gly Ser Trp
            500                 505                 510 tat tac ctc aac gct aat ggt gat atg gcg aca ggt tgg gtg aaa gat      1584
Tyr Tyr Leu Asn Ala Asn Gly Asp Met Ala Thr Gly Trp Val Lys Asp
        515                 520                 525 gga gat acc tgg tac tat ctt gaa gca tca ggt gct atg aaa gca agc      1632
Gly Asp Thr Trp Tyr Tyr Leu Glu Ala Ser Gly Ala Met Lys Ala Ser
    530                 535                 540 caa tgg ttc aaa gta tca gat aaa tgg tac tat gtc aat ggc tca ggt      1680
Gln Trp Phe Lys Val Ser Asp Lys Trp Tyr Tyr Val Asn Gly Ser Gly
545                 550                 555                 560 gcc ctt gca gtc aac aca act gta gat ggc tat gga gtc aat gcc aat      1728
Ala Leu Ala Val Asn Thr Thr Val Asp Gly Tyr Gly Val Asn Ala Asn
                565                 570                 575 ggt gaa tgg gta aac taa                                              1746
Gly Glu Trp Val Asn
            580

<210> SEQ ID NO 56
<211> LENGTH: 581
<212> TYPE: PRT
<213> ORGANISM: Streptococcus pneumoniae

<400> SEQUENCE: 56

Met Phe Ala Ser Lys Ser Glu Arg Lys Val His Tyr Ser Ile Arg Lys
  1               5                  10                  15

Phe Ser Ile Gly Val Ala Ser Val Ala Val Ala Ser Leu Val Met Gly
             20                  25                  30

Ser Val Val His Ala Thr Glu Asn Glu Gly Ser Thr Gln Ala Ala Thr
         35                  40                  45

-continued

```
Ser Ser Asn Met Ala Lys Thr Glu His Arg Lys Ala Ala Lys Gln Val
    50                  55                  60

Val Asp Glu Tyr Ile Glu Lys Met Leu Arg Glu Ile Gln Leu Asp Arg
65                  70                  75                  80

Arg Lys His Thr Gln Asn Val Ala Leu Asn Ile Lys Leu Ser Ala Ile
                85                  90                  95

Lys Thr Lys Tyr Leu Arg Glu Leu Asn Val Leu Glu Glu Lys Ser Lys
            100                 105                 110

Asp Glu Leu Pro Ser Glu Ile Lys Ala Lys Leu Asp Ala Ala Phe Glu
        115                 120                 125

Lys Phe Lys Lys Asp Thr Leu Lys Pro Gly Glu Lys Val Ala Glu Ala
    130                 135                 140

Lys Lys Lys Val Glu Glu Ala Lys Lys Lys Ala Glu Asp Gln Lys Glu
145                 150                 155                 160

Glu Asp Arg Arg Asn Tyr Pro Thr Asn Thr Tyr Lys Thr Leu Glu Leu
                165                 170                 175

Glu Ile Ala Glu Phe Asp Val Lys Val Lys Glu Ala Glu Leu Glu Leu
            180                 185                 190

Val Lys Glu Glu Ala Lys Glu Ser Arg Asn Glu Gly Thr Ile Lys Gln
        195                 200                 205

Ala Lys Glu Lys Val Glu Ser Lys Lys Ala Glu Ala Thr Arg Leu Glu
    210                 215                 220

Asn Ile Lys Thr Asp Arg Lys Lys Ala Glu Glu Glu Ala Lys Arg Lys
225                 230                 235                 240

Ala Asp Ala Lys Leu Lys Glu Ala Asn Val Ala Thr Ser Asp Gln Gly
                245                 250                 255

Lys Pro Lys Gly Arg Ala Lys Arg Gly Val Pro Gly Glu Leu Ala Thr
            260                 265                 270

Pro Asp Lys Lys Glu Asn Asp Ala Lys Ser Ser Asp Ser Ser Val Gly
        275                 280                 285

Glu Glu Thr Leu Pro Ser Ser Ser Leu Lys Ser Gly Lys Lys Val Ala
    290                 295                 300

Glu Ala Glu Lys Lys Val Glu Glu Ala Glu Lys Lys Ala Lys Asp Gln
305                 310                 315                 320

Lys Glu Glu Asp Arg Arg Asn Tyr Pro Thr Asn Thr Tyr Lys Thr Leu
                325                 330                 335

Asp Leu Glu Ile Ala Glu Ser Asp Val Lys Val Lys Glu Ala Glu Leu
            340                 345                 350

Glu Leu Val Lys Glu Glu Ala Lys Glu Pro Arg Asp Glu Glu Lys Ile
        355                 360                 365

Lys Gln Ala Lys Ala Lys Val Glu Ser Lys Lys Ala Glu Ala Thr Arg
    370                 375                 380

Leu Glu Asn Ile Lys Thr Asp Arg Lys Lys Ala Glu Glu Glu Ala Lys
385                 390                 395                 400

Arg Lys Ala Ala Glu Glu Asp Lys Val Lys Glu Lys Pro Ala Glu Gln
                405                 410                 415

Pro Gln Pro Ala Pro Ala Thr Gln Pro Glu Lys Pro Ala Pro Lys Pro
            420                 425                 430

Glu Lys Pro Ala Glu Gln Pro Lys Ala Glu Lys Thr Asp Asp Gln Gln
        435                 440                 445

Ala Glu Glu Asp Tyr Ala Arg Arg Ser Glu Glu Glu Tyr Asn Arg Leu
    450                 455                 460
```

-continued

```
Ile Gln Gln Gln Pro Pro Lys Thr Glu Lys Pro Ala Gln Pro Phe Thr
465                 470                 475                 480

Pro Lys Thr Gly Trp Lys Gln Glu Asn Gly Met Trp Tyr Phe Tyr Asn
                485                 490                 495

Thr Asp Gly Ser Met Ala Thr Gly Trp Leu Gln Tyr Asn Gly Ser Trp
            500                 505                 510

Tyr Tyr Leu Asn Ala Asn Gly Asp Met Ala Thr Gly Trp Val Lys Asp
        515                 520                 525

Gly Asp Thr Trp Tyr Tyr Leu Glu Ala Ser Gly Ala Met Lys Ala Ser
    530                 535                 540

Gln Trp Phe Lys Val Ser Asp Lys Trp Tyr Tyr Val Asn Gly Ser Gly
545                 550                 555                 560

Ala Leu Ala Val Asn Thr Thr Val Asp Gly Tyr Gly Val Asn Ala Asn
                565                 570                 575

Gly Glu Trp Val Asn
            580


<210> SEQ ID NO 57
<211> LENGTH: 2480
<212> TYPE: DNA
<213> ORGANISM: Streptococcus pneumoniae
<220> FEATURE:
<221> NAME/KEY: CDS
<222> LOCATION: (1)..(1992)
<223> OTHER INFORMATION: coding sequence for CbpA

<400> SEQUENCE: 57

gaa aac gaa gga agt acc caa gca gcc act tct tct aat atg gca aag       48
Glu Asn Glu Gly Ser Thr Gln Ala Ala Thr Ser Ser Asn Met Ala Lys
  1               5                  10                  15

aca gaa cat agg aaa gct gct aaa caa gtc gtc gat gaa tat ata gaa       96
Thr Glu His Arg Lys Ala Ala Lys Gln Val Val Asp Glu Tyr Ile Glu
             20                  25                  30

aaa atg ttg agg gag att caa cta gat aga aga aaa cat acc caa aat      144
Lys Met Leu Arg Glu Ile Gln Leu Asp Arg Arg Lys His Thr Gln Asn
         35                  40                  45

gtc gcc tta aac ata aag ttg agc gca att aaa acg aag tat ttg cgt      192
Val Ala Leu Asn Ile Lys Leu Ser Ala Ile Lys Thr Lys Tyr Leu Arg
     50                  55                  60

gaa tta aat gtt tta gaa gag aag tcg aaa gat gag ttg ccg tca gaa      240
Glu Leu Asn Val Leu Glu Glu Lys Ser Lys Asp Glu Leu Pro Ser Glu
 65                  70                  75                  80

ata aaa gca aag tta gac gca gct ttt gag aag ttt aaa aaa gat aca      288
Ile Lys Ala Lys Leu Asp Ala Ala Phe Glu Lys Phe Lys Lys Asp Thr
                 85                  90                  95

ttg aaa cca gga gaa aag gta gca gaa gct aag aag aag gtt gaa gaa      336
Leu Lys Pro Gly Glu Lys Val Ala Glu Ala Lys Lys Lys Val Glu Glu
            100                 105                 110

gct aag aaa aaa gcc gag gat caa aaa gaa gaa gat cgt cgt aac tac      384
Ala Lys Lys Lys Ala Glu Asp Gln Lys Glu Glu Asp Arg Arg Asn Tyr
        115                 120                 125

cca acc aat act tac aaa acg ctt gaa ctt gaa att gct gag ttc gat      432
Pro Thr Asn Thr Tyr Lys Thr Leu Glu Leu Glu Ile Ala Glu Phe Asp
    130                 135                 140

gtg aaa gtt aaa gaa gcg gag ctt gaa cta gta aaa gag gaa gct aaa      480
Val Lys Val Lys Glu Ala Glu Leu Glu Leu Val Lys Glu Glu Ala Lys
145                 150                 155                 160

gaa tct cga aac gag ggc aca att aag caa gca aaa gag aaa gtt gag      528
Glu Ser Arg Asn Glu Gly Thr Ile Lys Gln Ala Lys Glu Lys Val Glu
                165                 170                 175
```

-continued

```
agt aaa aaa gct gag gct aca agg tta gaa aac atc aag aca gat cgt       576
Ser Lys Lys Ala Glu Ala Thr Arg Leu Glu Asn Ile Lys Thr Asp Arg
            180                 185                 190

aaa aaa gca gaa gaa gaa gct aaa cga aaa gca gat gct aag ttg aag       624
Lys Lys Ala Glu Glu Glu Ala Lys Arg Lys Ala Asp Ala Lys Leu Lys
        195                 200                 205

gaa gct aat gta gcg act tca gat caa ggt aaa cca aag ggg cgg gca       672
Glu Ala Asn Val Ala Thr Ser Asp Gln Gly Lys Pro Lys Gly Arg Ala
    210                 215                 220

aaa cga gga gtt cct gga gag cta gca aca cct gat aaa aaa gaa aat       720
Lys Arg Gly Val Pro Gly Glu Leu Ala Thr Pro Asp Lys Lys Glu Asn
225                 230                 235                 240

gat gcg aag tct tca gat tct agc gta ggt gaa gaa act ctt cca agc       768
Asp Ala Lys Ser Ser Asp Ser Ser Val Gly Glu Glu Thr Leu Pro Ser
                245                 250                 255

tca tcc ctg aaa tca gga aaa aag gta gca gaa gct gag aag aag gtt       816
Ser Ser Leu Lys Ser Gly Lys Lys Val Ala Glu Ala Glu Lys Lys Val
            260                 265                 270

gaa gaa gct gag aaa aaa gcc aag gat caa aaa gaa gaa gat cgc cgt       864
Glu Glu Ala Glu Lys Lys Ala Lys Asp Gln Lys Glu Glu Asp Arg Arg
        275                 280                 285

aac tac cca acc aat act tac aaa acg ctt gac ctt gaa att gct gag       912
Asn Tyr Pro Thr Asn Thr Tyr Lys Thr Leu Asp Leu Glu Ile Ala Glu
    290                 295                 300

tcc gat gtg aaa gtt aaa gaa gcg gag ctt gaa cta gta aaa gag gaa       960
Ser Asp Val Lys Val Lys Glu Ala Glu Leu Glu Leu Val Lys Glu Glu
305                 310                 315                 320

gct aag gaa cct cga gac gag gaa aaa att aag caa gca aaa gcg aaa      1008
Ala Lys Glu Pro Arg Asp Glu Glu Lys Ile Lys Gln Ala Lys Ala Lys
                325                 330                 335

gtt gag agt aaa aaa gct gag gct aca agg tta gaa aac atc aag aca      1056
Val Glu Ser Lys Lys Ala Glu Ala Thr Arg Leu Glu Asn Ile Lys Thr
            340                 345                 350

gat cgt aaa aaa gca gaa gaa gaa gct aaa cga aaa gca gca gaa gaa      1104
Asp Arg Lys Lys Ala Glu Glu Glu Ala Lys Arg Lys Ala Ala Glu Glu
        355                 360                 365

gat aaa gtt aaa gaa aaa cca gct gaa caa cca caa cca gcg ccg gct      1152
Asp Lys Val Lys Glu Lys Pro Ala Glu Gln Pro Gln Pro Ala Pro Ala
    370                 375                 380

act caa cca gaa aaa cca gct cca aaa cca gag aag cca gct gaa caa      1200
Thr Gln Pro Glu Lys Pro Ala Pro Lys Pro Glu Lys Pro Ala Glu Gln
385                 390                 395                 400

cca aaa gca gaa aaa aca gat gat caa caa gct gaa gaa gac tat gct      1248
Pro Lys Ala Glu Lys Thr Asp Asp Gln Gln Ala Glu Glu Asp Tyr Ala
                405                 410                 415

cgt aga tca gaa gaa gaa tat aat cgc ttg act caa cag caa ccg cca      1296
Arg Arg Ser Glu Glu Glu Tyr Asn Arg Leu Thr Gln Gln Gln Pro Pro
            420                 425                 430

aaa act gaa aaa cca gca caa cca tct act cca aaa aca ggc tgg aaa      1344
Lys Thr Glu Lys Pro Ala Gln Pro Ser Thr Pro Lys Thr Gly Trp Lys
        435                 440                 445

caa gaa aac ggt atg tgg tac ttc tac aat act gat ggt tca atg gca      1392
Gln Glu Asn Gly Met Trp Tyr Phe Tyr Asn Thr Asp Gly Ser Met Ala
    450                 455                 460

aca gga tgg ctc caa aac aac ggt tca tgg tac tat cta aac gct aat      1440
Thr Gly Trp Leu Gln Asn Asn Gly Ser Trp Tyr Tyr Leu Asn Ala Asn
465                 470                 475                 480

ggt gct atg gcg aca gga tgg ctc caa aac aat ggt tca tgg tac tat      1488
Gly Ala Met Ala Thr Gly Trp Leu Gln Asn Asn Gly Ser Trp Tyr Tyr
```

-continued

```
                485                 490                 495

cta aac gct aat ggt tca atg gca aca gga tgg ctc caa aac aat ggt     1536
Leu Asn Ala Asn Gly Ser Met Ala Thr Gly Trp Leu Gln Asn Asn Gly
            500                 505                 510

tca tgg tac tac cta aac gct aat ggt gct atg gcg aca gga tgg ctc     1584
Ser Trp Tyr Tyr Leu Asn Ala Asn Gly Ala Met Ala Thr Gly Trp Leu
        515                 520                 525

caa tac aat ggt tca tgg tac tac cta aac agc aat ggc gct atg gcg     1632
Gln Tyr Asn Gly Ser Trp Tyr Tyr Leu Asn Ser Asn Gly Ala Met Ala
    530                 535                 540

aca gga tgg ctc caa tac aat ggc tca tgg tac tac ctc aac gct aat     1680
Thr Gly Trp Leu Gln Tyr Asn Gly Ser Trp Tyr Tyr Leu Asn Ala Asn
545                 550                 555                 560

ggt gat atg gcg aca gga tgg ctc caa aac aac ggt tca tgg tac tac     1728
Gly Asp Met Ala Thr Gly Trp Leu Gln Asn Asn Gly Ser Trp Tyr Tyr
                565                 570                 575

ctc aac gct aat ggt gat atg gcg aca gga tgg ctc caa tac aac ggt     1776
Leu Asn Ala Asn Gly Asp Met Ala Thr Gly Trp Leu Gln Tyr Asn Gly
            580                 585                 590

tca tgg tat tac ctc aac gct aat ggt gat atg gcg aca ggt tgg gtg     1824
Ser Trp Tyr Tyr Leu Asn Ala Asn Gly Asp Met Ala Thr Gly Trp Val
        595                 600                 605

aaa gat gga gat acc tgg tac tat ctt gaa gca tca ggt gct atg aaa     1872
Lys Asp Gly Asp Thr Trp Tyr Tyr Leu Glu Ala Ser Gly Ala Met Lys
    610                 615                 620

gca agc caa tgg ttc aaa gta tca gat aaa tgg tac tat gtc aat ggc     1920
Ala Ser Gln Trp Phe Lys Val Ser Asp Lys Trp Tyr Tyr Val Asn Gly
625                 630                 635                 640

tca ggt gcc ctt gca gtc aac aca act gta gat ggc tat gga gtc aat     1968
Ser Gly Ala Leu Ala Val Asn Thr Thr Val Asp Gly Tyr Gly Val Asn
                645                 650                 655

gcc aat ggt gaa tgg gta aac taa acctaatata actagttaat actgacttcc    2022
Ala Asn Gly Glu Trp Val Asn
            660

tgtaagaact ttttaaagta ttccctacaa ataccatatc ctttcagtag ataatatacc   2082

cttgtaggaa gtttagatta aaaaataact ctgtaatctc tagccggatt tatagcgcta   2142

gagactacgg agttttttg atgaggaaag aatggcggca ttcaagagac tctttaagag    2202

agttacgggt tttaaactat taagccttct ccaattgcaa gaggcttcaa tctctgctag   2262

ggtgctagct tgcgaaatgg ctccacggag tttggcagcg ccagatgttc cacggagata   2322

gtgaggagcg aggccgcgga attcacgaac tgcgacgttt tctcctttga ggttaatcaa   2382

tcgtttcaag tgttcgtagg cgatcttcat cttgtcttca aaggtcaaat caggtaggat   2442

ttctcctgtt tcaaagttta tggtggccct ggttgaag                           2480


<210> SEQ ID NO 58
<211> LENGTH: 663
<212> TYPE: PRT
<213> ORGANISM: Streptococcus pneumoniae

<400> SEQUENCE: 58

Glu Asn Glu Gly Ser Thr Gln Ala Ala Thr Ser Ser Asn Met Ala Lys
  1               5                  10                  15

Thr Glu His Arg Lys Ala Ala Lys Gln Val Val Asp Glu Tyr Ile Glu
            20                  25                  30

Lys Met Leu Arg Glu Ile Gln Leu Asp Arg Arg Lys His Thr Gln Asn
        35                  40                  45
```

-continued

```
Val Ala Leu Asn Ile Lys Leu Ser Ala Ile Lys Thr Lys Tyr Leu Arg
     50                  55                  60

Glu Leu Asn Val Leu Glu Glu Lys Ser Lys Asp Glu Leu Pro Ser Glu
 65                  70                  75                  80

Ile Lys Ala Lys Leu Asp Ala Ala Phe Glu Lys Phe Lys Lys Asp Thr
                 85                  90                  95

Leu Lys Pro Gly Glu Lys Val Ala Glu Ala Lys Lys Lys Val Glu Glu
            100                 105                 110

Ala Lys Lys Lys Ala Glu Asp Gln Lys Glu Glu Asp Arg Arg Asn Tyr
        115                 120                 125

Pro Thr Asn Thr Tyr Lys Thr Leu Glu Leu Glu Ile Ala Glu Phe Asp
    130                 135                 140

Val Lys Val Lys Glu Ala Glu Leu Glu Leu Val Lys Glu Glu Ala Lys
145                 150                 155                 160

Glu Ser Arg Asn Glu Gly Thr Ile Lys Gln Ala Lys Glu Lys Val Glu
                165                 170                 175

Ser Lys Lys Ala Glu Ala Thr Arg Leu Glu Asn Ile Lys Thr Asp Arg
            180                 185                 190

Lys Lys Ala Glu Glu Glu Ala Lys Arg Lys Ala Asp Ala Lys Leu Lys
        195                 200                 205

Glu Ala Asn Val Ala Thr Ser Asp Gln Gly Lys Pro Lys Gly Arg Ala
    210                 215                 220

Lys Arg Gly Val Pro Gly Glu Leu Ala Thr Pro Asp Lys Lys Glu Asn
225                 230                 235                 240

Asp Ala Lys Ser Ser Asp Ser Ser Val Gly Glu Glu Thr Leu Pro Ser
                245                 250                 255

Ser Ser Leu Lys Ser Gly Lys Lys Val Ala Glu Ala Glu Lys Lys Val
            260                 265                 270

Glu Glu Ala Glu Lys Lys Ala Lys Asp Gln Lys Glu Glu Asp Arg Arg
        275                 280                 285

Asn Tyr Pro Thr Asn Thr Tyr Lys Thr Leu Asp Leu Glu Ile Ala Glu
    290                 295                 300

Ser Asp Val Lys Val Lys Glu Ala Glu Leu Glu Leu Val Lys Glu Glu
305                 310                 315                 320

Ala Lys Glu Pro Arg Asp Glu Glu Lys Ile Lys Gln Ala Lys Ala Lys
                325                 330                 335

Val Glu Ser Lys Lys Ala Glu Ala Thr Arg Leu Glu Asn Ile Lys Thr
            340                 345                 350

Asp Arg Lys Lys Ala Glu Glu Glu Ala Lys Arg Lys Ala Ala Glu Glu
        355                 360                 365

Asp Lys Val Lys Glu Lys Pro Ala Glu Gln Pro Gln Pro Ala Pro Ala
    370                 375                 380

Thr Gln Pro Glu Lys Pro Ala Pro Lys Pro Glu Lys Pro Ala Glu Gln
385                 390                 395                 400

Pro Lys Ala Glu Lys Thr Asp Asp Gln Gln Ala Glu Glu Asp Tyr Ala
                405                 410                 415

Arg Arg Ser Glu Glu Glu Tyr Asn Arg Leu Thr Gln Gln Gln Pro Pro
            420                 425                 430

Lys Thr Glu Lys Pro Ala Gln Pro Ser Thr Pro Lys Thr Gly Trp Lys
        435                 440                 445

Gln Glu Asn Gly Met Trp Tyr Phe Tyr Asn Thr Asp Gly Ser Met Ala
    450                 455                 460

Thr Gly Trp Leu Gln Asn Asn Gly Ser Trp Tyr Tyr Leu Asn Ala Asn
```

-continued

```
465                 470                 475                 480

Gly Ala Met Ala Thr Gly Trp Leu Gln Asn Asn Gly Ser Trp Tyr Tyr
                485                 490                 495

Leu Asn Ala Asn Gly Ser Met Ala Thr Gly Trp Leu Gln Asn Asn Gly
            500                 505                 510

Ser Trp Tyr Tyr Leu Asn Ala Asn Gly Ala Met Ala Thr Gly Trp Leu
        515                 520                 525

Gln Tyr Asn Gly Ser Trp Tyr Tyr Leu Asn Ser Asn Gly Ala Met Ala
    530                 535                 540

Thr Gly Trp Leu Gln Tyr Asn Gly Ser Trp Tyr Tyr Leu Asn Ala Asn
545                 550                 555                 560

Gly Asp Met Ala Thr Gly Trp Leu Gln Asn Asn Gly Ser Trp Tyr Tyr
                565                 570                 575

Leu Asn Ala Asn Gly Asp Met Ala Thr Gly Trp Leu Gln Tyr Asn Gly
            580                 585                 590

Ser Trp Tyr Tyr Leu Asn Ala Asn Gly Asp Met Ala Thr Gly Trp Val
        595                 600                 605

Lys Asp Gly Asp Thr Trp Tyr Tyr Leu Glu Ala Ser Gly Ala Met Lys
    610                 615                 620

Ala Ser Gln Trp Phe Lys Val Ser Asp Lys Trp Tyr Tyr Val Asn Gly
625                 630                 635                 640

Ser Gly Ala Leu Ala Val Asn Thr Thr Val Asp Gly Tyr Gly Val Asn
                645                 650                 655

Ala Asn Gly Glu Trp Val Asn
            660


<210> SEQ ID NO 59
<211> LENGTH: 3463
<212> TYPE: DNA
<213> ORGANISM: Streptococcus pneumoniae
<220> FEATURE:
<221> NAME/KEY: CDS
<222> LOCATION: (319)..(3105)
<223> OTHER INFORMATION: coding sequence for PspA

<400> SEQUENCE: 59

aagcttatgc ttgtcaataa tcacaaatat gtagatcata tcttgtttag gacagtaaaa      60

catcctaatt actttttaaa tattttacct gagttgattg gcttgacctt gttgagtcat     120

gcctatatga cttttgtttt agtttttcca gtttatgcag ttattttgta tcgacgaata     180

gctgaagagg aaaagttatt acatgaagtt ataatcccaa atggaagcat aaagagataa     240

atacaaaatt cgatttatat acagttcata ttgaagtgat atagtaaggt taaagaaaaa     300

atatagaagg aaataaac atg ttt gca tca aaa agc gaa aga aaa gta cat       351
                    Met Phe Ala Ser Lys Ser Glu Arg Lys Val His
                      1               5                  10

tat tca att cgt aaa ttt agt att gga gta gct agt gta gct gtt gcc       399
Tyr Ser Ile Arg Lys Phe Ser Ile Gly Val Ala Ser Val Ala Val Ala
            15                  20                  25

agc ttg ttc tta gga gga gta gtc cat gca gaa ggg gtt aga agt ggg       447
Ser Leu Phe Leu Gly Gly Val Val His Ala Glu Gly Val Arg Ser Gly
        30                  35                  40

aat aac ctc acg gtt aca tct agt ggg caa gat ata tcg aag aag tat       495
Asn Asn Leu Thr Val Thr Ser Ser Gly Gln Asp Ile Ser Lys Lys Tyr
     45                  50                  55

gct gat gaa gtc gag tcg cat cta gaa agt ata ttg aag gat gtc aaa       543
Ala Asp Glu Val Glu Ser His Leu Glu Ser Ile Leu Lys Asp Val Lys
 60                  65                  70                  75
```

-continued

```
aaa aat ttg aaa aaa gtt caa cat acc caa aat gtc ggc tta att aca      591
Lys Asn Leu Lys Lys Val Gln His Thr Gln Asn Val Gly Leu Ile Thr
                 80                  85                  90

aag ttg agc gaa att aaa aag aag tat ttg tat gac tta aaa gtt aat      639
Lys Leu Ser Glu Ile Lys Lys Lys Tyr Leu Tyr Asp Leu Lys Val Asn
             95                 100                 105

gtt tta tcg gaa gct gag ttg acg tca aaa aca aaa gaa aca aaa gaa      687
Val Leu Ser Glu Ala Glu Leu Thr Ser Lys Thr Lys Glu Thr Lys Glu
        110                 115                 120

aag tta acc gca act ttt gag cag ttt aaa aaa gat aca tta cca aca      735
Lys Leu Thr Ala Thr Phe Glu Gln Phe Lys Lys Asp Thr Leu Pro Thr
    125                 130                 135

gaa cca gaa aaa aag gta gca gaa gct cag aag aag gtt gaa gaa gct      783
Glu Pro Glu Lys Lys Val Ala Glu Ala Gln Lys Lys Val Glu Glu Ala
140                 145                 150                 155

aag aaa aaa gcc gag gat caa aaa gaa aaa gat cgc cgt aac tac cca      831
Lys Lys Lys Ala Glu Asp Gln Lys Glu Lys Asp Arg Arg Asn Tyr Pro
                160                 165                 170

acc att act tac aaa acg ctt gaa ctt gaa att gct gag tcc gat gtg      879
Thr Ile Thr Tyr Lys Thr Leu Glu Leu Glu Ile Ala Glu Ser Asp Val
            175                 180                 185

gaa gtt aaa aaa gcg gag ctt gaa cta gta aaa gtg aaa gct aag gaa      927
Glu Val Lys Lys Ala Glu Leu Glu Leu Val Lys Val Lys Ala Lys Glu
        190                 195                 200

tct caa gac gag gaa aaa att aag caa gca gaa gcg gaa gtt gag agt      975
Ser Gln Asp Glu Glu Lys Ile Lys Gln Ala Glu Ala Glu Val Glu Ser
    205                 210                 215

aaa caa gct gag gct aca agg tta aaa aaa atc aag aca gat cgt gaa     1023
Lys Gln Ala Glu Ala Thr Arg Leu Lys Lys Ile Lys Thr Asp Arg Glu
220                 225                 230                 235

gaa gct aaa cga aaa gca gat gct aag ttg aag gaa gct gtt gaa aag     1071
Glu Ala Lys Arg Lys Ala Asp Ala Lys Leu Lys Glu Ala Val Glu Lys
                240                 245                 250

aat gta gcg act tca gag caa gat aaa cca aag agg cgg gca aaa cga     1119
Asn Val Ala Thr Ser Glu Gln Asp Lys Pro Lys Arg Arg Ala Lys Arg
            255                 260                 265

gga gtt tct gga gag cta gca aca cct gat aaa aaa gaa aat gat gcg     1167
Gly Val Ser Gly Glu Leu Ala Thr Pro Asp Lys Lys Glu Asn Asp Ala
        270                 275                 280

aag tct tca gat tct agc gta ggt gaa gaa act ctt cca agc cca tcc     1215
Lys Ser Ser Asp Ser Ser Val Gly Glu Glu Thr Leu Pro Ser Pro Ser
    285                 290                 295

ctt aat atg gca aat gaa agt cag aca gaa cat agg aaa gat gtc gat     1263
Leu Asn Met Ala Asn Glu Ser Gln Thr Glu His Arg Lys Asp Val Asp
300                 305                 310                 315

gaa tat ata aaa aaa atg ttg agt gag atc caa tta gat aga aga aaa     1311
Glu Tyr Ile Lys Lys Met Leu Ser Glu Ile Gln Leu Asp Arg Arg Lys
                320                 325                 330

cat acc caa aat gtc aac tta aac ata aag ttg agc gca att aaa acg     1359
His Thr Gln Asn Val Asn Leu Asn Ile Lys Leu Ser Ala Ile Lys Thr
            335                 340                 345

aag tat ttg tat gaa tta agt gtt tta aaa gag aac tcg aaa aaa gaa     1407
Lys Tyr Leu Tyr Glu Leu Ser Val Leu Lys Glu Asn Ser Lys Lys Glu
        350                 355                 360

gag ttg acg tca aaa acc aaa gca gag tta acc gca gct ttt gag cag     1455
Glu Leu Thr Ser Lys Thr Lys Ala Glu Leu Thr Ala Ala Phe Glu Gln
    365                 370                 375

ttt aaa aaa gat aca ttg aaa cca gaa aaa aag gta gca gaa gct gag     1503
Phe Lys Lys Asp Thr Leu Lys Pro Glu Lys Lys Val Ala Glu Ala Glu
```

-continued

```
380                 385                 390                 395

aag aag gtt gaa gaa gct aag aaa aaa gcc aag gat caa aaa gaa gaa     1551
Lys Lys Val Glu Glu Ala Lys Lys Lys Ala Lys Asp Gln Lys Glu Glu
                400                 405                 410

gat cgc cgt aac tac cca acc aat act tac aaa acg ctt gaa ctt gaa     1599
Asp Arg Arg Asn Tyr Pro Thr Asn Thr Tyr Lys Thr Leu Glu Leu Glu
            415                 420                 425

att gct gag tcc gat gtg aaa gtt aaa gaa gcg gag ctt gaa cta gta     1647
Ile Ala Glu Ser Asp Val Lys Val Lys Glu Ala Glu Leu Glu Leu Val
        430                 435                 440

aaa gag gaa gct aac gaa tct cga aac gag gaa aaa att aag caa gca     1695
Lys Glu Glu Ala Asn Glu Ser Arg Asn Glu Glu Lys Ile Lys Gln Ala
    445                 450                 455

aaa gag aaa gtt gag agt aaa aaa gct gag gct aca agg tta gaa aaa     1743
Lys Glu Lys Val Glu Ser Lys Lys Ala Glu Ala Thr Arg Leu Glu Lys
460                 465                 470                 475

atc aag aca gat cgt aaa aaa gca gaa gaa gaa gct aaa cga aaa gca     1791
Ile Lys Thr Asp Arg Lys Lys Ala Glu Glu Glu Ala Lys Arg Lys Ala
                480                 485                 490

gaa gaa tct gag aaa aaa gct gct gaa gcc aaa caa aaa gtg gat gct     1839
Glu Glu Ser Glu Lys Lys Ala Ala Glu Ala Lys Gln Lys Val Asp Ala
            495                 500                 505

gaa gaa tat gct ctt gaa gct aaa atc gct gag ttg gaa tat gaa gtt     1887
Glu Glu Tyr Ala Leu Glu Ala Lys Ile Ala Glu Leu Glu Tyr Glu Val
        510                 515                 520

cag aga cta gaa aaa gag ctc aaa gag att gat gag tct gac tca gaa     1935
Gln Arg Leu Glu Lys Glu Leu Lys Glu Ile Asp Glu Ser Asp Ser Glu
    525                 530                 535

gat tat ctt aaa gaa ggc ctc cgt gct cct ctt caa tct aaa ttg gat     1983
Asp Tyr Leu Lys Glu Gly Leu Arg Ala Pro Leu Gln Ser Lys Leu Asp
540                 545                 550                 555

acc aaa aaa gct aaa cta tca aaa ctt gaa gag ttg agt gat aag att     2031
Thr Lys Lys Ala Lys Leu Ser Lys Leu Glu Glu Leu Ser Asp Lys Ile
                560                 565                 570

gat gag tta gac gct gaa att gca aaa ctt gaa gtt caa ctt aaa gat     2079
Asp Glu Leu Asp Ala Glu Ile Ala Lys Leu Glu Val Gln Leu Lys Asp
            575                 580                 585

gct gaa gga aac aat aat gta gaa gcc tac ttt aaa gaa ggt tta gag     2127
Ala Glu Gly Asn Asn Asn Val Glu Ala Tyr Phe Lys Glu Gly Leu Glu
        590                 595                 600

aaa act act gct gag aaa aaa gct gaa tta gaa aaa gct gaa gct gac     2175
Lys Thr Thr Ala Glu Lys Lys Ala Glu Leu Glu Lys Ala Glu Ala Asp
    605                 610                 615

ctt aag aaa gca gtt gat gag cca gaa act cca gct ccg gct cct caa     2223
Leu Lys Lys Ala Val Asp Glu Pro Glu Thr Pro Ala Pro Ala Pro Gln
620                 625                 630                 635

cca gct cca gct cca gaa aaa cca gct gaa aaa cca gct cca gct cca     2271
Pro Ala Pro Ala Pro Glu Lys Pro Ala Glu Lys Pro Ala Pro Ala Pro
                640                 645                 650

gaa aaa cca gct cca gct cca gaa aaa cca gct cca gct cca gaa aaa     2319
Glu Lys Pro Ala Pro Ala Pro Glu Lys Pro Ala Pro Ala Pro Glu Lys
            655                 660                 665

cca gct cca gct cca gaa aaa cca gct cca gct cca gaa aaa cca gct     2367
Pro Ala Pro Ala Pro Glu Lys Pro Ala Pro Ala Pro Glu Lys Pro Ala
        670                 675                 680

cca act cca gaa act cca aaa aca ggc tgg aaa caa gaa aac ggt atg     2415
Pro Thr Pro Glu Thr Pro Lys Thr Gly Trp Lys Gln Glu Asn Gly Met
    685                 690                 695

tgg tac ttc tac aat act gat ggt tca atg gca aca ggc tgg ctc caa     2463
```

-continued

```
Trp Tyr Phe Tyr Asn Thr Asp Gly Ser Met Ala Thr Gly Trp Leu Gln
700                 705                 710                 715

aac aat ggc tca tgg tac tac ctc aac agc aat ggc gct atg gcg aca      2511
Asn Asn Gly Ser Trp Tyr Tyr Leu Asn Ser Asn Gly Ala Met Ala Thr
                720                 725                 730

gga tgg ctc caa aac aat ggc tca tgg tac tac ctc aac agc aat ggc      2559
Gly Trp Leu Gln Asn Asn Gly Ser Trp Tyr Tyr Leu Asn Ser Asn Gly
            735                 740                 745

gct atg gcg aca gga tgg ctc caa tac aat ggt tca tgg tac tac ctc      2607
Ala Met Ala Thr Gly Trp Leu Gln Tyr Asn Gly Ser Trp Tyr Tyr Leu
        750                 755                 760

aac gct aat ggt gat atg gcg aca gga tgg ctc caa tac aat ggt tca      2655
Asn Ala Asn Gly Asp Met Ala Thr Gly Trp Leu Gln Tyr Asn Gly Ser
    765                 770                 775

tgg tac tac ctc aac gct aat ggt gat atg gcg aca gga tgg ttc caa      2703
Trp Tyr Tyr Leu Asn Ala Asn Gly Asp Met Ala Thr Gly Trp Phe Gln
780                 785                 790                 795

tac aat ggt tca tgg tac tac ctc aac gct aat ggt gat atg gcg aca      2751
Tyr Asn Gly Ser Trp Tyr Tyr Leu Asn Ala Asn Gly Asp Met Ala Thr
                800                 805                 810

gga tgg ttc caa tac aat ggt tca tgg tac tac ctc aac gct aat ggt      2799
Gly Trp Phe Gln Tyr Asn Gly Ser Trp Tyr Tyr Leu Asn Ala Asn Gly
            815                 820                 825

gat atg gcg aca gga tgg ctc caa tac aat ggt tca tgg tac tac cta      2847
Asp Met Ala Thr Gly Trp Leu Gln Tyr Asn Gly Ser Trp Tyr Tyr Leu
        830                 835                 840

aac agc aat ggt gct atg gta aca gga tgg ctc caa aac aat ggc tca      2895
Asn Ser Asn Gly Ala Met Val Thr Gly Trp Leu Gln Asn Asn Gly Ser
    845                 850                 855

tgg tac tac cta aac gct aac ggt tca atg gca aca gat tgg gtg aaa      2943
Trp Tyr Tyr Leu Asn Ala Asn Gly Ser Met Ala Thr Asp Trp Val Lys
860                 865                 870                 875

gat gga gat acc tgg tac tat ctt gaa gca tca ggt gct atg aaa gca      2991
Asp Gly Asp Thr Trp Tyr Tyr Leu Glu Ala Ser Gly Ala Met Lys Ala
                880                 885                 890

agc caa tgg ttc aaa gta tca gat aaa tgg tac tat gtc aat ggc tca      3039
Ser Gln Trp Phe Lys Val Ser Asp Lys Trp Tyr Tyr Val Asn Gly Ser
            895                 900                 905

ggt gcc ctt gca gtc aac aca act gta gat agc tat aga gtc aat gcc      3087
Gly Ala Leu Ala Val Asn Thr Thr Val Asp Ser Tyr Arg Val Asn Ala
        910                 915                 920

aat ggt gaa tgg gta aac taaacttaat ataactagtt aatactgact             3135
Asn Gly Glu Trp Val Asn
    925

tcctgtaaga actctttaaa gtattcccta caaataccat atcctttcag tagataatat   3195

acccttgtag gaagtttaga ttaaaaaata actctgtaat ctctagccgg atttatagcg   3255

ctagagacta cggagttttt ttgatgagga aagaatggcg gcattcaaga gactctttaa   3315

gagagttacg ggttttaaac tattaagctt tctccaattg caagagggct tcaatctctg   3375

ctaggtgcta gcttgcgaaa tggctcccac ggagtttggc rgcgccagat gttccacgga   3435

ggtagtgagg agcgaggccg cggaattc                                        3463
```

<210> SEQ ID NO 60
<211> LENGTH: 929
<212> TYPE: PRT
<213> ORGANISM: Streptococcus pneumoniae

<400> SEQUENCE: 60

-continued

```
Met Phe Ala Ser Lys Ser Glu Arg Lys Val His Tyr Ser Ile Arg Lys
  1               5                  10                  15

Phe Ser Ile Gly Val Ala Ser Val Ala Val Ala Ser Leu Phe Leu Gly
             20                  25                  30

Gly Val Val His Ala Glu Gly Val Arg Ser Gly Asn Asn Leu Thr Val
         35                  40                  45

Thr Ser Ser Gly Gln Asp Ile Ser Lys Lys Tyr Ala Asp Glu Val Glu
     50                  55                  60

Ser His Leu Glu Ser Ile Leu Lys Asp Val Lys Lys Asn Leu Lys Lys
 65                  70                  75                  80

Val Gln His Thr Gln Asn Val Gly Leu Ile Thr Lys Leu Ser Glu Ile
                 85                  90                  95

Lys Lys Lys Tyr Leu Tyr Asp Leu Lys Val Asn Val Leu Ser Glu Ala
            100                 105                 110

Glu Leu Thr Ser Lys Thr Lys Glu Thr Lys Glu Lys Leu Thr Ala Thr
        115                 120                 125

Phe Glu Gln Phe Lys Lys Asp Thr Leu Pro Thr Glu Pro Glu Lys Lys
    130                 135                 140

Val Ala Glu Ala Gln Lys Lys Val Glu Glu Ala Lys Lys Lys Ala Glu
145                 150                 155                 160

Asp Gln Lys Glu Lys Asp Arg Arg Asn Tyr Pro Thr Ile Thr Tyr Lys
                165                 170                 175

Thr Leu Glu Leu Glu Ile Ala Glu Ser Asp Val Glu Val Lys Lys Ala
            180                 185                 190

Glu Leu Glu Leu Val Lys Val Lys Ala Lys Glu Ser Gln Asp Glu Glu
        195                 200                 205

Lys Ile Lys Gln Ala Glu Ala Glu Val Glu Ser Lys Gln Ala Glu Ala
    210                 215                 220

Thr Arg Leu Lys Lys Ile Lys Thr Asp Arg Glu Glu Ala Lys Arg Lys
225                 230                 235                 240

Ala Asp Ala Lys Leu Lys Glu Ala Val Glu Lys Asn Val Ala Thr Ser
                245                 250                 255

Glu Gln Asp Lys Pro Lys Arg Arg Ala Lys Arg Gly Val Ser Gly Glu
            260                 265                 270

Leu Ala Thr Pro Asp Lys Lys Glu Asn Asp Ala Lys Ser Ser Asp Ser
        275                 280                 285

Ser Val Gly Glu Glu Thr Leu Pro Ser Pro Ser Leu Asn Met Ala Asn
    290                 295                 300

Glu Ser Gln Thr Glu His Arg Lys Asp Val Asp Glu Tyr Ile Lys Lys
305                 310                 315                 320

Met Leu Ser Glu Ile Gln Leu Asp Arg Arg Lys His Thr Gln Asn Val
                325                 330                 335

Asn Leu Asn Ile Lys Leu Ser Ala Ile Lys Thr Lys Tyr Leu Tyr Glu
            340                 345                 350

Leu Ser Val Leu Lys Glu Asn Ser Lys Lys Glu Glu Leu Thr Ser Lys
        355                 360                 365

Thr Lys Ala Glu Leu Thr Ala Ala Phe Glu Gln Phe Lys Lys Asp Thr
    370                 375                 380

Leu Lys Pro Glu Lys Lys Val Ala Glu Ala Glu Lys Lys Val Glu Glu
385                 390                 395                 400

Ala Lys Lys Lys Ala Lys Asp Gln Lys Glu Glu Asp Arg Arg Asn Tyr
                405                 410                 415

Pro Thr Asn Thr Tyr Lys Thr Leu Glu Leu Glu Ile Ala Glu Ser Asp
```

-continued

```
            420                 425                 430

Val Lys Val Lys Glu Ala Glu Leu Glu Leu Val Lys Glu Glu Ala Asn
        435                 440                 445

Glu Ser Arg Asn Glu Glu Lys Ile Lys Gln Ala Lys Glu Lys Val Glu
    450                 455                 460

Ser Lys Lys Ala Glu Ala Thr Arg Leu Glu Lys Ile Lys Thr Asp Arg
465                 470                 475                 480

Lys Lys Ala Glu Glu Glu Ala Lys Arg Lys Ala Glu Glu Ser Glu Lys
                485                 490                 495

Lys Ala Ala Glu Ala Lys Gln Lys Val Asp Ala Glu Glu Tyr Ala Leu
            500                 505                 510

Glu Ala Lys Ile Ala Glu Leu Glu Tyr Glu Val Gln Arg Leu Glu Lys
        515                 520                 525

Glu Leu Lys Glu Ile Asp Glu Ser Asp Ser Glu Asp Tyr Leu Lys Glu
    530                 535                 540

Gly Leu Arg Ala Pro Leu Gln Ser Lys Leu Asp Thr Lys Lys Ala Lys
545                 550                 555                 560

Leu Ser Lys Leu Glu Glu Leu Ser Asp Lys Ile Asp Glu Leu Asp Ala
                565                 570                 575

Glu Ile Ala Lys Leu Glu Val Gln Leu Lys Asp Ala Glu Gly Asn Asn
            580                 585                 590

Asn Val Glu Ala Tyr Phe Lys Glu Gly Leu Glu Lys Thr Thr Ala Glu
        595                 600                 605

Lys Lys Ala Glu Leu Glu Lys Ala Glu Ala Asp Leu Lys Lys Ala Val
    610                 615                 620

Asp Glu Pro Glu Thr Pro Ala Pro Ala Pro Gln Pro Ala Pro Ala Pro
625                 630                 635                 640

Glu Lys Pro Ala Glu Lys Pro Ala Pro Ala Pro Glu Lys Pro Ala Pro
                645                 650                 655

Ala Pro Glu Lys Pro Ala Pro Ala Pro Glu Lys Pro Ala Pro Ala Pro
            660                 665                 670

Glu Lys Pro Ala Pro Ala Pro Glu Lys Pro Ala Pro Thr Pro Glu Thr
        675                 680                 685

Pro Lys Thr Gly Trp Lys Gln Glu Asn Gly Met Trp Tyr Phe Tyr Asn
    690                 695                 700

Thr Asp Gly Ser Met Ala Thr Gly Trp Leu Gln Asn Asn Gly Ser Trp
705                 710                 715                 720

Tyr Tyr Leu Asn Ser Asn Gly Ala Met Ala Thr Gly Trp Leu Gln Asn
                725                 730                 735

Asn Gly Ser Trp Tyr Tyr Leu Asn Ser Asn Gly Ala Met Ala Thr Gly
            740                 745                 750

Trp Leu Gln Tyr Asn Gly Ser Trp Tyr Tyr Leu Asn Ala Asn Gly Asp
        755                 760                 765

Met Ala Thr Gly Trp Leu Gln Tyr Asn Gly Ser Trp Tyr Tyr Leu Asn
    770                 775                 780

Ala Asn Gly Asp Met Ala Thr Gly Trp Phe Gln Tyr Asn Gly Ser Trp
785                 790                 795                 800

Tyr Tyr Leu Asn Ala Asn Gly Asp Met Ala Thr Gly Trp Phe Gln Tyr
                805                 810                 815

Asn Gly Ser Trp Tyr Tyr Leu Asn Ala Asn Gly Asp Met Ala Thr Gly
            820                 825                 830

Trp Leu Gln Tyr Asn Gly Ser Trp Tyr Tyr Leu Asn Ser Asn Gly Ala
        835                 840                 845
```

-continued

```
Met Val Thr Gly Trp Leu Gln Asn Asn Gly Ser Trp Tyr Tyr Leu Asn
    850                 855                 860

Ala Asn Gly Ser Met Ala Thr Asp Trp Val Lys Asp Gly Asp Thr Trp
865                 870                 875                 880

Tyr Tyr Leu Glu Ala Ser Gly Ala Met Lys Ala Ser Gln Trp Phe Lys
                885                 890                 895

Val Ser Asp Lys Trp Tyr Tyr Val Asn Gly Ser Gly Ala Leu Ala Val
            900                 905                 910

Asn Thr Thr Val Asp Ser Tyr Arg Val Asn Ala Asn Gly Glu Trp Val
        915                 920                 925

Asn


<210> SEQ ID NO 61
<211> LENGTH: 690
<212> TYPE: PRT
<213> ORGANISM: Streptococcus pneumoniae

<400> SEQUENCE: 61

Met Phe Ala Ser Lys Ser Glu Arg Lys Val His Tyr Ser Ile Arg Lys
  1               5                  10                  15

Phe Ser Ile Gly Val Ala Ser Val Ala Val Ala Ser Leu Phe Leu Gly
             20                  25                  30

Gly Val Val His Ala Glu Gly Val Arg Ser Gly Asn Asn Leu Thr Val
         35                  40                  45

Thr Ser Ser Gly Gln Asp Ile Ser Lys Lys Tyr Ala Asp Glu Val Glu
     50                  55                  60

Ser His Leu Glu Ser Ile Leu Lys Asp Val Lys Lys Asn Leu Lys Lys
 65                  70                  75                  80

Val Gln His Thr Gln Asn Val Gly Leu Ile Thr Lys Leu Ser Glu Ile
                 85                  90                  95

Lys Lys Lys Tyr Leu Tyr Asp Leu Lys Val Asn Val Leu Ser Glu Ala
            100                 105                 110

Glu Leu Thr Ser Lys Thr Lys Glu Thr Lys Glu Lys Leu Thr Ala Thr
        115                 120                 125

Phe Glu Gln Phe Lys Lys Asp Thr Leu Pro Thr Glu Pro Glu Lys Lys
    130                 135                 140

Val Ala Glu Ala Gln Lys Lys Val Glu Glu Ala Lys Lys Lys Ala Glu
145                 150                 155                 160

Asp Gln Lys Glu Lys Asp Arg Arg Asn Tyr Pro Thr Ile Thr Tyr Lys
                165                 170                 175

Thr Leu Glu Leu Glu Ile Ala Glu Ser Asp Val Glu Val Lys Lys Ala
            180                 185                 190

Glu Leu Glu Leu Val Lys Val Lys Ala Lys Glu Ser Gln Asp Glu Glu
        195                 200                 205

Lys Ile Lys Gln Ala Glu Ala Glu Val Glu Ser Lys Gln Ala Glu Ala
    210                 215                 220

Thr Arg Leu Lys Lys Ile Lys Thr Asp Arg Glu Glu Ala Lys Arg Lys
225                 230                 235                 240

Ala Asp Ala Lys Leu Lys Glu Ala Val Glu Lys Asn Val Ala Thr Ser
                245                 250                 255

Glu Gln Asp Lys Pro Lys Arg Arg Ala Lys Arg Gly Val Ser Gly Glu
            260                 265                 270

Leu Ala Thr Pro Asp Lys Lys Glu Asn Asp Ala Lys Ser Ser Asp Ser
        275                 280                 285
```

-continued

```
Ser Val Gly Glu Glu Thr Leu Pro Ser Pro Ser Leu Asn Met Ala Asn
    290                 295                 300

Glu Ser Gln Thr Glu His Arg Lys Asp Val Asp Glu Tyr Ile Lys Lys
305                 310                 315                 320

Met Leu Ser Glu Ile Gln Leu Asp Arg Arg Lys His Thr Gln Asn Val
                325                 330                 335

Asn Leu Asn Ile Lys Leu Ser Ala Ile Lys Thr Lys Tyr Leu Tyr Glu
            340                 345                 350

Leu Ser Val Leu Lys Glu Asn Ser Lys Lys Glu Glu Leu Thr Ser Lys
        355                 360                 365

Thr Lys Ala Glu Leu Thr Ala Ala Phe Glu Gln Phe Lys Lys Asp Thr
    370                 375                 380

Leu Lys Pro Glu Lys Lys Val Ala Glu Ala Glu Lys Lys Val Glu Glu
385                 390                 395                 400

Ala Lys Lys Lys Ala Lys Asp Gln Lys Glu Glu Asp Arg Arg Asn Tyr
                405                 410                 415

Pro Thr Asn Thr Tyr Lys Thr Leu Glu Leu Glu Ala Glu Ser Asp Val
            420                 425                 430

Lys Val Lys Glu Ala Glu Leu Glu Leu Val Lys Glu Glu Ala Asn Glu
        435                 440                 445

Ser Arg Asn Glu Glu Lys Ile Lys Gln Ala Lys Glu Lys Val Glu Ser
    450                 455                 460

Lys Lys Ala Glu Ala Thr Arg Leu Glu Lys Ile Lys Thr Asp Arg Lys
465                 470                 475                 480

Lys Ala Glu Glu Glu Ala Lys Arg Lys Ala Glu Glu Ser Glu Lys Lys
                485                 490                 495

Ala Ala Glu Ala Lys Gln Lys Val Asp Ala Glu Glu Tyr Ala Leu Glu
            500                 505                 510

Ala Lys Ile Ala Glu Leu Glu Tyr Glu Val Gln Arg Leu Glu Lys Glu
        515                 520                 525

Leu Lys Glu Ile Asp Glu Ser Asp Ser Glu Asp Tyr Leu Lys Glu Gly
    530                 535                 540

Leu Arg Ala Pro Leu Gln Ser Lys Leu Asp Thr Lys Lys Ala Lys Leu
545                 550                 555                 560

Ser Lys Leu Glu Glu Leu Ser Asp Lys Ile Asp Glu Leu Asp Ala Glu
                565                 570                 575

Ile Ala Lys Leu Glu Val Gln Leu Lys Asp Ala Glu Gly Asn Asn Asn
            580                 585                 590

Val Glu Ala Tyr Phe Lys Glu Gly Leu Glu Lys Thr Thr Ala Glu Lys
        595                 600                 605

Lys Ala Glu Leu Glu Lys Ala Glu Ala Asp Leu Lys Lys Ala Val Asp
    610                 615                 620

Glu Pro Glu Thr Pro Ala Pro Ala Pro Gln Pro Ala Pro Ala Pro Glu
625                 630                 635                 640

Lys Pro Ala Glu Lys Pro Ala Pro Ala Pro Glu Lys Pro Ala Pro Ala
                645                 650                 655

Pro Glu Lys Pro Ala Pro Ala Pro Glu Lys Pro Ala Pro Ala Pro Glu
            660                 665                 670

Lys Pro Ala Pro Ala Pro Glu Lys Pro Ala Pro Thr Pro Glu Thr Pro
        675                 680                 685

Lys Thr
    690
```

-continued

<210> SEQ ID NO 62
<211> LENGTH: 701
<212> TYPE: PRT
<213> ORGANISM: Streptococcus pneumoniae

<400> SEQUENCE: 62

```
Met Phe Ala Ser Lys Ser Glu Arg Lys Val His Tyr Ser Ile Arg Lys
  1               5                  10                  15

Phe Ser Ile Gly Val Ala Ser Val Ala Val Ala Ser Leu Phe Leu Gly
             20                  25                  30

Gly Val Val His Ala Glu Gly Val Arg Ser Gly Asn Asn Leu Thr Val
         35                  40                  45

Thr Ser Ser Gly Gln Asp Ile Ser Lys Lys Tyr Ala Asp Glu Val Glu
     50                  55                  60

Ser His Leu Glu Ser Ile Leu Lys Asp Val Lys Lys Asn Leu Lys Lys
 65                  70                  75                  80

Val Gln His Thr Gln Asn Val Gly Leu Ile Thr Lys Leu Ser Glu Ile
                 85                  90                  95

Lys Lys Lys Tyr Leu Tyr Asp Leu Lys Val Asn Val Leu Ser Glu Ala
            100                 105                 110

Glu Leu Thr Ser Lys Thr Lys Glu Thr Lys Glu Lys Leu Thr Ala Thr
        115                 120                 125

Phe Glu Gln Phe Lys Lys Asp Thr Leu Pro Thr Glu Pro Glu Lys Lys
    130                 135                 140

Val Ala Glu Ala Gln Lys Lys Val Glu Glu Ala Lys Lys Lys Ala Glu
145                 150                 155                 160

Asp Gln Lys Glu Lys Asp Arg Arg Asn Tyr Pro Thr Ile Thr Tyr Lys
                165                 170                 175

Thr Leu Glu Leu Glu Ile Ala Glu Ser Asp Val Glu Val Lys Lys Ala
            180                 185                 190

Glu Leu Glu Leu Val Lys Val Lys Ala Lys Glu Ser Gln Asp Glu Glu
        195                 200                 205

Lys Ile Lys Gln Ala Glu Ala Glu Val Glu Ser Lys Gln Ala Glu Ala
    210                 215                 220

Thr Arg Leu Lys Lys Ile Lys Thr Asp Arg Glu Glu Ala Lys Arg Lys
225                 230                 235                 240

Ala Asp Ala Lys Leu Lys Glu Ala Val Glu Lys Asn Val Ala Thr Ser
                245                 250                 255

Glu Gln Asp Lys Pro Lys Arg Arg Ala Lys Arg Gly Val Ser Gly Glu
            260                 265                 270

Leu Ala Thr Pro Asp Lys Lys Glu Asn Asp Ala Lys Ser Ser Asp Ser
        275                 280                 285

Ser Val Gly Glu Glu Thr Leu Pro Ser Pro Ser Leu Asn Met Ala Asn
    290                 295                 300

Glu Ser Gln Thr Glu His Arg Lys Asp Val Asp Glu Tyr Ile Lys Lys
305                 310                 315                 320

Met Leu Ser Glu Ile Gln Leu Asp Arg Arg Lys His Thr Gln Asn Val
                325                 330                 335

Asn Leu Asn Ile Lys Leu Ser Ala Ile Lys Thr Lys Tyr Leu Tyr Glu
            340                 345                 350

Leu Ser Val Leu Lys Glu Asn Ser Lys Lys Glu Glu Leu Thr Ser Lys
        355                 360                 365

Thr Lys Ala Glu Leu Thr Ala Ala Phe Glu Gln Phe Lys Lys Asp Thr
    370                 375                 380
```

-continued

```
Leu Lys Pro Glu Lys Lys Val Ala Glu Ala Glu Lys Lys Val Glu Glu
385                 390                 395                 400

Ala Lys Lys Lys Ala Lys Asp Gln Lys Glu Glu Asp Arg Arg Asn Tyr
                405                 410                 415

Pro Thr Asn Thr Tyr Lys Thr Leu Glu Leu Glu Ala Glu Ser Asp Val
            420                 425                 430

Lys Val Lys Glu Ala Glu Leu Glu Leu Val Lys Glu Glu Ala Asn Glu
        435                 440                 445

Ser Arg Asn Glu Glu Lys Ile Lys Gln Ala Lys Glu Lys Val Glu Ser
    450                 455                 460

Lys Lys Ala Glu Ala Thr Arg Leu Glu Lys Ile Lys Thr Asp Arg Lys
465                 470                 475                 480

Lys Ala Glu Glu Glu Ala Lys Arg Lys Ala Glu Glu Ser Glu Lys Lys
                485                 490                 495

Ala Ala Glu Ala Lys Gln Lys Val Asp Ala Glu Glu Tyr Ala Leu Glu
            500                 505                 510

Ala Lys Ile Ala Glu Leu Glu Tyr Glu Val Gln Arg Leu Glu Lys Glu
        515                 520                 525

Leu Lys Glu Ile Asp Glu Ser Asp Ser Glu Asp Tyr Leu Lys Glu Gly
    530                 535                 540

Leu Arg Ala Pro Leu Gln Ser Lys Leu Asp Thr Lys Lys Ala Lys Leu
545                 550                 555                 560

Ser Lys Leu Glu Glu Leu Ser Asp Lys Ile Asp Glu Leu Asp Ala Glu
                565                 570                 575

Ile Ala Lys Leu Glu Val Gln Leu Lys Asp Ala Glu Gly Asn Asn Asn
            580                 585                 590

Val Glu Ala Tyr Phe Lys Glu Gly Leu Glu Lys Thr Thr Ala Glu Lys
        595                 600                 605

Lys Ala Glu Leu Glu Lys Ala Glu Ala Asp Leu Lys Lys Ala Val Asp
    610                 615                 620

Glu Pro Glu Thr Pro Ala Pro Ala Pro Gln Pro Ala Pro Ala Pro Glu
625                 630                 635                 640

Lys Pro Ala Glu Lys Pro Ala Pro Ala Pro Ala Pro Glu Lys Pro Ala
                645                 650                 655

Pro Ala Pro Glu Lys Pro Ala Pro Ala Pro Glu Lys Pro Ala Pro Ala
            660                 665                 670

Pro Glu Lys Pro Ala Pro Ala Pro Glu Lys Pro Ala Pro Ala Pro Glu
        675                 680                 685

Lys Pro Ala Pro Ala Pro Lys Pro Glu Thr Pro Glu Thr
    690                 695                 700
```

<210> SEQ ID NO 63
<211> LENGTH: 670
<212> TYPE: PRT
<213> ORGANISM: Streptococcus pneumoniae

<400> SEQUENCE: 63

```
Met Phe Ala Ser Lys Ser Glu Arg Lys Val His Tyr Ser Ile Arg Lys
  1               5                  10                  15

Phe Ser Ile Gly Val Ala Ser Val Val Val Ala Ser Leu Val Met Gly
            20                  25                  30

Ser Val Val His Ala Thr Glu Asn Glu Gly Ile Thr Gln Val Ala Thr
        35                  40                  45

Ser Tyr Asn Lys Ala Asn Glu Ser Gln Thr Glu His Arg Lys Ala Ala
```

-continued

```
    50                  55                  60

Lys Gln Val Asp Glu Asp Ile Lys Lys Met Leu Ser Glu Ile Gln Glu
 65                  70                  75                  80

Tyr Ile Lys Lys Met Leu Ser Glu Ile Gln Leu Asp Lys Arg Lys His
                 85                  90                  95

Thr Gln Asn Val Asn Leu Asn Arg Lys Leu Ser Ala Ile Gln Thr Lys
            100                 105                 110

Tyr Leu Tyr Glu Leu Arg Val Leu Lys Glu Lys Ser Lys Lys Glu Glu
        115                 120                 125

Leu Thr Ser Asn Tyr Pro Thr Asn Thr Tyr Lys Thr Leu Glu Leu Glu
    130                 135                 140

Ile Ala Glu Phe Asp Val Lys Val Lys Glu Ala Glu Leu Glu Leu Val
145                 150                 155                 160

Lys Glu Glu Ala Lys Pro Arg Asn Glu Glu Lys Ile Lys Gln Ala Lys
                165                 170                 175

Ala Lys Val Glu Ser Lys Lys Ala Glu Ala Thr Arg Leu Glu Glu Ile
            180                 185                 190

Lys Thr Glu Arg Lys Lys Ala Glu Glu Glu Ala Lys Arg Lys Ala Glu
        195                 200                 205

Glu Ser Glu Lys Lys Ala Ala Glu Ala Lys Gln Lys Val Asp Thr Lys
    210                 215                 220

Glu Gln Gly Lys Pro Lys Arg Arg Ala Lys Arg Gly Val Ser Gly Glu
225                 230                 235                 240

Leu Ala Thr Pro Asp Lys Lys Glu Asn Asp Ala Lys Ser Ser Asp Ser
                245                 250                 255

Ser Val Gly Glu Glu Thr Leu Pro Ser Pro Ser Leu Asn Met Ala Asn
            260                 265                 270

Glu Ser Gln Thr Glu His Arg Lys Asp Val Asp Glu Tyr Ile Lys Lys
        275                 280                 285

Met Leu Ser Glu Ile Gln Leu Asp Arg Arg Lys His Thr Gln Asn Val
    290                 295                 300

Asn Leu Asn Ile Lys Leu Ser Ala Ile Lys Thr Lys Tyr Leu Tyr Glu
305                 310                 315                 320

Leu Ser Val Leu Lys Glu Asn Ser Lys Lys Glu Glu Leu Thr Ser Lys
                325                 330                 335

Thr Lys Ala Glu Leu Thr Ala Ala Phe Glu Gln Phe Lys Lys Asp Thr
            340                 345                 350

Leu Lys Pro Glu Lys Lys Val Ala Glu Ala Glu Lys Lys Val Glu Glu
        355                 360                 365

Ala Lys Lys Lys Ala Lys Asp Gln Lys Glu Glu Asp Arg Arg Asn Tyr
    370                 375                 380

Pro Thr Asn Thr Tyr Lys Thr Leu Glu Leu Glu Ala Glu Ser Asp Val
385                 390                 395                 400

Lys Val Asp Lys Ala Glu Leu Glu Leu Val Lys Glu Glu Ala Asn Glu
                405                 410                 415

Ser Arg Asn Glu Glu Lys Ile Lys Gln Ala Lys Glu Lys Val Glu Ser
            420                 425                 430

Lys Lys Ala Glu Ala Thr Arg Leu Glu Lys Ile Lys Thr Asp Asp Arg
        435                 440                 445

Lys Lys Ala Glu Glu Glu Ala Lys Arg Lys Ala Glu Glu Ser Glu Lys
    450                 455                 460

Lys Ala Ala Glu Ala Lys Gln Lys Val Asp Ala Glu Glu Tyr Ala Leu
465                 470                 475                 480
```

-continued

```
Glu Ala Lys Ile Ala Glu Leu Glu Tyr Glu Val Gln Arg Leu Glu Lys
                485                 490                 495

Glu Leu Lys Glu Ile Asp Glu Ser Asp Ser Glu Asp Tyr Leu Lys Glu
            500                 505                 510

Gly Leu Arg Ala Pro Leu Gln Ser Lys Leu Asp Thr Lys Lys Ala Lys
        515                 520                 525

Leu Ser Lys Leu Glu Glu Leu Ser Asp Lys Ile Asp Glu Leu Asp Ala
    530                 535                 540

Glu Ile Ala Lys Leu Glu Val Gln Leu Lys Asp Ala Glu Gly Asn Asn
545                 550                 555                 560

Asn Val Glu Ala Tyr Phe Lys Glu Gly Leu Glu Lys Thr Thr Ala Glu
                565                 570                 575

Lys Lys Ala Glu Leu Glu Lys Ala Glu Ala Asp Leu Lys Lys Ala Val
            580                 585                 590

Asp Glu Pro Glu Thr Pro Ala Pro Ala Pro Gln Pro Ala Pro Ala Pro
        595                 600                 605

Glu Lys Pro Ala Glu Lys Pro Ala Pro Ala Pro Ala Pro Glu Lys Pro
    610                 615                 620

Ala Pro Ala Pro Glu Lys Pro Ala Glu Lys Pro Ala Glu Lys Pro Ala
625                 630                 635                 640

Glu Glu Pro Ala Glu Lys Pro Ala Pro Ala Pro Glu Lys Pro Ala Pro
                645                 650                 655

Thr Pro Glu Lys Pro Ala Pro Thr Pro Glu Thr Pro Lys Thr
            660                 665                 670


<210> SEQ ID NO 64
<211> LENGTH: 437
<212> TYPE: PRT
<213> ORGANISM: Streptococcus pneumoniae

<400> SEQUENCE: 64

Met Phe Ala Ser Lys Ser Glu Arg Lys Val His Tyr Ser Ile Arg Lys
  1               5                  10                  15

Phe Ser Ile Gly Val Ala Ser Val Ala Val Ala Ser Leu Val Met Gly
             20                  25                  30

Ser Val Val His Ala Thr Glu Asn Glu Gly Ser Thr Gln Ala Ala Thr
         35                  40                  45

Ser Ser Asn Met Ala Lys Thr Glu His Arg Lys Ala Ala Lys Gln Val
     50                  55                  60

Val Asp Glu Tyr Ile Glu Lys Met Leu Ser Glu Ile Gln Leu Asp Arg
 65                  70                  75                  80

Arg Lys His Thr Gln Asn Val Ala Leu Asn Ile Lys Leu Ser Ala Ile
                 85                  90                  95

Lys Thr Lys Tyr Leu Arg Glu Leu Asn Val Leu Glu Glu Lys Ser Lys
            100                 105                 110

Asp Glu Leu Pro Ser Asn Tyr Pro Thr Asn Thr Tyr Lys Thr Leu Glu
        115                 120                 125

Leu Glu Ile Ala Glu Phe Asp Val Lys Val Lys Glu Ala Glu Leu Glu
    130                 135                 140

Leu Val Lys Glu Glu Ala Lys Glu Ser Arg Asn Glu Gly Thr Ile Lys
145                 150                 155                 160

Gln Ala Lys Glu Lys Val Glu Ser Lys Lys Ala Glu Ala Thr Arg Leu
                165                 170                 175

Glu Asn Glu Ile Lys Thr Asp Arg Lys Lys Ala Glu Glu Glu Ala Lys
```

-continued

```
                180                 185                 190

Arg Lys Ala Asp Gly Lys Leu Lys Glu Ala Asn Val Ala Thr Ser Asp
        195                 200                 205

Gln Gly Lys Pro Lys Gly Arg Ala Lys Arg Gly Val Pro Gly Glu Leu
    210                 215                 220

Ala Thr Pro Asp Lys Lys Glu Asn Asp Ala Lys Ser Ser Asp Ser Ser
225                 230                 235                 240

Val Gly Glu Glu Thr Leu Pro Ser Ser Ser Leu Lys Ser Gly Lys Lys
                245                 250                 255

Val Ala Glu Ala Glu Lys Lys Val Glu Glu Ala Glu Lys Lys Ala Lys
            260                 265                 270

Asp Gln Lys Glu Glu Asp Arg Arg Asn Tyr Pro Thr Asn Thr Tyr Lys
        275                 280                 285

Thr Leu Asp Glu Leu Glu Ala Glu Ser Asp Val Lys Val Lys Glu Ala
    290                 295                 300

Glu Leu Glu Leu Val Lys Glu Glu Ala Lys Glu Pro Arg Asp Glu Glu
305                 310                 315                 320

Lys Ile Lys Gln Ala Lys Ala Lys Val Glu Ser Lys Lys Ala Glu Ala
                325                 330                 335

Thr Arg Leu Glu Asn Ile Lys Thr Asp Arg Lys Lys Ala Glu Glu Glu
            340                 345                 350

Ala Lys Arg Lys Ala Ala Glu Glu Asp Lys Val Lys Glu Lys Pro Ala
        355                 360                 365

Glu Gln Pro Gln Pro Ala Pro Ala Pro Gln Pro Glu Lys Pro Ala Pro
    370                 375                 380

Lys Pro Glu Lys Pro Ala Glu Gln Pro Lys Ala Glu Lys Thr Asp Asp
385                 390                 395                 400

Gln Gln Ala Glu Glu Asp Tyr Ala Arg Arg Ser Glu Glu Glu Tyr Asn
                405                 410                 415

Arg Leu Thr Gln Gln Gln Pro Pro Lys Thr Glu Lys Pro Ala Gln Pro
            420                 425                 430

Ser Thr Pro Lys Thr
        435
```

<210> SEQ ID NO 65
<211> LENGTH: 478
<212> TYPE: PRT
<213> ORGANISM: Streptococcus pneumoniae

<400> SEQUENCE: 65

```
Met Phe Ala Ser Lys Ser Glu Arg Lys Val His Tyr Ser Ile Arg Lys
  1               5                  10                  15

Phe Ser Ile Gly Val Ala Ser Val Ala Val Ala Ser Leu Phe Leu Gly
             20                  25                  30

Gly Val Val His Ala Glu Gly Val Arg Ser Glu Asn Thr Pro Val Thr
         35                  40                  45

Ser Ser Gly Asp Glu Val Asp Glu Tyr Ile Lys Lys Met Leu Ser Glu
     50                  55                  60

Ile Gln Leu Asp Lys Arg Lys His Thr His Asn Phe Ala Leu Asn Leu
 65                  70                  75                  80

Lys Leu Ser Arg Ile Lys Thr Glu Tyr Leu Tyr Lys Leu Lys Val Asn
                 85                  90                  95

Val Leu Glu Glu Lys Ser Lys Ala Glu Leu Thr Ser Lys Thr Lys Lys
            100                 105                 110
```

-continued

```
Glu Val Asp Ala Ala Phe Glu Lys Phe Lys Lys Asp Thr Leu Lys Leu
        115                 120                 125

Gly Glu Lys Val Ala Glu Ala Gln Lys Lys Val Glu Glu Ala Lys Lys
    130                 135                 140

Lys Ala Lys Asp Gln Lys Glu Glu Asp His Arg Asn Tyr Pro Thr Asn
145                 150                 155                 160

Thr Tyr Lys Thr Leu Glu Leu Glu Ile Ala Glu Ser Asp Val Lys Val
                165                 170                 175

Lys Glu Ala Glu Leu Glu Leu Leu Lys Glu Glu Ala Lys Thr Arg Asn
            180                 185                 190

Glu Asp Thr Ile Asn Gln Ala Lys Ala Lys Val Lys Ser Glu Gln Ala
        195                 200                 205

Glu Ala Thr Arg Leu Lys Lys Ile Lys Thr Asp Arg Glu Gln Ala Glu
    210                 215                 220

Ala Thr Arg Leu Glu Asn Ile Lys Thr Asp Arg Glu Lys Ala Glu Glu
225                 230                 235                 240

Ala Lys Arg Lys Ala Glu Ala Glu Glu Val Lys Asp Lys Leu Lys Arg
                245                 250                 255

Arg Thr Lys Arg Ala Val Pro Gly Glu Pro Ala Thr Pro Asp Lys Lys
            260                 265                 270

Glu Asn Asp Ala Lys Ser Ser Asp Ser Ser Val Gly Glu Glu Thr Leu
        275                 280                 285

Pro Ser Pro Ser Leu Lys Ser Gly Lys Lys Val Ala Glu Ala Gln Lys
    290                 295                 300

Lys Val Ala Glu Ala Glu Lys Lys Ala Lys Asp Gln Lys Glu Glu Asp
305                 310                 315                 320

Arg Arg Asn Tyr Pro Thr Asn Thr Tyr Lys Thr Leu Asp Leu Glu Ala
                325                 330                 335

Glu Ser Asp Val Lys Val Lys Glu Ala Glu Leu Glu Leu Val Lys Glu
            340                 345                 350

Glu Ala Lys Glu Ser Arg Asn Glu Glu Lys Val Lys Gln Ala Lys Ala
        355                 360                 365

Lys Val Glu Ser Lys Lys Ala Glu Ala Thr Arg Leu Glu Lys Ile Lys
    370                 375                 380

Thr Asp Arg Lys Lys Ala Glu Glu Ala Lys Arg Arg Ala Ala Glu Glu
385                 390                 395                 400

Asp Lys Val Lys Glu Lys Pro Ala Glu Gln Pro Glu Lys Pro Thr Glu
                405                 410                 415

Glu Pro Glu Asn Pro Ala Pro Ala Pro Lys Pro Glu Asn Pro Ala Glu
            420                 425                 430

Gln Pro Lys Ala Glu Lys Pro Ala Asp Gln Gln Ala Glu Glu Asp Tyr
        435                 440                 445

Ala Arg Arg Ser Glu Glu Glu Tyr Asn Arg Leu Thr Gln Gln Gln Pro
    450                 455                 460

Pro Lys Thr Glu Lys Pro Ala Gln Pro Ser Thr Pro Lys Thr
465                 470                 475
```

<210> SEQ ID NO 66
<211> LENGTH: 487
<212> TYPE: PRT
<213> ORGANISM: Streptococcus pneumoniae

<400> SEQUENCE: 66

```
Met Phe Ala Ser Lys Asn Glu Arg Lys Val His Tyr Ser Ile Arg Lys
  1               5                  10                  15
```

-continued

```
Phe Ser Ile Gly Val Ala Ser Val Ala Val Ala Ser Leu Phe Met Gly
            20                  25                  30

Ser Val Val His Ala Thr Glu Lys Glu Val Thr Thr Gln Val Ala Thr
        35                  40                  45

Ser Phe Asn Lys Ala Asn Lys Ser Gln Thr Glu His Met Lys Ala Ala
    50                  55                  60

Lys Gln Val Asp Glu Tyr Ile Thr Lys Lys Leu Gln Leu Asp Arg Arg
65                  70                  75                  80

Lys His Thr Gln Asn Val Gly Leu Leu Thr Lys Leu Gly Val Ile Lys
                85                  90                  95

Thr Glu Tyr Leu His Arg Leu Ser Val Ser Lys Glu Lys Ser Glu Ala
            100                 105                 110

Glu Leu Pro Ser Glu Ile Lys Ala Lys Leu Asp Ala Ala Phe Glu Gln
        115                 120                 125

Phe Lys Lys Asp Thr Leu Pro Thr Glu Pro Gly Lys Lys Val Ala Glu
    130                 135                 140

Ala Glu Lys Lys Val Glu Glu Ala Lys Lys Lys Ala Glu Asp Gln Lys
145                 150                 155                 160

Glu Glu Asp Arg Arg Asn Tyr Pro Thr Ile Thr Tyr Lys Thr Leu Glu
                165                 170                 175

Leu Glu Ile Ala Glu Ser Asp Val Glu Val Lys Lys Ala Glu Leu Glu
            180                 185                 190

Leu Val Lys Glu Glu Ala Lys Gly Ser Arg Asn Glu Gln Lys Val Asn
        195                 200                 205

Gln Ala Lys Ala Lys Val Glu Ser Lys Gln Ala Glu Ala Thr Arg Leu
    210                 215                 220

Lys Lys Ile Lys Thr Asp Arg Glu Gln Ala Glu Ala Thr Arg Leu Glu
225                 230                 235                 240

Asn Ile Lys Thr Asp Arg Glu Lys Ala Glu Glu Ala Lys Arg Lys Ala
                245                 250                 255

Glu Ala Glu Glu Val Lys Asp Lys Leu Lys Arg Arg Thr Lys Arg Ala
            260                 265                 270

Val Pro Gly Glu Pro Ala Thr Pro Asp Lys Lys Glu Asn Asp Ala Lys
        275                 280                 285

Ser Ser Asp Ser Ser Val Gly Glu Glu Thr Leu Pro Ser Pro Ser Leu
    290                 295                 300

Lys Ser Gly Lys Lys Val Ala Glu Ala Glu Lys Lys Val Ala Glu Ala
305                 310                 315                 320

Glu Lys Lys Ala Lys Asp Gln Lys Glu Glu Asp Arg Arg Asn Tyr Pro
                325                 330                 335

Thr Asn Thr Tyr Lys Thr Leu Glu Leu Glu Ala Glu Ser Asp Val Lys
            340                 345                 350

Val Lys Glu Ala Glu Leu Glu Leu Val Lys Glu Glu Ala Lys Glu Ser
        355                 360                 365

Arg Asn Glu Glu Lys Val Lys Gln Ala Lys Ala Glu Val Glu Ser Lys
    370                 375                 380

Lys Ala Glu Ala Thr Arg Leu Glu Lys Ile Lys Thr Asp Arg Lys Lys
385                 390                 395                 400

Ala Glu Glu Ala Lys Arg Lys Ala Ala Glu Glu Asp Lys Val Lys Glu
                405                 410                 415

Lys Pro Ala Glu Gln Pro Gln Pro Ala Pro Ala Pro Gln Pro Glu Lys
            420                 425                 430
```

-continued

```
Pro Ala Pro Ala Pro Lys Pro Glu Asn Pro Ala Glu Gln Pro Lys Ala
        435                 440                 445

Glu Lys Pro Ala Asp Gln Gln Ala Glu Glu Asp Tyr Ala Arg Arg Ser
    450                 455                 460

Glu Glu Glu Tyr Asn Arg Leu Thr Gln Gln Gln Pro Pro Lys Thr Glu
465                 470                 475                 480

Lys Pro Ala Gln Pro Ser Thr
                485


<210> SEQ ID NO 67
<211> LENGTH: 451
<212> TYPE: PRT
<213> ORGANISM: Streptococcus pneumoniae

<400> SEQUENCE: 67

Met Phe Ala Ser Lys Ser Glu Arg Lys Val His Tyr Ser Ile Arg Lys
  1               5                  10                  15

Phe Ser Val Gly Val Ala Ser Val Val Val Ala Ser Leu Val Met Gly
             20                  25                  30

Ser Val Val His Ala Thr Glu Asn Glu Gly Ala Thr Gln Val Pro Thr
         35                  40                  45

Ser Ser Asn Arg Ala Asn Glu Ser Gln Ala Glu Gln Gly Glu Gln Pro
     50                  55                  60

Lys Lys Leu Asp Ser Glu Arg Asp Lys Ala Arg Lys Glu Val Glu Glu
 65                  70                  75                  80

Tyr Val Lys Lys Ile Val Gly Glu Ser Tyr Ala Lys Ser Thr Lys Lys
                 85                  90                  95

Arg His Thr Ile Thr Val Ala Leu Val Asn Glu Leu Asn Asn Ile Lys
            100                 105                 110

Asn Glu Tyr Leu Asn Lys Ile Val Glu Ser Thr Ser Glu Ser Gln Leu
        115                 120                 125

Gln Ile Leu Met Met Asn Tyr Pro Thr Ile Thr Tyr Lys Thr Leu Glu
    130                 135                 140

Leu Glu Ile Ala Glu Ser Asp Val Glu Val Lys Lys Ala Glu Leu Glu
145                 150                 155                 160

Leu Val Lys Val Lys Ala Asn Glu Pro Arg Asp Glu Gln Lys Ile Lys
                165                 170                 175

Gln Ala Glu Ala Glu Val Glu Ser Lys Gln Ala Glu Ala Thr Arg Leu
            180                 185                 190

Lys Lys Ile Lys Thr Asp Arg Glu Glu Ala Glu Glu Glu Ala Lys Arg
        195                 200                 205

Arg Ala Asp Ala Lys Glu Gln Gly Lys Pro Lys Gly Arg Ala Lys Arg
    210                 215                 220

Gly Val Pro Gly Glu Leu Ala Thr Pro Asp Lys Lys Glu Asn Asp Ala
225                 230                 235                 240

Lys Ser Ser Asp Ser Ser Val Gly Glu Glu Thr Leu Pro Ser Pro Ser
                245                 250                 255

Leu Lys Pro Glu Lys Lys Val Ala Glu Ala Glu Lys Lys Val Glu Glu
            260                 265                 270

Ala Lys Lys Lys Ala Glu Asp Gln Lys Glu Glu Asp Arg Arg Asn Tyr
        275                 280                 285

Pro Thr Asn Thr Tyr Lys Thr Leu Glu Leu Glu Ala Glu Ser Asp Val
    290                 295                 300

Glu Val Lys Lys Ala Glu Leu Glu Leu Val Lys Glu Glu Ala Lys Glu
305                 310                 315                 320
```

-continued

```
Pro Arg Asn Glu Glu Lys Val Lys Gln Ala Lys Ala Glu Val Glu Ser
                325                 330                 335

Lys Lys Ala Glu Val Glu Ser Lys Lys Ala Glu Ala Thr Arg Leu Glu
            340                 345                 350

Lys Ile Lys Thr Asp Arg Lys Lys Ala Glu Glu Glu Ala Lys Arg Lys
        355                 360                 365

Ala Ala Glu Glu Asp Lys Val Lys Glu Lys Pro Ala Glu Gln Pro Gln
    370                 375                 380

Pro Ala Pro Ala Pro Lys Ala Glu Lys Pro Ala Pro Ala Pro Lys Pro
385                 390                 395                 400

Glu Asn Pro Ala Glu Gln Pro Lys Ala Glu Lys Pro Ala Asp Gln Gln
                405                 410                 415

Ala Glu Glu Glu Tyr Ala Arg Arg Ser Glu Glu Glu Tyr Asn Arg Leu
            420                 425                 430

Thr Leu Gln Gln Pro Pro Lys Thr Glu Lys Pro Ala Gln Pro Ser Thr
        435                 440                 445

Pro Lys Thr
    450


<210> SEQ ID NO 68
<211> LENGTH: 730
<212> TYPE: PRT
<213> ORGANISM: Streptococcus pneumoniae

<400> SEQUENCE: 68

Met Phe Ala Ser Lys Ser Glu Arg Lys Val His Tyr Ser Ile Arg Lys
  1               5                  10                  15

Phe Ser Ile Gly Val Ala Ser Val Val Val Ala Ser Leu Phe Leu Gly
             20                  25                  30

Gly Val Val His Ala Glu Glu Val Arg Arg Gly Asn Asn Leu Thr Val
         35                  40                  45

Thr Ser Ser Gly Asp Glu Val Glu Ser His Tyr Gln Ser Ile Leu Glu
     50                  55                  60

Lys Val Arg Lys Ser Leu Glu Lys Asp Arg His Thr Gln Asn Val Asp
 65                  70                  75                  80

Leu Ile Lys Lys Leu Gln Asp Ile Lys Arg Thr Tyr Leu Tyr Asn Leu
                 85                  90                  95

Lys Glu Lys Pro Glu Ala Glu Leu Thr Ser Lys Thr Asn Lys Glu Leu
            100                 105                 110

Asp Ala Ala Phe Glu Lys Phe Lys Lys Glu Pro Glu Leu Thr Lys Lys
        115                 120                 125

Leu Ala Glu Ala Glu Lys Lys Ala Lys Asp Gln Lys Glu Glu Asp His
    130                 135                 140

Arg Asn Tyr Pro Thr Asn Thr Tyr Lys Thr Ile Glu Leu Glu Ile Ala
145                 150                 155                 160

Glu Ala Glu Val Gly Val Ala Lys Ala Glu Leu Glu Leu Ala Gln Ala
                165                 170                 175

Gln Val Gln Ile Pro Gln Asp Thr Glu Lys Ile Asn Ala Ala Lys Ala
            180                 185                 190

Lys Val Glu Ala Ala Lys Ser Asn Val Lys Lys Leu Glu Lys Ile Lys
        195                 200                 205

Ser Asp Ile Glu Lys Thr Tyr Leu Tyr Lys Leu Asp Asn Ser Thr Lys
    210                 215                 220

Glu Thr Pro Lys Ser Arg Val Arg Arg Asn Ser Pro Gln Val Gly Asp
```

-continued

```
225                 230                 235                 240

Ser Arg Glu Leu Lys Glu Thr Ile Asp Lys Ala Lys Glu Thr Leu Ser
                245                 250                 255

Thr Tyr Met Val Thr Arg Leu Thr Lys Leu Asp Pro Ser Val Phe Trp
            260                 265                 270

Phe Ala Asp Leu Leu Met Asp Ala Lys Lys Val Val Glu Glu Tyr Lys
        275                 280                 285

Thr Lys Leu Glu Asp Ala Ser Asp Lys Lys Ser Val Glu Asp Leu Arg
    290                 295                 300

Lys Glu Ala Glu Gly Lys Ile Glu Ser Leu Ile Val Thr His Gln Asn
305                 310                 315                 320

Arg Glu Lys Glu Asn Gln Pro Ala Pro Gln Pro Gly Gly Gln Ala Gly
                325                 330                 335

Gly Ser Met Val Val Pro Pro Val Thr Gln Thr Pro Pro Ser Thr Ser
            340                 345                 350

Gln Ser Pro Gly Gln Lys Ala Thr Glu Ala Glu Lys Lys Lys Leu Gln
        355                 360                 365

Asp Leu Ile Arg Gln Phe Gln Glu Ala Leu Asn Lys Leu Asp Asp Glu
    370                 375                 380

Thr Lys Thr Val Pro Asp Gly Ala Lys Leu Thr Gly Glu Ala Gly Lys
385                 390                 395                 400

Ala Tyr Asn Glu Thr Arg Thr Tyr Ala Lys Glu Val Val Asp Lys Ser
                405                 410                 415

Lys Lys Leu Leu Ser Gln Thr Ala Val Thr Met Asp Glu Leu Ala Met
            420                 425                 430

Gln Leu Thr Lys Leu Asn Asp Ala Met Ser Lys Leu Lys Glu Ala Lys
        435                 440                 445

Ala Lys Leu Val Pro Glu Val Lys Pro Gln Pro Glu Asn Pro Glu Pro
    450                 455                 460

Lys Pro Gln Pro Glu Gly Glu Lys Pro Ser Val Pro Asp Ile Asn Gln
465                 470                 475                 480

Glu Lys Glu Lys Ala Lys Leu Ala Ile Ala Thr Tyr Met Ser Lys Ile
                485                 490                 495

Leu Asp Asp Ile Lys Lys His His Leu Lys Lys Glu Lys His His Gln
            500                 505                 510

Ile Val Ala Leu Ile Lys Asp Leu Asp Lys Leu Arg Lys Gln Ala Leu
        515                 520                 525

Ser Glu Ile Asp Asn Val Asn Thr Lys Val Glu Ile Glu Asn Thr Val
    530                 535                 540

His Lys Val Phe Ala Asp Met Asp Thr Val Val Thr Lys Phe Gln Lys
545                 550                 555                 560

Gly Leu Ile Gln Asn Thr Pro Gln Val Pro Glu Ala Gln Arg Ala Gln
                565                 570                 575

Arg Tyr Gln Arg Phe Gln Ile His Gln Lys Ala Pro Asp Thr Pro Gln
            580                 585                 590

Val Pro Glu Ala Pro Lys Ser Pro Glu Val Pro Lys Val Pro Glu Ala
        595                 600                 605

Pro Lys Ala Pro Asp Thr Pro Gln Val Pro Glu Ala Pro Lys Ser Pro
    610                 615                 620

Glu Val Pro Lys Val Ser Asp Thr Pro Lys Ala Pro Asp Thr Pro Gln
625                 630                 635                 640

Val Pro Glu Ala Pro Lys Ser Pro Glu Val Pro Lys Val Pro Glu Ala
                645                 650                 655
```

-continued

```
Pro Lys Ala Pro Asp Thr Pro Gln Val Pro Glu Ala Pro Lys Ser Pro
            660                 665                 670

Glu Val Pro Lys Val Pro Asp Thr Pro Lys Ala Pro Asp Thr Pro Gln
        675                 680                 685

Val Pro Glu Ala Pro Lys Ala Pro Asp Thr Pro Gln Ile Pro Glu Ala
    690                 695                 700

Pro Ala Pro Glu Thr Pro Ala Pro Ala Pro Glu Ala Pro Lys Thr Gly
705                 710                 715                 720

Trp Lys Gln Glu Asn Gly Met Trp Lys Gly
                725                 730


<210> SEQ ID NO 69
<211> LENGTH: 2349
<212> TYPE: DNA
<213> ORGANISM: Streptococcus pneumoniae

<400> SEQUENCE: 69

aattcgccct tcgacgaata gctgaagagg aaaagctatt acatgaagtt ataatcccaa      60

atggaagcat aaagagataa atacaaaatt cgatttatat acagttcata ttgaagtgat     120

atagtaaggc taaagaaaaa atatagaagg aaataaacat gtttgcatca aaaagcgaaa     180

gaaaagtaca ttattcaatt cgtaaattta gtattggagt agctagtgta gtagttgcta     240

gtttgttctt aggaggagta gttcacgcag aagaggttag aagagggaat aacctcacgg     300

ttacatctag tggggatgaa gtcgagtcgc attatcaaag tatattggag aaggtcagaa     360

aaagtttgga aaaagatcga catacccaaa atgtcgactt aatcaaaaag ttgcaagaca     420

ttaagagaac gtatttgtat aatttaaaag agaagccgga agctgagttg acgtcaaaaa     480

caaataaaga gttagacgca gcttttgaga agtttaaaaa agaaccagaa cttactaaaa     540

aattagcaga agctgagaaa aaagccaagg atcaaaaaga agaagatcac cgtaactacc     600

caaccaatac ttacaaaaca atcgaactgg aaattgcgga agcagaagta ggggtcgcca     660

aggcagagct tgagcttgca caagctcaag tccaaatacc tcaagatact gagaaaatta     720

atgctgctaa agctaaagta gaagctgcta aaagtaatgt taaaaaacta gaaaaaatta     780

aatcagatat tgaaaaaacg tatttgtata aattagataa ctcaaccaaa gaaacgccaa     840

aatctagagt gcgaagaaat tctccgcaag taggcgattc gagagaactt aaggaaacga     900

tagacaaagc gaaagaaact ctgtctacct atatggtaac tcgtttaacg aagctggatc     960

catctgtttt ttggtttgca gatcttctta tggatgctaa gaaagttgtg gaagaataca    1020

agacaaaatt agaggatgct tcagataaaa aatcggtaga agacttgcga aaggaagcag    1080

aaggaaaaat agagtctctt atcgtgactc accaaaatag agaaaaagaa aaccaaccag    1140

caccccaacc aggaggacaa gcaggtggtt caatggttgt accaccggtg acgcaaacac    1200

ctccatcaac ttcccaaagt ccaggacaaa aggcgaccga agctgaaaag aaaaagttac    1260

aagacttgat tcgtcaattc caagaagcct tgaacaaact agacgatgaa acaaagactg    1320

ttccagatgg ggctaaactc acaggagaag ctggaaaagc ctataatgag actagaactt    1380

atgcgaaaga agttgttgac aagagcaaga agcttctatc acagacagca gtgacaatgg    1440

atgaattggc aatgcaatta accaaattga acgatgccat gtctaaattg aaagaagcta    1500

aagcgaaatt ggtaccagag gttaaaccac agccggaaaa cccagagcca aaaccacaac    1560

cagagggtga gaaaccaagc gtaccagata ttaatcagga gaaagaaaaa gctaaacttg    1620

ctatagcaac atacatgagc aagattttag atgatataaa gaaacatcat ctgaagaaag    1680
```

-continued aaaaacatca tcagattgtt gctcttatta aggaccttga taaacttaga aagcaagcac 1740
tttctgaaat tgataatgta aataccaaag tagaaattga gaatacagtc cacaaggtat 1800
ttgcagacat ggatacggtt gttactaaat tccaaaaagg cttaattcag aacacaccgc 1860
aggttccaga agcccaaaga gcccagaggt accaaaggtt tcagatacac caaaaggctc 1920
cggacacacc gcaggttcca gaagcaccaa agagcccaga ggtaccaaag gttccagaag 1980
caccaaaggc tccggacaca ccgcaagttc cggaagcacc aaagagccca gaggtaccaa 2040
aggtttcaga tacaccaaag gctccggaca caccgcaggt tccagaagca ccaaagagcc 2100
cagaggtacc aaaggttcca gaagcaccaa aggctccgga cacaccgcaa gttccggaag 2160
caccaaagag cccagaggta ccaaaggttc cagatacacc aaaggctccg gacacaccgc 2220
aggttccaga agcaccaaag gctccagaca caccgcaaat tccggaagca ccagctccag 2280
aaactccggc tccagctcca gaagctccaa aaacaggctg gaaacaagaa aacggtatgt 2340
ggaagggcg 2349

<210> SEQ ID NO 70
<211> LENGTH: 2405
<212> TYPE: DNA
<213> ORGANISM: Streptococcus pneumoniae

<400> SEQUENCE: 70
cggccgccag tgtgatggat atctgcagaa ttcgcccttc gacgaatagc tgaagaggaa 60
aagctattac atgaagttat aatcccaaat ggaagcataa agagataaat acaaaattcg 120
atttatatac agttcatatt gaagtgatat agtaaggtta aagaaaaaat atagaaggaa 180
ataaacatgt ttgcatcaaa aagcgaaaga aaagtacatt attcaattcg taaatttagt 240
attggagtag ctagtgtagt agttgctagt cttgttatgg gaagtgtggt tcatgcgacg 300
gagaatgagg gaattaccca agtagccact tcttataata aggcaaatga aagtcagaca 360
gaacatagga aagctgctaa acaagtcgat gaagatataa aaaaaatgtt gagtgagatc 420
caagaatata taaaaaaaat gttgagtgag atccaattag ataaaagaaa acatacccaa 480
aatgtcaact taaacagaaa gttgagcgca attcaaacga agtatttgta tgaattaaga 540
gttttaaaag agaagtcgaa aaaagaagag ttgacgtcaa aaacaaaaaa agagttagac 600
gcagcttttg agaagtttaa aaaagaacca gaacttacta aaaaattagc agaagctaaa 660
caaaaagcca aggctcaaaa agaagaagat ttccgtaact acccaaccaa tacttacaaa 720
acgcttgaac ttgaaattgc tgagttcgat gtgaaagtta aagaagcgga gcttgaacta 780
gtaaaagagg aagctaaacc ccgaaacgag gaaaaaatta agcaagcaaa agcgaaagtt 840
gagagtaaaa aagctgaggc tacaaggtta gaagaaatca agacagaacg taaaaaagca 900
gaagaagaag ctaaacgaaa agcagaagaa tctgagaaaa aagctgctga agccaaacaa 960
aaagtggata ctaaagagca aggtaaacca aagaggcggg caaaacgagg agtttctgga 1020
gagctagcaa cacctgataa aaaagaaaat gatgcgaagt cttcagattc tagcgtaggt 1080
gaagaaactc ttccaagccc atcccttaat atggcaaatg aaagtcagac agaacatagg 1140
aaagatgtcg atgaatatat aaaaaaaatg ttgagtgaga tccaattaga tagaagaaaa 1200
catacccaaa atgtcaactt aaacataaag ttgagcgcaa ttaaaacgaa gtatttgtat 1260
gaattaagtg ttttaaaaga gaactcgaaa aaagaagagt tgacgtcaaa aaccaaagca 1320
gagttaaccg cagcttttga gcagtttaaa aaagatacat tgaaaccaga aaaaaaggta 1380

-continued

```
gcagaagctg agaagaaggt tgaagaagct aagaaaaaag ccaaggatca aaaagaagaa   1440

gatcgccgta actacccaac caatacttac aaaacgcttg aacttgaaat tgctgagtcc   1500

gatgtgaaag ttaaaaaagc ggagcttgaa ctagtaaaag aggaagctaa cgaatctcga   1560

aacgaggaaa aaattaagca agcaaaagag aaagttgaga gtaaaaaagc tgaggctaca   1620

aggttagaaa aaatcaagac agatcgtaaa aaagcagaag aagaagctaa acgaaaagca   1680

gaagaatctg agaaaaaagc tgctgaagcc aaacaaaaag tggatgctga agaatatgct   1740

cttgaagcta aaatcgctga gttggaatat gaagttcaga gactagaaaa agagctcaaa   1800

gagattgatg agtctgactc agaagattat cttaaagaag gcctccgtgc tcctcttcaa   1860

tctaaattgg ataccaaaaa agctaaacta tcaaaacttg aagagttgag tgataagatt   1920

gatgagttag acgctgaaat tgcaaaactt gaagttcaac ttaaagatgc tgaaggaaac   1980

aataatgtag aagcctactt taaagaaggt ttagagaaaa ctactgctga gaaaaaagct   2040

gaattagaaa aagctgaagc tgaccttaag aaagcagttg atgagccaga aactccagct   2100

ccggctcctc aaccagctcc agctccagaa aaaccagctg aaaaaccagc tccagctcca   2160

gctccagaaa aaccagctcc agctccagaa aaaccagctg aaaaaccagc tgaaaaacca   2220

gctgaagaac cagctgaaaa accagctcca gctccagaaa aaccagctcc aactccagaa   2280

aaaccagctc caactccaga aactccaaaa acaggctgga aacaagaaaa cggtatgtgg   2340

tacttctaca atactgatgg ttcaatggca acaggctggc tccaaaacaa tggttcatgg   2400

tacta                                                               2405
```

<210> SEQ ID NO 71
<211> LENGTH: 2773
<212> TYPE: DNA
<213> ORGANISM: Streptococcus pneumoniae
<220> FEATURE:
<221> NAME/KEY: misc_feature
<222> LOCATION: (1)..(2773)
<223> OTHER INFORMATION: nucleotide “n” can be any of the nucleotides “a”,“c”,“g” or “t”.

<400> SEQUENCE: 71

```
ccaagctatt aggtgacact atagaatact caagctatgc atcaagctta tgcttgtcaa     60

taatcacaaa tatgtagatc atatcttgtt taggacagta aaacatccta attacttttt    120

aaatattctt cctgagttga ttggcttgac cttgttgagt catgcttatg tgacttttgt    180

tttagttttt ccagtttatg cagttatttt gtatcgacga atagctgaag aggaaaagct    240

attacatgaa gttataatcc caaatggaag cataaagaga taaatacaaa attcgattta    300

tatacagttc atattgaagt aatatagtaa ggttaaagaa aaaatataga aggaaataaa    360

catgtttgca tcaaaaagcg aaagaaaagt acattattca attcgtaaat ttagtattgg    420

agtagctagt gtagctgttg ccagtcttgt tatgggaagt gtggttcatg cgacagagaa    480

cgagggaagt acccaagcag ccacttcttc taatatggca aagacagaac ataggaaagc    540

tgctaaacaa gtcgtcgatg aatatataga aaaaatgttg agggagattc aactagatag    600

aagaaaacat acccaaaatg tcgccttaaa cataaagttg agcgcaatta aaacgaagta    660

tttgcgtgaa ttaaatgttt tagaagagaa gtcgaaagat gagttgccgt cagaaataaa    720

agcaaagtta gacgcagctt ttgagaagtt taaaaaagat acattgaaac caggagaaaa    780

ggtagcagaa gctaagaaga aggttgaaga agctaagaaa aaagccgagg atcaaaaaga    840

agaagatcgt cgtaactacc caaccaatac ttacaaaacg cttgaacttg aaattgctga    900
```

-continued

```
gttcgatgtg aaagttaaag aagcggagct tgaactagta aaagaggaag ctaaagaatc    960
tcgaaacgag ggcacaatta agcaagcaaa agagaaagtt gagagtaaaa aagctgaggc   1020
tacaaggtta gaaaacatca agacagatcg taaaaaagca gaagaagaag ctaaacgaaa   1080
agcagatggt aagttgaagg aagctaatgt agcgacttca gatcaaggta aaccaaaggg   1140
gcgggcaaaa cgaggagttc ctggagagct agcaacacct gataaaaaag aaaatgatgc   1200
gaagtcttca gattctagcg taggtgaaga aactcttcca agctcatccc tgaaatcagg   1260
aaaaaaggta gcagaagctg agaagaaggt tgaagaagct gagaaaaaag ccaaggatca   1320
aaaagaagaa gatcgccgta actacccaac caatacttac aaaacgcttg accttgaaat   1380
tgctgagtcc gatgtgaaag ttaaagaagc ggagcttgaa ctagtaaaag aggaagctaa   1440
ggaacctcga gacgaggaaa aaattaagca agcaaaagcg aaagttgaga gtaaaaaagc   1500
tgaggctaca aggttagaaa acatcaagac agatcgtaaa aaagcagaag aagaagctaa   1560
acgaaaagca gcagaagaag ataaagttaa agaaaaacca gctgaacaac cacaaccagc   1620
gccggctact caaccagaaa aaccagctcc aaaaccagag aagccagctg aacaaccaaa   1680
agcagaaaaa acagatgatc aacaagctga agaagactat gctcgtagat cagaagaaga   1740
atataatcgc ttgactcaac agcaaccgcc aaaaaactgaa aaaccagcac aaccatctac   1800
tccaaaaaca ggctggaaac aagaaaacgg tatgtggtac ttctacaata ctgatggttc   1860
aatggcaaca ggatggctcc aaaacaacgg ttcatggtac tatctaaacg ctaatggtgc   1920
tatggcgaca ggatggctcc aaaacaatgg ttcatggtac tatctaaacg ctaatggttc   1980
aatggcaaca ggatggctcc aaaacaatgg ttcatggtac tacctaaacg ctaatggtgc   2040
tatggcgaca ggatggctcc aatacaatgg ttcatggtac tacctaaaca gcaatggcgc   2100
tatggcgaca ggatggctcc aatacaatgg ctcatggtac tacctcaacg ctaatggtga   2160
tatggcgaca ggatggctcc aaaacaacgg ttcatggtac tacctcaacg ctaatggtga   2220
tatggcgaca ggatggctcc aatacaacgg ttcatggtat tacctcaacg ctaatggtga   2280
tatggcgaca ggttgggtga aagatggana tacctggtac tatcttaaag catcaggtgc   2340
tatgaaagca agccaatggt tcaaagtatc agataaatgg tactatgtca atggctcagg   2400
tgcccttgca gtcaacacaa ctgtagatgg ctatggagtc aatgccaatg gtgaatgggt   2460
aaactaaacc taatataact agttaatact gacttcctgt aagaactttt taaagtattc   2520
cctacaaata ccatatcctt tcagtagata atataccctt gtaggaagtt tagattaaaa   2580
aataactctg taatctctag ccggatttat agcgctagag actacggagt ttttttgatg   2640
aggaaagaat ggcggcattc aagagactct ttaagagagt tacgggtttt aaactattaa   2700
gccttctcca attgcaagag ggcttcaatc tctgctaggg tgctagcttg cgaaatggct   2760
ccacggagtt tgc                                                      2773
```

<210> SEQ ID NO 72
<211> LENGTH: 2489
<212> TYPE: DNA
<213> ORGANISM: Streptococcus pneumoniae

<400> SEQUENCE: 72

```
gattgtatac gaccactata gggcgaattg ggcccgacgt cgcatgctcc cggccgccat     60
ggccgcgggt attcgacgaa tagctgaaga ggaaaagcta ttacatgaag ttataatccc    120
aaatggaagc ataaagagat aaatacaaca ttcgatttat atacagttcc tattgaagtg    180
atataataag gttaaagaaa aaatatagaa ggaaataaac atgtttgcat caaaaagcga    240
```

-continued

```
aagaaaagta cattattcaa ttcgtaaatt tagtattgga gtagctagtg tagctgttgc    300
cagcttgttc ttaggaggag tagtccatgc agaaggggtt agaagtggga ataacctcac    360
ggttacatct agtgggcaag atatatcgaa gaagtatgct gatgaagtcg agtcgcatct    420
agaaagtata ttgaaggatg tcaaaaaaaa tttgaaaaaa gttcaacata cccaaaatgt    480
cggcttaatt acaaagttga gcgaaattaa aaagaagtat ttgtatgact taaaagttaa    540
tgttttatcg gaagctgagt tgacgtcaaa aacaaaagaa acaaaagaaa agttaaccgc    600
aacttttgag cagtttaaaa aagatacatt accaacagaa ccagaaaaaa aggtagcaga    660
agctcagaag aaggttgaag aagctaagaa aaaagccgag gatcaaaaag aaaaagatcg    720
ccgtaactac ccaaccatta cttacaaaac gcttgaactt gaaattgctg agtccgatgt    780
ggaagttaaa aaagcggagc ttgaactagt aaaagtgaaa gctaaggaat ctcaagacga    840
ggaaaaaatt aagcaagcag aagcggaagt tgagagtaaa caagctgagg ctacaaggtt    900
aaaaaaaatc aagacagatc gtgaagaagc taaacgaaaa gcagatgcta agttgaagga    960
agctgttgaa aagaatgtag cgacttcaga gcaagataaa ccaaagaggc gggcaaaacg   1020
aggagtttct ggagagctag caacacctga taaaaaagaa aatgatgcga agtcttcaga   1080
ttctagcgta ggtgaagaaa ctcttccaag cccatccctt aatatggcaa atgaaagtca   1140
gacagaacat aggaaagatg tcgatgaata tataaaaaaa atgttgagtg agatccaatt   1200
agatggaaga aaacataccc caaatgtcaa cttaaacata aagttgagcg caattaaaac   1260
gaagtatttg tatgaattaa gtgttttaaa agagaactcg aaaaaagaag agttgacgtc   1320
aaaaaccaaa gcagagttaa ccgcagcttt tgagcagttt aaaaaagata cattgaaacc   1380
agaaaaaaaa gtagcagaag ctgagaagaa ggttgaagaa gctaagaaaa aagccaagga   1440
tcaaaaagaa gaagatcgcc gtaactaccc aaccaatact tacaaaacgc ttgaacttga   1500
aattgctgag tccgatgtga aagttaaaga agcggagctt gaactagtaa aagaggaagc   1560
taacgaatct cgaaacgagg aaaaaattaa gcaagcaaaa gagaaagttg agagtaaaaa   1620
agctgaggct acaaggttag aaaaaatcaa gacagatcgt aaaaaagcag aagaagaagc   1680
taaacgaaaa gcagaagaat ctgagaaaaa agctgctgaa gccaaacaaa aagtggatgc   1740
tgaagaatat gctcttgaag ctaaaatcgc tgagttggaa tatgaagttc agagactaga   1800
aaaagagctc aaagagattg atgagtctga ctcagaagat tatcttaaag aaggcctccg   1860
tgctcctctt caatctaaat tggataccaa aaaagctaaa ctatcaaaac ttgaagagtt   1920
gagtgataag attgatgagt tagacgctga aattgcaaaa cttgaagttc aacttaaaga   1980
tgctgaagga aacaataatg tagaagccta ctttaaagaa ggtttagaga aaactactgc   2040
tgagaaaaaa gctgaattag aaaaagctga agctgacctt aagaaagcag ttgatgagcc   2100
agaaactcca gctccggctc ctcaaccagc tccggctcca gaaaaaccag ctgaaaaacc   2160
agctccagct ccagctccag aaaaaccagc tccagctcca gaaaaaccag ctccagctcc   2220
agaaaaacca gctccagctc cagaaaaacc agctccagct ccagaaaaac cagctccagc   2280
tccagaaaaa ccagctccag ctccagaaaa accagctcca gctcctaaac cagaaactcc   2340
agaaacaggc tggaaacaag aaaacggtat gtggtacttc tacaatactg atggttcaat   2400
ggcaacaggc tggctccaaa acaatggctc atggtactac ctcaacagca atggcgttat   2460
ggcgacagga tggttcccaa acaatggtc                                     2489
```

<210> SEQ ID NO 73

-continued

<211> LENGTH: 1680
<212> TYPE: DNA
<213> ORGANISM: Streptococcus pneumoniae

<400> SEQUENCE: 73
attgtatacg actcactata gggcgaattg ggcccgacgt cgcatgctcc cggccgccat 60
ggccgcggga ttcgacgaat agctgaagag gaaaagctat tacatgaagt tataatccca 120
aatggaagca taaagagata aatacaaaat tcgatttata tacagttcat attgaagtga 180
tatagtaagg ttaaagaaaa aatatagaag gaaataaaca tgtttgcatc aaaaaacgaa 240
agaaaagtac attattcaat tcgtaaattt agtattggag tagctagtgt agctgttgcc 300
agtcttttta tgggaagtgt ggttcatgcg acagagaagg aggtaactac ccaagtagcc 360
acttctttta ataaggcaaa taaaagtcag acagaacata tgaaagctgc taaacaagtc 420
gatgaatata taacaaaaaa gctccaatta gatagaagaa aacataccca aaatgtcggc 480
ttactcacaa agttgggcgt aattaaaacg gagtatttgc atagattaag tgtttcaaaa 540
gagaagtcgg aagctgagtt gccgtcagaa ataaaagcaa agttagacgc agcttttgag 600
cagtttaaaa aagatacatt accaacagaa ccaggaaaaa aggtagcaga agctgagaag 660
aaggttgaag aagctaagaa aaaagccgag gatcaaaaag aagaagatcg tcgtaactac 720
ccaaccatta cttacaaaac gcttgaactt gaaattgctg agtccgatgt ggaagttaaa 780
aaagcggagc ttgaactagt aaaagaggaa gctaagggat ctcgaaacga gcaaaaagtt 840
aaccaagcaa aagcgaaagt tgagagtaaa caagctgagg ctacaaggtt aaaaaaaatc 900
aagacagatc gtgaacaagc tgagactaca aggttagaaa acatcaagac agatcgtgaa 960
aaagcagaag aagctaaacg aaaagcagat gctaaagagc aagatgaatc aaagaggcgg 1020
gtaaaaggag gagttccggg agagcaagca acacttgata aaaaagaaaa tgatgcgaag 1080
tcttcagatt ctagcgtagg tgaagaaact cttccaagcc catccctgaa atcaggaaaa 1140
aaggtagcag aagctgagaa gaaggttgca gaagctgaga aaaaagccaa ggatcaaaaa 1200
gaagaagatc gccgtaacta cccaaccaat acttacaaaa cgcttgaact tgaaattgct 1260
gagtccgatg tgaaagttaa agaagcggag cttgaactag taaaagagga agctaaggaa 1320
tctcgaaacg aggaaaaagt taagcaagca aaagcggaag ttgagagtaa aaaagctgag 1380
gctacaaggt tagaaaaaat caagacagat cgtaaaaaag cagaagaagc taaacgaaaa 1440
gcagcagaag aagataaagt taaagaaaaa ccagctgaac aaccacaacc agcgccggct 1500
cctcaaccag aaaaaccagc tccagctcca aaaccagaga atccagctga acaaccaaaa 1560
gcagaaaaac cagctgatca acaagctgaa gaagactatg ctcgtagatc agaagaagaa 1620
tataatcgct tgactcaaca gcaaccgcca aaaactgaaa aaccagcaca accatctact 1680

<210> SEQ ID NO 74
<211> LENGTH: 1766
<212> TYPE: DNA
<213> ORGANISM: Streptococcus pneumoniae
<220> FEATURE:
<221> NAME/KEY: misc_feature
<222> LOCATION: (1)..(1766)
<223> OTHER INFORMATION: nucleotide "n" can be any of the nucleotides "a","c","g" or "t".

<400> SEQUENCE: 74
gtatacgact cactataggg cgaattgggc ccgacgtcgc atgctcccgg ccgccatggc 60
cgcgggattc gacgaatagc tgaagaggaa aagctattac atgaagttat aatcccaaat 120

-continued

```
ggaagcataa agagataaat acaaaattcg atttatatac agttcatatt gaagtgatat    180

agtaaggtta aagaaaaaat atagaaggaa ataaacatgt ttgcatcaaa aagcgaaaga    240

aaagtacatt attcaattcg taaatttagt gttggagtag ctagtgtagt tgttgccagt    300

cttgttatgg gaagtgtggt tcatgcgaca gagaacgagg gagctaccca agtacccact    360

tcttctaata gggcaaatga aagtcaggca gaacaaggag aacaacctaa aaaactcgat    420

tcagaacgag ataaggcaag gaaagaggtc gaggaatatg taaaaaaaat agtgggtgag    480

agctatgcaa aatcaactaa aaagcgacat acaattactg tagctctagt taacgagttg    540

aacaacatta agaacgagta tttgaataaa atagttgaat caacctcaga aagccaacta    600

cagatactga tgatggagag tcgatcaaaa gtagatgaag ctgtgtctaa gtttgaaaag    660

gactcatctt cttcgtcaag ttcagactct tccactaaac cggaagcttc agatacagcg    720

aagccaaaca agccgacaga accaggagaa aaggtagcag aagctaagaa gaaggttgaa    780

gaagctgaga aaaaagccaa ggatcaaaaa gaagaagatc gtcgtaacta cccaaccatt    840

acttacaaaa cgcttgaact tgaaattgct gagtccgatg tggaagttaa aaaagcggag    900

cttgaactag taaaagtgaa agctaacgaa cctcgagacg agcaaaaaat taagcaagca    960

gaagcggaag ttgagagtaa acaagctgag gctacaaggt taaaaaaaat caagacagat   1020

cgtgaagaag cagaagaaga agctaaacga agagcagatg ctaaagagca aggtaaacca   1080

aaggggcggg caaaacgagg agttcctgga gagctagcaa cacctgataa aaaagaaaat   1140

gatgcgaagt cttcagattc tagcgtaggt gaagaaactc ttccaagccc atccctgaaa   1200

ccagaaaaaa aggtagcaga agctgagaag aaggttgaag aagctaagaa aaaagccgag   1260

gatcaaaaag aagaagatcg ccgtaactac ccaaccaata cttacaaaac gcttgaactt   1320

gaaattgctg agtccgatgt ggaagttaaa aaagcggagc ttgaactagt aaaagaggaa   1380

gctaaggaac ctcgaaacga ggaaaaagtt aagcaagcaa aagcggaagt tgagagtaaa   1440

aaagctgagg ctactaggtt agaaaaaatc aagacagatc gtaaaaaagc agaagaagaa   1500

gctaaacgaa aagcagcaga agaagataaa gttaaagaaa aaccagctga acaaccacaa   1560

ccagcgccgg ctccaaaagc agaaaaacca gctccagctc caaaaccaga gaatccagct   1620

gaacaaccaa aagcagaaaa accagctgat caacaagctg aagaagagta tgctcgtaga   1680

tcagaagaag aatataatcg cttgactcta cagcaaccgc caaaaactga aaaaccagca   1740

caaccatcta ctccaaaaac aaanac                                        1766
```

<210> SEQ ID NO 75
<211> LENGTH: 1590
<212> TYPE: DNA
<213> ORGANISM: Streptococcus pneumoniae

<400> SEQUENCE: 75

```
aaactattac atgaagttat aatcccaaat ggaagcataa agagataaat acaaaattcg     60

atttatatac agttcatatt gaagtgatat agtaaggtta aagaaaaaat atagaaggaa    120

ataattatgt ttgcatcyaa aagcgaaaga aaagtacatt attcaattcg taaatttagt    180

attggagtag ctagtgtagc tgttgctagc ttgttcttag gaggagtagt ccatgcagaa    240

ggggttagaa gtgagaatac ccccaaggtt acatctagtg gggatgaagt cgatgaatat    300

ataaaaaaaa tgttgagtga gatccaatta gataaaagaa aacataccca caatttcgcc    360
```

-continued

```
ttaaacctaa agttgagcag aattaaaacg gagtatttgt ataaattaaa agttaatgtt        420

ttagaagaaa agtcaaaagc tgagttgacg tcaaaaacaa aaaaagaggt agacgcagct        480

tttgagaagt ttaaaaaaga tacattgaaa ctaggagaaa aggtagcaga agctcagaag        540

aaggttgaag aagctaagaa aaaagccaag gatcaaaaag aagaagatca ccgtaactac        600

ccaaccaata cttacaaaac gcttgaactt gaaattgctg agtccgatgt gaaagttaaa        660

gaagcggagc ttgaactatt gaaagaggaa gctaaaactc gaaacgagga cacaattaac        720

caagcaaaag cgaaagttaa gagtgaacaa gctgaggcta caaggttaaa aaaaatcaag        780

acagatcgtg aacaagctga ggctacaagg ttagaaaaca tcaagacaga tcgtgaaaaa        840

gcagaagaag ctaaacgaaa agcagaagca gaagaagtta aagataaact aaagaggcgg        900

acaaaacgag cagttcctgg agagccagca acacctgata aaaaagaaaa tgatgcgaag        960

tcttcagatt ctagcgtagg tgaagaaact cttccaagcc catccctgaa atcaggaaaa       1020

aaggtagcag aagctcagaa gaaggtagca gaagctgaga aaaaagccaa ggatcaaaaa       1080

gaagaagatc gccgtaacta cccaaccaat acttacaaaa cgcttgacct tgaaattgct       1140

gagtccgatg tgaaagttaa agaagcggag cttgaactag taaaagagga agctaaggaa       1200

tctcgaaacg aggaaaaagt taagcaagca aaagcgaaag ttgagagtaa aaaagctgag       1260

gctacaaggt tagaaaaaat caagacagat cgtaaaaaag cagaagaagc taaacgaaga       1320

gcagcagaag aagataaagt taaagaaaaa ccagctgaac aaccacaacc agcgccggct       1380

cctcaaccag aaaaaccaac tgaagagcct gagaatccag ctccagctcc aaaacctgag       1440

aatccagctg aacaaccaaa agcagaaaaa ccagctgatc aacaagctga agaagactat       1500

gctcgtagat cagaagaaga atataatcgc ttgactcaac agcaaccgcc aaaaactgaa       1560

aaaccagcac aaccatctac tccaaaaaca                                        1590
```

<210> SEQ ID NO 76
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 76
cgacgaatag ctgaagagg                                                     19

<210> SEQ ID NO 77
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 77
cataccgttt tcttgtttcc agcc                                               24